United States Patent
Yoshikuni et al.

(10) Patent No.: US 8,137,949 B2
(45) Date of Patent: Mar. 20, 2012

(54) BIOSYNTHESIS OF COMMODITY CHEMICALS

(75) Inventors: Yasuo Yoshikuni, Albany, CA (US); Adam Joseph Wargacki, Berkeley, CA (US); Asael Herman, Nes Ziona (IL)

(73) Assignee: Bio Architecture Lab, Inc., Berkeley, CA (US)

( * ) Notice: Subject to any disclaimer, the term of this patent is extended or adjusted under 35 U.S.C. 154(b) by 0 days.

(21) Appl. No.: 13/191,389

(22) Filed: Jul. 26, 2011

(65) Prior Publication Data
US 2011/0287521 A1   Nov. 24, 2011

Related U.S. Application Data

(63) Continuation of application No. 12/636,046, filed on Dec. 11, 2009, now Pat. No. 8,003,365.

(60) Provisional application No. 61/121,869, filed on Dec. 11, 2008.

(51) Int. Cl.
*C12N 1/12* (2006.01)

(52) U.S. Cl. .................................. 435/252.1

(58) Field of Classification Search .................. None
See application file for complete search history.

(56) References Cited

OTHER PUBLICATIONS

International Preliminary Report on Patentability mailed Jun. 14, 2011, for PCT/US2009/067750 filed Dec. 11, 2009, 9 pages.
Marshall et al. (1983). "Threonine aldolase and alcohol dehydrogenase activities in *Lactobacillus bulgaricus* and *Lactobacillus acidophilus* and their contribution to flavour production in fermented milks," J. Dairy Res. 50:375-379.
Notice of Allowance mailed Jun. 28, 2011, for U.S. Appl. No. 12/636,046 filed Dec. 11, 2009, 7 pages.

*Primary Examiner* — Alexander Kim
(74) *Attorney, Agent, or Firm* — Morrison & Foerster LLP

(57) ABSTRACT

Methods, enzymes, recombinant microorganism, and microbial systems are provided for converting suitable monosaccharides or oligosaccharides, such as those derived from biomass, as well as various aldehydes and/or ketones, into commodity chemicals, such as biofuels. Commodity chemicals produced by the methods described herein are also provided. Commodity chemical enriched, refinery-produced petroleum products are also provided, as well as methods for producing the same.

3 Claims, 4 Drawing Sheets

Biosynthetic pathway for 2,2,4-trimethyl-1,3-pentanediol

Production of 3-hydroxy-2,2,4-trimethylpentanal from DH10B strain harboring pTrcTM1559 (A) and it's control plasmid (B).

BIOSYNTHESIS OF COMMODITY CHEMICALS

CROSS-REFERENCE TO RELATED APPLICATION

This application is a continuation of copending U.S. patent application Ser. No. 12/636,046, with a filing date of Dec. 11, 2009, which claims the benefit under 35 U.S.C. §119(e) of U.S. Provisional Patent Application No. 61/121,869 filed Dec. 11, 2008, all of which are incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 690212000901SEQLIST.txt, date recorded: Jul. 18, 2011, size: 179 KB).

TECHNICAL FIELD

The present application relates generally to the use of recombinant microorganisms and chemical/enzymatic systems to convert aldehydes and/or ketones to various commodity chemicals or biofuels, such as isooctane.

BACKGROUND

Petroleum is facing declining global reserves and contributes to more than 30% of greenhouse gas emissions driving global warming. Annually 800 billion barrels of transportation fuel are consumed globally. Diesel and jet fuels account for greater than 50% of global transportation fuels.

Significant legislation has been passed, requiring fuel producers to cap or reduce the carbon emissions from the production and use of transportation fuels. Fuel producers are seeking substantially similar, low carbon fuels that can be blended and distributed through existing infrastructure (e.g., refineries, pipelines, tankers).

Due to increasing petroleum costs and reliance on petrochemical feedstocks, the chemical industry is also looking for ways to improve margin and price stability, while reducing its environmental footprint. The chemical industry is striving to develop greener products that are more energy, water, and $CO_2$ efficient than current products. Fuels produced from biological sources, such as biomass, represent one aspect of that process.

Many present methods for converting biomass into biofuels focus on the use of lignocellulolic biomass. However, there are many problems associated with using this process. Large-scale cultivation of lignocellulolic biomass requires a substantial amount of cultivated land, which can be only achieved by replacing food crop production with energy crop production, deforestation, and by recultivating currently uncultivated land. Other problems include a decrease in water availability and quality as well as an increase in the use of pesticides and fertilizers.

The degradation of lignocellulolic biomass using biological systems presents a significant challenge due to its substantial mechanical strength and the complex chemical components. Approximately thirty different enzymes are required to fully convert lignocellulose to monosaccharides. The only available alternate to this complex approach requires a substantial amount of heat, pressure, and strong acids. The art therefore needs an economic and technically simple process for converting biomass into hydrocarbons for use as biofuels or biopetrols. U.S. application Ser. Nos. 12/245,537 and 12/245,540 describe the use of recombinant microorganisms to produce various biofuels from biomass, and also describe the use of such recombinant microorganisms to produce various aldehydes, such as butyraldehyde and isobutyraldehyde, from biomass derived saccharides.

2,2,4-Trimethylpentane, also known as isooctane, is an octane isomer that defines the 100 point on the octane rating scale. Isooctane represents an important component of gasoline. Isooctane is produced on a massive scale in the petroleum industry, often as a mixture with related hydrocarbons. The petroleum industry typically relies on the alkylation process to produce isooctane, which alkylates isobutane with isobutylene using a strong acid catalyst.

Moreover, existing petroleum reserves are less and less useful for gasoline because of low octane content, and the ability to add octane can increase the useability of current petroleum reserves. The art therefore needs an environmentally friendly and technically simple process for producing isooctane, as well as other related biofuels.

BRIEF SUMMARY

Figure 1:
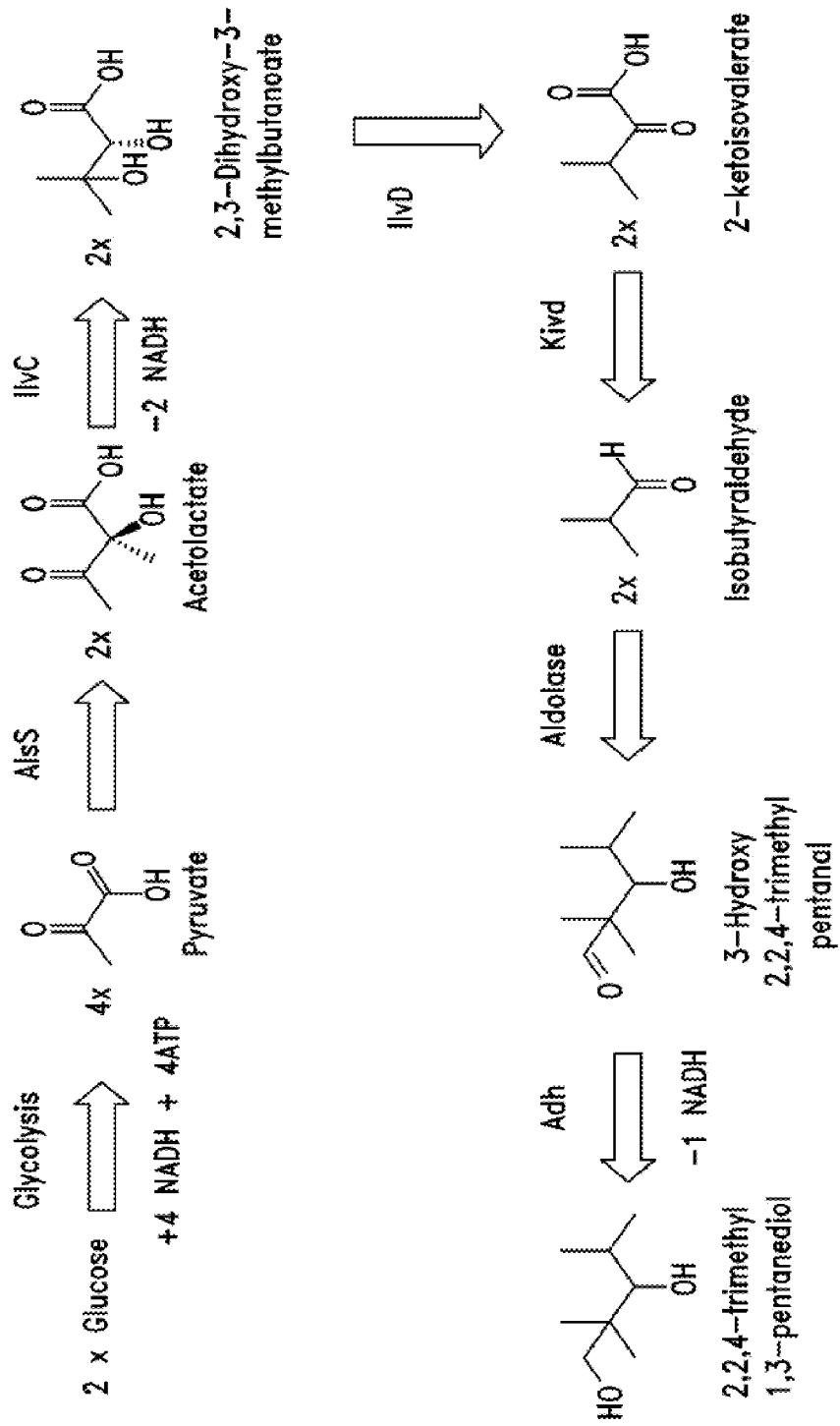
FIG. 1 shows an exemplary pathway by which isobutyraldehyde may be converted in vivo to 2,4,4-trimethyl-1,3-pentanediol.

Embodiments of the present invention relate generally to methods of producing a commodity chemical, or an intermediate thereof, comprising growing a recombinant microorganism with a source of an aldehyde, a ketone, or both, wherein the recombinant microorganism comprises: (i) at least one exogenous polynucleotide encoding and expressing a polypeptide having an aldolase activity; and (ii) at least one exogenous polynucleotide encoding and expressing a polypeptide having an alcohol dehydrogenase activity, wherein at least one of the polynucleotides is exogenous, thereby producing the commodity chemical, or the intermediate thereof.

In certain embodiments, the commodity chemical, or the intermediate thereof, is selected from the following formulas:

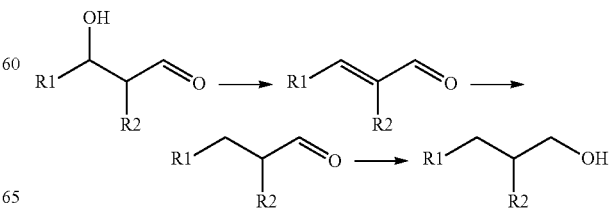

wherein R1 is selected from the group consisting of H, CH$_3$, CH$_3$CH$_2$, CH$_3$CH(CH$_3$), CH$_3$(CH$_2$)$_n$CH$_2$, CH$_3$CH(CH$_3$)(CH$_2$)$_n$CH$_2$, and CH$_3$CH$_2$CH(CH$_3$)(CH$_2$)$_n$CH$_2$; and wherein R2 is selected from the group consisting of H, CH$_3$, CH$_3$CH$_2$, CH$_3$CH(CH$_3$), CH$_3$(CH$_2$)$_n$CH$_2$, CH$_3$CH(CH$_3$)(CH$_2$)$_n$CH$_2$, CH$_3$CH$_2$CH(CH$_3$)(CH$_2$)$_n$CH$_2$, wherein n=0-30. In certain embodiments, the commodity chemical is further enzymatically or chemically converted to its corresponding alkane.

In certain embodiments, the commodity chemical is selected from the group consisting of 3-hydroxy-2,2,4 trimethylpentanal and 2,2,4-trimethyl-1,3-pentanediol. In certain embodiments, the 2,2,4-trimethyl-1,3-pentanediol is further enzymatically or chemically converted to 2,2,4-trimethylpentane.

In certain embodiments, the commodity chemical is selected from the group consisting of 3-hydroxy-2-ethylhexanal, 2-ethyl-2-hexene-1-al, 2-ethylhexanal, and 2-ethylhexanol. In certain embodiments, the 2-ethylhexanol is further enzymatically or chemically converted to 2-ethylhexane.

In certain embodiments, the commodity chemical is selected from the group consisting of 3-hydroxy-2-butyl-1-octanol, 2-butyl-2-octene-1-al, 2-butyl-octanal, and 2-butyl-octanol. In certain embodiments, the 2-butyl-octanol is further enzymatically or chemically converted to 2-butyl-octane.

In certain embodiments, the source of the aldehyde, ketone, or both is a recombinant microorganism that comprises an aldehyde and/or ketone biosynthesis pathway selected from an acetoaldehyde, propionaldehyde, glutaraldehyde, butyraldehyde, isobutyraldehyde, 2-methyl-butyraldehyde, 3-methyl-butyraldehyde, 4-methylpentaldehyde, hexanaldehyde, octanaldehyde, phenylacetoaldehyde, 2-phenyl acetoaldehyde, 2-(4-hydroxyphenyl)acetoaldehyde, 2-Indole-3-acetoaldehyde, 5-amino-pentaldehyde, succinate semialdehyde, and a succinate 4-hydroxyphenyl acetaldehyde biosynthesis pathway, and combinations thereof.

In certain embodiments, the recombinant microorganism that comprises the aldehyde and/or ketone biosynthesis pathway is the same as the recombinant microorganism that produces or synthesizes the commodity chemical. In certain embodiments, the recombinant microorganism that comprises the aldehyde and/or ketone biosynthesis pathway is different than the recombinant microorganism that produces or synthesizes the commodity chemical.

In certain embodiments, the aldehyde and/or ketone biosynthesis pathway comprises an isobutyraldehyde biosynthesis pathway, and wherein the aldehyde is isobutyraldehyde. In certain embodiments, the aldehyde and/or ketone biosynthesis pathway comprises a butyraldehyde biosynthesis pathway, and wherein the aldehyde is butyraldehyde. In certain embodiments, the aldehyde and/or ketone biosynthesis pathway comprises a hexanaldehyde biosynthesis pathway, and wherein the aldehyde is hexanaldehyde.

In certain embodiments, the at least one exogenous polynucleotide encoding and expressing the polypeptide having the aldolase activity comprises (i) a nucleotide sequence that is at least 80%, 90%, 95%, 98%, or 99% identical to at least one nucleotide sequence set forth in SEQ ID NOS:51-82, or (ii) a nucleotide sequence that hybridizes to at least one nucleotide sequence set forth in SEQ ID NOS:51-82, or a complement thereof, under conditions of medium stringency. In certain embodiments, the polypeptide having the aldolase activity comprises at least one biologically active motif selected from the amino acid sequences set forth in SEQ ID NOS:223-244, 255-260.

In certain embodiments, the at least one exogenous polynucleotide encoding and expressing the polypeptide having the alcohol dehydrogenase activity comprises (i) a nucleotide sequence that is at least 80%, 90%, 95%, 98%, or 99% identical to the nucleotide sequence set forth in SEQ ID NOS: 1, 3, 5, 7, 9, 11, 13, 15, 17, 19, 21, 23, 25, 27, 29, 30, 31, 33, or 83-96, or (ii) a nucleotide sequence that hybridizes to at least one nucleotide sequence set forth in SEQ ID NOS:1, 3, 5, 7, 9, 11, 13, 15, 17, 19, 21, 23, 25, 27, 29, 30, 31, 33, or 83-96, or a complement thereof, under conditions of medium stringency. In certain embodiments, the polypeptide having the alcohol dehydrogenase activity comprises at least one of a nicotinamide adenine dinucleotide (NAD+), a NADH, nicotinamide adenine dinucleotide phosphate (NADP+), or a NADPH binding motif. In certain embodiments, the NAD+, NADH, NADP+, or NADPH binding motif is selected from the group consisting of Y-X-G-G-X-Y (SEQ ID NO:245), Y-X-X-G-G-X-Y (SEQ ID NO:246), Y-X X-X-G-G-X-Y (SEQ ID NO:247), Y-X-G-X-X-Y (SEQ ID NO:248), Y-X-X-G-G-X-X-Y (SEQ ID NO:249), Y-X-X-X-G-G-X-X-Y (SEQ ID NO:250), Y-X-G-X-Y (SEQ ID NO:251), Y-X-X-G-X-Y (SEQ ID NO:252), Y-X-X-X-G-X-Y (SEQ ID NO:253), and Y-X-X-X-X-G-X-Y (SEQ ID NO:254); wherein Y is independently selected from alanine, glycine, and serine, wherein G is glycine, and wherein X is independently selected from a genetically encoded amino acid.

In certain embodiments, the recombinant microorganism further comprises at least one exogenous polynucleotide encoding and expressing a polypeptide having a double bond reductase activity and/or at least one polynucleotide encoding and expressing a polypeptide having a dehydratase activity. In certain embodiments, the at least one exogenous polynucleotide encoding and expressing the polypeptide having the double bond reductase activity comprises (i) a nucleotide sequence that is at least 80%, 90%, 95%, 98%, or 99% identical to the nucleotide sequence set forth in SEQ ID NOS:35-50, or (ii) a nucleotide sequence that hybridizes to at least one nucleotide sequence set forth in SEQ ID NOS:35-50, or a complement thereof, under conditions of medium stringency.

Embodiments of the present invention also relate generally to recombinant microorganisms, comprising (i) at least one exogenous polynucleotide encoding and expressing a polypeptide having an aldolase activity; and (ii) at least one exogenous polynucleotide encoding and expressing a polypeptide having an alcohol dehydrogenase activity.

In certain embodiments, the recombinant microorganism is capable of converting a source of an aldehyde, a ketone, or both, to a commodity chemical, or an intermediate thereof, wherein the commodity chemical, or the intermediate thereof, is selected from the following formulas:

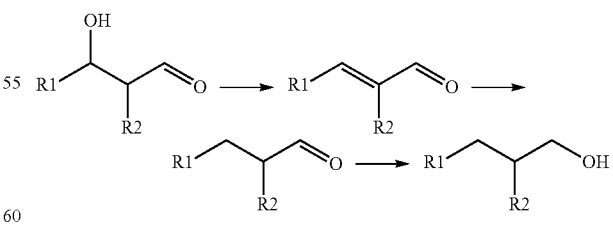

wherein R1 is selected from the group consisting of H, CH$_3$, CH$_3$CH$_2$, CH$_3$CH(CH$_3$), CH$_3$(CH$_2$)$_n$CH$_2$, CH$_3$CH(CH$_3$)(CH$_2$)$_n$CH$_2$, and CH$_3$CH$_2$CH(CH$_3$)(CH$_2$)$_n$CH$_2$; and wherein R2 is selected from the group consisting of H, CH$_3$, CH$_3$CH$_2$, CH$_3$CH(CH$_3$), CH$_3$(CH$_2$)$_n$CH$_2$, CH$_3$CH(CH$_3$)(CH$_2$)$_n$CH$_2$, CH$_3$CH$_2$CH(CH$_3$)(CH$_2$)$_n$CH$_2$, wherein n=0-30.

In certain embodiments, the recombinant microorganism further comprises (iii) at least one exogenous polynucleotide encoding and expressing an aldehyde and/or ketone biosynthesis pathway. In certain embodiments, the microorganism that further comprises the aldehyde and/or ketone biosynthesis pathway is capable of converting a suitable monosaccharide or suitable oligosaccharide to a commodity chemical, or an intermediate thereof, wherein the commodity chemical, or the intermediate thereof, is selected from the following formulas:

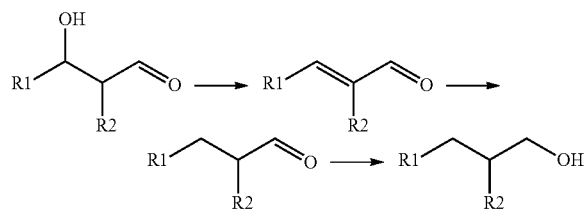

wherein R1 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, and $CH_3CH_2CH(CH_3)(CH_2)_nCH_2$; and wherein R2 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, $CH_3CH_2CH(CH_3)(CH_2)_nCH_2$, wherein n=0-30.

In certain embodiments, the at least one exogenous polynucleotide encoding and expressing the aldehyde and/or ketone biosynthesis pathway comprises a pathway selected from an acetoaldehyde, propionaldehyde, glutaraldehyde, butyraldehyde, isobutyraldehyde, 2-methyl-butyraldehyde, 3-methyl-butyraldehyde, 4-methylpentaldehyde, hexanaldehyde, octanaldehyde, phenylacetoaldehyde, 2-phenyl acetoaldehyde, 2-(4-hydroxyphenyl)acetoaldehyde, 2-Indole-3-acetoaldehyde, 5-amino-pentaldehyde, succinate semialdehyde, and succinate 4-hydroxyphenyl acetaldehyde biosynthesis pathway, and combinations thereof.

In certain embodiments, the aldehyde and/or ketone biosynthesis pathway comprises an isobutyraldehyde biosynthesis pathway, and wherein the aldehyde is isobutyraldehyde. In certain embodiments, the aldehyde and/or ketone biosynthesis pathway comprises a butyraldehyde biosynthesis pathway, and wherein the aldehyde is butyraldehyde. In certain embodiments, the aldehyde and/or ketone biosynthesis pathway comprises a hexanaldehyde biosynthesis pathway, and wherein the aldehyde is hexanaldehyde.

In certain embodiments, the at least one exogenous polynucleotide encoding and expressing the polypeptide having the aldolase activity comprises (i) a nucleotide sequence that is at least 80%, 90%, 95%, 98%, or 99% identical to at least one nucleotide sequence set forth in SEQ ID NOS:51-82, or (ii) a nucleotide sequence that hybridizes to at least one nucleotide sequence set forth in SEQ ID NOS:51-82, or a complement thereof, under conditions of medium stringency. In certain embodiments, the polypeptide having the aldolase activity comprises at least one biologically active motif selected from the amino acid sequences set forth in SEQ ID NOS:223-244, 255-260.

In certain embodiments, the at least one exogenous polynucleotide encoding and expressing the polypeptide having the alcohol dehydrogenase activity comprises (i) a nucleotide sequence that is at least 80%, 90%, 95%, 98%, or 99% identical to the nucleotide sequence set forth in SEQ ID NOS: 1, 3, 5, 7, 9, 11, 13, 15, 17, 19, 21, 23, 25, 27, 29, 30, 31, 33, or 83-96, or (ii) a nucleotide sequence that hybridizes to at least one nucleotide sequence set forth in SEQ ID NOS:1, 3, 5, 7, 9, 11, 13, 15, 17, 19, 21, 23, 25, 27, 29, 30, 31, 33, or 83-96, or a complement thereof, under conditions of medium stringency. In certain embodiments, the polypeptide having the alcohol dehydrogenase activity comprises at least one of a nicotinamide adenine dinucleotide (NAD+), a NADH, nicotinamide adenine dinucleotide phosphate (NADP+), or a NADPH binding motif. In certain embodiments, the NAD+, NADH, NADP+, or NADPH binding motif is selected from the group consisting of Y-X-G-G-X-Y (SEQ ID NO:245), Y-X-X-G-G-X-Y (SEQ ID NO:246), Y-X-X-X-G-G-X-Y (SEQ ID NO:247), Y-X-G-X-X-Y (SEQ ID NO:248), Y-X-X-G-G-X-X-Y (SEQ ID NO:249), Y-X-X-X-G-X-X-Y (SEQ ID NO:250), Y-X-G-X-Y (SEQ ID NO:251), Y-X-X-G-X-Y (SEQ ID NO:252), Y-X-X-X-G-X-Y (SEQ ID NO:253), and Y-X-X-X-X-G-X-Y (SEQ ID NO:254); wherein Y is independently selected from alanine, glycine, and serine, wherein G is glycine, and wherein X is independently selected from a genetically encoded amino acid.

In certain embodiments, the recombinant microorganism further comprises at least one exogenous polynucleotide encoding and expressing a polypeptide having a double bond reductase activity and/or at least one polynucleotide encoding and expressing a polypeptide having a dehydratase activity. In certain embodiments, the at least one exogenous polynucleotide encoding and expressing the polypeptide having the double bond reductase activity comprises (i) a nucleotide sequence that is at least 80%, 90%, 95%, 98%, or 99% identical to the nucleotide sequence set forth in SEQ ID NOS:35-50, or (ii) a nucleotide sequence that hybridizes to at least one nucleotide sequence set forth in SEQ ID NOS:35-50, or a complement thereof, under conditions of medium stringency.

Embodiments of the present invention also relate generally to methods of producing a commodity chemical, or an intermediate thereof, comprising growing a first recombinant microorganism with a source of a suitable monosaccharide or oligosaccharide, wherein the first recombinant microorganism comprises, (i) an aldehyde or ketone biosynthesis pathway, (ii) at least one polynucleotide encoding and expressing a polypeptide having an aldolase activity; and (iii) at least one polynucleotide encoding and expressing a polypeptide having an alcohol dehydrogenase activity; wherein at least one of the polynucleotides is exogenous, thereby producing the commodity chemical, or the intermediate thereof. In certain embodiments, the source of the suitable monosaccharide or oligosaccharide comprises a second recombinant microorganism that is capable of growing on a biomass-derived polysaccharide as a sole source of carbon. In certain embodiments, the biomass-derived polysaccharide is selected from alginate and pectin.

Embodiments of the present invention also relate generally to methods of producing a commodity chemical, or an intermediate thereof, comprising growing a recombinant microorganism with a biomass-derived polysaccharide, wherein the recombinant microorganism is capable of growing on the biomass-derived polysaccharide as a sole source of carbon, and wherein the recombinant microorganism comprises (i) an aldehyde or ketone biosynthesis pathway, (ii) at least one polynucleotide encoding and expressing a polypeptide having an aldolase activity; and (iii) at least one polynucleotide encoding and expressing a polypeptide having an alcohol dehydrogenase activity, wherein at least one of the polynucleotides is exogenous, thereby producing the commodity chemical, or the intermediate thereof. In certain embodiments, the biomass-derived polysaccharide is selected from alginate and pectin.

Embodiments of the present invention also relate to recombinant microorganisms, comprising (i) an aldehyde or ketone biosynthesis pathway, (ii) at least one exogenous polynucleotide encoding and expressing a polypeptide having an aldolase activity; and (iii) at least one exogenous polynucleotide encoding and expressing a polypeptide having an alcohol dehydrogenase activity. In certain embodiments, the recombinant microorganism is capable of growing on a biomass-derived polysaccharide as a sole source of carbon.

In certain embodiments, the microorganism is selected from *Acetobacter aceti, Achromobacter, Acidiphilium, Acinetobacter, Actinomadura, Actinoplanes, Aeropyrum pernix, Agrobacterium, Alcaligenes, Ananas comosus* (M), *Arthrobacter, Aspargillus niger, Aspargillus oryze, Aspergillus melleus, Aspergillus pulverulentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus lentus, Bacillus licheniformis, Bacillus macerans, Bacillus stearothermophilus, Bacillus subtilis, Bifidobacterium, Brevibacillus brevis, Burkholderia cepacia, Candida cylindracea, Candida rugosa, Carica papaya* (L), *Cellulosimicrobium, Cephalosporium, Chaetomium erraticum, Chaetomium gracile, Clostridium, Clostridium butyricum, Clostridium acetobutylicum, Clostridium thermocellum, Corynebacterium* (*glutamicum*), *Corynebacterium efficiens, Escherichia coli, Enterococcus, Erwina chrysanthemi, Gliconobacter, Gluconacetobacter, Haloarcula, Humicola insolens, Humicola nsolens, Kitasatospora setae, Klebsiella, Klebsiella oxytoca, Kluyveromyces, Kluyveromyces fragilis, Kluyveromyces lactis, Kocuria, Lactlactis, Lactobacillus, Lactobacillus fermentum, Lactobacillus sake, Lactococcus, Lactococcus lactis, Leuconostoc, Methylocystis, Methanolobus siciliae, Methanogenium organophilum, Methanobacterium bryantii, Microbacterium imperiale, Micrococcus lysodeikticus, Microlunatus, Mucor javanicus, Mycobacterium, Myrothecium, Nitrobacter, Nitrosomonas, Nocardia, Papaya carica, Pediococcus, Pediococcus halophilus, Penicillium, Penicillium camemberti, Penicillium citrinum, Penicillium emersonii, Penicillium roqueforti, Penicillum lilactinum, Penicillum multicolor, Paracoccus pantotrophus, Propionibacterium, Pseudomonas, Pseudomonas fluorescens, Pseudomonas denitrificans, Pyrococcus, Pyrococcus furiosus, Pyrococcus horikoshii, Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, Sccharomyces cerevisiae, Sclerotina libertina, Sphingobacterium multivorum, Sphingobium, Sphingomonas, Streptococcus, Streptococcus thermophilus* Y-1, *Streptomyces, Streptomyces griseus, Streptomyces lividans, Streptomyces murinus, Streptomyces rubiginosus, Streptomyces violaceoruber, Streptoverticillium mobaraense, Tetragenococcus, Thermus, Thiosphaera pantotropha, Trametes, Trichoderma, Trichoderma longibrachiatum, Trichoderma reesei, Trichoderma viride, Trichosporon penicillatum, Vibrio alginolyticus, Xanthomonas*, yeast, *Zygosaccharomyces rouxii, Zymomonas*, and *Zymomonus mobilis*.

Embodiments of the present invention also relate to commodity chemicals produced by any of the methods or recombinant microorganisms described herein. Certain embodiments also include blended commodity chemicals comprising any of the commodity chemicals described herein and a refinery-produced petroleum product. In certain embodiments, the commodity chemical is selected from isooctane, 2-ethylhexane, and 2-butyl-octane. In certain embodiments, the refinery-produced petroleum product is selected from gasoline, jet fuel, and diesel fuel.

The present invention also relates to methods of producing a commodity chemical enriched refinery-produced petroleum product, comprising (a) blending a refinery-produced petroleum product with any of the commodity chemicals produced by the methods or recombinant microorganisms described herein, thereby producing the commodity chemical enriched refinery-produced petroleum product.

DETAILED DESCRIPTION

Embodiments of the present invention relate to the discovery that recombinant microorganisms can be engineered to utilize various aldehydes and/or ketones in the production of a variety of commodity chemicals or biofuels. For instance, the insertion of one or more exogenous polynucleotides that encode an enzyme having an aldolase activity and one or more exogenous polynucleotides that encode an enzyme having an alcohol dehydrogenase activity may render a microorganism capable of converting aldehydes and/or ketones into various commodity chemicals, or intermediates thereof. In certain aspects, these commodity chemicals may then be further chemically or enzymatically converted to other commodity chemicals, including biofuels. Such biofuels may include, for example, medium to long chain alkanes, such as isooctane and 2-ethylhexane.

In certain embodiments, the methods and recombinant microorganisms provided herein may be utilized to produce a variety of commodity chemicals, especially medium to long chain hydrocarbons. For instance, recombinant microorganisms of the present invention may be utilized generally to catalyze the following reactions:

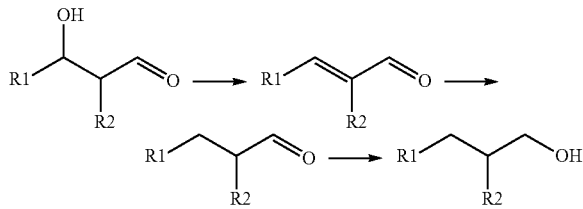

wherein R1 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, and $CH_3CH_2CH(CH_3)(CH_2)_nCH_2$; and wherein R2 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, $CH_3CH_2CH(CH_3)(CH_2)_nCH_2$, wherein n=0-30, and any corresponding alkanes produced therefrom.

Typically, the first chemical from left to right in the reaction exemplified above is produced from the condensation of two aldehydes and/or ketones, which may be the same or different, and which may be catalyzed by an enzyme having an aldolase activity, as described herein and known in the art.

After the aldolase condensation step, the first step in the reaction exemplified above typically occurs spontaneously, or may be catalyzed by a dehydratase. The second reaction may be catalyzed by an endogenous double bond reductase, or may be enhanced by the addition of an exogenous double bond reductase. The third reaction to produce the diol or alcohol may be catalyzed by an alcohol dehydrogenase, as described herein and known in the art. Thus, certain recombinant microorganisms of the invention may comprise an exogenous aldolase, optionally an exogenous double bond reductase, and/or an exogenous alcohol dehydrogenase.

As noted above, 2,2,4-trimethylpentane, also known as isooctane, is an octane isomer that defines the 100 point on the octane rating scale, and represents an important component of gasoline. As one particular illustration of the in vivo biological production of this molecule, a biosynthetic pathway to produce isooctane may be initiated in a recombinant microorganism that has access to a source of isobutyraldehyde. In certain embodiments, isobutyraldehyde may be obtained from a recombinant microorganism that comprises a isobutyraldehyde biosynthesis pathway, as described herein, and which can convert a suitable monosaccharide or oligosaccharide to isobutyraldehyde.

Briefly, regardless of the source of isobutyraldehyde, a recombinant microorganism of the invention may be utilized to condense two molecules of isobutyraldehyde to form 3-hydroxy-2,2,4-trimethyl pentanal, which has been shown herein to be catalyzed in vivo by a recombinant microorganism that comprises an exogenous enzyme having an aldolase activity. In certain embodiments, 3-hydroxy-2,2,4-trimethyl pentanal may then be readily reduced in vivo to 2,2,4-trimethyl-1,3-pentanediol by a recombinant microorganism that comprises an exogenous enzyme having an alcohol dehydrogenase (Adh) activity. Thus, in certain embodiments, a recombinant microorganism comprising one or more polynucleotides encoding an aldolase enzyme and one or more polynucleotides encoding an alcohol dehydrogenase enzyme may be utilized to synthesize 3-hydroxy-2,2,4-trimethyl pentanal and 2,2,4-trimethyl-1,3-pentanediol from a source of isobutyraldehyde, which may then be further converted to isooctane.

For the final steps in the production of isooctane, if desired, 2,2,4-trimethyl-1,3-pentanediol may then be converted to 2,2,4-trimethylpentane, or isooctane, by various processes, such as chemical or enzymatic processes. One example of such a process includes "hydrotreating," as described herein and known in the art.

As an additional example of converting an aldehyde or ketone to a commodity chemical, a recombinant microorganism provided herein may be utilized to condense two molecules of butyraldehyde to form 3-hydroxy-2-ethylhexanal, which has been shown herein to be catalyzed in vivo by a recombinant microorganism that comprises an exogenous enzyme having an aldolase activity. 3-hydroxy-2-ethylhexanal may then be spontaneously or enzymatically dehydrated to form 2-ethyl-2-hexene-1-al, as also described herein. In certain embodiments, 2-ethyl-2-hexene-1-al may then be consecutively reduced to form 2-ethylhexanal and 2-ethylhexanol, catalyzed by a double bond reductase and an alcohol dehydrogenase, respectively (see Example 4). For the final step, if desired, 2-ethylhexanol may then be converted to 2-ethylhexane according to techniques known in the art and described herein, such as by chemical or enzymatic conversion (e.g., hydrotreating).

Thus, in certain embodiments, a recombinant microorganism comprising one or more exogenous polynucleotides encoding an aldolase enzyme and one or more exogenous polynucleotides encoding an alcohol dehydrogenase enzyme may be utilized to synthesize 2-ethyl-2-hexene-1-al and 2-ethylhexanol from a source of butyraldehyde, which may then be converted to 2-ethylhexane. In certain embodiments, butyraldehyde may be obtained from a recombinant microorganism that comprises a butyraldehyde biosynthesis pathway, as described herein, and which can convert a monosaccharide or oligosaccharide to butyraldehyde.

The methods described herein produce biofuels with significant advantages over other biofuels. In particular, isooctane and other medium to long chain alkanes provide a number of important advantages over the existing common biofuels, such as ethanol and butanol, and are attractive long-term replacements of petroleum-based fuels such as gasoline, diesels, kerosene, and heavy oils in the future. As one example, isooctane and other medium to long chain alkanes and alcohols are major components in all petroleum products and jet fuel in particular, and hence alkanes we produce can be utilized directly by existing engines. By way of further example, medium to long chain alcohols are far better fuels than ethanol, and have a nearly comparable energy density to gasoline. As noted above, isooctane is a major component of gasoline.

As another example, n-alkanes are major components of all oil products including gasoline, diesels, kerosene, and heavy oils. Recombinant microorganisms may be used to produce n-alkanes with different carbon lengths ranging, for example, from C7 to over C20: C7 for gasoline (e.g., motor vehicles), C10-C15 for diesels (e.g., motor vehicles, trains, and ships), and C8-C16 for kerosene (e.g., aviations and ships), and for all heavy oils.

Certain embodiments of the present invention relate generally to methods for producing isooctane and other medium to long chain alkanes from biomass-derived feedstock, thereby providing a low carbon source of biofuels. For instance, in producing a commodity chemical or biofuel (e.g., isooctane) from biomass, a suitable biomass-derived monosaccharide or oligosaccharide may be first obtained directly from any available source, such as a microorganism that is capable of growing on a biomass-derived polysaccharide, such as pectin or alginate, as a sole source of carbon. This monosaccharide or oligosaccharide may then converted to an aldehyde and/or ketone by contacting that monosaccharide or oligosaccharide with a recombinant microorganism that comprises an aldehyde and/or ketone biosynthesis pathway.

The aldehyde and/or ketone produced by such a recombinant microorganism may then be converted to a commodity chemical or biofuel by contacting that aldehyde and/or ketone with a recombinant microorganism of the present invention, such as a microorganism that comprises both an aldolase enzyme and an alcohol dehydrogenase enzyme. In certain embodiments, the recombinant microorganism that comprises the aldehyde and/or ketone biosynthesis pathway may be the same or different as the recombinant microorganism that comprises the aldolase enzyme and the alcohol dehydrogenase enzyme.

Among other uses apparent to a person skilled in the art, the commodity chemicals and biofuels produced by the methods and recombinant microorganisms described herein may be utilized by existing petroleum refineries for blending with petroleum products produced by traditional refinery methods, to produce commodity chemical enriched, refinery-produced petroleum products. To this end, as noted above, fuel producers are seeking substantially similar, low carbon fuels that can be blended and distributed through existing infrastructure (refineries, pipelines, tankers). As hydrocarbons, the commodity chemicals produced according to the methods herein are substantially similar to petroleum derived fuels, reduce green house gas emissions by more than 80% from petroleum derived fuels, and are compatible with existing infrastructure in the oil and gas industry.

For instance, certain of the commodity chemicals produced herein, including, for example, isooctane, among others, are blendable directly into refinery-produced petroleum products, such as gasoline, jet and diesel fuels. By using such biologically produced commodity chemicals as a blendstock for gasoline, jet and diesel fuels, refineries may reduce Green House Gas emissions by more than 80%.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *A Practical Guide to Molecular Cloning* (B. Perbal, ed., 1984).

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All references referred to herein are incorporated by reference in their entirety.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment," as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence.

The term "reference sequence" refers generally to a nucleic acid coding sequence, or amino acid sequence, of any polypeptide or enzyme having a biological activity described herein (e.g., aldolase, alcohol dehydrogenase, dehydratase, diol dehydrogenase, double bond reductase etc.), such as a "wild-type" sequence, including those polynucleotide and polypeptide reference sequences exemplified by SEQ ID NOS:1-96 and 215-222, and including those motif sequences exemplified by SEQ ID NOS:223-260. A reference sequence may also include naturally-occurring, functional variants (i.e., orthologs or homologs) of the sequences described herein.

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an enzymatic activity of a reference polynucleotide or polypeptide. Representative biologically active fragments generally participate in an interaction, e.g., an intra-molecular or an inter-molecular interaction. An inter-molecular interaction can be a specific binding interaction or an enzymatic interaction. Examples of enzymatic interactions or activities include aldolase activities, alcohol dehydrogenase activities, dehydratases activities, lyase activities, transporter activities, isomerase activities, kinase activities, among others described herein. Biologically active fragments typically comprise one or more active sites or enzymatic/binding motifs, as described herein and known in the art.

A "biomolecule" refers generally to an organic molecule that is produced by a living organism, including large polymeric molecules (biopolymers) such as proteins, polysaccharides, and nucleic acids as well, as small molecules such as primary secondary metabolites, lipids, phospholipids, glycolipids, sterols, glycerolipids, vitamins, and hormones. Organic molecules (e.g., biomolecules) consist primarily of carbon and hydrogen, nitrogen, and oxygen, and, to a smaller extent, phosphorus and sulfur, although other elements may be incorporated into a biomolecule.

A "biopolymer" refers generally to a large molecule or macromolecule composed of repeating structural units, which are typically connected by covalent chemical bonds, and which can be produced by living organisms. Examples of biopolymers include, without limitation, polysaccharides, nucleic acids, and proteins.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, the terms "function" and "functional" and the like refer to a biological or enzymatic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected, transformed, or infected in vivo or in vitro with a recombinant vector or a polynucleotide of the invention. A host cell which comprises a recombinant vector of the invention is a recombinant host cell, recombinant cell, or recombinant microorganism.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

By "enhance," "enhancing," "increase," or "increasing" is meant the ability of one or more recombinant microorganisms to produce a greater amount of a given product or molecule (e.g., commodity chemical, biofuel, or intermediate product thereof) as compared to a control microorganism, such as an unmodified microorganism or a differently modified microorganism. An "increased" amount is typically a "statistically significant" amount, and may include an increase that is 1, 2, 3, 4, 5, 6, 7, 8, 9, 10, 15, 20, 30, 40, 50, 60, 70, 80, 90, 100 or more times (including all integers and decimal points in between, e.g., 1.5, 1.6, 1.7. 1.8, etc.) the amount produced by an unmodified microorganism or a differently modified microorganism. An increased amount may be measured according to routine techniques in the art. For instance, an "increased" amount of a commodity chemical may be measured according to a percentage of a theoretical maximum yield. For instance, in certain embodiments, the methods of the present invention may enhance the yield of a target molecule (e.g., commodity chemical) to at least about 30%, 35%, 40%, 45%, 50%, 55%, 60%, 65%, 70%, 75%, 80%, 85%, 88%, 90%, 91%, 92%, 93%, 94%, 95%, 96%, 97%, 98%, 99%, or 100% of a theoretical maximum yield. In certain embodiments, the method may be characterized by increasing the percentage of the theoretical maximum yield of the target molecule by at least about 10% (e.g., from about 30% to about 40% of the theoretical maximum yield), 15% (e.g., from about 30% to about 45%), 20%, 25%, 30%, 35%, 40%, 50%, 60%, 70%, 80%, or 90% as compared to incubating the same recombinant microorganism under control or different conditions, or as compared to incubating a control (e.g., unmodified or differently modified) microorganism under the same or similar conditions.

The term "reduce" relates generally to a "decrease" in a relevant cellular response, such as NADH or acetate production, as measured according to routine techniques in the diagnostic art. Other relevant cellular responses (in vivo or in vitro) will be apparent to persons skilled in the art. A "decrease" in a response may be "statistically significant" amount as compared to the response produced by an unmodified microorganism or a differently modified microorganism, or by a microorganism growing under different conditions, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

By "obtained from" is meant that a sample such as, for example, a polynucleotide extract or polypeptide extract is isolated from, or derived from, a particular source, such as a desired organism, typically a microorganism. "Obtained from" can also refer to the situation in which a polynucleotide or polypeptide sequence is isolated from, or derived from, a particular organism or microorganism. For example, a polynucleotide sequence encoding a benzaldehyde lyase enzyme may be isolated from a variety of prokaryotic or eukaryotic microorganisms, such as *Pseudomonas*. As another example, a polynucleotide sequence encoding an aldolase enzyme may be isolated from a variety of prokaryotic or eukarotic microrganisms, such as *Thermotoga maritima* and *Escherichia coli* DH10B.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., $CO_2$ concentration, nutrient levels, light, heat). In the absence of that condition, inducible promoters typically do not allow significant or measurable levels of transcriptional activity.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide, and preferably such that the enzymatic activity of the encoded polypeptide is improved (e.g., optimized) relative to the unmodified polypeptide. The effect on the enzymatic activity of the encoded polypeptide may generally be assessed as described herein.

In certain embodiments, the present invention provides isolated polynucleotides comprising various lengths of contiguous stretches of sequence identical to or complementary to an aldolase or an alcohol dehydrogenase, among others described herein, wherein the isolated polynucleotides encode a biologically active, truncated enzyme.

Exemplary nucleotide sequences that encode the enzymes of the application encompass full-length aldolases and alcohol dehydrogenases, as well as portions of the full-length or substantially full-length nucleotide sequences of these genes or their transcripts or DNA copies of these transcripts. Portions of a nucleotide sequence may encode polypeptide portions or segments that retain the biological activity of the reference polypeptide. A portion of a nucleotide sequence that encodes a biologically active fragment of an enzyme provided herein may encode at least about 20, 21, 22, 23, 24, 25, 30, 40, 50, 60, 70, 80, 90, 100, 120, 150, 200, 300, 400, 500, 600, or more contiguous amino acid residues, almost up to the total number of amino acids present in a full-length enzyme. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The terms "polynucleotide variant" and "variant" and the like refer to polynucleotides that display substantial sequence identity with any of the reference polynucleotide sequences or genes described herein, and to polynucleotides that hybridize with any polynucleotide reference sequence described herein, or any polynucleotide coding sequence of any gene or polypeptide referred to herein, under low stringency, medium stringency, high stringency, or very high stringency conditions that are defined hereinafter and known in the art. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between) sequence identity with a reference polynucleotide described herein.

The terms "polynucleotide variant" and "variant" also include naturally-occurring allelic variants that encode these enzymes. Examples of naturally-occurring variants include allelic variants (same locus), homologs (different locus), and orthologs (different organism). Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having a suitable enzymatic activity described herein (e.g., C—C ligase, aldolase, alcohol dehydrogenase, reductase, etc.).

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in a given microorganism (e.g., *E. coli*), such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide.

Generally, variants of a particular reference nucleotide sequence may have at least about 30%, 40% 50%, 55%, 60%, 65%, 70%, generally at least about 75%, 80%, 85%, 90% to 95% or more, and even about 97% or 98% or more sequence identity to that particular nucleotide sequence as determined by sequence alignment programs described elsewhere herein using default parameters.

Known aldolase, alcohol dehydrogenase, double bond reductase, and other nucleotide reference sequences can be used to isolate corresponding sequences and alleles from other organisms, particularly other microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other reference coding sequences present in a population of cloned genomic DNA fragments or cDNA fragments (i.e., genomic or cDNA libraries) from a chosen organism.

The present invention also contemplates polynucleotides that hybridize to reference aldolase, alcohol dehydrogenase, double bond reductase, or other nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., "Current Protocols in Molecular Biology", John Wiley & Sons Inc, 1994-1998, Sections 6.3.1-6.3.6. Aqueous and non-aqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

One embodiment of "very high stringency" conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al., Current Protocols in Molecular Biology (1989), at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6$ ($\log_{10}$ M)+0.41 (% G+C)−0.63 (% formamide)−(600/length) wherein: M is the concentration of Na$^+$, preferably in the range of 0.01 molar to 0.4 molar; % G+C is the sum of guano sine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5× Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C. Based on the above, embodiments of the present invention include recombinant microorganisms that comprise a polynucleotide sequence that hybridizes to the complement of any of the reference polynucleotide sequences described herein, such as a polynucleotide sequence that encodes an aldolase or an alcohol dehydrogenase enzyme, under conditions of medium, high, or very high stringency, as described herein and known in the art.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a selected enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life that is longer than that of a transcript generated from the naturally occurring sequence. Such nucleotides are typically referred to as "codon-optimized." Any of the nucleotide sequences described herein may be utilized in such a "codon-optimized" form.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct localization of the encoded polypeptide to a desired site within the cell. Other recombinant constructions may be used to join sequences encoding a polypeptide of interest to nucleotide sequence encoding a polypeptide domain which will direct secretion of the encoded protein.

Embodiments of the present invention contemplate the use of recombinant microorganisms comprising "polypeptides" having an aldolase activity, alcohol dehydrogenase activity, double bond reductase activity, or other activity described herein, including truncated, variant and/or modified polypeptides thereof, for producing commodity chemicals. "Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant may be distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

Variant proteins encompassed by the present application are "biologically active," that is, they continue to possess the enzymatic activity of a reference polypeptide. Such variants may result from, for example, genetic polymorphism or from human manipulation. Biologically active variants of a reference polypeptide sequence or fragment thereof may have at least about 40%, 50%, 60%, 70%, generally at least about 75%, 80%, 85%, usually about 90% to 95% or more, and typically about 98% or more sequence similarity or identity with the amino acid sequence for a reference protein as determined by sequence alignment programs described elsewhere herein using default parameters. A biologically active variant of a reference polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from a reference polypeptide sequences by at least one but by less than 15, 10 or 5 amino acid residues. In other embodiments, it differs from the reference sequences by at least one residue but less than 20%, 15%, 10% or 5% of the residues.

The present invention contemplates the use in the methods described herein of variants of full-length reference polypeptides having any of the enzymatic activities described herein (e.g., aldolase, alcohol dehydrogenase, double bond reductase etc.), truncated fragments of these full-length polypeptides, variants of truncated fragments, as well as their related biologically active fragments. Typically, biologically active fragments of a polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken). Biologically active fragments of a polypeptide/enzyme an enzymatic activity described herein include peptides comprising amino acid sequences sufficiently similar to, or derived from, the amino acid sequences of a (putative) full-length reference polypeptide sequence. Typically, biologically active fragments comprise a domain or motif with at least one enzymatic activity, and may include one or more (and in some cases all) of the various active domains. A biologically active fragment of an enzyme can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

An aldolase, alcohol dehydrogenase, double bond reductase, or other reference polypeptide may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of aldolase or alcohol dehydrogenase polypeptides. Recursive ensemble mutagenesis (REM), a technique which enhances the frequency of functional mutants in the libraries, can be used in combination with the screening assays to identify polypeptide variants (Arkin and Yourvan (1992) *Proc. Natl. Acad. Sci. USA* 89: 7811-7815; Delgrave et al., (1993) *Protein Engineering*, 6: 327-331). Conservative substitutions, such as exchanging one amino acid with another having similar properties, may be desirable as discussed in more detail below.

Polypeptide variants may contain conservative amino acid substitutions at various locations along their sequence, as compared to a reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science*, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE 1

| Amino acid sub-classification | |
|---|---|
| Sub-classes | Amhio acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |

TABLE 1-continued

Amino acid sub-classification

| Sub-classes | Amino acids |
|---|---|
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant polypeptide can readily be determined by assaying its enzymatic activity, as described herein (see, e.g., Examples 2-4). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in an aldolase or alcohol dehydrogenase polypeptide is typically replaced with another amino acid residue from the same side chain family. Alternatively, mutations can be introduced randomly along all or part of a coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference polypeptide, results in abolition of an activity of the parent molecule such that less than 20% of the wild-type activity is present. For example, such essential amino acid residues include those that are conserved in aldolase, alcohol dehydrogenase, double bond reductase, or other reference polypeptides across different species, including those sequences that are conserved in the enzymatic sites of polypeptides from various sources.

Accordingly, the present invention also contemplates variants of the naturally-occurring reference polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference polypeptide sequence. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60,70, 80, 90, 100 or more amino acids but which retain the properties of a parent or reference polypeptide sequence are contemplated.

In some embodiments, variant polypeptides differ from a reference aldolase or alcohol dehydrogenase polypeptide sequence by at least one but by less than 50, 40, 30, 20, 15, 10, 8, 6, 5, 4, 3 or 2 amino acid residue(s). In other embodiments, variant polypeptides differ from a reference by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98%, or 99% or more sequence identity or similarity to a corresponding sequence of a reference polypeptide, and retains the enzymatic activity of that reference polypeptide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, H is, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The term "endogenous" refers generally to naturally occurring copies of a gene, polynucleotide sequence, or polypeptide that may be found in a genetically unmodified wild-type cell or organism. For example, certain naturally-occurring bacterial or yeast species do not typically contain an aldolase gene, and, therefore, do not comprise an "endogenous" polynucleotide sequence that encodes a aldolase enzyme.

The term "exogenous" refers generally to a copy of a gene, copy of polynucleotide sequence or nucleic acid molecule, or a polypeptide that does not naturally occur in a wild-type cell or organism, but is typically introduced into the cell by molecular biological techniques, i.e., engineering to produce a recombinant microorganism. Examples of "exogenous" genes or polynucleotides include vectors, plasmids, and/or man-made nucleic acid constructs encoding a desired protein or enzyme.

In this regard, it is also noted that even though an organism may comprise an endogenous or naturally-occurring copy of a given polynucleotide sequence or gene, the introduction of a plasmid or vector encoding that sequence or a related sequence, such as to over-express or otherwise regulate the expression of the encoded polypeptide, represents an "exogenous" copy of that gene or polynucleotide sequence. Also, in certain embodiments, the placing of an otherwise endogenous gene or polynucleotide under the control of an exogenous promoter sequence, such as a constitutive or inducible promoter, to increase the level of expression of the endogenous gene, may also be considered an exogenous gene or polynucleotide within the meaning of the present invention. Similarly, the modification of an otherwise endogenous gene or polynucleotide by the addition of non-naturally occurring sequences, such as to produce a chimeric gene or polypeptide, may also be considered an exogenous gene or polynucleotide within the meaning of the present invention.

Any of the of pathways, genes, polynucleotides, nucleic acid molecules, polypeptides, or enzymes described herein may utilize or rely on an "endogenous" sequence, or may be provided as one or more "exogenous" sequences.

The present invention also contemplates chimeric or fusion polypeptides. As used herein, a "chimeric protein," "fusion protein," or "fusion polypeptide" may include, without limitation, a first polypeptide or fragment thereof linked to a second, third, or fourth (or more) polypeptide, or fragment thereof (e.g., to create multiple fragments). The second, third or fourth polypeptide may refer to the same polypeptide as the first polypeptide, such as to selectively link together certain fragments of that first polypeptide, or may refer to a "heterologous polypeptide," which typically has an amino acid sequence corresponding to a protein that is different from the first polypeptide, and which may be derived from the same or a different organism. In certain embodiments, a fusion protein includes at least one (or two, three, four, or more) biologically active portion of a given polypeptide protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the activity of the polypeptide. For example, in one embodiment, a fusion partner may comprise a sequence that assists in expressing the protein (an expression enhancer) at higher yields than the native recombinant protein. Other fusion partners may be selected so as to increase the solubility of the protein, target the protein to desired intracellular compartments, secrete the protein, or tether the protein to the cell surface. As one example, the fusion protein can contain a heterologous signal peptide sequence at its N-terminus. In certain host cells, secretion or cell-surface tethering of fusion polypeptides can be increased through the use of one or more heterologous signal peptide sequences, typically fused at or near to the N-terminus of the polypeptide.

A "recombinant" microorganism typically comprises one or more exogenous genes or polynucleotide sequences, such as in a plasmid or vector. Examples of microorganisms that can be utilized as recombinant microorganisms include, without limitation, *Escherichia coli, Acetobacter aceti, Achromobacter, Acidiphilium, Acinetobacter, Actinomadura, Actinoplanes, Aeropyrum pernix, Agrobacterium, Alcaligenes, Ananas comosus* (M), *Arthrobacter, Aspergillus niger, Aspergillus oryze, Aspergillus melleus, Aspergillus pulveru-*

*lentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus lentus, Bacillus licheniformis, Bacillus macerans, Bacillus stearothermophilus, Bacillus subtilis, Bifidobacterium, Brevibacillus brevis, Burkholderia cepacia, Candida cylindracea, Candida rugosa, Carica papaya (L), Cellulosimicrobium, Cephalosporium, Chaetomium erraticum, Chaetomium gracile, Clostridium, Clostridium butyricum, Clostridium acetobutylicum, Clostridium thermocellum, Corynebacterium (glutamicum), Corynebacterium efficiens, Enterococcus, Erwina chrysanthemi, Gliconobacter, Gluconacetobacter, Haloarcula, Humicola insolens, Humicola nsolens, Kitasatospora setae, Klebsiella, Klebsiella oxytoca, Kluyveromyces, Kluyveromyces fragilis, Kluyveromyces lactis, Kocuria, Lactlactis, Lactobacillus, Lactobacillus fermentum, Lactobacillus sake, Lactococcus, Lactococcus lactis, Leuconostoc, Methylocystis, Methanolobus siciliae, Methanogenium organophilum, Methanobacterium bryantii, Microbacterium imperiale, Micrococcus lysodeikticus, Microlunatus, Mucor javanicus, Mycobacterium, Myrothecium, Nitrobacter, Nitrosomonas, Nocardia, Papaya carica, Pediococcus, Pediococcus halophilus, Penicillium, Penicillium camemberti, Penicillium citrinum, Penicillium emersonii, Penicillium roqueforti, Penicillum lilactinum, Penicillum multicolor, Paracoccus pantotrophus, Propionibacterium, Pseudomonas, Pseudomonas fluorescens, Pseudomonas denitrificans, Pyrococcus, Pyrococcus furiosus, Pyrococcus horikoshii, Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, Saccharophagus degradans, Sccharomyces cerevisiae, Sclerotina libertina, Sphingobacterium multivorum, Sphingobium, Sphingomonas, Streptococcus, Streptococcus thermophilus Y-1, Streptomyces, Streptomyces griseus, Streptomyces lividans, Streptomyces murinus, Streptomyces rubiginosus, Streptomyces violaceoruber, Streptoverticillium mobaraense, Tetragenococcus, Thermus, Thiosphaera pantotropha, Trametes, Trichoderma, Trichoderma longibrachiatum, Trichoderma reesei, Trichoderma viride, Trichosporon penicillatum, Vibrio alginolyticus, Vibrio splendidus, Xanthomonas, yeast, Yarrowia lipolytica, Zygosaccharomyces rouxii, Zymomonas, or Zymomonus mobilis.*

"Transformation" refers generally to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome.

A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell, such as a cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

Examples of "biomass" include aquatic or marine biomass, fruit-based biomass such as fruit waste, and vegetable-based biomass such as vegetable waste, among others. Examples of aquatic or marine biomass include, but are not limited to, kelp, giant kelp, seaweed, algae, and marine microflora, microalgae, sea grass, and the like. Examples of fruit and/or vegetable biomass include, but are not limited to, any source of pectin such as plant peel and pomace including citrus, orange, grapefruit, potato, tomato, grape, mango, gooseberry, carrot, sugar-beet, and apple, among others. In certain aspects, biomass does not include fossilized sources of carbon, such as hydrocarbons that are typically found within the top layer of the Earth's crust (e.g., natural gas, nonvolatile materials composed of almost pure carbon, like anthracite coal, etc).

A "commodity chemical," or an "intermediate thereof," relates generally to chemicals, such as biofuels, having the following formulas:

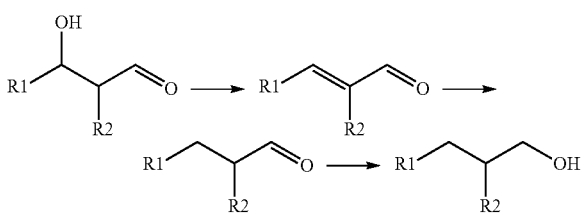

wherein R1 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, and $CH_3CH_2CH(CH_3)(CH_2)_nCH_2$; and wherein R2 is selected from the group consisting of H, $CH_3$, $CH_3CH_2$, $CH_3CH(CH_3)$, $CH_3(CH_2)_nCH_2$, $CH_3CH(CH_3)(CH_2)_nCH_2$, $CH_3CH_2CH(CH_3)(CH_2)_nCH_2$, wherein n=0-30, including any corresponding alkanes that can be produced therefrom.

In certain embodiments, the commodity chemical may be 3-hydroxy-2,2,4 trimethylpentanal, 2,2,4-trimethyl-1,3-pentanediol, and/or 2,2,4-trimethylpentane. In certain embodiments, the commodity chemical may be 3-hydroxy-2-ethylhexanal, 2-ethyl-2-hexene-1-al, 2-ethylhexanal, 2-ethylhexanol, and/or 2-ethylhexane. In certain embodiments, the commodity chemical may be 3-hydroxy-2-butyl-1-octanol, 2-butyl-2-octene-1-al, 2-butyl-octanal, or 2-butyl-octanol.

In certain aspects, the diol or alcohol, such as 2,2,4-trimethyl-1,3-pentanediol or 2-ethylhexanol, may be further chemically or enzymatically converted to its corresponding alkane, such as 2,2,4-trimethylpentane or 2-ethylhexane, respectively. One example of such a process includes "hydrotreating," also known as "hydrogenation." For instance, alcohols such as 2,2,4-trimethyl-1,3-pentanediol, 2-ethylhexanol, and 2-butyl-octanol may be "hydrotreated" to form their corresponding alkanes, 2,2,4-trimethylpentane, 2-ethylhexane, and 2-butyl-octane, respectively. The process of "hydrotreating" in petroleum refining systems refers generally to the catalytic addition of hydrogen to a molecule containing a functional group. A hydrotreating catalyst is generally formulated by placing some combination of molybdenum, nickel and cobalt oxide on a calcined alumina particle. The alumina particle may then be formulated and manufactured to have an extremely high internal surface area (very porous) and the catalytic metals may be deposited and distributed "mono-atomically" on the internal surface of the particle. In hydrotreating (vs. "hydrocracking") the alumina surface is typically formulated and manufactured to be as inert (i.e., chemically passive) as possible.

General examples of "biomass-derived polysaccharides" include, but are not limited to, alginate, agar, carrageenan, fucoidan, pectin, polygalacturonate, cellulose, hemicellulose, xylan, arabinan, and mannan. Examples of polysaccharides, oligosaccharides, monosaccharides or other sugar components of biomass include, but are not limited to, alginate (e.g., polyG, polyMG, polyM), oligoalginate (e.g., ΔM, ΔG, ΔMM, ΔMG, ΔGM, ΔGG, MM, MG, GM, GG, MMM, MGM, MMG, MGG, GMM, GMG, GGM, GGG), agar, carrageenan, fucoidan, pectin, gluronate, guluronate, mannuronate, mannitol, lyxose, cellulose, hemicellulose, cellobiose, glycerol, xylitol, glucose, mannose, galactose, xylose, xylan, mannan, arabinan, arabinose, glucuronate, galacturonate (including di- and tri-galacturonates), rhamnose, and the like.

Certain examples of alginate-derived polysaccharides include saturated polysaccharides, such as β-D-mannuronate, α-L-gluronate, dialginate, trialginate, pentalginate, hexylginate, heptalginate, octalginate, nonalginate, decalginate, undecalginate, dodecalginate and polyalginate, as well as unsaturated polysaccharides such as 4-deoxy-L-erythro-5-hexoseulose uronic acid, 4-(4-deoxy-beta-D-mann-4-enuronosyl)-D-mannuronate or L-guluronate, 4-(4-deoxy-beta-D-mann-4-enuronosyl)-dialginate, 4-(4-deoxy-beta-D-mann-4-enuronosyl)-trialginate, 4-(4-deoxy-beta-D-mann-4-enuronosyl)-tetralginate, 4-(4-deoxy-beta-D-mann-4-enuronosyl)-pentalginate, 4-(4-deoxy-beta-D-mann-4-enuronosyl)-hexylginate, 4-(4-deoxy-beta-D-mann-4-enuronosyl)-heptalginate, 4-(4-deoxy-beta-D-mann-4-enuronosyl)-octalginate, 4-(4-deoxy-beta-D-mann-4-enuronosyl)-non alginate, 4-(4-deoxy-beta-D-mann-4-enuronosyl)-undecalginate, and 4-(4-deoxy-beta-D-mann-4-enuronosyl)-dodecalginate.

Certain examples of pectin-derived polysaccharides include saturated polysaccharides, such as galacturonate, digalacturonate, trigalacturonate, tetragalacturonate, pentagalacturonate, hexagalacturonate, heptagalacturonate, octagalacturonate, nonagalacturonate, decagalacturonate, dodecagalacturonate, polygalacturonate, and rhamnopolygalacturonate, as well as saturated polysaccharides such as 4-deoxy-L-threo-5-hexosulose uronate, 4-(4-Deoxy-alpha-D-gluc-4-enuronosyl)-D-galacturonate, 4-(4-Deoxy-alpha-D-gluc-4-enuronosyl)-D-digalacturonate, 4-(4-Deoxy-alpha-D-gluc-4-enuronosyl)-D-trigalacturonate, 4-(4-Deoxy-alpha-D-gluc-4-enuronosyl)-D-tetragalacturonate, 4-(4-Deoxy-alpha-D-gluc-4-enuronosyl)-D-pentagalacturonate, 4-(4-Deoxy-alpha-D-gluc-4-enuronosyl)-D-hexagalacturonate, 4-(4-Deoxy-alpha-D-gluc-4-enuronosyl)-D-heptagalacturonate, 4-(4-Deoxy-alpha-D-gluc-4-enuronosyl)-D-octagalacturonate, 4-(4-Deoxy-alpha-D-gluc-4-enuronosyl)-D-nonagalacturonate, 4-(4-Deoxy-alpha-D-gluc-4-enuronosyl)-D-decagalacturonate, and 4-(4-Deoxy-alpha-D-gluc-4-enuronosyl)-D-dodecagalacturonate.

A "suitable monosaccharide" or "suitable saccharide" refers generally to any saccharide that may be produced by a recombinant microorganism growing on pectin, alginate, or other saccharide (e.g., biomass-derived polysaccharides including galacturonate, cellulose, hemi-cellulose etc.) as a source or sole source of carbon, and also refers generally to any saccharide that may be utilized in a biofuel biosynthesis pathway of the present invention to produce hydrocarbons such as biofuels or biopetrols. Examples of suitable monosaccharides or oligosaccharides include, but are not limited to, 2-keto-3-deoxy D-gluconate (KDG), D-mannitol, gluronate, mannuronate, mannitol, lyxose, glycerol, xylitol, glucose, mannose, galactose, xylose, arabinose, glucuronate, galacturonates, and rhamnose, and the like. As noted herein, a "suitable monosaccharide" or "suitable saccharide" as used herein may be produced by an engineered or recombinant microorganism described in U.S. application Ser. Nos. 12/245,537 and 12/245,540, herein incorporated by reference for the disclosure of such microorganisms, or may be obtained from commercially available sources.

The recitation "optimized" as used herein refers to a pathway, gene, polypeptide, enzyme, or other molecule having an altered biological activity, such as by the genetic alteration of a polypeptide's amino acid sequence or by the alteration/modification of the polypeptide's surrounding cellular environment, to improve its functional characteristics in relation to the original molecule or original cellular environment (e.g., a wild-type sequence of a given polypeptide or a wild-type microorganism). Any of the polypeptides or enzymes described herein may be optionally "optimized," and any of the genes or nucleotide sequences described herein may optionally encode an optimized polypeptide or enzyme. Any of the pathways described herein may optionally contain one or more "optimized" enzymes, or one or more nucleotide sequences encoding for an optimized enzyme or polypeptide.

Typically, the improved functional characteristics of the polypeptide, enzyme, or other molecule relate to the suitability of the polypeptide or other molecule for use in a biological pathway (e.g., an aldehyde and/or ketone biosynthesis pathway, an aldolase, an alcohol dehydrogenase) to convert an aldehyde and/or ketone to a biofuel, such as isooctane. Certain embodiments, therefore, contemplate the use of "optimized" biological pathways. An exemplary "optimized" polypeptide may contain one or more alterations or mutations in its amino acid coding sequence (e.g., point mutations, deletions, addition of heterologous sequences) that facilitate improved expression and/or stability in a given microbial system or microorganism, allow regulation of polypeptide activity in relation to a desired substrate (e.g., inducible or repressible activity), modulate the localization of the polypeptide within a cell (e.g., intracellular localization, extracellular secretion), and/or effect the polypeptide's overall level of activity in relation to a desired substrate (e.g., reduce or increase enzymatic activity). A polypeptide or other molecule may also be "optimized" for use with a given microbial system or microorganism by altering one or more pathways within that system or organism, such as by altering a pathway that regulates the expression (e.g., up-regulation), localization, and/or activity of the "optimized" polypeptide or other molecule, or by altering a pathway that minimizes the production of undesirable by-products, among other alterations. In this manner, a polypeptide or other molecule may be "optimized" with or without altering its wild-type amino acid sequence or original chemical structure. Optimized polypeptides or biological pathways may be obtained, for example, by direct mutagenesis or by natural selection for a desired phenotype, according to techniques known in the art.

In certain aspects, "optimized" genes or polypeptides may comprise a nucleotide coding sequence or amino acid sequence that is 50% to 99% identical (including all integers in between) to the nucleotide or amino acid sequence of a reference (e.g., wild-type) gene or polypeptide. In certain aspects, an "optimized" polypeptide or enzyme may have about 1, 2, 3, 4, 5, 6, 7, 8, 9, 10, 20, 30, 40, 50, 100 (including all integers and decimal points in between e.g., 1.2, 1.3, 1.4, 1.5, 5.5, 5.6, 5.7, 60, 70, etc.), or more times the biological activity of a reference polypeptide.

Certain aspects of the invention also include a commodity chemical, such as a biofuel, that is produced according to the methods and recombinant microorganisms described herein. Such a biofuel (e.g., medium to long chain alkane, isooctane) may be distinguished from other fuels, such as those fuels produced by traditional refinery from crude carbon sources, by radio-carbon dating techniques. For instance, carbon has two stable, nonradioactive isotopes: carbon-12 ($^{12}C$), and carbon-13 ($^{13}C$). In addition, there are trace amounts of the unstable isotope carbon-14 ($^{14}C$) on Earth. Carbon-14 has a half-life of 5730 years, and would have long ago vanished from Earth were it not for the unremitting impact of cosmic rays on nitrogen in the Earth's atmosphere, which create more of this isotope. The neutrons resulting from the cosmic ray interactions participate in the following nuclear reaction on the atoms of nitrogen molecules ($N_2$) in the atmospheric air:

$$n + {}_7^{14}N \rightarrow {}_6^{14}C + p$$

Plants and other photosynthetic organisms take up atmospheric carbon dioxide by photosynthesis. Since many plants are ingested by animals, every living organism on Earth is constantly exchanging carbon-14 with its environment for the duration of its existence. Once an organism dies, however, this exchange stops, and the amount of carbon-14 gradually decreases over time through radioactive beta decay.

Most hydrocarbon-based fuels, such as crude oil and natural gas derived from mining operations, are the result of compression and heating of ancient organic materials (i.e., kerogen) over geological time. Formation of petroleum typically occurs from hydrocarbon pyrolysis, in a variety of mostly endothermic reactions at high temperature and/or pressure. Today's oil formed from the preserved remains of prehistoric zooplankton and algae, which had settled to a sea or lake bottom in large quantities under anoxic conditions (the remains of prehistoric terrestrial plants, on the other hand, tended to form coal). Over geological time the organic matter mixed with mud, and was buried under heavy layers of sediment resulting in high levels of heat and pressure (known as diagenesis). This process caused the organic matter to chemically change, first into a waxy material known as kerogen which is found in various oil shales around the world, and then with more heat into liquid and gaseous hydrocarbons in a process known as catagenesis. Most hydrocarbon based fuels derived from crude oil have been undergoing a process of carbon-14 decay over geological time, and, thus, will have little to no detectable carbon-14. In contrast, certain biofuels produced by the living microorganisms of the present invention will comprise carbon-14 at a level comparable to all other presently living things (i.e., an equilibrium level). In this manner, by measuring the carbon-12 to carbon-14 ratio of a hydrocarbon-based biofuel of the present invention, and comparing that ratio to a hydrocarbon based fuel derived from crude oil, the biofuels produced by the methods provided herein can be structurally distinguished from typical sources of hydrocarbon based fuels.

Embodiments of the present invention include methods of producing a commodity chemical, comprising growing a recombinant microorganism with a source of an aldehyde, a ketone, or both, wherein the recombinant microorganism comprises: (i) at least one polynucleotide (i.e., one or more polynucleotides) encoding and expressing a polypeptide having an aldolase activity; and (ii) at least one polynucleotide (i.e., one or more polynucleotides) encoding and expressing a polypeptide having an alcohol dehydrogenase activity, thereby producing the commodity chemical. In certain embodiments, the recombinant microorganism may also comprise at least one polynucleotide (i.e., one or more polynucleotides) encoding and expressing a polypeptide having a double bond reductase activity, and/or at least one polynucleotide encoding and expressing a polypeptide having a dehydratase activity. In certain embodiments, at least one or two of the polynucleotides is an exogenous polynucleotide. In certain embodiments, each of the polynucleotides is exogenous.

Embodiments of the present invention also include recombinant microorganisms that comprise (i) at least one polynucleotide encoding and expressing a polypeptide having an aldolase activity; and (ii) at least one polynucleotide encoding and expressing a polypeptide having an alcohol dehydrogenase activity. In certain embodiments, such microorganisms may also comprise may also comprise at least one polynucleotide encoding and expressing a polypeptide having a double bond reductase activity. In certain embodiments, at least one or two of the polynucleotides is an exogenous polynucleotide. In certain embodiments, each of the polynucleotides is exogenous. These recombinant microorganisms are typically capable of producing a commodity chemical, or an intermediate thereof, from a source of an aldehyde, a ketone, or both.

Embodiments of the present invention also include recombinant microorganisms that comprise (i) at least one polynucleotide encoding and expressing an aldehyde and/or ketone biosynthesis pathway (ii) at least one polynucleotide encoding and expressing a polypeptide having an aldolase activity; and (ii) at least one polynucleotide encoding and expressing a polypeptide having an alcohol dehydrogenase activity. In certain embodiments, such microorganisms may also comprise may also comprise at least one polynucleotide encoding and expressing a polypeptide having a double bond reductase activity. In certain embodiments, at least one or two of the polynucleotides is an exogenous polynucleotide. In certain embodiments, each of the polynucleotides is exogenous. These recombinant microorganisms are typically capable of producing a commodity chemical, or an intermediate thereof, from a source of an aldehyde, a ketone, or both, and may also capable of producing said source of an aldehyde, a ketone, or both, from a suitable monosaccharide or oligosaccharide.

As noted above, in certain embodiments, a recombinant microorganism may also comprise at least one exogenous polynucleotide encoding and expressing a polypeptide having a double bond reductase activity, and/or a polypeptide having a deyhdratase activity. In these and related embodiments, the presence or over-expression of an exogenous double bond reductase or dehydratase may not be necessary to achieve the desired product (e.g., isooctane), as such reactions may be catalyzed by endogenous reductase and dehydratase enzymes, but may be used to increase the amount of desired product produced by the recombinant microorganism.

As used herein, an enzyme or polypeptide having an "aldolase" activity refers generally to a class of enzymes that are capable of catalyzing the reversible reaction of cleaving D-fructose-1,6-bisphosphate to form dihydroxyacetone phosphate and D-glyceraldehyde-3-phosphate. Aldolase enzymes are present in all animal and plant tissue and in most microorganisms. Class I aldolases, found in animal and higher plant tissue, are typically characterized by not requiring a bivalent metal cofactor and by the formation of a ketimine Schiff base intermediate with the substrate dihydroxyacetone phosphate. Class II aldolases, typically found in microorganisms such as yeast and bacteria, require a metal cofactor and may be inhibited by EDTA.

As one exemplary aldolase, fructose 1,6-biphosphate aldolase (aldolase A) catalyzes a key reaction in glycolysis and energy production. Aldolase B is an isoenzyme of aldolase A, which is capable of cleaving fructose 1-phosphate to form glyceraldehyde and dihydroxyacetone phosphate. This reaction, however, is reversible, and can be utilized to condense glyceraldehyde and dihydroxyacetone phosphate.

Beyond the condensation of glyceraldehye and dihydroxyacetone phosphate, it has been discovered that aldolase enzymes catalyze other useful condensation reactions between aldehydes and/or ketones. In particular, the reversible nature of their catalytic activity has been shown herein to be useful in generating a variety of commodity chemicals, or intermediates thereof, from the condensation products of various combinations of aldehydes and/or ketonees. For instance, an aldolase enzyme of the present invention may be capable of catalyzing the condensation of two molecules of isobutyraldehyde to form 3-hydroxy-2,2,4-trimethyl pentanal. As another example, an aldolase enzyme of the present invention may be capable of catalyzing the condensation of two butyraldehyde molecules to form 3-hydroxy-2-ethylhexanal. As another example, aldolase enzyme of the present invention may be capable of catalyzing the condensation of two hexanaldehyde molecules to form 2-butyl-octanal.

Thus, in certain aspects, the recitation "aldolase" refers to an enzyme that is capable of catalyzing the condensation of various aldehydes and/or ketones, such as acetoaldehyde, propionaldehyde, glutaraldehyde, butyraldehyde, isobutyraldehyde, 2-methyl-butyraldehyde, 3-methyl-butyraldehyde, 4-methylpentaldehyde, hexanaldehyde, heptanaldehyde, octanaldehyde, phenylacetoaldehyde, 2-phenyl acetoaldehyde, 2-(4-hydroxyphenyl)acetaldehyde, 2-Indole-3-acetoaldehyde, 5-amino-pentaldehyde, succinate semialdehyde, and/or succinate 4-hydroxyphenyl acetoaldehyde, among others, including combinations thereof. The condensation of aldehydes and/or ketones may be utilized to produce such chemicals as propanal, butanal, isobutanal, pentanal, 2-methylbutanal, 3-methylbutanal, hexanal, 2-methylpentanal, 3-methylpentanal, 4-methylpentanal, heptanal, octanal, 2-methylheptanal, nonanal, decanal, undecanal, dodecanal, among others recognizable to a person skilled in the art.

"Aldolase" enzymes or "aldolases," as used herein, also include those enzymes having an acyl-acyl carrier protein (ACP) activity, such as an ACP thioesterase activity. Such ACP esterases typically have the ability to catalyze the production of free fatty acid(s) from fatty acyl-ACP substrates (e.g., C8-C14) under enzyme reactive conditions. However, it is believed that acyl-ACP esterases are also capable of catalyzing the condensation of two aldehydes and/or ketones, such as isobutyeraldehyde and butyeraldehyde, to form a corresponding alkyl aldehyde, such as 3-hydroxy-2,2,4-trimethylpentanal and 2-ethyl-2-hexene-1-al, respectively.

Such esterases are obtainable from the specific exemplified sequences provided herein and from related sources. For example, several species in the genus *Cuphea* accumulate triglycerides containing medium-chain fatty acids in their seeds, e.g., procumbens, lutea, hookeriana, hyssopifolia, wrightii and inflata. Another natural plant source of medium-chain fatty acids are seeds of the Lauraceae family (e.g., Pisa (*Actinodophne hookeri*) and Sweet Bay (*Laurus nobilis*)). Other plant sources include Myristicaceae, Simarubaceae, Vochysiaceae, and Salvadoraceae, and rainforest species of *Erisma, Picramnia* and *Virola*, which have been reported to accumulate C14 fatty acids. Exemplary esterases having aldolase activity, including FATB1 and FATB2, are described in U.S. Pat. Nos. 5,298,421, 5,304,481, 5,344,771, 5,455,167, and 5,667,997, and Yuan et al. (*PNAS USA* 92:10639-634, 1995), which are incorporated by reference for their ACP-acyl thioesterase polynucleotide and polypeptide sequences.

In certain embodiments, a recombinant microorganism may comprise comprise one or more polynucleotide sequences that encode a polypeptide having an aldolase activity, wherein the polynucleotide has 80%, 85%, 90%, 95%, 97%, 98%, 99% sequence identity to SEQ ID NOS: 215-222, or polynucleotide sequences that hybridize to their complements under conditions described herein and known in the art. SEQ ID NO:215 encodes a FATB2 enzyme from *Cuphea hookeriana*. SEQ ID NO:216 encodes a FATB3 enzyme from *Cuphea lanceolata*. SEQ ID NOS:217 and 218 each encode a ketoacyl-ACP synthase IV (KASIV) from *Cuphea lanceolata*. SEQ ID NO:219 encodes an ACP1-2 enzyme from *Cuphea lanceolata*, SEQ ID NO:220 encodes an ACP1-3 enzyme from *Cuphea lanceolata*, and SEQ ID NO:221 encodes an ACP1-1 enzyme from *Cuphea lanceolata*. SEQ ID NO:222 encodes an Acl1 from *Cuphea lanceolata*.

Aldolase enzymes may also be obtained from such organisms as *Thermotoga maritima* and *Escherichia coli* DH10B, among others. For instance, in certain embodiments, an aldolase enzyme may be based on the polynucleotide reference sequences set forth in SEQ ID NOS:51-82, and/or the polypeptide reference sequences encoded by these polynucleotide reference sequences. Thus, certain recombinant microorganisms of the invention may comprise one or more polynucleotide sequences having 80%, 85%, 90%, 95%, 97%, 98%, 99% sequence identity to SEQ ID NOS: 51-82, or polynucleotide sequences that hybridize the their complements under conditions of medium or high stringency, as described herein and known in the art.

Certain "aldolase" enzymes of the present invention, or the polynucleotide sequences encoding such enzymes, may also be characterized by certain conserved motifs or domains. In this regard, various amino acid sequences comprising 20 aldolase enzymes from *Escerichia coli* DH10β were analyzed for common sequence motifs using the PROSITE database. Many of these sequences produced strong matches to known sequence profiles. For instance, ALDOL1, encoded by ECDH10B0008 (SEQ ID NO:63), ALDOL2, encoded by EC ECDH10B0894 (SEQ ID NO:64), ALDOL10, encoded by ECDH10B2629 (SEQ ID NO:72), and ALDOL19, encoded by ECDH10B4135 (SEQ ID NO:81), shared the motifs "Transaldolase signature 1" and "Transaldolase signature 2" (see Table 4, below). Also, ALDOL 5, encoded by ECDH10B1991 (SEQ ID NO:67), contains two motifs, the "KDPG and KHG aldolases active site" motif and the "KDPG and KHG aldolases Schiff-base forming residue" motif (see Table 4, below), and ALDOL6, encoded by ECDH10B2249

(SEQ ID NO:68), ALDOL12, encoded by ECDH10B3100 (SEQ ID NO:74), and ALDOL16, encoded by ECDH10B3310 (SEQ ID NO:78), share the motifs, "Fructose-bisphosphate aldolase class-II signature 1" and "Fructose-bisphosphate aldolase class-II signature 2" (see Table 4, below).

Exemplary aldolase motifs are given below in Table 3, and matching ECDH10B (*E. coli* DH10B) aldol sequence fragments are given in Table 4.

TABLE 3

Aldolase motifs.

| Motif Name | Sequence |
|---|---|
| Transaldolase signature 1 | [DGH]-[IVSAC]-T-[ST]-N-P-[STA]-[LIVMF] (SEQ ID NO: 223) |
| Transaldolase signature 2 | [LIVMA]-x-[LIVM]-K-[LIVM]-[PAS]-x-[STC]-x-[DENQPAS]-[GC]-[LIVM]-x-[AGV]-x(0,1)-[QEKRSTH]-x-[LIVMF] (SEQ ID NOS: 224 and 255) |
| KDPG and KHG aldolases active site | G-[LIVM]-x(3)-E-[LIV]-T-[LF]-R (SEQ ID NO: 225) |
| KDPG and KHG aldolases Schiff-base forming residue | G-x(3)-[LIVMF]-K-[LF]-F-P-[SA]-x(3)-G (SEQ ID NO: 226) |
| Fructose-bisphosphate aldolase class-II signature 1 | [FYVMT]-x(1,3)-[LIVMH]-[APNT]-[LIVM]-x(1,2)-[LIVM]-H-x-D-H-[GACH] (SEQ ID NOS: 227, 256-260) |
| Fructose-bisphosphate aldolase class-II signature 2 | [LIVM]-E-x-E-[LIVM]-G-x(2)-[GM]-[GSTA]-x-E (SEQ ID NO: 228) |

TABLE 4

Motif matches within aldolase sequences.

| Gene | Residues | Sequence | Match |
|---|---|---|---|
| ECDH10B0008 | 31-39 | DATTNPSLI (SEQ ID NO: 229) | Transaldolase signature 1 |
| ECDH10B0008 | 129-146 | ILIKLASTWQGIRAAEQL (SEQ ID NO: 230) | Transaldolase signature 2 |
| ECDH10B0894 | 24-32 | GVTTNPSII (SEQ ID NO: 231) | Transaldolase signature 1 |
| ECDH10B0894 | 82-99 | IVVKVPVTAEGLAAIKM (SEQ ID NO: 232) | Transaldolase signature 2 |
| ECDH10B2629 | 30-38 | DATTNPSLL (SEQ ID NO: 233) | Transaldolase signature 1 |
| ECDH10B2629 | 128-145 | ILIKLASTWEGIRAAEEL (SEQ ID NO: 234) | Transaldolase signature 2 |
| ECDH10B4135 | 24-32 | GVTTNPSII (SEQ ID NO: 235) | Transaldolase signature 1 |
| ECDH10B4135 | 82-99 | IVVKIPVTSEGLAAIKI (SEQ ID NO: 236) | Transaldolase signature 2 |
| ECDH10B1991 | 40-49 | GVRVLEVTLR (SEQ ID NO: 237) | KDPG and KHG aldolases active site |
| ECDH10B1991 | 128-141 | GLKEFKFEPAEANG (SEQ ID NO: 238) | KDPG and KHG aldolases Schiff-base forming residue |
| ECDH10B2249 | 73-84 | YHHPLAIHLDHH (SEQ ID NO: 239) | Fructose-bisphosphate aldolase class-II signature 1 |
| ECDH10B2249 | 131-142 | VEAELGQLGGQE (SEQ ID NO: 240) | Fructose-bisphosphate aldolase class-II signature 2 |
| ECDH10B3100 | 101-112 | YGVPVILHTDHC (SEQ ID NO: 241) | Fructose-bisphosphate aldolase class-II signature 1 |
| ECDH10B3100 | 172-183 | LEIELGCTGGE (SEQ ID NO: 242) | Fructose-bisphosphate aldolase class-II signature 2 |
| ECDH10B3310 | 71-84 | TTYNMPLALHLDHH (SEQ ID NO: 243) | Fructose-bisphosphate aldolase class-II signature 1 |
| ECDH10B3100 | 131-142 | VEAELGRLGGVE (SEQ ID NO: 244) | Fructose-bisphosphate aldolase class-II signature 2 |

Thus, in certain embodiments, a recombinant microorganism of the invention may comprise one or more polynucleotides that encode an aldolase enzyme or polypeptide, where the aldolase enzyme or polypeptide comprises one or more of the domains or motifs exemplified in Tables 3 and 4, or biologically active variants of these motifs that are capable of facilitating the catalysis of the condensation of various combinations of aldehydes and/or ketones.

An enzyme or polypeptide having an "alcohol dehydrogenase" activity refers generally to an enzyme that catalyzes the conversion of aldehyde or ketone substituents to alcohols or diols, and may include secondary alcohol dehydrogenases. For instance, 2,2,4-trimethylpentanal may be reduced to 2,2,4-trimethyl-1,3-pentanediol by an enzyme having alcohol dehydrogenase (Adh) activity, representing one enzymatic step in the conversion of isobutyraldehyde to isooctane.

In certain aspects, a recombinant microorganism may comprise one or more alcohol dehydrogenases encoded by a nucleotide reference sequence selected from SEQ ID NOS:1, 3, 5, 7, 9, 11, 13, 15, 17, 19, 21, 23, 25, 27, 29, 30, 31, 33, and 83-96, or a polypeptide or enzyme encoded by any of these polynucleotide sequences, such as a polypeptide sequence selected from SEQ ID NOS:2, 4, 6, 8, 10, 12, 14, 16, 18, 20, 22, 24, 26, 28, 30, 32, and 34, including biologically active fragments or variants thereof, such as optimized variants. Certain recombinant microorganisms of the invention may comprise one or more nucleotide sequences or polypeptide sequences having 80%, 85%, 90%, 95%, 97%, 98%, 99% sequence identity to SEQ ID NOS:1-34 or 83-96.

For certain of the alcohol dehydrogenase sequences referred to above, SEQ ID NO:1 is the nucleotide sequence and SEQ ID NO:2 is the polypeptide sequence of a secondary alcohol dehydrogenase (2adh-1: PP_1946) isolated from *Pseudomonas putida* KT2440. SEQ ID NO:3 is the nucleotide sequence and SEQ ID NO:4 is the polypeptide sequence of a secondary alcohol dehydrogenase (2adh-2: PP_1817) isolated from *Pseudomonas putida* KT2440.

SEQ ID NO:5 is the nucleotide sequence and SEQ ID NO:6 is the polypeptide sequence of a secondary alcohol dehydrogenase (2adh-3: PP_1953) isolated from *Pseudomonas putida* KT2440. SEQ ID NO:7 is the nucleotide sequence and SEQ ID NO:8 is the polypeptide sequence of a secondary alcohol dehydrogenase (2adh-4: PP_3037) isolated from *Pseudomonas putida* KT2440.

SEQ ID NO:9 is the nucleotide sequence and SEQ ID NO:10 is the polypeptide sequence of a secondary alcohol dehydrogenase (2adh-5: PP_1852) isolated from *Pseudomonas putida* KT2440. SEQ ID NO:11 is the nucleotide sequence and SEQ ID NO:12 is the polypeptide sequence of a secondary alcohol dehydrogenase (2adh-6: PP_2723) isolated from *Pseudomonas putida* KT2440.

SEQ ID NO:13 is the nucleotide sequence and SEQ ID NO:14 is the polypeptide sequence of a secondary alcohol dehydrogenase (2adh-7: PP_2002) isolated from *Pseudomonas putida* KT2440. SEQ ID NO:15 is the nucleotide sequence and SEQ ID NO:16 is the polypeptide sequence of a secondary alcohol dehydrogenase (2adh-8: PP_1914) isolated from *Pseudomonas putida* KT2440.

SEQ ID NO:17 is the nucleotide sequence and SEQ ID NO:18 is the polypeptide sequence of a secondary alcohol dehydrogenase (2adh-9: PP_1914) isolated from *Pseudomonas putida* KT2440. SEQ ID NO:19 is the nucleotide sequence and SEQ ID NO:20 is the polypeptide sequence of a secondary alcohol dehydrogenase (2adh-10: PP_3926) isolated from *Pseudomonas putida* KT2440.

SEQ ID NO:21 is the nucleotide sequence and SEQ ID NO:22 is the polypeptide sequence of a secondary alcohol dehydrogenase (2adh-11: PFL_1756) isolated from *Pseudomonas fluorescens* Pf-5. SEQ ID NO:23 is the nucleotide sequence and SEQ ID NO:24 is the polypeptide sequence of a secondary alcohol dehydrogenase (2adh-12: KPN_01694) isolated from *Klebsiella pneumoniae* subsp. *pneumoniae* MGH 78578.

SEQ ID NO:25 is the nucleotide sequence and SEQ ID NO:26 is the polypeptide sequence of a secondary alcohol dehydrogenase (2adh-13: KPN_02061) isolated from *Klebsiella pneumoniae* subsp. *pneumoniae* MGH 78578. SEQ ID NO:27 is the nucleotide sequence and SEQ ID NO:28 is the polypeptide sequence of a secondary alcohol dehydrogenase (2adh-14: KPN_00827) isolated from *Klebsiella pneumoniae* subsp. *pneumoniae* MGH 78578.

SEQ ID NO:29 is the nucleotide sequence and SEQ ID NO:30 is the polypeptide sequence of a secondary alcohol dehydrogenase (2adh-16: KPN_01350) isolated from *Klebsiella pneumoniae* subsp. *pneumoniae* MGH 78578. SEQ ID NO:31 is the nucleotide sequence and SEQ ID NO:32 is the polypeptide sequence of a secondary alcohol dehydrogenase (2adh-17: KPN_03369) isolated from *Klebsiella pneumoniae* subsp. *pneumoniae* MGH 78578. SEQ ID NO:33 is the nucleotide sequence and SEQ ID NO:34 is the polypeptide sequence of a secondary alcohol dehydrogenase (2adh-18: KPN_03363) isolated from *Klebsiella pneumoniae* subsp. *pneumoniae* MGH 78578.

The alcohol dehydrogenase encoding polynucleotide sequences of SEQ ID NOS: 83-96 were obtained from *Pseudomonas putida*.

In certain aspects, an alcohol dehydrogenase (adh), a secondary alcohol dehydrogenase (2adh), a fragment, variant, or derivative thereof, or any other enzyme that utilizes such an active site, may comprise at least one of a nicotinamide adenine dinucleotide (NAD+), NADH, nicotinamide adenine dinucleotide phosphate (NADP+), or NADPH binding motif. In certain embodiments, the NAD+, NADH, NADP+, or NADPH binding motif may be selected from the group consisting of Y-X-G-G-X-Y (SEQ ID NO:245), Y-X-X-G-G-X-Y (SEQ ID NO:246), Y-X-X-X-G-G-X-Y (SEQ ID NO:247), Y-X-G-X-X-Y (SEQ ID NO:248), Y-X-X-G-G-X-X-Y (SEQ ID NO:249), Y-X-X-X-G-X-X-Y (SEQ ID NO:250), Y-X-G-X-Y (SEQ ID NO:251), Y-X-X-G-X-Y (SEQ ID NO:252), Y-X-X-X-G-X-Y (SEQ ID NO:253), and Y-X-X-X-X-G-X-Y (SEQ ID NO:254); wherein Y is independently selected from alanine, glycine, and serine, wherein G is glycine, and wherein X is independently selected from a genetically encoded amino acid.

In certain embodiments, a microbial system or recombinant microorganism may comprise natural or optimized alcohol dehydrogenases from *Pseudomonads*, *Rhodococcus erythropolis* ATCC4277, *Norcadia fusca* AKU2123, *Klebsialla*, or other suitable organisms. Genes encoding alcohol dehydrogenases may be isolated from these and other organisms according to known techniques in the art and incorporated into the recombinant microorganisms as described herein.

An enzyme or polypeptide having a "double bond reductase" activity refers generally to an enzyme that catalyzes the following general reaction:

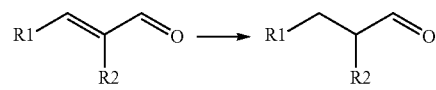

As noted herein, in certain embodiments, the above reaction may be catalyzed by the endogenous enzymes in a given microorganism, such that the addition of an exogenous enzyme having double bond reductase activity may not be necessary to practice the present invention. Nonetheless, it is believed that in certain aspects the over-expression of a double bond reductase enzyme, or the expression of a particular double bond reductase having increased affinity for the components of the specific reaction contemplated, may allow increased production of the desired commodity chemical, or intermediate thereof.

Double bond reductases may be obtained, for example, from such organisms as *Saccharomyces cerevisiae, Pichia angusta, Zymomonas mobilis, E. coli, Klebsiella pneumoniae, Pseudomonas fluorescens*, and *Pseudomonas putida*, among others.

In certain embodiments, a double bond reductase enzyme may be based on the polynucleotide reference sequences set forth in SEQ ID NOS:35-50, and/or the corresponding polypeptide reference sequences encoded by these polynucleotides. Thus, certain recombinant microorganisms of the invention may comprise one or more polynucleotide sequences having 80%, 85%, 90%, 95%, 97%, 98%, 99% sequence identity to SEQ ID NOS: 35-50, or polynucleotide sequences that hybridize the their complements under conditions described herein and known in the art.

The "double bond reductase" enzymes of the present invention, or the polynucleotide sequences encoding such enzymes, may also be characterized by certain conserved motifs or domains, as described herein and known in the art.

In certain embodiments, the source of the aldehyde, the ketone, or both, which is condensed by an enzyme having aldolase activity to form a commodity chemical, or intermediate thereof, may include a recombinant microorganism that comprises an aldehyde and/or ketone biosynthesis pathway. In certain embodiments, such a biosynthesis pathway may include an aldehyde biosynthesis pathway, a ketone biosynthesis pathway, or both.

In certain embodiments, the biosynthesis pathway may include one or more of an acetoaldehyde, propionaldehyde, glutaraldehyde, butyraldehyde, isobutyraldehyde, 2-methylbutyraldehyde, 3-methyl-butyraldehyde, 4-methylpentaldehyde, phenylacetoaldehyde, 2-phenyl acetoaldehyde, 2-(4-hydroxyphenyl)acetoaldehyde, 2-Indole-3-acetoaldehyde, 5-amino-pentaldehyde, succinate semialdehyde, and/or succinate 4-hydroxyphenyl acetaldehyde biosynthesis pathway, including various combinations thereof.

In certain aspects, the biosynthesis pathway comprises a butyraldehyde or isobutyraldehyde biosynthesis pathway. Exemplary aldehyde and ketone biosynthesis pathways are described herein and in U.S. application Ser. Nos. 12/245,537 and 12/245,540, which are incorporated by reference for their description of aldehyde/ketone biosynthesis pathways.

In certain aspects, a propionaldehyde biosynthesis pathway may comprise a threonine deaminase (ilvA) gene from an organism such as *Escherichia coli* and a keto-isovalerate decarboxylase (kivd) gene from an organism such as *Lactococcus lactis*, and/or functional variants of these enzymes, including homologs or orthologs thereof, as well as optimized variants. These enzymes may be utilized generally to convert L-threonine to propionaldehyde.

In certain aspects, a butyraldehyde biosynthesis pathway may comprise at least one of a thiolase (atoB) gene from an organism such as *E. coli*, a β-hydroxy butyryl-CoA dehydrogenase (hbd) gene, a crotonase (crt) gene, a butyryl-CoA dehydrogenase (bcd) gene, an electron transfer flavoprotein A (etfA) gene, and/or an electron transfer flavoprotein B (etfB) gene from an organism such as *Clostridium acetobutyricum* (e.g., ATCC 824), as well as a coenzyme A-linked butyraldehyde dehydrogenase (ald) gene from an organism such as *Clostridium beijerinckii acetobutyricum* ATCC 824. In certain aspects, a coenzyme A-linked alcohol dehydrogenase (adhE2) gene from an organism such as *Clostridium acetobutyricum* ATCC 824 may be used as an alternative to an ald gene.

In certain aspects, an isobutyraldehyde biosynthetic pathway may comprise an acetolactate synthase (alsS) from an organism such as *Bacillus subtilis* or an als gene from an organism such as *Klebsiella pneumoniae* subsp. *pneumoniae* MGH 78578 (codon usage may be optimized for *E. coli* protein expression). Such a pathway may also comprise acetolactate reductoisomerase (ilvC) and/or 2,3-dihydroxy-isovalerate dehydratase (ilvD) genes from an organism such as *E. coli*, as well as a keto-isovalerate decarboxylase (kivd) gene from an organism such as *Lactococcus lactis*.

In certain aspects, a 3-methylbutyraldehyde and 2-methylbutyraldehyde biosynthesis pathway may comprise an acetolactate synthase (alsS) gene from an organism such as *Bacillus subtilis* or an (als) gene from an organism such as *Klebsiella pneumoniae* subsp. *pneumoniae* MGH 78578 (codon usage may be optimized for *E. coli* protein expression). Certain aspects of such a pathway may also comprise acetolactate reductoisomerase (ilvC), 2,3-dihydroxyisovalerate dehydratase (ilvD), isopropylmalate synthase (LeuA), isopropylmalate isomerase (LeuC and LeuD), and 3-isopropylmalate dehydrogenase (LeuB) genes from an organism such as *E. coli*, as well as a keto-isovalerate decarboxylase (kivd) from an organism such as *Lactococcus lactis*.

In certain aspects, a phenylacetoaldehyde and 4-hydroxyphenylacetoaldehyde biosynthesis pathway may comprise one or more of 3-deoxy-7-phosphoheptulonate synthase (aroF, aroG, and aroH), 3-dehydroquinate synthase (aroB), a 3-dehydroquinate dehydratase (aroD), dehydroshikimate reductase (aroE), shikimate kinase II (aroL), shikimate kinase I (aroK), 5-enolpyruvylshikimate-3-phosphate synthetase (aroA), chorismate synthase (aroC), fused chorismate mutase P/prephenate dehydratase (pheA), and/or fused chorismate mutase T/prephenate dehydrogenase (tyrA) genes from an organism such as *E. coli*, as well as a keto-isovalerate decarboxylase (kivd) from an organism such as *Lactococcus lactis*.

In certain embodiments, the recombinant microrganism that is the source of the aldehyde, the ketone, or both, may be the same recombinant microorganism that converts the aldehyde or ketone to the commodity chemical. For example, in the production of isooctane, such a recombinant microorganism may comprise an isobutyraldehyde biosynthesis pathway, an aldolase enzyme, optionally a double bond reductase enzyme, and an alcohol dehydrogenase enzyme, and would be capable of converting a suitable monosaccharide to isobutyraldehyde, and then to 3-hydroxy-2,2,4-trimethyl pentanal and 2,2,4-trimethyl-1,3-pentanediol. In these and related aspects, 2,2,4-trimethyl-1,3-pentanediol may be further converted to isooctane, such as by "hydrotreating," as described herein and known in the art.

As a further example, in the production of commodity chemicals such as 2-ethylhexanol and 2-ethylhexane, such a recombinant microorganism may comprise a butyraldehyde biosynthesis pathway, an aldolase enzyme, optionally a double bond reductase enzyme, and an alcohol dehydrogenase enzyme, and would be capable of converting a suitable monosaccharide to butyraldehyde, and then to 3-hydroxy-2-ethyl hexanal, 2-ethyl-2-hexene-1-al, 2-ethylhexanal, and finally to 2-ethylhexanol. In these and related aspects, 2-ethylhexanol may be further converted to 2-ethylhexane, such as by "hydrotreating," as described herein and known in the art.

In certain embodiments, the recombinant microorganism that is the source of the aldehyde, the ketone, or both may be different than the recombinant microorganism that converts the aldehyde or ketone to the commodity chemical. In these and related embodiments, a first recombinant microorganism that comprises an aldehyde and/or ketone biosynthesis pathway may be utilized as a source or feedstock to produce one or more aldehydes and or ketones, which may then be converted to the desired commodity chemical, such as 2,2,4-trimethyl-1,3-pentanediol or 2-ethylhexanol, by a second recombinant microorganism that comprises an aldolase, optionally an exogenous double bond reductase, and an alchohol dehydrogenase. In these and related embodiments, the two recombinant microorganisms may be cultured together. Alternatively, the aldehyde, ketone, or both may be produced separately by the first recombinant microorganism and then later incubated with the second recombinant microorganism that comprises the aldolase and the alcohol dehydrogenase. Various other combinations and aspects of the invention will be apparent to a person skilled in the art in this regard.

In other embodiments, the source of an aldehyde and/or ketone, such as isobutyraldehyde, may be any other suitable source, such as a commercially available source. In these and any embodiments, the "source" of the aldehyde, ketone, or both may include the aldehyde or the ketone itself, which may be added directly to a microbial culture system as needed.

As for all other pathways and enzymes described herein, the aldolases, optional double bond reductases, and alcohol dehydrogenases, and the components for each of the aldehyde and/or ketone biosynthesis pathways described herein may be present in a recombinant microorganism either endogenously or exogenously. To improve the efficiency of a given biosynthesis pathway, endogenous genes, for example, may be upregulated or over-expressed, such as by introducing an additional copy ((i.e., exogenous gene) of that otherwise endogenous gene into the recombinant microorganism. Such pathways may also be optimized by altering via mutagenesis the endogenous version of a gene to improve functionality, followed by introduction of the altered gene into the microorganism. The expression of endogenous genes may be up or down-regulated, or even eliminated, according to known techniques in the art and described herein. Similarly, the expression levels of exogenous genes or polynucleotide sequences may be regulated as desired, such as by using various constitutive or inducible promoters. Such genes or polynucleotides may also be "codon-optimized," as described herein and known in the art. Also included are functional naturally-occurring variants of the genes and enzymes/polypeptides described herein, including homologs or orthologs thereof.

Any microorganism may be utilized according to the present invention. In certain aspects, a microorganism is a eukaryotic or prokaryotic microorganism. In certain aspects, a microrganism is a yeast, such as *S. cerevisiae*. In certain aspects, a microorganism is a bacteria, such as a gram-positive bacteria or a gram-negative bacteria. Given its rapid growth rate, well-understood genetics, the variety of available genetic tools, and its capability in producing heterologous proteins, genetically modified *E. coli* may be used in certain embodiments of a microbial system as described herein, whether for the degradation and metabolism of a polysaccharide, such as alginate or pectin, or the formation or biosynthesis of commodity chemicals, such as biofuels.

Other microorganisms may be used according to the present invention, based in part on the compatibility of enzymes and metabolites to host organisms. For example, other organisms such as *Acetobacter aceti, Achromobacter, Acidiphilium, Acinetobacter, Actinomadura, Actinoplanes, Aeropyrum pernix, Agrobacterium, Alcaligenes, Ananas comosus* (M), *Arthrobacter, Aspargillus niger, Aspargillus oryze, Aspergillus melleus, Aspergillus pulverulentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus lentus, Bacillus licheniformis, Bacillus macerans, Bacillus stearothermophilus, Bacillus subtilis, Bifidobacterium, Brevibacillus brevis, Burkholderia cepacia, Candida cylindracea, Candida rugosa, Carica papaya* (L), *Cellulosimicrobium, Cephalosporium, Chaetomium erraticum, Chaetomium gracile, Clostridium, Clostridium butyricum, Clostridium acetobutylicum, Clostridium thermocellum, Corynebacterium* (glutamicum), *Corynebacterium efficiens, Escherichia coli, Enterococcus, Erwina chrysanthemi, Gliconobacter, Gluconacetobacter, Haloarcula, Humicola insolens, Humicola nsolens, Kitasatospora setae, Klebsiella, Klebsiella oxytoca, Kluyveromyces, Kluyveromyces fragilis, Kluyveromyces lactis, Kocuria, Lactlactis, Lactobacillus, Lactobacillus fermentum, Lactobacillus sake, Lactococcus, Lactococcus lactis, Leuconostoc, Methylocystis, Methanolobus siciliae, Methanogenium organophilum, Methanobacterium bryantii, Microbacterium imperiale, Micrococcus lysodeikticus, Microlunatus, Mucor javanicus, Mycobacterium, Myrothecium, Nitrobacter, Nitrosomonas, Nocardia, Papaya carica, Pediococcus, Pediococcus halophilus, Penicillium, Penicillium camemberti, Penicillium citrinum, Penicillium emersonii, Penicillium roqueforti, Penicillum lilactinum, Penicillum multicolor, Paracoccus pantotrophus, Propionibacterium, Pseudomonas, Pseudomonas fluorescens, Pseudomonas denitrificans, Pyrococcus, Pyrococcus furiosus, Pyrococcus horikoshii, Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, Sccharomyces cerevisiae, Sclerotina libertina, Sphingobacterium multivorum, Sphingobium, Sphingomonas, Streptococcus, Streptococcus thermophilus* Y-1, *Streptomyces, Streptomyces griseus, Streptomyces lividans, Streptomyces murinus, Streptomyces rubiginosus, Streptomyces violaceoruber, Streptoverticillium mobaraense, Tetragenococcus, Thermus, Thiosphaera pantotropha, Trametes, Trichoderma, Trichoderma longibrachiatum, Trichoderma reesei, Trichoderma viride, Trichosporon penicillatum, Vibrio alginolyticus, Xanthomonas*, yeast, *Zygosaccharomyces rouxii, Zymomonas*, and *Zymomonus mobilis*, may be utilized as recombinant microorganisms provided herein, and, thus, may be utilized according to the various methods of the present invention.

The various embodiments described herein can be combined to provide further embodiments. All of the U.S. patents, U.S. patent application publications, U.S. patent applications, foreign patents, foreign patent applications and nonpatent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The following Examples are offered by way of illustration, not limitation.

EXAMPLES

Example 1

Aldehyde/Ketone Biosynthesis Pathways

To provide a useful source of aldehydes and/or ketones, such as butyraldehyde and isobutyraldehyde, recombinant microorganisms that comprise an aldehyde and/or ketone biosynthesis pathway, and which are capable of converting a suitable monosaccharide or oligosaccharide to an aldehyde or ketone, were constructed.

A butyraldehyde biosynthetic pathway comprising a thiolase (atoB) gene from *E. coli*, β-hydroxy butyryl-CoA dehydrogenase (hbd), crotonase (crt), butyryl-CoA dehydrogenase (bcd), electron transfer flavoprotein A (etfA), and electron transfer flavoprotein B (etfB) genes from *Clostridium acetobutyricum* ATCC 824, and a coenzyme A-linked butyraldehyde dehydrogenase (ald) gene from *Clostridium beijerinckii acetobutyricum* ATCC 824 was constructed in *E. coli* and tested for the ability to produce butyraldehyde. Also, a coenzyme A-linked alcohol dehydrogenase (adhE2) gene from *Clostridium acetobutyricum* ATCC 824 was used as an alternative to ald and tested for the ability to produce butanol.

An isobutyraldehyde biosynthetic pathway comprising an acetolactate synthase (alsS) from *Bacillus subtilis* or (als) from *Klebsiella pneumoniae* subsp. *pneumoniae* MGH 78578 (codon usage was optimized for *E. coli* protein expression) and acetolactate reductoisomerase (ilvC) and 2,3-dihydroxyisovalerate dehydratase (ilvD), genes from *E. coli* and keto-isovalerate decarboxylase (kivd) from *Lactococcus lactis* was constructed and tested for the ability to produce isobutyraldehyde, as measured by isobutanal production.

Construction of pBADButP.

The DNA sequence encoding hbd, crt, bcd, etfA, and etfA of *Clostridium acetobutyricum* ATCC 824 was amplified by polymerase chain reaction (PCR) from 50 ng *Clostridium acetobutyricum* ATCC 824 genome (ATCC) in 50 μl. Amplified DNA fragment was digested with BamHI and XbaI and ligated into pBAD33 pre-digested with the same restriction enzymes.

Construction of pBADButP-atoB.

The DNA sequence encoding atoB of *Escherichia coli* DH10B was amplified by polymerase chain reaction (PCR) from 50 ng *Escherichia coli* DH10B genome in 50 μl. Amplified DNA fragment was digested with XbaI and PstI and ligated into pBADButP pre-digested with the same restriction enzymes.

Construction of pBADatoB-ald.

The DNA sequence encoding atoB of *Escherichia coli* DH10B and ald from *Clostridium beijerinckii* were amplified separately by polymerase chain reaction (PCR) from either 50 ng *Escherichia coli* DH10B or *Clostridium beijerinckii* genome (ATCC) in 50 μl, respectively. The amplified DNA fragments were gel purified and eluted into 30 ul of EB buffer (Qiagen). 5 ul from each DNA solution was combined and each DNA fragment was spliced by another round of PCR. The spliced fragment was digested with SacI and HindIII and ligated into pBADButP pre-digested with the same restriction enzymes.

Construction of pBADButP-atoB-ALD.

The DNA fragment 1 encoding chloramphenicol acetyltransferase (CAT), P15 origin of replication, araBAD promoter, atoB of *Escherichia coli* DH10B and ald of *Clostridium beijerinckii* and the DNA fragment 2 encoding araBAD promoter, hbd, crt, bcd, etfA, and etfB of *Clostridium acetobutyricum* ATCC 824 were amplified separately by polymerase chain reaction (PCR) from 50 ng of either pBADatoB-ald or pBADButP in 50 μl, respectively. Amplified DNA fragments were digested with NotI and KpnI and ligated each other.

Construction of pBADals-ilvCD.

The DNA fragment encoding als of *Klebsiella pneumoniae* subsp. *pneumoniae* MGH 78578 of its codon usage optimized for over-expression in *E. coli* was amplified by polymerase chain reaction (PCR) from 50 ng pETals in 50 μl. The amplified DNA fragment was digested with SacI and XbaI and ligated into pBADilvCD pre-digested with the same restriction enzymes.

Construction of pBADalsS-ilvCD.

The DNA fragments encoding front and bottom halves of alsS of *Bacillus subtilis* B26 were amplified by polymerase chain reaction (PCR) from 50 ng *Bacillus subtilis* B26 genome (ATCC) in 50 μl. The amplified DNA fragments were gel purified and eluted into 30 ul of EB buffer (Qiagen). 5 ul from each DNA solution was combined and each DNA fragment was spliced by another round of PCR. The spliced fragment was internal XbaI site free and thus was digested with SacI and XbaI and ligated into pBADilvCD pre-digested with the same restriction enzymes.

Construction of pTrcBALK.

A DNA sequence encoding ketoisovalerate decarboxylase (kivd) of *Lactococcus lavtis* was amplified by polymerase chain reaction (PCR) 50 ng pETBAL in 50 μl. Amplified DNA fragment was digested with SacI and XbaI and ligated into pTrcBAL pre-digested with the same restriction enzymes.

Construction of pTrcBALD.

A DNA sequence encoding CoA-linked aldehyde dehydrogenase (ald) of *Clostridium beijerinckii* was amplified by polymerase chain reaction (PCR) from 50 ng pETBAL in 50 μl. Amplified DNA fragment was digested with SacI and HndIII and ligated into pTrcBAL pre-digested with the same restriction enzymes.

Construction of pBBRPduCDEGH.

A DNA sequence encoding propanediol dehydratase medium (pduD) and small (pduE) subunits and propanediol dehydratase reactivation large (pduG) and small (pduH) subunits of *Klebsiella pneumoniae* subsp. *pneumoniae* MGH 78578 was amplified by polymerase chain reaction (PCR) from 50 ng *Klebsiella pneumoniae* subsp. *pneumoniae* MGH 78578 in 50 μl. Amplified DNA fragment was digested with SacII and XbaI and ligated into pTrc99A pre-digested with the same restriction enzymes to form pBBRPduDEGH.

A DNA sequence encoding propanediol dehydratase large subunit (pduC) of *Klebsiella pneumoniae* subsp. *pneumoniae* MGH 78578 was amplified by polymerase chain reaction (PCR) from 50 ng *Klebsiella pneumoniae* subsp. *pneumoniae* MGH 78578 in 50 μl. Amplified DNA fragment was digested with XhoI and XbaI and ligated into pBBRPduDEGH pre-digested with the same restriction enzymes.

To test the butyraldehyde biosynthesis pathway, DH10B harboring pBADButP-atoB/pTrcBALD and pBADButP-atoB-ALD/pTrcB2DH/pBBRpduCDEGH were grown overnight in LB media containing 50 ug/ml chroramphenicol ($Cm^{50}$) and 100 ug/ml ampicillin ($Amp^{100}$) at 37 C, 200 rpm. An aliquot of each seed culture was inoculated into fresh TB media containing $Cm^{50}$ and $Amp^{100}$ and was grown in incubation shaker at 37 C, 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS.

Figure 2A:
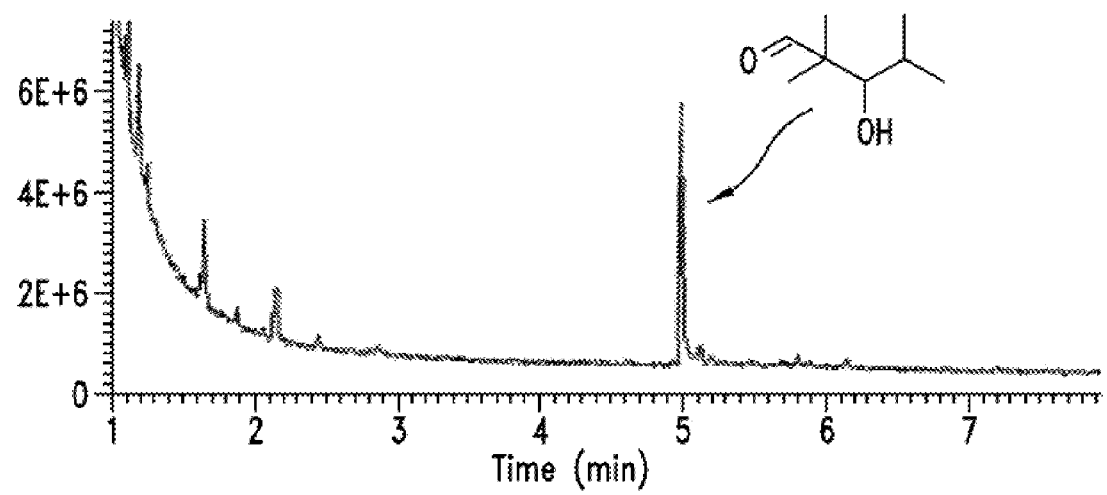
FIG. 2 shows the production of 3-hydroxy-2,2,4-trimethylpentanal from DH10B strain harboring pTrcTM1559 (A) and its control plasmid (B), as measured by GC-MS.
Figure 2B:
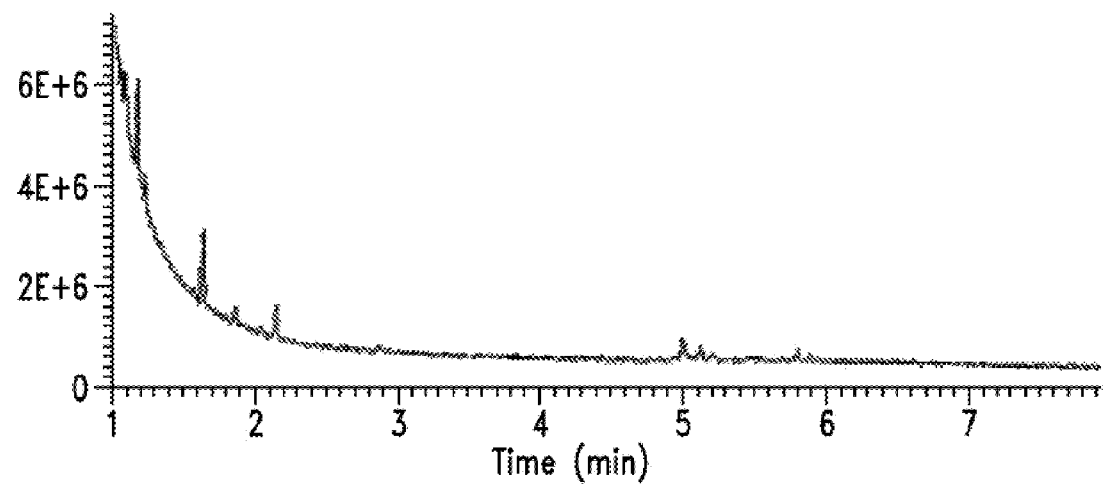

To test the isobutyeraldehyde biosynthesis pathway, DH10B cells harboring pBADals-ilvCD/pTrcBALK or pBADalsS-ilvCD/pTrcBALK were grown overnight in LB media containing 50 ug/ml chroramphenicol ($Cm^{50}$) and 100 ug/ml ampicillin ($Amp^{100}$) at 37 C, 200 rpm. An aliquot of each seed culture was inoculated into fresh TB media containing $Cm^{50}$ and $Amp^{100}$ and was grown in an incubation shaker at 37° C., 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS for the production of isobutyraldehyde, as measured by isobutanal production. FIG. 2 shows the production of isobutanal from these cultures. This strain also produced 2-methylbutyraldehyde and 3-methylbutyraldehyde as minor components (not shown).

Example 2

Production of 3-Hydroxy-2,2,4 Trimethylpentanal from Isobutyraldehyde

The ability of an enzyme having aldolase activity to condense two molecules of isobutyraldehyde to form 3-hydroxy-2,2,4-trimethylpentanal was tested in vivo. Plasmid TrcTM1559 was constructed as described in Example 5 below, and contains an aldose-encoding polynucleotide sequence that was obtained from Thermotoga maritima.

A single colony of E. coli DH10B stain harboring pTrcTM1559 was inoculated into fresh LB media containing $Amp^{100}$ and the culture was grown in an incubation shaker at 37° C. for overnight. One percent of this culture was inoculated into fresh TB media containing $Amp^{100}$ and the culture was grown in incubation shaker at 37° C. When the culture was grown to an $OD_{600nm}$ of 0.6, the culture was induced with 0.5 mM IPTG. 50 mM isobutyraldehyde was added and the cultures were grown for a day. 500 ul of culture was extracted with 500 ul of ethylacetate, and the extracts were analyzed by GC-MS. The formation of 3-hydroxy-2,2,4-trimethylpentanal was observed (see FIG. 2).

Example 3

Production of 2,2,4-Trimethyl-1,3-Pentanediol from Isobutyraldehyde

The ability of a recombinant microorganism comprising an aldolase enzymen and an alcohol dehydrogenase to convert isobutyraldehyde to 2,2,4-trimethyl-1,3-pentanediol is tested. Plasmid TrcTM1559 is described in Example 2 above.

Various alcohol dehydrogenases were isolated from Pseudomonas putida KT2440, Pseudomonas fluorescens Pf-5, and Klebsiella pneumoniae MGH 78578 (see SEQ ID NO:1-34) and cloned into expression plasmids, as described in U.S. application Ser. Nos. 12/245,537 and 12/245,540, which are incorporated by reference for their description, construction and testing of alcohol dehydrogenase enzymes. Additional alcohol dehydrogenases were also obtained from Pseudomonas putida (see SEQ ID NOS:83-96).

A single colony of E. coli DH10B stain harboring both pTrcTM1559 and an alcohol dehydrogenase expressing plasmid is inoculated into fresh LB media containing $Amp^{100}$ and the culture is grown in incubation shaker at 37° C. for overnight. One percent of this culture is inoculated into fresh TB media containing $Amp^{100}$ and the culture is grown in incubation shaker at 37° C. When the culture is grown to an $OD_{600nm}$ of 0.6, the culture is induced with 0.5 mM IPTG. 50 mM isobutyraldehyde is added and the cultures are grown for a day. 500 ul of culture is extracted with 500 ul of ethylacetate, and the extracts are analyzed by GC-MS. The formation of 2,2,4-trimethylpentandiol is observed.

Example 4

Production of Other Medium to Long Chain Hydrocarbons

In addition to abovementioned pathway to produce 2,2,4-trimethyl-1,3-pentanediol and then 2,2,4, trimethylpentane (isooctane), enzymatic aldol condensation followed by alcohol dehydrogenation can yield variety of medium to long chain hydrocarbons from various aldehydes and ketones as starting materials. These aldehydes and/or ketones can be produced by recombinant microorganisms according to the aldehyde and/or ketone biosynthesis pathways described in U.S. application Ser. Nos. 12/245,537 and 12/245,540, which are incorporated by reference for the description, construction, and testing of these pathways.

One example is illustrated herein, in which two molecules of butyraldehyde were condensed by an aldolase to form 3-hydroxy-2-ethyl hexanal. This molecule was then spontaneously or enzymatically dehydrated to form 2-ethyl-2-hexene-1-al, which may then be consecutively reduced to form 2-ethylhexanal and 2-ethylhexanol, catalyzed by double bond reductase and alcohol dehydrogenase, respectively.

Also illustrated herein is a reaction in which two molecules of hexanaldehyde were condensed by an aldolase to form 3-hydroxy-2-butyl-1-octanal. This molecule was then spontaneously or enzymatically dehydrated to form 2-butyl-2-octene-1-al, which may then be consecutively reduced to for 2-butyl-octanal and 2-butyl octanol.

Figure 3A:
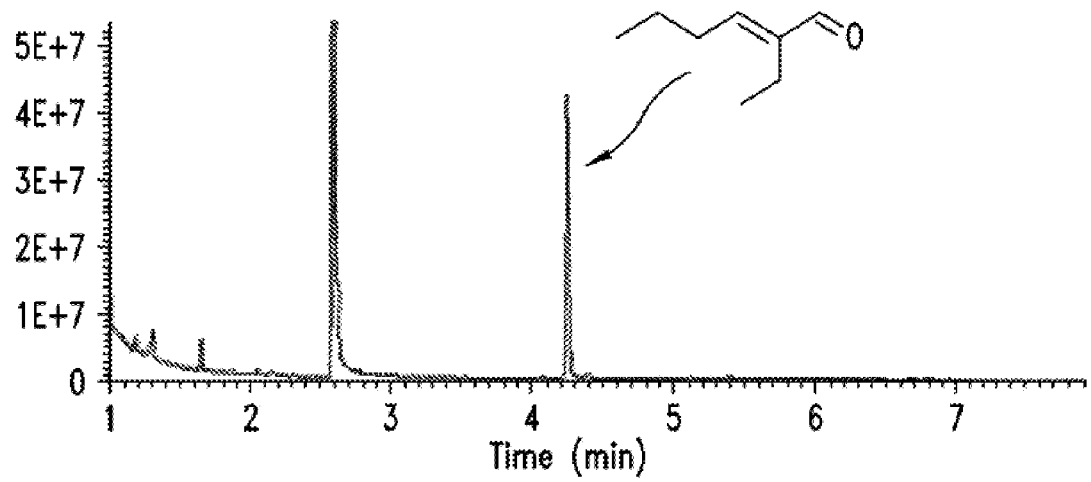
FIG. 3 shows the production of 2-ethyl-2-hexene-1-al from DH10B strain harboring pTrcTM1559 (A) and its control plasmid (B), as measured by GC-MS.
Figure 3B:
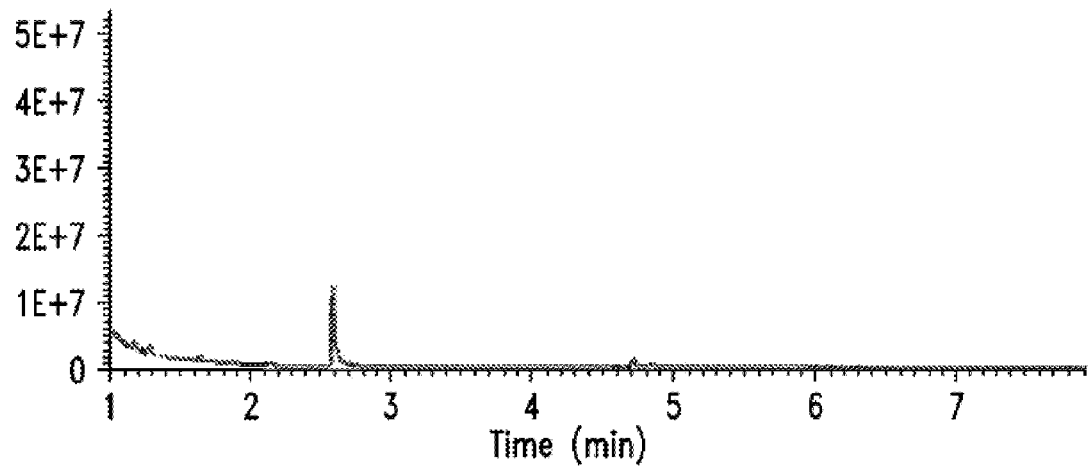
Figure 4A:
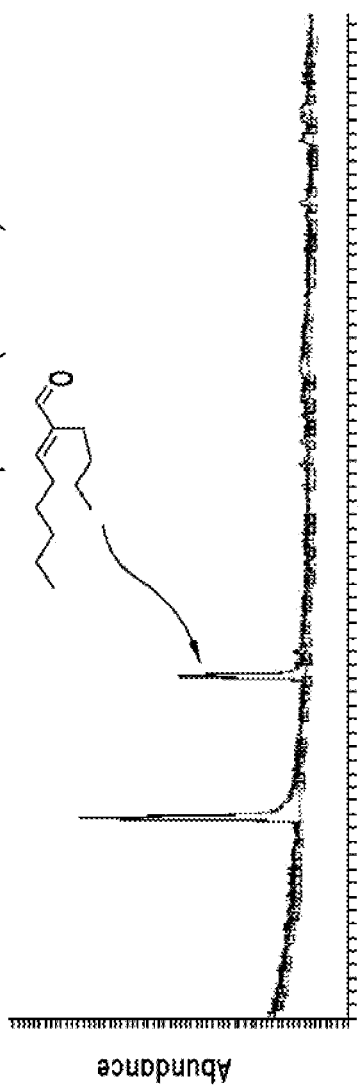
FIG. 4 shows the production of 2-butyl-2-octene-1-al from DH10B strain harboring pTrcTM1559 (A) and its control plasmid (B), as measured by GC-MS
Figure 4B:
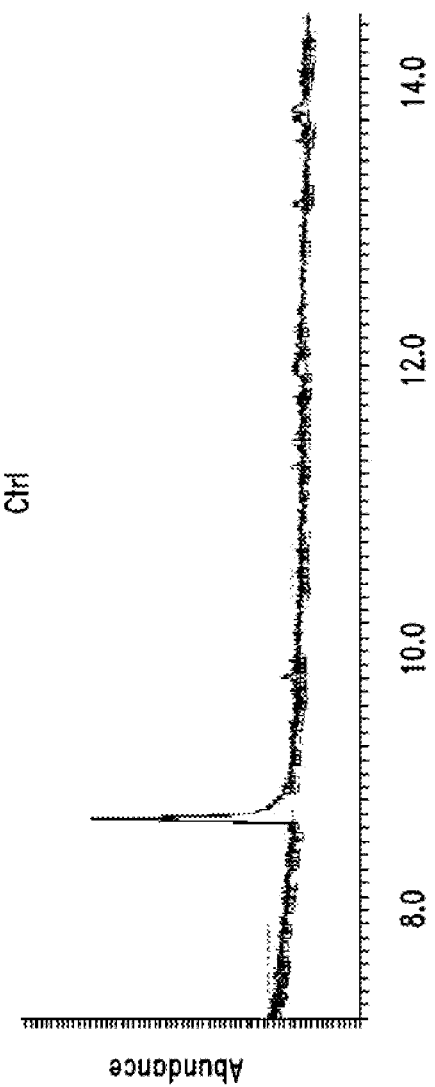

To test the production of 2-ethyl-2-hexene-1-al, a single colony of E. coli DH10B stain harboring pTrcTM1559 was inoculated into fresh LB media containing $Amp^{100}$ and the culture grown in incubation shaker at 37 C for overnight. One percent of this culture was inoculated into fresh TB media containing $Amp^{100}$ and the culture was grown in incubation shaker at 37 C. When the culture was grown $OD_{600nm}$ of 0.6, the culture was induced with 0.5 mM IPTG. Either 50 mM butyraldehyde or 50 mm hexanaldehyde was added and the cultures were grown for a day. 500 ul of the culture was extracted with 500 ul of ethylacetate, and the extracts were analyzed by GC-MS. The formation of 2-ethyl-2-hexene-1-al was observed (see FIG. 3). Also, the formation of 2-butyl-2-octene-1-al was observed (see FIG. 4).

Example 5

Isolation and Cloning of Aldolases

Polynucleotide sequences that encode enzymes having aldolase activity were isolated from *Thermotoga maritima* and *Escherichia coli* DH10B and cloned into expression vectors.

Construction of pTrcTM0040, pTrcTM0066, pTrcTM0273, pTrcTM0283, pTrcTM0295, pTrcTM0343, pTrcTM0720, pTrcTM1072, pTrcTM1419, pTrcTM1521, pTrcTM1559, and pTrcTM1744

As the DNA sequences encoding TM0273, TM0283, TM0720, TM 1559, and TM1744 contain an internal NcoI site, flanking regions of NcoI site for each gene were amplified separately by polymerase chain reaction (PCR): 98° C. for 10 sec, 60° C. for 15 sec, and 72° C. for 30 min, repeated 30 times. The reaction mixture contained 1× Phusion buffer (NEB), 2 mM dNTP, 0.5 µM forward and reverse primers (see Table 5), 1U Phusion High Fidelity DNA polymerase (NEB), and 50 ng *Thermotoga maritima* genome in 50 µl.

TABLE 5

| Gene name | Forward 5' -> 3' | Reverse 5' -> 3' |
| --- | --- | --- |
| TM0273 fragment 1 | CATGCCATGGGG ATGACAATGCCTTATGTAAAGAACA (SEQ ID NO: 97) | CTGCGGTACCATAGAAGCTCCGTGA (SEQ ID NO: 98) |
| TM0273 fragment 2 | TCACGGAGCTTCTATGGTACCGCAG (SEQ ID NO: 99) | GCTCTAGA TTACGCCTTTCCGCTGGATCCGAAT (SEQ ID NO: 100) |
| TM0283 fragment 1 | CATGCCATGGGG ATGAGGAGTACAGACAGGTTACTGT (SEQ ID NO: 101) | TGCCCACACCATCGCGAATGTTGAA (SEQ ID NO: 102) |
| TM0283 fragment 2 | TTCAACATTCGCGATGGTGTGGGCA (SEQ ID NO: 103) | GCTCTAGA TTACTTCTGACCGTACTTGGTGTGG (SEQ ID NO: 104) |
| TM0720 fragment 1 | CATGCCATGGGG ATGTGGAAGCATGTAAAACAGGTTG (SEQ ID NO: 105) | CATGCTTCCCATTGTTTCTATGACA (SEQ ID NO: 106) |
| TM0720 fragment 2 | TGTCATAGAAACAATGGGAAGCATG (SEQ ID NO: 107) | CACCGGTGCTCCGTGGGTGAGATGT (SEQ ID NO: 108) |
| TM0720 fragment 3 | ACATCTCACCCACGGAGCACCGGTG (SEQ ID NO: 109) | GCTCTAGA TTATATTTCCACCCCTTCGATCTTG (SEQ ID NO: 110) |
| TM1559 fragment 1 | CATGCCATGGGG ATGATAGAGTACAGGATTGAGGAGG (SEQ ID NO: 111) | CACACAGACTCCGTGGAAACGATTT (SEQ ID NO: 112) |
| TM1559 fragment 2 | AAATCGTTTCCACGGAGTCTGTGTG (SEQ ID NO: 113) | GCTCTAGA TTAACCTCCATATCTCTCTTCTCCC (SEQ ID NO: 114) |
| TM1744 fragment 1 | CATGCCATGGGG ATGATCGATCTCAGGTCCGACACCG (SEQ ID NO: 115) | AGCCTGTGCCATCGCTTTTCTCATC (SEQ ID NO: 116) |
| TM1744 fragment 2 | GATGAGAAAAGCGATGGCACAGGCT (SEQ ID NO: 117) | TTGATTTCCCATTGTGCCGGAGGGT (SEQ ID NO: 118) |
| TM1744 fragment 3 | ACCCTCCGGCACAATGGGAAATCAA (SEQ ID NO: 119) | GAGAACCGCCATCGCTCCGACCTCG (SEQ ID NO: 120) |
| TM1744 fragment 4 | CGAGGTCGGAGCGATGGCGGTTCTC (SEQ ID NO: 121) | ATCGGGGTCCATCGCTCCATTTTTT (SEQ ID NO: 122) |
| TM1744 fragment 5 | AAAAAATGGAGCGATGGACCCCGAT (SEQ ID NO: 123) | GCTCTAGA TTAGGAGAATTTTCTGAAGAGTTTT (SEQ ID NO: 124) |

The DNA sequences encoding TM0040, TM0066, TM0273, TM0283, TM0295, TM0343, TM0720, TM1072, TM1419, TM1521, TM1559, and TM1744 of Themotoga maritima were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 μM forward and reverse primers (see Table 6), 1U Phusion High Fidelity DNA polymerase (NEB), and 50 ng Thermotoga maritima genome in 50 μl (Note: For TM0273, TM0283, TM0720, TM 1559, and TM1744, fragments prepared as described in the preceding paragraph were used). The amplified DNA fragments were digested with NcoI and XbaI and ligated into pTrc99A pre-digested with the same restriction enzymes.

TABLE 6

| Gene name | Forward 5' -> 3' | Reverse 5' -> 3' |
|---|---|---|
| TM0044 | CATGCC ATGGTTTACACAACTCCCTGGAACAGAAAG (SEQ ID NO: 125) | GCTCTAGA TTACAACCTTTGCCAGAGTATCGCC (SEQ ID NO: 126) |
| TM0066 | CATGCCATGGGG ATGAAGATGGAAGAGCTCTTCAAAA (SEQ ID NO: 127) | GCTCTAGA TTATTCTGTGCACCCCCTGATCTTT (SEQ ID NO: 128) |
| TM0273 | CATGCCATGGGG ATGACAATGCCTTATGTAAAGAACA (SEQ ID NO: 129) | GCTCTAGA TTACGCCTTTCCGCTGGATCCGAAT (SEQ ID NO: 130) |
| TM0283 | CATGCCATGGGG ATGAGGAGTACAGACAGGTTACTGT (SEQ ID NO: 131) | GCTCTAGA TTACTTCTGACCGTACTTGGTGTGG (SEQ ID NO: 132) |
| TM0295 | CATGCCATGGGG ATGAAGATCTTTCTGGACACAGCAA (SEQ ID NO: 133) | GCTCTAGA TTATTTCTTCAGGTTCTCCAAATAC (SEQ ID NO: 134) |
| TM0343 | CATGCCATGGGG ATGATAGTCGTTTTGAAACCCGGTT (SEQ ID NO: 135) | GCTCTAGA TTAATTCACCTTCACCCCCAGGGCA (SEQ ID NO: 136) |
| TM0720 | CATGCCATGGGG ATGTGGAAGCATGTAAAACAGGTTG (SEQ ID NO: 137) | GCTCTAGA TTATATTTCCACCCCTTCGATCTTG (SEQ ID NO: 138) |
| TM1072 | CATGCCATGGGG ATGAGAGAGACGATAAGAGAGATTC (SEQ ID NO: 139) | GCTCTAGA TTACAGCCATCCCTCCGGAACACCC (SEQ ID NO: 140) |
| TM1419 | CATGCC ATGGTCAAGGTCCTGATCCTCGGTC (SEQ ID NO: 141) | GCTCTAGA TTACAGCCACTTCGGTTTCAATCCC (SEQ ID NO: 142) |
| TM1521 | CATGCCATGGGG ATGTTCAGAGGAGTAGGAACTGCTA (SEQ ID NO: 143) | GCTCTAGA TTATAGCAATCCACTCTCCTTGAGA (SEQ ID NO: 144) |
| TM1559 | CATGCCATGGGG ATGATAGAGTACAGGATTGAGGAGG (SEQ ID NO: 145) | GCTCTAGA TTAACCTCCATATCTCTCTTCTCCC (SEQ ID NO: 146) |
| TM1744 | CATGCCATGGGG ATGATCGATCTCAGGTCCGACACCG (SEQ ID NO: 147) | GCTCTAGA TTAGGAGAATTTTCTGAAGAGTTTT (SEQ ID NO: 148) |

Construction of pTrcDH10Bxxx

The DNA sequences encoding EC1648 and EC4071 contain an internal NcoI site, and the DNA sequence encoding EC2249 contained an XbaI site. Flanking regions of the restriction sites for each gene were amplified separately by polymerase chain reaction (PCR): 98° C. for 30 sec, 55° C. for 15 sec, and 72° C. for 45 sec, repeated 30 times. The reaction mixture contained 1× Phusion buffer (NEB), 2 mM dNTP, 0.3 µM forward and reverse primers (see Table 7), 1U Phusion High Fidelity DNA polymerase (NEB), and 20 ng *E. coli* DH10β.

TABLE 7

| Gene name | Forward 5' -> 3' | Reverse 5' -> 3' |
|---|---|---|
| EC1648 fragment 1 | CATGCCATGGGGATGGCAGATTTAGACGATATTAAAG (SEQ ID NO: 149) | CTGAAAATAACCGTGGTCAAAAGCC (SEQ ID NO: 150) |
| EC1648 fragment 2 | GGCTTTTGACCACGGTTATTTTCAG (SEQ ID NO: 151) | CAGTCACGGCCATCGTCGGCATTCCC (SEQ ID NO: 152) |
| EC1648 fragment 3 | GGGAATGCCGACGATGGCCGTGACTG (SEQ ID NO: 153) | GCTCTAGATTACTGTTTTTCACTCAGATAG (SEQ ID NO: 154) |
| EC2249 fragment 1 | CATGCCATGGGGATGTACGTGGTATCGACAAAG (SEQ ID NO: 155) | GTTCTCCAGTCTCGAAAAATCAAGC (SEQ ID NO: 156) |
| EC2249 fragment 2 | GCTTGATTTTTCGAGACTGGAGAAC (SEQ ID NO: 157) | GCTCTAGATTATGCCCTGCCCTCGCAGC (SEQ ID NO: 158) |
| EC4071 fragment 1 | CATGCCATGGGGATGAATAAGTACACCATCAAC (SEQ ID NO: 159) | GAGGATCACCCACGGCATATTGATATG (SEQ ID NO: 160) |
| EC4071 fragment 2 | CATATCAATATGCCGTGGGTGATCCTC (SEQ ID NO: 161) | GCTCTAGATTAGCGGCGTTTAGCCATC (SEQ ID NO: 162) |

The DNA sequences encoding EC0008, EC0894, EC0940, EC1648, EC1991, EC2249, EC2250, EC2465, EC2629, EC2969, EC3100, EC3233, EC3299, EC3305, EC3310, EC4071, EC4092, EC4135 and EC4539 of *Escherichia coli* DH10β were amplified by polymerase chain reaction (PCR): 98° C. for 30 sec, 55° C. for 30 sec, and 72° C. for 1 min, repeated 30 times. The reaction mixture contained 1× Phusion buffer (NEB), 2 mM dNTP, 0.3 µM forward and reverse primers (see Table 8), 1U Phusion High Fidelity DNA polymerase (NEB), and 20 ng *Escherichia coli* DH10β genome in 50 µl (Note: For EC1648, EC2249 and EC4071 fragments prepared in the preceding paragraph were used).

TABLE 8

| Gene name | Forward 5' -> 3' | Reverse 5' -> 3' |
|---|---|---|
| EC0008 | CATGCCATGGGGATGACGGACAAATTGACCTC (SEQ ID NO: 163) | GCTCTAGATTACAGCAGATCGCCGATC (SEQ ID NO: 164) |
| EC0894 | CATGCCATGGGGATGGAACTGTATCTGGATAC (SEQ ID NO: 165) | GCTCTAGATTAAATCGACGTTCTGCCAAAC (SEQ ID NO: 166) |
| EC0940 | CATGCCATGGGGATGATTGATTTACGCAGTGATAC (SEQ ID NO: 167) | GCTCTAGATTAACGCGCCAGGAATGCAC (SEQ ID NO: 168) |
| EC1648 | CATGCCATGGGGATGGCAGATTTAGACGATATTAAAG (SEQ ID NO: 169) | GCTCTAGATTACTGTTTTTCACTCAGATAG (SEQ ID NO: 170) |
| EC1991 | CATGCCATGGGGATGAAAAACTGGAAAACAAG (SEQ ID NO: 171) | GCTCTAGATTACAGCTTAGCGCCTTCTAC (SEQ ID NO: 172) |
| EC2249 | CATGCCATGGGGATGTACGTGGTATCGACAAAG (SEQ ID NO: 173) | GCTCTAGATTATGCCCTGCCCTCGCAGC (SEQ ID NO: 174) |
| EC2250 | CATGCCATGGGGATGACAGATATTGCGCAGTTG (SEQ ID NO: 175) | GCTCTAGATCAGGCGATAGTAATTTTGC (SEQ ID NO: 176) |
| EC2465 | CATGCCATGGGGATGGCACAACCTGCCGCTATTATTC (SEQ ID NO: 177) | GCTCTAGATTAACGCTGCCAGCTTAAGG (SEQ ID NO: 178) |
| EC2629 | CATGCCATGGGGATGAACGAGTTAGACGGCATC (SEQ ID NO: 179) | GCTCTAGATTATAGTTTGGCGGCAAGAAG (SEQ ID NO: 180) |
| EC2969 | CATGCCATGGGGATGGAACGAAATAAACTTGC (SEQ ID NO: 181) | GCTCTAGATTACTCTTCAATTCGTAACC (SEQ ID NO: 182) |
| EC3100 | CATGCCATGGGGATGTCTAAGATTTTTGATTTC (SEQ ID NO: 183) | GCTCTAGATTACAGAACGTCGATCGCGTTC (SEQ ID NO: 184) |
| EC3233 | CATGCCATGGGGATGGATATTGTATTTATAGAG (SEQ ID NO: 185) | GCTCTAGATTAATTATTTTCTTTCAGATTATTG (SEQ ID NO: 186) |
| EC3299 | CATGCCATGGGGATGAATAACGATGTTTTCCC (SEQ ID NO: 187) | GCTCTAGATTATTTTTTAAAGGTATCAG (SEQ ID NO: 188) |

TABLE 8-continued

| Gene name | Forward 5' -> 3' | Reverse 5' -> 3' |
|---|---|---|
| EC3305 | CATGCCATGGGGATGA AACATCTGACAGAAAT G (SEQ ID NO: 189) | GCTCATATATATATCC TCCTTTATTGGCCTTC ACAGGCTGTG (SEQ ID NO: 190) |
| EC3310 | CAATAAAGGAGGATAT ATATATGAGCATTATC TCCACTAAATATC (SEQ ID NO: 191) | GCTCTAGATTATGCTG AAATTCGATTCG (SEQ ID NO: 192) |
| EC4071 | CATGCCATGGGGATG AATAAGTACACCATC AAC (SEQ ID NO: 193) | GCTCTAGATTAGCGGC GTTTAGCCATC (SEQ ID NO: 194) |
| EC4092 | CATGCCATGGGGATGC AAAACATTACTCAGTC (SEQ ID NO: 195) | GCTCTAGATTACAGCG CCAGCGCACTGG (SEQ ID NO: 196) |
| EC4135 | CATGCCATGGGGATGG AACTGTATCTGGACAC (SEQ ID NO: 197) | GCTCTAGATTAGAGAT GAGTAGTGCCAAATG (SEQ ID NO: 198) |
| EC4539 | CATGCCATGGGGATGA CTGATCTGAAAGCAAG (SEQ ID NO: 199) | GCTCTAGATTAGTAGC TGCTGGCGCTC (SEQ ID NO: 200) |

The amplified fragments encoding EC3305 and EC3310 were ligated together using the overlap-PCR method. (PCR): 98° C. for 30 sec, 55° C. for 30 sec, and 72° C. for 1 min, repeated 30 times. The reaction mixture contained 1× Phusion buffer (NEB), 2 mM dNTP, 0.3 μM forward and reverse primers (forward primer: catgccatggggatgaaacatctgacagaaatg (SEQ ID NO:189), reverse primer: gctctagattatgctgaaattcgattcg (SEQ ID NO:190)), 1U Phusion High Fidelity DNA polymerase (NEB), and 3 μL PCR product from the previous paragraph.

Amplified DNA fragment was digested with NcoI and XbaI and ligated into pTrc99A pre-digested with the same restriction enzymes.

The invention claimed is:

1. A recombinant microorganism, comprising:
   a) hexanal;
   b) 2-butyl-2-octene-1-al and
   c) recombinant DNA comprising SEQ ID NO:51 wherein said recombinant DNA encodes an aldolase wherein said aldolase is expressed in said microorganism and said hexanal is converted to 2-butyl-2-octene-1-al by said aldolase.

2. The microorganism of claim 1 wherein the microorganism is yeast.

3. The microorganism of claim 1 wherein the microorganism is *E. coli*.

* * * * *

SEQUENCE LISTING

<160> NUMBER OF SEQ ID NOS: 260

<210> SEQ ID NO 1
<211> LENGTH: 789
<212> TYPE: DNA
<213> ORGANISM: Pseudomonas putida KT2440

<400> SEQUENCE: 1

```
atgacagtca attatgattt tccggaaaaa gtcgtgctgg ttaccggcgc tggctctggt    60
attggccgtg ccactgcgct tgccttcgcg cagtcgggcg catccgttgc ggtcgcagac   120
atctcgactg accacggttt gaaaaccgta gagttggtca aagccgaagg aggcgaggcg   180
accttcttcc atgtcgatgt aggctctgaa cccagcgtcc agtcgatgct ggctggtgtc   240
gtggcgcatt acggcggcct ggacattgcg cacaacaacg ccggcattga ggccaatatc   300
gtgccgctgg ccgagctgga ctccgacaac tggcgtcgtg tcatcgatgt gaacctttcc   360
tcggtgttct attgcctgaa aggtgaaatc cctctgatgc tgaaaggggg cggcggcgcc   420
attgtgaata ccgcatcggc ctccgggctg attggcggct atcgcctttc cgggtatacc   480
gccacgaagc acggcgtagt ggggctgact aaggctgctg ctatcgatta tgcaaaccag   540
aatatccgga ttaatgccgt gtgccctggt ccagttgact ccccattcct ggctgacatg   600
ccgcaaccca tgcgcgatcg acttctcttt ggcactccaa ttggacgatt ggccaccgca   660
gaggagatcg cgcgttcggt tctgtggctg tgttctgacg atgcaaaata cgtggtgggc   720
cattcgatgt cagtcgacgg tggcgtggca gtgactgcgg ttggtactcg aatggatgat   780
ctctttttaa                                                          789
```

<210> SEQ ID NO 2
<211> LENGTH: 262
<212> TYPE: PRT
<213> ORGANISM: Pseudomonas putida KT2440

<400> SEQUENCE: 2

```
Met Thr Val Asn Tyr Asp Phe Ser Gly Lys Val Val Leu Val Thr Gly
1               5                   10                  15
```

```
Ala Gly Ser Gly Ile Gly Arg Ala Thr Ala Leu Ala Phe Ala Gln Ser
             20                  25                  30

Gly Ala Ser Val Ala Val Ala Asp Ile Ser Thr Asp His Gly Leu Lys
         35                  40                  45

Thr Val Glu Leu Val Lys Ala Glu Gly Glu Ala Thr Phe Phe His
 50                  55                  60

Val Asp Val Gly Ser Glu Pro Ser Val Gln Ser Met Leu Ala Gly Val
 65                  70                  75                  80

Val Ala His Tyr Gly Gly Leu Asp Ile Ala His Asn Asn Ala Gly Ile
                 85                  90                  95

Glu Ala Asn Ile Val Pro Leu Ala Glu Leu Asp Ser Asp Asn Trp Arg
            100                 105                 110

Arg Val Ile Asp Val Asn Leu Ser Ser Val Phe Tyr Cys Leu Lys Gly
            115                 120                 125

Glu Ile Pro Leu Met Leu Lys Arg Gly Gly Ala Ile Val Asn Thr
        130                 135                 140

Ala Ser Ala Ser Gly Leu Ile Gly Gly Tyr Arg Leu Ser Gly Tyr Thr
145                 150                 155                 160

Ala Thr Lys His Gly Val Val Gly Leu Thr Lys Ala Ala Ala Ile Asp
                165                 170                 175

Tyr Ala Asn Gln Asn Ile Arg Ile Asn Ala Val Cys Pro Gly Pro Val
            180                 185                 190

Asp Ser Pro Phe Leu Ala Asp Met Pro Gln Pro Met Arg Asp Arg Leu
        195                 200                 205

Leu Phe Gly Thr Pro Ile Gly Arg Leu Ala Thr Ala Glu Glu Ile Ala
210                 215                 220

Arg Ser Val Leu Trp Leu Cys Ser Asp Asp Ala Lys Tyr Val Val Gly
225                 230                 235                 240

His Ser Met Ser Val Asp Gly Gly Val Ala Val Thr Ala Val Gly Thr
                245                 250                 255

Arg Met Asp Asp Leu Phe
            260

<210> SEQ ID NO 3
<211> LENGTH: 762
<212> TYPE: DNA
<213> ORGANISM: Pseudomonas putida KT2440

<400> SEQUENCE: 3
atgagcatga cctttctgg ccaggtagcc ctggtgaccg gcgcgggtgc cggcatcggc      60
cgggcaaccg ccctggcgtt cgcccacgag ggcatgaaag tggtggtggc ggacctcgac    120
ccggtcggcg gcgaggccac cgtggcgcag atccacgcgg caggcggcga agcgctgttc    180
attgcctgcg acgtgacccg cgacgccgag gtgcgccagt tgcatgagcg cctgatggcc    240
gcctacggcc ggctggacta cgccttcaac aacgccggga tcgagatcga gcaacaccgc    300
ctggccgaag cagcgaagc ggagttcgat gccatcatgg gcgtgaacgt gaagggcgtg    360
tggttgtgca tgaagtatca gttgcccttg ttgctggccc aaggcggtgg ggccatcgtc    420
aataccgcgt cggtggcggg gctaggggcg gcgccaaaga tgagcatcta cagcgccagc    480
aagcatgcgg tcatcggtct gaccaagtcg gcggccatcg agtacgccaa gaagggcatc    540
cgcgtgaacg ccgtgtgccc ggccgtgatc gacaccgaca tgttccgccg gcttaccag    600 gccgacccgc gcaaggccga gttcgccgca gccatgcacc ggtagggcg cattggcaag    660 gtcgaggaaa tcgccagcgc cgtgctgtat ctgtgcagtg acggcgcggc gtttaccacc    720
```

```
gggcattgcc tgacggtgga tggtggggct acggcgatct ga                762
```

<210> SEQ ID NO 4
<211> LENGTH: 253
<212> TYPE: PRT
<213> ORGANISM: Pseudomonas putida KT2440

<400> SEQUENCE: 4

```
Met Ser Met Thr Phe Ser Gly Gln Val Ala Leu Val Thr Gly Ala Gly
 1               5                  10                  15

Ala Gly Ile Gly Arg Ala Thr Ala Leu Ala Phe Ala His Glu Gly Met
            20                  25                  30

Lys Val Val Ala Asp Leu Asp Pro Val Gly Gly Glu Ala Thr Val
        35                  40                  45

Ala Gln Ile His Ala Ala Gly Gly Glu Ala Leu Phe Ile Ala Cys Asp
    50                  55                  60

Val Thr Arg Asp Ala Glu Val Arg Gln Leu His Glu Arg Leu Met Ala
 65                  70                  75                  80

Ala Tyr Gly Arg Leu Asp Tyr Ala Phe Asn Asn Ala Gly Ile Glu Ile
                85                  90                  95

Glu Gln His Arg Leu Ala Glu Gly Ser Glu Ala Glu Phe Asp Ala Ile
            100                 105                 110

Met Gly Val Asn Val Lys Gly Val Trp Leu Cys Met Lys Tyr Gln Leu
        115                 120                 125

Pro Leu Leu Leu Ala Gln Gly Gly Ala Ile Val Asn Thr Ala Ser
    130                 135                 140

Val Ala Gly Leu Gly Ala Ala Pro Lys Met Ser Ile Tyr Ser Ala Ser
145                 150                 155                 160

Lys His Ala Val Ile Gly Leu Thr Lys Ser Ala Ala Ile Glu Tyr Ala
                165                 170                 175

Lys Lys Gly Ile Arg Val Asn Ala Val Cys Pro Ala Val Ile Asp Thr
            180                 185                 190

Asp Met Phe Arg Arg Ala Tyr Gln Ala Asp Pro Arg Lys Ala Glu Phe
        195                 200                 205

Ala Ala Ala Met His Pro Val Gly Arg Ile Gly Lys Val Glu Glu Ile
    210                 215                 220

Ala Ser Ala Val Leu Tyr Leu Cys Ser Asp Gly Ala Ala Phe Thr Thr
225                 230                 235                 240

Gly His Cys Leu Thr Val Asp Gly Gly Ala Thr Ala Ile
                245                 250
```

<210> SEQ ID NO 5
<211> LENGTH: 810
<212> TYPE: DNA
<213> ORGANISM: Pseudomonas putida KT2440

<400> SEQUENCE: 5

```
atgtcttttc aaacaaaat cgttgtgctc acaggcgcag cttctggcat cggcaaagcg    60
acagcacagc tgctagtgga gcagggcgcc catgtggttg ccatggatct taaaagcgac   120
ttgcttcaac aagcattcgg cagtgaggag cacgttctgt gcatccctac cgacgtcagc   180
gatagcgaag ccgtgcgagc cgccttccag gcagtggacg cgaaatttgg ccgtgtcgac   240
gtgattatta cgccgcgggg catcaacgca cctacgcgag aagccaacca gaaaatggtt   300
gatgccaacg tcgctgccct cgatgccatg aagagcgggc gggcgcccac tttcgacttc   360
ctggccgata cctcggatca ggatttccgg cgcgtaatgg aagtcaattt gttcagccag   420
```

-continued

```
ttttactgca ttcgagaggg tgttccgctg atgcgccgag cgggtggcgg cagcatcgtc    480
aacatctcca gcgtggcagc gctcctgggc gtggcaatgc cactttacta ccccgcctcc    540
aaggcggcgg tgctgggcct cacccgtgca gcggcagctg agttggcacc ttacaacatt    600
cgtgtgaatg ccatcgctcc aggctctgtc gacacaccat tgatgcatga gcaaccaccg    660
gaagtcgttc agttcctggt cagcatgcaa cccatcaagc ggctggccca acccgaggag    720
cttgcccaaa gcatcctgtt ccttgccggt gagcattcgt ccttcatcac cggacagacg    780
ctttctccca acggcgggat gcacatgtaa                                     810
```

<210> SEQ ID NO 6
<211> LENGTH: 269
<212> TYPE: PRT
<213> ORGANISM: Pseudomonas putida KT2440

<400> SEQUENCE: 6

```
Met Ser Phe Gln Asn Lys Ile Val Val Leu Thr Gly Ala Ala Ser Gly
  1               5                  10                  15

Ile Gly Lys Ala Thr Ala Gln Leu Leu Val Glu Gln Gly Ala His Val
             20                  25                  30

Val Ala Met Asp Leu Lys Ser Asp Leu Leu Gln Gln Ala Phe Gly Ser
         35                  40                  45

Glu Glu His Val Leu Cys Ile Pro Thr Asp Val Ser Asp Ser Glu Ala
     50                  55                  60

Val Arg Ala Ala Phe Gln Ala Val Asp Ala Lys Phe Gly Arg Val Asp
 65                  70                  75                  80

Val Ile Ile Asn Ala Ala Gly Ile Asn Ala Pro Thr Arg Glu Ala Asn
                 85                  90                  95

Gln Lys Met Val Asp Ala Asn Val Ala Ala Leu Asp Ala Met Lys Ser
            100                 105                 110

Gly Arg Ala Pro Thr Phe Asp Phe Leu Ala Asp Thr Ser Asp Gln Asp
        115                 120                 125

Phe Arg Arg Val Met Glu Val Asn Leu Phe Ser Gln Phe Tyr Cys Ile
    130                 135                 140

Arg Glu Gly Val Pro Leu Met Arg Arg Ala Gly Gly Ser Ile Val
145                 150                 155                 160

Asn Ile Ser Ser Val Ala Ala Leu Leu Gly Val Ala Met Pro Leu Tyr
                165                 170                 175

Tyr Pro Ala Ser Lys Ala Ala Val Leu Gly Leu Thr Arg Ala Ala Ala
            180                 185                 190

Ala Glu Leu Ala Pro Tyr Asn Ile Arg Val Asn Ala Ile Ala Pro Gly
        195                 200                 205

Ser Val Asp Thr Pro Leu Met His Glu Gln Pro Pro Glu Val Val Gln
    210                 215                 220

Phe Leu Val Ser Met Gln Pro Ile Lys Arg Leu Ala Gln Pro Glu Glu
225                 230                 235                 240

Leu Ala Gln Ser Ile Leu Phe Leu Ala Gly Glu His Ser Ser Phe Ile
                245                 250                 255

Thr Gly Gln Thr Leu Ser Pro Asn Gly Gly Met His Met
            260                 265
```

<210> SEQ ID NO 7
<211> LENGTH: 771
<212> TYPE: DNA
<213> ORGANISM: Pseudomonas putida KT2440

-continued

```
<400> SEQUENCE: 7
atgacccttg aaggcaaaac tgcactcgtc accggttcca ccagcggcat tggcctgggc    60
atcgcccagg tattggcccg ggctggcgcc aacatcgtgc tcaacggctt ggtgacccg    120 ggccccgcca tggcggaaat tgcccggcac ggggtgaagg ttgtgcacca cccggccgac    180
ctgtcggatg tggtccagat cgaggctttg ttcaacctgg ccgaacgcga gttcggcggc    240
gtcgacatcc tggtcaacaa cgccggtatc cagcatgtgg caccggttga gcagttcccg    300
ccagaaagct gggacaagat catcgccctg aacctgtcgg ccgtattcca tggcacgcgc    360
ctggcgctgc cgggcatgcg cacgcgcaac tgggggcgca tcatcaatat cgcttcggtg    420
catggcctgg tcggctcgat tggcaaggca gcctacgtgg cagccaagca tggcgtgatc    480
ggcctgacca aggtggtcgg cctggaaacc gccaccagtc atgtcacctg caatgccata    540
tgcccgggct gggtgctgac accgctggtg caaaagcaga tcgacgatcg tgcggccaag    600
ggtggcgatc ggctgcaagc gcagcacgat ctgctggcag aaaagcaacc gtcgctggct    660
ttcgtcaccc ccgaacacct cggtgagctg gtactctttc tgtgcagcga ggccggtagc    720
caggttcgcg cgccgccctg gaacgtcgat ggtggctggt tggcccagtg a             771

<210> SEQ ID NO 8
<211> LENGTH: 256
<212> TYPE: PRT
<213> ORGANISM: Pseudomonas putida KT2440

<400> SEQUENCE: 8

Met Thr Leu Glu Gly Lys Thr Ala Leu Val Thr Gly Ser Thr Ser Gly
 1               5                   10                  15

Ile Gly Leu Gly Ile Ala Gln Val Leu Ala Arg Ala Gly Ala Asn Ile
                20                  25                  30

Val Leu Asn Gly Phe Gly Asp Pro Gly Pro Ala Met Ala Glu Ile Ala
            35                  40                  45

Arg His Gly Val Lys Val Val His His Pro Ala Asp Leu Ser Asp Val
        50                  55                  60

Val Gln Ile Glu Ala Leu Phe Asn Leu Ala Glu Arg Glu Phe Gly Gly
65                  70                  75                  80

Val Asp Ile Leu Val Asn Asn Ala Gly Ile Gln His Val Ala Pro Val
                85                  90                  95

Glu Gln Phe Pro Pro Glu Ser Trp Asp Lys Ile Ile Ala Leu Asn Leu
            100                 105                 110

Ser Ala Val Phe His Gly Thr Arg Leu Ala Leu Pro Gly Met Arg Thr
        115                 120                 125

Arg Asn Trp Gly Arg Ile Ile Asn Ile Ala Ser Val His Gly Leu Val
    130                 135                 140

Gly Ser Ile Gly Lys Ala Ala Tyr Val Ala Ala Lys His Gly Val Ile
145                 150                 155                 160

Gly Leu Thr Lys Val Val Gly Leu Glu Thr Ala Thr Ser His Val Thr
                165                 170                 175

Cys Asn Ala Ile Cys Pro Gly Trp Val Leu Thr Pro Leu Val Gln Lys
            180                 185                 190

Gln Ile Asp Asp Arg Ala Ala Lys Gly Gly Asp Arg Leu Gln Ala Gln
        195                 200                 205

His Asp Leu Leu Ala Glu Lys Gln Pro Ser Leu Ala Phe Val Thr Pro
    210                 215                 220

Glu His Leu Gly Glu Leu Val Leu Phe Leu Cys Ser Glu Ala Gly Ser
225                 230                 235                 240
```

Gln Val Arg Gly Ala Ala Trp Asn Val Asp Gly Gly Trp Leu Ala Gln
            245                 250                 255

<210> SEQ ID NO 9
<211> LENGTH: 750
<212> TYPE: DNA
<213> ORGANISM: Pseudomonas putida KT2440

<400> SEQUENCE: 9

```
atgtccaagc aacttacact cgaaggcaaa gtggccctgg ttcagggcgg ttcccgaggc      60
attggcgcag ctatcgtaag gcgcctggcc cgcgaaggcg cgcaagtggc cttcacctat     120
gtcagctctg ccggcccggc tgaagaactg gctcgggaaa ttaccgagaa cggcggcaaa     180
gccttggccc tgcgggctga cagcgctgat gccgcggccg tgcagctggc ggttgatgac     240
accgagaaag ccttgggccg gctggatatc ctggtcaaca cgccggtgt gctggcagtg     300
gccccagtga cagagttcga cctggccgac ttcgatcata tgctggccgt gaacgtacgc     360
agcgtgttcg tcgccagcca ggccgcggca cgctatatgg gccagggcgg tcgtatcatc     420
aacattggca gcaccaacgc cgagcgcatg ccgtttgccg gtggtgcacc gtacgccatg     480
agcaagtcgg cactggttgg tctgacccgc ggcatggcac gcgacctcgg gccgcagggc     540
attaccgtga caacgtgca gcccggcccg gtggacaccg acatgaaccc ggccagtggc     600
gagtttgccg agagcctgat tccgctgatg gccattgggc gatatggcga gccggaggag     660
attgccagct tcgtggctta cctggcaggg cctgaagccg ggtatatcac cggggccagc     720
ctgactgtag atggtgggtt tgcagcctga                                      750
```

<210> SEQ ID NO 10
<211> LENGTH: 249
<212> TYPE: PRT
<213> ORGANISM: Pseudomonas putida KT2440

<400> SEQUENCE: 10

Met Ser Lys Gln Leu Thr Leu Glu Gly Lys Val Ala Leu Val Gln Gly
1               5                   10                  15

Gly Ser Arg Gly Ile Gly Ala Ala Ile Val Arg Arg Leu Ala Arg Glu
            20                  25                  30

Gly Ala Gln Val Ala Phe Thr Tyr Val Ser Ser Ala Gly Pro Ala Glu
        35                  40                  45

Glu Leu Ala Arg Glu Ile Thr Glu Asn Gly Gly Lys Ala Leu Ala Leu
    50                  55                  60

Arg Ala Asp Ser Ala Asp Ala Ala Ala Val Gln Leu Ala Val Asp Asp
65                  70                  75                  80

Thr Glu Lys Ala Leu Gly Arg Leu Asp Ile Leu Val Asn Asn Ala Gly
                85                  90                  95

Val Leu Ala Val Ala Pro Val Thr Glu Phe Asp Leu Ala Asp Phe Asp
            100                 105                 110

His Met Leu Ala Val Asn Val Arg Ser Val Phe Val Ala Ser Gln Ala
        115                 120                 125

Ala Ala Arg Tyr Met Gly Gln Gly Gly Arg Ile Ile Asn Ile Gly Ser
    130                 135                 140

Thr Asn Ala Glu Arg Met Pro Phe Ala Gly Gly Ala Pro Tyr Ala Met
145                 150                 155                 160

Ser Lys Ser Ala Leu Val Gly Leu Thr Arg Gly Met Ala Arg Asp Leu
                165                 170                 175

Gly Pro Gln Gly Ile Thr Val Asn Asn Val Gln Pro Gly Pro Val Asp

```
                          180                 185                 190
Thr Asp Met Asn Pro Ala Ser Gly Glu Phe Ala Glu Ser Leu Ile Pro
            195                 200                 205

Leu Met Ala Ile Gly Arg Tyr Gly Glu Pro Glu Glu Ile Ala Ser Phe
    210                 215                 220

Val Ala Tyr Leu Ala Gly Pro Glu Ala Gly Tyr Ile Thr Gly Ala Ser
225                 230                 235                 240

Leu Thr Val Asp Gly Gly Phe Ala Ala
                245

<210> SEQ ID NO 11
<211> LENGTH: 858
<212> TYPE: DNA
<213> ORGANISM: Pseudomonas putida KT2440

<400> SEQUENCE: 11
atgagcgact accctacccc tccattccca tcccaaccgc aaagcgttcc cggttcccag      60
cgcaagatgg atccgtatcc ggactgcggt gagcagagct acaccggcaa caatcgcctc    120
gcaggcaaga tcgccttgat aaccggtgct gacagcggca tcgggcgtgc ggtggcgatt    180
gcctatgccc gagaaggcgc tgacgttgcc attgcctatc tgaatgaaca cgacgatgcg    240
caggaaaccg cgcgctgggt caaagcggct ggccgccagt gcctgctgct gcccggcgac    300
ctggcacaga acagcactg ccacgacatc gtcgacaaga ccgtggcgca gtttggtcgc    360
atcgatatcc tggtcaacaa cgccgcgttc cagatggccc atgaaagcct ggacgacatt    420
gatgacgatg aatgggtgaa gaccttcgat accaacatca ccgccatttt ccgcatttgc    480
cagcgcgctt tgccctcgat gccaaagggc ggttcgatca tcaacaccag ttcggtcaac    540
tctgacgacc cgtcacccag cctgttggcc tatgccgcga ccaaaggggc tattgccaat    600
ttcactgcag gccttgcgca actgctgggc aagcagggca ttcgcgtcaa cagcgtcgca    660
cccggcccga tctggacccc gctgatcccg gccaccatgc tgatgaggc ggtgagaaac    720 ttcggttccg gttacccgat gggacggccg ggtcaacctg tggaggtggc gccaatctat    780
gtcttgctgg ggtccgatga agccagctac atctcgggtt cgcgttacgc cgtgacggga    840
ggcaaaccta ttctgtga                                                  858

<210> SEQ ID NO 12
<211> LENGTH: 285
<212> TYPE: PRT
<213> ORGANISM: Pseudomonas putida KT2440

<400> SEQUENCE: 12

Met Ser Asp Tyr Pro Thr Pro Pro Phe Pro Ser Gln Pro Gln Ser Val
1               5                   10                  15

Pro Gly Ser Gln Arg Lys Met Asp Pro Tyr Pro Asp Cys Gly Glu Gln
            20                  25                  30

Ser Tyr Thr Gly Asn Asn Arg Leu Ala Gly Lys Ile Ala Leu Ile Thr
        35                  40                  45

Gly Ala Asp Ser Gly Ile Gly Arg Ala Val Ala Ile Ala Tyr Ala Arg
    50                  55                  60

Glu Gly Ala Asp Val Ala Ile Ala Tyr Leu Asn Glu His Asp Asp Ala
65                  70                  75                  80

Gln Glu Thr Ala Arg Trp Val Lys Ala Ala Gly Arg Gln Cys Leu Leu
                85                  90                  95

Leu Pro Gly Asp Leu Ala Gln Lys Gln His Cys His Asp Ile Val Asp
            100                 105                 110
```

```
Lys Thr Val Ala Gln Phe Gly Arg Ile Asp Ile Leu Val Asn Asn Ala
            115                 120                 125

Ala Phe Gln Met Ala His Glu Ser Leu Asp Asp Ile Asp Asp Asp Glu
        130                 135                 140

Trp Val Lys Thr Phe Asp Thr Asn Ile Thr Ala Ile Phe Arg Ile Cys
145                 150                 155                 160

Gln Arg Ala Leu Pro Ser Met Pro Lys Gly Gly Ser Ile Ile Asn Thr
                165                 170                 175

Ser Ser Val Asn Ser Asp Asp Pro Ser Pro Ser Leu Leu Ala Tyr Ala
            180                 185                 190

Ala Thr Lys Gly Ala Ile Ala Asn Phe Thr Ala Gly Leu Ala Gln Leu
        195                 200                 205

Leu Gly Lys Gln Gly Ile Arg Val Asn Ser Val Ala Pro Gly Pro Ile
    210                 215                 220

Trp Thr Pro Leu Ile Pro Ala Thr Met Pro Asp Glu Ala Val Arg Asn
225                 230                 235                 240

Phe Gly Ser Gly Tyr Pro Met Gly Arg Pro Gly Gln Pro Val Glu Val
                245                 250                 255

Ala Pro Ile Tyr Val Leu Leu Gly Ser Asp Glu Ala Ser Tyr Ile Ser
            260                 265                 270

Gly Ser Arg Tyr Ala Val Thr Gly Gly Lys Pro Ile Leu
        275                 280                 285

<210> SEQ ID NO 13
<211> LENGTH: 774
<212> TYPE: DNA
<213> ORGANISM: Pseudomonas putida KT2440

<400> SEQUENCE: 13
atgatcgaaa tcagcggcag caccccgggc cacaatggcc gggtagcctt ggtcacgggc      60
gccgcccgcg gcatcggtct gggcattgcc gcatggctga tctgcgaagg ctggcaagtg     120
gtgctgagtg atctggaccg ccagcgtggt accaaagtgg ccaaggcgtt gggcgacaac     180
gcctggttca tcaccatgga cgttgccgac gaggcccagg tcagtgccgg cgtgtccgaa     240
gtgctcgggc agttcggccg gctggacgcg ctggtgtgca atgcggccat tgccaacccg     300
cacaaccaga cgctggaaag cctgagcctg cacaatggaa ccgggtgct ggggtcaac      360
ctcagcggcc ccatgctgct ggccaagcat tgtgcgccgt acctgcgtgc gcacaatggg     420
gcgatcgtca acctgacctc tacccgtgct cggcagtccg aacccgacac cgaggcttac     480
gcggcaagca agggcggcct ggtggctttg accatgccc tggccatgag cctgggcccg     540
gagattcgcg tcaatgcggt gagcccgggc tggatcgatg cccgtgatcc gtcgcagcgc     600
cgtgccgagc cgttgagcga agctgaccat gcccagcatc aacgggcag gtagggacc      660
gtggaagatg tcgcggccat ggttgcctgg ttgctgtcac gccaggcggc atttgtcacc     720
ggccaggagt ttgtggtcga tggcggcatg acccgcaaga tgatctatac ctga          774

<210> SEQ ID NO 14
<211> LENGTH: 257
<212> TYPE: PRT
<213> ORGANISM: Pseudomonas putida KT2440

<400> SEQUENCE: 14

Met Ile Glu Ile Ser Gly Ser Thr Pro Gly His Asn Gly Arg Val Ala
1               5                   10                  15

Leu Val Thr Gly Ala Ala Arg Gly Ile Gly Leu Gly Ile Ala Ala Trp
```

```
                    20                  25                  30
Leu Ile Cys Glu Gly Trp Gln Val Val Leu Ser Asp Leu Asp Arg Gln
                35                  40                  45
Arg Gly Thr Lys Val Ala Lys Ala Leu Gly Asp Asn Ala Trp Phe Ile
 50                  55                  60
Thr Met Asp Val Ala Asp Glu Ala Gln Val Ser Ala Gly Val Ser Glu
 65                  70                  75                  80
Val Leu Gly Gln Phe Gly Arg Leu Asp Ala Leu Val Cys Asn Ala Ala
                85                  90                  95
Ile Ala Asn Pro His Asn Gln Thr Leu Glu Ser Leu Ser Leu Ala Gln
                100                 105                 110
Trp Asn Arg Val Leu Gly Val Asn Leu Ser Gly Pro Met Leu Leu Ala
                115                 120                 125
Lys His Cys Ala Pro Tyr Leu Arg Ala His Asn Gly Ala Ile Val Asn
                130                 135                 140
Leu Thr Ser Thr Arg Ala Arg Gln Ser Glu Pro Asp Thr Glu Ala Tyr
145                 150                 155                 160
Ala Ala Ser Lys Gly Gly Leu Val Ala Leu Thr His Ala Leu Ala Met
                165                 170                 175
Ser Leu Gly Pro Glu Ile Arg Val Asn Ala Val Ser Pro Gly Trp Ile
                180                 185                 190
Asp Ala Arg Asp Pro Ser Gln Arg Arg Ala Glu Pro Leu Ser Glu Ala
                195                 200                 205
Asp His Ala Gln His Pro Thr Gly Arg Val Gly Thr Val Glu Asp Val
                210                 215                 220
Ala Ala Met Val Ala Trp Leu Leu Ser Arg Gln Ala Ala Phe Val Thr
225                 230                 235                 240
Gly Gln Glu Phe Val Val Asp Gly Gly Met Thr Arg Lys Met Ile Tyr
                245                 250                 255
Thr

<210> SEQ ID NO 15
<211> LENGTH: 741
<212> TYPE: DNA
<213> ORGANISM: Pseudomonas putida KT2440

<400> SEQUENCE: 15
atgagcctgc aaggtaaagt tgcactggtt accggcgcca gccgtggcat tggccaggcc      60
atcgccctcg agctgggccg ccagggcgcg accgtgatcg gtaccgccac gtcggcgtcc     120
ggtgccgagc gcatcgctgc caccctgaaa gaacacggca ttaccggcac tggcatggag     180
ctgaacgtga ccagcgccga atcggttgaa gccgtactgg ccgccattgg cgagcagttc     240
ggcgcgccgg ccatcttggt caacaatgcc ggtatcaccc gcgacaacct catgctgcgc     300
atgaaagacg acgagtggtt tgatgtcatc gacaccaacc tgaacagcct ctaccgtctg     360
tccaagggcg tgctgcgtgg catgaccaag gcgcgttggg gtcgtatcat cagcatcggc     420
tcggtcgttg gtgccatggg taacgcaggt caggccaact acgcggctgc caaggccggt     480
ctggaaggtt tcagccgcgc cctggcgcgt gaagtgggtt cgcgtggtat caccgtcaac     540
tcggtgaccc caggcttcat cgataccgac atgaccccgcg agctgccaga agctcagcgc     600
gaagccctgc agacccagat tccgctgggc cgcctgggcc aggctgacga aattgccaag     660
gtggtttcgt tcctggcatc cgacggcgcc gcctacgtga ccggcgctac cgtgccggtc     720
aacggcggga tgtacatgta a                                               741
```

<210> SEQ ID NO 16
<211> LENGTH: 246
<212> TYPE: PRT
<213> ORGANISM: Pseudomonas putida KT2440

<400> SEQUENCE: 16

```
Met Ser Leu Gln Gly Lys Val Ala Leu Val Thr Gly Ala Ser Arg Gly
1               5                   10                  15

Ile Gly Gln Ala Ile Ala Leu Glu Leu Gly Arg Gln Gly Ala Thr Val
            20                  25                  30

Ile Gly Thr Ala Thr Ser Ala Ser Gly Ala Glu Arg Ile Ala Ala Thr
        35                  40                  45

Leu Lys Glu His Gly Ile Thr Gly Thr Gly Met Glu Leu Asn Val Thr
    50                  55                  60

Ser Ala Glu Ser Val Glu Ala Val Leu Ala Ala Ile Gly Glu Gln Phe
65                  70                  75                  80

Gly Ala Pro Ala Ile Leu Val Asn Asn Ala Gly Ile Thr Arg Asp Asn
                85                  90                  95

Leu Met Leu Arg Met Lys Asp Asp Glu Trp Phe Asp Val Ile Asp Thr
            100                 105                 110

Asn Leu Asn Ser Leu Tyr Arg Leu Ser Lys Gly Val Leu Arg Gly Met
        115                 120                 125

Thr Lys Ala Arg Trp Gly Arg Ile Ile Ser Ile Gly Ser Val Val Gly
    130                 135                 140

Ala Met Gly Asn Ala Gly Gln Ala Asn Tyr Ala Ala Ala Lys Ala Gly
145                 150                 155                 160

Leu Glu Gly Phe Ser Arg Ala Leu Ala Arg Glu Val Gly Ser Arg Gly
                165                 170                 175

Ile Thr Val Asn Ser Val Thr Pro Gly Phe Ile Asp Thr Asp Met Thr
            180                 185                 190

Arg Glu Leu Pro Glu Ala Gln Arg Glu Ala Leu Gln Thr Gln Ile Pro
        195                 200                 205

Leu Gly Arg Leu Gly Gln Ala Asp Glu Ile Ala Lys Val Val Ser Phe
    210                 215                 220

Leu Ala Ser Asp Gly Ala Ala Tyr Val Thr Gly Ala Thr Val Pro Val
225                 230                 235                 240

Asn Gly Gly Met Tyr Met
                245
```

<210> SEQ ID NO 17
<211> LENGTH: 738
<212> TYPE: DNA
<213> ORGANISM: Pseudomonas putida KT2440

<400> SEQUENCE: 17

```
atgactcaga aaatagctgt cgtgaccggc ggcagtcgcg gcattggcaa gtccatcgtg      60
ctggccctgg ccggcgcggg ttatcaggtt gccttcagtt atgtccgtga cgaggcgtca     120
gccgctgcct tgcaggcgca ggtcgaaggg ctcggccggg actgcctggc cgtgcagtgt     180
gatgtcaagg aagcgccgag cattcaggcg ttttttgaac gggtcgagca acgtttcgag     240
cgtatcgact tgttggtcaa caacgccggt attacccgtg acggtttgct cgccacgcaa     300
tcgttgaacg acatcaccga ggtcatccag accaacctgg tcggcacgtt gttgtgctgt     360
cagcaggtgc tgccctgcat gatgcgccaa cgcagcgggt gcatcgtcaa cctcagttcg     420
gtggccgcgc aaaagcccgg caagggccag agcaactacg ccgccgccaa aggcggtgta     480
```

-continued

```
gaagcattga cacgcgcact ggcggtggag ttggcgccgc gcaacatccg ggtcaacgcg      540
gtggcgcccg gcatcgtcag caccgacatg agccaagccc tggtcggcgc ccatgagcag      600
gaaatccagt cgcggctgtt gatcaaacgg ttcgcccggc ctgaagaaat tgccgacgcg      660
gtgctgtatc tggccgagcg cggcctgtac atcacgggcg aagtcctgtc cgtcaacggc      720
ggattgaaaa tgccatga                                                    738
```

<210> SEQ ID NO 18
<211> LENGTH: 245
<212> TYPE: PRT
<213> ORGANISM: Pseudomonas putida KT2440

<400> SEQUENCE: 18

```
Met Thr Gln Lys Ile Ala Val Val Thr Gly Gly Ser Arg Gly Ile Gly
  1               5                  10                  15
Lys Ser Ile Val Leu Ala Leu Ala Gly Ala Gly Tyr Gln Val Ala Phe
                 20                  25                  30
Ser Tyr Val Arg Asp Glu Ala Ser Ala Ala Ala Leu Gln Ala Gln Val
             35                  40                  45
Glu Gly Leu Gly Arg Asp Cys Leu Ala Val Gln Cys Asp Val Lys Glu
 50                  55                  60
Ala Pro Ser Ile Gln Ala Phe Phe Glu Arg Val Glu Gln Arg Phe Glu
 65                  70                  75                  80
Arg Ile Asp Leu Leu Val Asn Asn Ala Gly Ile Thr Arg Asp Gly Leu
                 85                  90                  95
Leu Ala Thr Gln Ser Leu Asn Asp Ile Thr Glu Val Ile Gln Thr Asn
            100                 105                 110
Leu Val Gly Thr Leu Leu Cys Cys Gln Gln Val Leu Pro Cys Met Met
            115                 120                 125
Arg Gln Arg Ser Gly Cys Ile Val Asn Leu Ser Ser Val Ala Ala Gln
130                 135                 140
Lys Pro Gly Lys Gly Gln Ser Asn Tyr Ala Ala Lys Gly Gly Val
145                 150                 155                 160
Glu Ala Leu Thr Arg Ala Leu Ala Val Glu Leu Ala Pro Arg Asn Ile
                165                 170                 175
Arg Val Asn Ala Val Ala Pro Gly Ile Val Ser Thr Asp Met Ser Gln
            180                 185                 190
Ala Leu Val Gly Ala His Glu Gln Glu Ile Gln Ser Arg Leu Leu Ile
            195                 200                 205
Lys Arg Phe Ala Arg Pro Glu Glu Ile Ala Asp Ala Val Leu Tyr Leu
        210                 215                 220
Ala Glu Arg Gly Leu Tyr Ile Thr Gly Glu Val Leu Ser Val Asn Gly
225                 230                 235                 240
Gly Leu Lys Met Pro
                245
```

<210> SEQ ID NO 19
<211> LENGTH: 768
<212> TYPE: DNA
<213> ORGANISM: Pseudomonas putida KT2440

<400> SEQUENCE: 19

```
atgtccaaga cccacctgtt cgacctcgac ggcaagattg cctttgtttc ggcgccagc       60 cgtggcatcg cgaggccat cgcccacttg ctcgcgcagc aaggggccca tgtgatcgtt      120
tccagccgca agcttgacgg gtgccagcag gtggccgacg ccatcattgc cgccggcggc     180
```

```
aaggccacgg ctgtggcctg ccacattggt gagctggaac agattcagca ggtgttcgcc    240
ggcattcgcg aacagttcgg gcgactggac gtgctggtca acaatgcagc caccaacccg    300
caattctgca atgtgctgga caccgaccca ggggcgttcc agaagaccgt ggacgtgaac    360
atccgtggtt acttcttcat gtcggtggag gctggcaagc tgatgcgcga aacggcggc    420 ggcagcatca tcaacgtggc gtcgatcaac ggtgtttcac ccgggctgtt ccaaggcatc    480
tactcggtga ccaaggcggc ggtcatcaac atgaccaagg tgttcgccaa agagtgtgca    540
cccttcggta ttcgctgcaa cgcgctactg ccggggctga ccgataccaa gttcgcttcg    600
gcattggtga gaacgaagc catcctcaac gccgccttgc agcagatccc cctcaaacgc    660
gtggccgacc caaggaaat ggcgggtgcg gtgctgtacc tggccagcga tgcctccagc    720
tacaccaccg gcaccacgct caatgtcgac ggtggcttcc tgtcctga              768
```

<210> SEQ ID NO 20
<211> LENGTH: 255
<212> TYPE: PRT
<213> ORGANISM: Pseudomonas putida KT2440

<400> SEQUENCE: 20

```
Met Ser Lys Thr His Leu Phe Asp Leu Asp Gly Lys Ile Ala Phe Val
 1               5                   10                  15

Ser Gly Ala Ser Arg Gly Ile Gly Glu Ala Ile Ala His Leu Leu Ala
            20                  25                  30

Gln Gln Gly Ala His Val Ile Val Ser Ser Arg Lys Leu Asp Gly Cys
        35                  40                  45

Gln Gln Val Ala Asp Ala Ile Ile Ala Ala Gly Lys Ala Thr Ala
    50                  55                  60

Val Ala Cys His Ile Gly Glu Leu Glu Gln Ile Gln Gln Val Phe Ala
 65                  70                  75                  80

Gly Ile Arg Glu Gln Phe Gly Arg Leu Asp Val Leu Val Asn Asn Ala
                85                  90                  95

Ala Thr Asn Pro Gln Phe Cys Asn Val Leu Asp Thr Asp Pro Gly Ala
            100                 105                 110

Phe Gln Lys Thr Val Asp Val Asn Ile Arg Gly Tyr Phe Phe Met Ser
        115                 120                 125

Val Glu Ala Gly Lys Leu Met Arg Glu Asn Gly Gly Ser Ile Ile
    130                 135                 140

Asn Val Ala Ser Ile Asn Gly Val Ser Pro Gly Leu Phe Gln Gly Ile
145                 150                 155                 160

Tyr Ser Val Thr Lys Ala Ala Val Ile Asn Met Thr Lys Val Phe Ala
                165                 170                 175

Lys Glu Cys Ala Pro Phe Gly Ile Arg Cys Asn Ala Leu Leu Pro Gly
            180                 185                 190

Leu Thr Asp Thr Lys Phe Ala Ser Ala Leu Val Lys Asn Glu Ala Ile
        195                 200                 205

Leu Asn Ala Ala Leu Gln Gln Ile Pro Leu Lys Arg Val Ala Asp Pro
    210                 215                 220

Lys Glu Met Ala Gly Ala Val Leu Tyr Leu Ala Ser Asp Ala Ser Ser
225                 230                 235                 240

Tyr Thr Thr Gly Thr Thr Leu Asn Val Asp Gly Gly Phe Leu Ser
                245                 250                 255
```

<210> SEQ ID NO 21
<211> LENGTH: 762
<212> TYPE: DNA

<213> ORGANISM: Pseudomonas fluorescens Pf-5

<400> SEQUENCE: 21

```
atgagcatga cgttttccgg ccaggtggcc ctagtgaccg gcgcagccaa tggtatcggc    60
cgcgccaccg cccaggcatt tgccgcacaa ggcttgaagg tggtggtggc ggacctggac   120
acggcggggg gcgagggcac cgtggcgctg atccgcgagg ccggtggcga ggcattgttc   180
gtgccgtgca acgttaccct ggaggcggat gtgcaaagcc tcatggcccg caccatcgaa   240
gcctatgggc gcctggatta cgccttcaac aatgccggta tcgagatcga aaagggccgc   300
cttgcgagg gctccatgga tgagttcgac gccatcatgg gggtcaacgt caaagggctc   360
tggctgtgca tgaagtacca gttgccgctg ctgctggccc agggcggtgg ggcgatcgtc   420
aacaccgcct cggtggcggg cctgggcgcg gcgccgaaga tgagcatcta tgcggcctcc   480
aagcatgcgg tgatcggcct gaccaagtcg gcggccatcg aatatgcgaa gaagaaaatc   540
cgcgtgaacg cggtatgccc ggcggtgatc gacaccgaca tgttccgccg tgcctacgag   600
gcggacccga agaaggccga gttcgccgcg gccatgcacc cggtggggcg catcggcaag   660
gtcgaggaga tcgccagtgc ggtgctctac ctgtgcagcg atggcgcggc ctttaccacc   720
ggccatgcac tggcggtcga cggcggggcc accgcgatct ga                      762
```

<210> SEQ ID NO 22
<211> LENGTH: 253
<212> TYPE: PRT
<213> ORGANISM: Pseudomonas fluorescens Pf-5

<400> SEQUENCE: 22

```
Met Ser Met Thr Phe Ser Gly Gln Val Ala Leu Val Thr Gly Ala Ala
  1               5                  10                  15

Asn Gly Ile Gly Arg Ala Thr Ala Gln Ala Phe Ala Ala Gln Gly Leu
             20                  25                  30

Lys Val Val Val Ala Asp Leu Asp Thr Ala Gly Gly Glu Gly Thr Val
         35                  40                  45

Ala Leu Ile Arg Glu Ala Gly Gly Glu Ala Leu Phe Val Pro Cys Asn
     50                  55                  60

Val Thr Leu Glu Ala Asp Val Gln Ser Leu Met Ala Arg Thr Ile Glu
 65                  70                  75                  80

Ala Tyr Gly Arg Leu Asp Tyr Ala Phe Asn Asn Ala Gly Ile Glu Ile
                 85                  90                  95

Glu Lys Gly Arg Leu Ala Glu Gly Ser Met Asp Glu Phe Asp Ala Ile
            100                 105                 110

Met Gly Val Asn Val Lys Gly Val Trp Leu Cys Met Lys Tyr Gln Leu
        115                 120                 125

Pro Leu Leu Leu Ala Gln Gly Gly Gly Ala Ile Val Asn Thr Ala Ser
    130                 135                 140

Val Ala Gly Leu Gly Ala Ala Pro Lys Met Ser Ile Tyr Ala Ala Ser
145                 150                 155                 160

Lys His Ala Val Ile Gly Leu Thr Lys Ser Ala Ala Ile Glu Tyr Ala
                165                 170                 175

Lys Lys Lys Ile Arg Val Asn Ala Val Cys Pro Ala Val Ile Asp Thr
            180                 185                 190

Asp Met Phe Arg Arg Ala Tyr Glu Ala Asp Pro Lys Lys Ala Glu Phe
        195                 200                 205

Ala Ala Ala Met His Pro Val Gly Arg Ile Gly Lys Val Glu Glu Ile
    210                 215                 220
```

```
Ala Ser Ala Val Leu Tyr Leu Cys Ser Asp Gly Ala Ala Phe Thr Thr
225                 230                 235                 240

Gly His Ala Leu Ala Val Asp Gly Gly Ala Thr Ala Ile
                245                 250
```

<210> SEQ ID NO 23
<211> LENGTH: 735
<212> TYPE: DNA
<213> ORGANISM: Klebsiella pneumoniae subsp. pneumoniae MGH78578

<400> SEQUENCE: 23

```
atgaaacttg ccagtaaaac cgccattgtc accggcgccg cacgcggtat cggctttggc      60
attgcccagg tgcttgcgcg ggaaggcgcg cgagtgatta tcgccgatcg tgatgcacac     120
ggcgaagccg ccgccgcttc cctgcgcgaa tcgggcgcac aggcgctgtt tatcagctgc     180
aatatcgctg aaaaaacgca ggtcgaagcc ctgtattccc aggccgaaga ggcgtttggc     240
ccggtagaca ttctggtgaa taacgccgga atcaaccgcg acgccatgct gcacaaatta     300
acggaagcgg actgggacac ggttatcgac gttaacctga aaggcacttt cctctgtatg     360
cagcaggccg ctatccgcat gcgcgagcgc ggtgcgggcc gcattatcaa tatcgcttcc     420
gccagttggc ttggcaacgt cgggcaaacc aactattcgg cgtcaaaagc cggcgtggtg     480
ggaatgacca aaaccgcctg ccgcgaactg gcgaaaaaag tgtcaccggt gaatgccatc     540
tgcccgggct ttatcgatac cgacatgacg cgcggcgtac cggaaaacgt ctggcaaatc     600
atggtcagca aaattcccgc gggttacgcc ggcgaggcga agacgtcgg cgagtgtgtg      660
gcgtttctgg cgtccgatgg cgcgcgctat atcaatggtg aagtgattaa cgtcggcggc     720
ggcatggtgc tgtaa                                                      735
```

<210> SEQ ID NO 24
<211> LENGTH: 253
<212> TYPE: PRT
<213> ORGANISM: Klebsiella pneumoniae subsp. pneumoniae MGH78578

<400> SEQUENCE: 24

```
Met Ser Met Thr Phe Ser Gly Gln Val Ala Leu Val Thr Gly Ala Ala
 1               5                  10                  15

Asn Gly Ile Gly Arg Ala Thr Ala Gln Ala Phe Ala Ala Gln Gly Leu
            20                  25                  30

Lys Val Val Ala Asp Leu Asp Thr Ala Gly Gly Glu Gly Thr Val
        35                  40                  45

Ala Leu Ile Arg Glu Ala Gly Gly Glu Ala Leu Phe Val Pro Cys Asn
    50                  55                  60

Val Thr Leu Glu Ala Asp Val Gln Ser Leu Met Ala Arg Thr Ile Glu
65                  70                  75                  80

Ala Tyr Gly Arg Leu Asp Tyr Ala Phe Asn Asn Ala Gly Ile Glu Ile
                85                  90                  95

Glu Lys Gly Arg Leu Ala Glu Gly Ser Met Asp Glu Phe Asp Ala Ile
            100                 105                 110

Met Gly Val Asn Val Lys Gly Val Trp Leu Cys Met Lys Tyr Gln Leu
        115                 120                 125

Pro Leu Leu Leu Ala Gln Gly Gly Ala Ile Val Asn Thr Ala Ser
    130                 135                 140

Val Ala Gly Leu Gly Ala Ala Pro Lys Met Ser Ile Tyr Ala Ala Ser
145                 150                 155                 160

Lys His Ala Val Ile Gly Leu Thr Lys Ser Ala Ala Ile Glu Tyr Ala
                165                 170                 175
```

```
Lys Lys Lys Ile Arg Val Asn Ala Val Cys Pro Ala Val Ile Asp Thr
            180                 185                 190

Asp Met Phe Arg Arg Ala Tyr Glu Ala Asp Pro Lys Lys Ala Glu Phe
        195                 200                 205

Ala Ala Ala Met His Pro Val Gly Arg Ile Gly Lys Val Glu Glu Ile
    210                 215                 220

Ala Ser Ala Val Leu Tyr Leu Cys Ser Asp Gly Ala Ala Phe Thr Thr
225                 230                 235                 240

Gly His Ala Leu Ala Val Asp Gly Gly Ala Thr Ala Ile
                245                 250

<210> SEQ ID NO 25
<211> LENGTH: 750
<212> TYPE: DNA
<213> ORGANISM: Klebsiella pneumoniae subsp. pneumoniae MGH78578

<400> SEQUENCE: 25
atgttattga aagataaagt cgccattatt actggcgcgg cctccgcacg cggtttgggc      60
ttcgcgactg cgaaattatt cgccgaaaac ggcgcgaaag tggtcattat cgacctcaat     120
ggcgaagcca gtaaaaccgc cgcggcggca ttaggcgaag accatctcgg cctggcggcc     180
aacgtcgctg atgaagtgca ggtgcaggcg gccatcgaac agatcctggc gaaatacggt     240
cgggttgatg tactggtcaa taacgccggg attacccagc cgctgaagct gatggatatc     300
aagcgcgcca actatgacgc ggtgcttgat gttagcctgc gcggcacgct gctgatgtcg     360
caggcggtta tccccaccat gcgggcgcaa aaatccggca gcatcgtctg catctcgtcc     420
gtctccgccc agcgcggcgg cggtattttc ggcggaccgc actacagcgc ggcaaaagcc     480
gggtgctgg gtctggcgcg gcgatggcg cgcgagcttg gcccggataa cgtccgcgtt       540
aactgcatca ccccggggct gattcagacc gacattaccg ccggcaagct gactgatgac     600
atgacggcca acattcttgc cggcattccg atgaaccgcc ttggcgacgc gatagacatc     660
gcgcgcgccg cgctgttcct cggcagcgat ctttcctcct actccaccgg catcaccctg     720
gacgttaacg gcggcatgtt aattcactaa                                      750

<210> SEQ ID NO 26
<211> LENGTH: 249
<212> TYPE: PRT
<213> ORGANISM: Klebsiella pneumoniae subsp. pneumoniae MGH78578

<400> SEQUENCE: 26

Met Leu Leu Lys Asp Lys Val Ala Ile Ile Thr Gly Ala Ala Ser Ala
1               5                   10                  15

Arg Gly Leu Gly Phe Ala Thr Ala Lys Leu Phe Ala Glu Asn Gly Ala
            20                  25                  30

Lys Val Val Ile Ile Asp Leu Asn Gly Glu Ala Ser Lys Thr Ala Ala
        35                  40                  45

Ala Ala Leu Gly Glu Asp His Leu Gly Leu Ala Ala Asn Val Ala Asp
    50                  55                  60

Glu Val Gln Val Gln Ala Ala Ile Glu Gln Ile Leu Ala Lys Tyr Gly
65                  70                  75                  80

Arg Val Asp Val Leu Val Asn Asn Ala Gly Ile Thr Gln Pro Leu Lys
                85                  90                  95

Leu Met Asp Ile Lys Arg Ala Asn Tyr Asp Ala Val Leu Asp Val Ser
            100                 105                 110

Leu Arg Gly Thr Leu Leu Met Ser Gln Ala Val Ile Pro Thr Met Arg
```

```
              115                 120                 125
Ala Gln Lys Ser Gly Ser Ile Val Cys Ile Ser Ser Val Ser Ala Gln
        130                 135                 140

Arg Gly Gly Gly Ile Phe Gly Gly Pro His Tyr Ser Ala Ala Lys Ala
145                 150                 155                 160

Gly Val Leu Gly Leu Ala Arg Ala Met Ala Arg Glu Leu Gly Pro Asp
                165                 170                 175

Asn Val Arg Val Asn Cys Ile Thr Pro Gly Leu Ile Gln Thr Asp Ile
            180                 185                 190

Thr Ala Gly Lys Leu Thr Asp Asp Met Thr Ala Asn Ile Leu Ala Gly
        195                 200                 205

Ile Pro Met Asn Arg Leu Gly Asp Ala Ile Asp Ile Ala Arg Ala Ala
    210                 215                 220

Leu Phe Leu Gly Ser Asp Leu Ser Ser Tyr Ser Thr Gly Ile Thr Leu
225                 230                 235                 240

Asp Val Asn Gly Gly Met Leu Ile His
                245
```

<210> SEQ ID NO 27
<211> LENGTH: 750
<212> TYPE: DNA
<213> ORGANISM: Klebsiella pneumoniae subsp. pneumoniae MGH78578

<400> SEQUENCE: 27

```
atgttattga aagataaagt cgccattatt actggcgcgg cctccgcacg cggtttgggc      60
ttcgcgactg cgaaattatt cgccgaaaac ggcgcgaaag tggtcattat cgacctcaat     120
ggcgaagcca gtaaaaccgc cgcggcggca ttaggcgaag accatctcgg cctggcggcc     180
aacgtcgctg atgaagtgca ggtgcaggcg gccatcgaac agatcctggc gaaatacggt     240
cgggttgatg tactggtcaa taacgccggg attacccagc cgctgaagct gatggatatc     300
aagcgcgcca actatgacgc ggtgcttgat gttagcctgc gcggcacgct gctgatgtcg     360
caggcggtta tccccaccat gcgggcgcaa aaatccggca gcatcgtctg catctcgtcc     420
gtctccgccc agcgcggcgg cggtattttc ggcggaccgc actacagcgc ggcaaaagcc     480
ggggtgctgg gtctggcgcg ggcgatggcg cgcgagcttg gcccggataa cgtccgcgtt     540
aactgcatca ccccggggct gattcagacc gacattaccg ccggcaagct gactgatgac     600
atgacggcca acattcttgc cggcattccg atgaaccgcc ttggcgacgc gatagacatc     660
gcgcgcgccg cgctgttcct cggcagcgat ctttcctcct actccaccgg catcaccctg     720
gacgttaacg gcggcatgtt aattcactaa                                     750
```

<210> SEQ ID NO 28
<211> LENGTH: 249
<212> TYPE: PRT
<213> ORGANISM: Klebsiella pneumoniae subsp. pneumoniae MGH78578

<400> SEQUENCE: 28

```
Met Leu Leu Lys Asp Lys Val Ala Ile Ile Thr Gly Ala Ala Ser Ala
1               5                  10                  15

Arg Gly Leu Gly Phe Ala Thr Ala Lys Leu Phe Ala Glu Asn Gly Ala
                20                  25                  30

Lys Val Val Ile Ile Asp Leu Asn Gly Glu Ala Ser Lys Thr Ala Ala
            35                  40                  45

Ala Ala Leu Gly Glu Asp His Leu Gly Leu Ala Ala Asn Val Ala Asp
        50                  55                  60
```

```
Glu Val Gln Val Gln Ala Ala Ile Glu Gln Ile Leu Ala Lys Tyr Gly
 65                  70                  75                  80

Arg Val Asp Val Leu Val Asn Asn Ala Gly Ile Thr Gln Pro Leu Lys
                 85                  90                  95

Leu Met Asp Ile Lys Arg Ala Asn Tyr Asp Ala Val Leu Asp Val Ser
            100                 105                 110

Leu Arg Gly Thr Leu Leu Met Ser Gln Ala Val Ile Pro Thr Met Arg
        115                 120                 125

Ala Gln Lys Ser Gly Ser Ile Val Cys Ile Ser Ser Val Ser Ala Gln
    130                 135                 140

Arg Gly Gly Gly Ile Phe Gly Gly Pro His Tyr Ser Ala Ala Lys Ala
145                 150                 155                 160

Gly Val Leu Gly Leu Ala Arg Ala Met Ala Arg Glu Leu Gly Pro Asp
                165                 170                 175

Asn Val Arg Val Asn Cys Ile Thr Pro Gly Leu Ile Gln Thr Asp Ile
            180                 185                 190

Thr Ala Gly Lys Leu Thr Asp Asp Met Thr Ala Asn Ile Leu Ala Gly
        195                 200                 205

Ile Pro Met Asn Arg Leu Gly Asp Ala Ile Asp Ile Ala Arg Ala Ala
    210                 215                 220

Leu Phe Leu Gly Ser Asp Leu Ser Ser Tyr Ser Thr Gly Ile Thr Leu
225                 230                 235                 240

Asp Val Asn Gly Gly Met Leu Ile His
                245

<210> SEQ ID NO 29
<211> LENGTH: 714
<212> TYPE: DNA
<213> ORGANISM: Klebsiella pneumoniae subsp. pneumoniae MGH78578

<400> SEQUENCE: 29
atgacagcgt tcacaacaa atcagtgctg gttttaggcg ggagtcgggg aattggcgcg      60
gcgatcgtca ggcgttttgt cgccgatggc gcgtcggtgg tgtttagcta ttccggttcg     120
ccggaagcgc cgagcggct ggcggcagag accggcagca cggcggtgca ggcggacagc     180
gccgatcgcg atgcggtgat aagcctggtc cgcgacagcg gcccgctgga cgtgttagtg     240
gtcaatgccg ggatcgcgct tttcggtgac gctctcgagc aggacagcga tgcaatcgat     300
cgcctgttcc acatcaatat tcacgccccc taccatgcct ccgtcgaagc ggcgcgccgc     360
atgccggaag gcgggcgcat tattgtcatc ggctcagtca atggcgatcg catgccgttg     420
ccgggaatgg cggcctatgc gctcagcaaa tcggccctgc aggggctggc gcgcggcctg     480
gcgcgggatt ttggcccgcg cggcatcacg gtcaacgtcg tccagcccgg cccaattgat     540
accgacgcca acccggagaa cggcccgatg aaagagctga tgcacagctt tatggccatt     600
aagcgccatg gccgtccgga agaggtggcg ggaatggtgg cgtggctggc cggtccggag     660
gcgtcgtttg tcactggcgc catgcacacc atcgacggag cgtttggcgc ctga           714

<210> SEQ ID NO 30
<211> LENGTH: 237
<212> TYPE: PRT
<213> ORGANISM: Klebsiella pneumoniae subsp. pneumoniae MGH78578

<400> SEQUENCE: 30

Met Thr Ala Phe His Asn Lys Ser Val Leu Val Leu Gly Gly Ser Arg
  1               5                  10                  15

Gly Ile Gly Ala Ala Ile Val Arg Arg Phe Val Ala Asp Gly Ala Ser
```

```
                20                  25                  30
Val Val Phe Ser Tyr Ser Gly Ser Pro Glu Ala Ala Glu Arg Leu Ala
            35                  40                  45

Ala Glu Thr Gly Ser Thr Ala Val Gln Ala Asp Ser Ala Asp Arg Asp
        50                  55                  60

Ala Val Ile Ser Leu Val Arg Asp Ser Gly Pro Leu Asp Val Leu Val
65                  70                  75                  80

Val Asn Ala Gly Ile Ala Leu Phe Gly Asp Ala Leu Glu Gln Asp Ser
                85                  90                  95

Asp Ala Ile Asp Arg Leu Phe His Ile Asn Ile His Ala Pro Tyr His
            100                 105                 110

Ala Ser Val Glu Ala Ala Arg Arg Met Pro Glu Gly Gly Arg Ile Ile
        115                 120                 125

Val Ile Gly Ser Val Asn Gly Asp Arg Met Pro Leu Pro Gly Met Ala
    130                 135                 140

Ala Tyr Ala Leu Ser Lys Ser Ala Leu Gln Gly Leu Ala Arg Gly Leu
145                 150                 155                 160

Ala Arg Asp Phe Gly Pro Arg Gly Ile Thr Val Asn Val Val Gln Pro
                165                 170                 175

Gly Pro Ile Asp Thr Asp Ala Asn Pro Glu Asn Gly Pro Met Lys Glu
            180                 185                 190

Leu Met His Ser Phe Met Ala Ile Lys Arg His Gly Arg Pro Glu Glu
        195                 200                 205

Val Ala Gly Met Val Ala Trp Leu Ala Gly Pro Glu Ala Ser Phe Val
    210                 215                 220

Thr Gly Ala Met His Thr Ile Asp Gly Ala Phe Gly Ala
225                 230                 235

<210> SEQ ID NO 31
<211> LENGTH: 750
<212> TYPE: DNA
<213> ORGANISM: Klebsiella pneumoniae subsp. pneumoniae MGH78578

<400> SEQUENCE: 31
atgaacggcc tgctaaacgg taaacgtatt gtcgtcaccg gtgcggcgcg cggtctcggg      60
taccactttg ccgaagcctg cgccgctcag ggcgcgacgg tggtgatgtg cgacatcctg     120
cagggagagc tggcggaaag cgctcatcgc ctgcagcaga agggctatca ggtcgaatct     180
cacgccatcg atcttgccag tcaagcatcg atcgagcagg tcttcagcgc catcggcgcg     240
caggggtcta tcgatggctt agtcaataac gcagcgatgg ccaccggcgt cggcggaaaa     300
aatatgatcg attacgatcc ggatctgtgg gatcgggtaa tgacggtcaa cgttaaaggc     360
acctggttgg tgacccgcgc ggcggtaccg ctgctgcgcg aaggggcggc gatcgtcaac     420
gtcgcttcgg ataccgcgct gtggggcgcg ccgcggctga tggcctatgt cgccagtaag     480
ggcgcggtga ttgcgatgac ccgctccatg gcccgcgagc tgggtgaaaa gcggatccgt     540
atcaacgcca tcgcgccggg actgacccgc gttgaggcca cggaatacgt tcccgccgag     600
cgtcatcagc tgtatgagaa cggccgcgcg ctcagcggcg cgcagcagcc ggaagatgtc     660
accggcagcg tggtctggct gctgagcgat cttcgcgct ttatcaccgg ccaactgatc     720
ccggtcaacg gcggttttgt ctttaactaa                                     750

<210> SEQ ID NO 32
<211> LENGTH: 249
<212> TYPE: PRT
<213> ORGANISM: Klebsiella pneumonia subsp. pneumonia MGH78578
```

<400> SEQUENCE: 32

Met Asn Gly Leu Leu Asn Gly Lys Arg Ile Val Thr Gly Ala Ala
1               5                   10                  15

Arg Gly Leu Gly Tyr His Phe Ala Glu Ala Cys Ala Ala Gln Gly Ala
            20                  25                  30

Thr Val Val Met Cys Asp Ile Leu Gln Gly Glu Leu Ala Glu Ser Ala
        35                  40                  45

His Arg Leu Gln Gln Lys Gly Tyr Gln Val Glu Ser His Ala Ile Asp
    50                  55                  60

Leu Ala Ser Gln Ala Ser Ile Glu Gln Val Phe Ser Ala Ile Gly Ala
65              70                  75                  80

Gln Gly Ser Ile Asp Gly Leu Val Asn Asn Ala Ala Met Ala Thr Gly
                85                  90                  95

Val Gly Gly Lys Asn Met Ile Asp Tyr Asp Pro Asp Leu Trp Asp Arg
            100                 105                 110

Val Met Thr Val Asn Val Lys Gly Thr Trp Leu Val Thr Arg Ala Ala
        115                 120                 125

Val Pro Leu Leu Arg Glu Gly Ala Ala Ile Val Asn Val Ala Ser Asp
    130                 135                 140

Thr Ala Leu Trp Gly Ala Pro Arg Leu Met Ala Tyr Val Ala Ser Lys
145                 150                 155                 160

Gly Ala Val Ile Ala Met Thr Arg Ser Met Ala Arg Glu Leu Gly Glu
                165                 170                 175

Lys Arg Ile Arg Ile Asn Ala Ile Ala Pro Gly Leu Thr Arg Val Glu
            180                 185                 190

Ala Thr Glu Tyr Val Pro Ala Glu Arg His Gln Leu Tyr Glu Asn Gly
        195                 200                 205

Arg Ala Leu Ser Gly Ala Gln Gln Pro Glu Asp Val Thr Gly Ser Val
    210                 215                 220

Val Trp Leu Leu Ser Asp Leu Ser Arg Phe Ile Thr Gly Gln Leu Ile
225                 230                 235                 240

Pro Val Asn Gly Gly Phe Val Phe Asn
                245

<210> SEQ ID NO 33
<211> LENGTH: 795
<212> TYPE: DNA
<213> ORGANISM: Klebsiella pneumoniae subsp. pneumoniae MGH78578

<400> SEQUENCE: 33
atgaatgcac aaattgaagg gcgcgtcgcg gtagtcaccg gcggttcgtc aggaatcggc      60
tttgaaacgc tgcgcctgct gctgggcgaa ggggcgaaag tcgccttttg cggccgcaac     120
ccggatcggc ttgccagcgc ccatgcggcg ttgcaaaacg aatatccaga aggtgaggtg     180
ttctcctggc gctgtgacgt actgaacgaa gctgaagttg aggcgttcgc cgccgcggtc     240
gccgcgcgtt cggcggcgt cgatatgctg attaataacg ccggccaggg ctatgtcgcc      300
cacttcgccg atacgccacg tgaggcctgg ctgcacgaag ccgaactgaa actgttcggc     360
gtgattaacc cggtaaaggc ctttcagtcc ctgctagagg cgtcggatat cgcctcgatt     420
acctgtgtga actcgctgct ggcgttacag ccggaagagc acatgatcgc cacctctgcc     480
gcccgcgccg cgctgctcaa tatgacgctg actctgtcga aagagctggt ggataaaggt     540
attcgtgtga attccattct gctggggatg gtggagtccg ggcagtggca cgccgtttt      600 gagagccgaa gcgataagag ccagagttgg cagcagtgga ccgccgatat cgcccgtaag     660

```
cgggggatcc cgatggcgcg tctcggtaag ccgcaggagc cagcgcaagc gctgctattc    720
ctcgcttcgc cgctggcctc ctttaccacc ggcgcggcgc tggacgtttc cggcggtttc    780
tgtcgccatc tgtaa                                                     795
```

```
<210> SEQ ID NO 34
<211> LENGTH: 264
<212> TYPE: PRT
<213> ORGANISM: Klebsiella pneumonia subsp. pneumoniae MGH78578

<400> SEQUENCE: 34
```

| Met | Asn | Ala | Gln | Ile | Glu | Gly | Arg | Val | Ala | Val | Thr | Gly | Gly | Ser |
|---|---|---|---|---|---|---|---|---|---|---|---|---|---|---|
| 1 | | | | 5 | | | | | 10 | | | | | 15 |

| Ser | Gly | Ile | Gly | Phe | Glu | Thr | Leu | Arg | Leu | Leu | Leu | Gly | Gly | Ala |
|---|---|---|---|---|---|---|---|---|---|---|---|---|---|---|
| | | | 20 | | | | | 25 | | | | | 30 | |

| Lys | Val | Ala | Phe | Cys | Gly | Arg | Asn | Pro | Asp | Arg | Leu | Ala | Ser | Ala | His |
|---|---|---|---|---|---|---|---|---|---|---|---|---|---|---|---|
| | | | 35 | | | | | 40 | | | | | 45 | | |

Ala Ala Leu Gln Asn Glu Tyr Pro Glu Gly Glu Val Phe Ser Trp Arg
         50                  55                  60

Cys Asp Val Leu Asn Glu Ala Glu Val Glu Ala Phe Ala Ala Ala Val
65                  70                  75                  80

Ala Ala Arg Phe Gly Gly Val Asp Met Leu Ile Asn Asn Ala Gly Gln
                 85                  90                  95

Gly Tyr Val Ala His Phe Ala Asp Thr Pro Arg Glu Ala Trp Leu His
            100                 105                 110

Glu Ala Glu Leu Lys Leu Phe Gly Val Ile Asn Pro Lys Ala Phe
        115                 120                 125

Gln Ser Leu Leu Glu Ala Ser Asp Ile Ala Ser Ile Thr Cys Val Asn
    130                 135                 140

Ser Leu Leu Ala Leu Gln Pro Glu Glu His Met Ile Ala Thr Ser Ala
145                 150                 155                 160

Ala Arg Ala Ala Leu Leu Asn Met Thr Leu Thr Leu Ser Lys Glu Leu
                165                 170                 175

Val Asp Lys Gly Ile Arg Val Asn Ser Ile Leu Leu Gly Met Val Glu
            180                 185                 190

Ser Gly Gln Trp Gln Arg Arg Phe Glu Ser Arg Ser Asp Lys Ser Gln
        195                 200                 205

Ser Trp Gln Gln Trp Thr Ala Asp Ile Ala Arg Lys Arg Gly Ile Pro
    210                 215                 220

Met Ala Arg Leu Gly Lys Pro Gln Glu Pro Gln Ala Leu Leu Phe
225                 230                 235                 240

Leu Ala Ser Pro Leu Ala Ser Phe Thr Thr Gly Ala Ala Leu Asp Val
                245                 250                 255

Ser Gly Gly Phe Cys Arg His Leu
            260

```
<210> SEQ ID NO 35
<211> LENGTH: 1204
<212> TYPE: DNA
<213> ORGANISM: Saccharomyces cerevisiae

<400> SEQUENCE: 35
atgccatttg taaaggtttt tgagccgatc tccctaagag acacaaacct ttttgaacca    60
attaagattg gtaacactca gctggcacat cgtgcggtta tgccccatt gaccagaatg    120 agggccactc accccggaaa tattccaaat aaggagtggg ctgctgtgta ttatggtcag    180
```

| | |
|---|---|
| cgtgctcaaa gacctggtac catgatcatc acggaaggta cgtttatttc ccctcaagcc | 240 |
| ggcggctatg acaacgcccc tgggatttgg tctgatgaac aggtcgctga gtggaagaat | 300 |
| atcttttag ccatccatga ttgtcagtcg ttcgcgtggg tacaactttg gtctttaggc | 360 |
| tgggcatcct tcccagacgt attggcaaga gacgggttac gctatgactg tgcatctgac | 420 |
| agagtgtata tgaatgctac gttacaagaa aaggccaaag atgcgaataa tctcgaacat | 480 |
| agtttgacta aagacgacat taaacagtat atcaaggatt acatccatgc cgctaagaat | 540 |
| tctatcgcgg ctggcgccga tggtgtagaa attcatagcg ccaatgggta cttgttgaat | 600 |
| cagttcttgg atccacattc taataagagg accgacgaat acggcggaac gatcgaaaac | 660 |
| agggcccgct ttacactgga ggttgtcgat gctcttatcg aaacaatcgg tcctgaacgg | 720 |
| gtgggtttga ggttgtcgcc atacggcact tttaacagta tgtctggagg tgctgaacca | 780 |
| ggtattatcg ctcaatatgc ttatgttttg ggtgaattag agaagagggc aaaggctggt | 840 |
| aagcgtttgg cctttgtgca ccttgttgaa ccacgtgtca cggacccatc gttggtggag | 900 |
| ggcgaaggag aatattccga gggtactaac gattttgcct actctatatg gaagggtcca | 960 |
| atcatcagag ctggtaatta cgctcttcat ccagaagtgg ttagagaaca agtaaaggat | 1020 |
| cccagaacct tgataggcta tggtagattc ttcatctcca acccagattt agtctaccgt | 1080 |
| ttagaagagg gcctgccatt gaacaagtat gacagaagta ccttctacac catgtccgcg | 1140 |
| gaaggttata ccgactaccc aacatatgaa gaggcagtag atttaggttg gaacaagaac | 1200 |
| tgat | 1204 |

<210> SEQ ID NO 36
<211> LENGTH: 1203
<212> TYPE: DNA
<213> ORGANISM: Saccharomyces cerevisiae

<400> SEQUENCE: 36

| | |
|---|---|
| atgccatttg ttaaggactt taagccacaa gctttgggtg acaccaactt attcaaacca | 60 |
| atcaaaattg gtaacaatga acttctacac cgtgctgtca ttcctccatt gactagaatg | 120 |
| agagcccaac atccaggtaa tattccaaac agagactggg ccgttgaata ctacgctcaa | 180 |
| cgtgctcaaa gaccaggaac cttgattatc actgaaggta cctttccctc tccacaatct | 240 |
| gggggttacg acaatgctcc aggtatctgg tccgaagaac aaattaaaga atggaccaag | 300 |
| attttcaagg ctattcatga gaagaaatcg ttcgcatggg tccaattatg ggttctaggt | 360 |
| tgggctgctt tcccagacac ccttgctagg gatggtttgc gttacgactc cgcttctgac | 420 |
| aacgtgtata tgaatgcaga acaagaagaa aaggctaaga aggctaacaa cccacaacac | 480 |
| agtataacaa aggatgaaat taagcaatac gtcaaagaat acgtccaagc tgccaaaaac | 540 |
| tccattgctg ctggtgccga tggtgttgaa atccacagcg ctaacggtta cttgttgaac | 600 |
| cagttcttgg acccacactc caataacaga accgatgagt atggtggatc catcgaaaac | 660 |
| agagcccgtt tcaccttgga agtggttgat gcagttgtcg atgctattgg ccctgaaaaa | 720 |
| gtcggtttga gattgtctcc atatggtgtc ttcaacagta tgtctggtgg tgctgaaacc | 780 |
| ggtattgttg ctcaatatgc ttatgtctta ggtgaactgg aaagaagagc taaagctggc | 840 |
| aagcgtttgg ctttcgtcca tctagttgaa cctcgtgtca ccaacccatt tttaactgaa | 900 |
| ggtgaaggtg aatacaatgg aggtagcaac gaatttgctt attctatctg gaagggtcca | 960 |
| attattagag caggtaactt tgctctgcac ccagaagttg tcagagaaga ggtgaaggat | 1020 |
| cctagaacat tgatcggtta cggtagattt tttatctcta atccagattt ggttgatcgt | 1080 |

-continued

| | |
|---|---|
| ttggaaaaag gggttaccatt aaacaaatat gacagagaca ctttctacaa aatgtcagct | 1140 |
| gagggataca ttgactaccc tacctacgaa gaagctctaa aactcggttg ggacaaaaat | 1200 |
| taa | 1203 |

<210> SEQ ID NO 37
<211> LENGTH: 1203
<212> TYPE: DNA
<213> ORGANISM: Saccharomyces cerevisiae

<400> SEQUENCE: 37

| | |
|---|---|
| atgccatttg taaaaggttt tgagccgatc tccctaagag acacaaacct ttttgaacca | 60 |
| attaagattg gtaacactca gcttgcacat cgtgcggtta tgcccccatt gaccagaatg | 120 |
| agggccactc accccggaaa tattccaaat aaggagtggg ctgctgtgta ttatggtcag | 180 |
| cgtgctcaaa gacctggtac catgatcatc acggaaggta cgtttatttc ccctcaagcc | 240 |
| ggcggctatg acaacgcccc tgggattttgg tctgatgagc aggtcgctga gtggaagaat | 300 |
| atcttttag ccatccatga ttgtcagtcg ttcgcgtggg tacaactttg gtctttaggc | 360 |
| tgggcatcct tcccagacgt attggcaaga gacgggttac gctatgactg tgcatctgac | 420 |
| agagtgtata tgaatgctac gttacaagaa aaggccaaag atgcgaataa tctcgaacat | 480 |
| agtttgacta aagacgacat taaacagtat atcaaggatt acatccatgc ggctaagaat | 540 |
| tctatcgcgg ctggcgccga tggtgtagaa attcatagcg ccaatgggta cttgttgaat | 600 |
| cagttcttgg atccacattc taataagagg accgacgaat acggcggaac gatcgaaaac | 660 |
| agggcccgct ttacactgga ggttgtcgat gctcttatcg aaactatcgg tcctgaacgg | 720 |
| gtgggtttga ggttgtcgcc gtacggcact tttaacagta tgtctggggg tgctgaacca | 780 |
| ggtattatcg ctcaatattc gtatgttttg ggtgaattag agaagagggc aaaggctggt | 840 |
| aagcgtttgg cctttgtgca cctcgttgaa ccacgtgtca cggacccatc gttggtggag | 900 |
| ggcgaaggag aatattccga gggtactaac gattttgcct actctatatg gaagggtcca | 960 |
| atcatcagag ctggtaatta cgctcttcat ccagaagtgg ttagagaaca agtaaaggat | 1020 |
| cccagaacct tgataggcta tggtagattc ttcatctcta acccagattt agtctaccgt | 1080 |
| ttagaagagg gcctgccatt gaacaagtat gacagaagta ccttctacac catgtccgcg | 1140 |
| gaaggttata ccgactaccc aacatatgaa gaggcagtag atttaggttg gaacaagaac | 1200 |
| tga | 1203 |

<210> SEQ ID NO 38
<211> LENGTH: 1203
<212> TYPE: DNA
<213> ORGANISM: Saccharomyces cerevisiae

<400> SEQUENCE: 38

| | |
|---|---|
| atgccatttg ttaaggactt taagccacaa gctttgggtg acaccaactt attcaaacca | 60 |
| atcaaaattg gtaacaatga acttctacac cgtgctgtca ttcctccatt gactagaatg | 120 |
| agagcccaac atccaggtaa tattccaaac agagactggg ccgttgaata ctacgctcaa | 180 |
| cgtgctcaaa gaccaggaac cttgattatc actgaaggta cctttcctct ccacaatctc | 240 |
| gggggttacg acaatgctcc aggtatccgg tccgaagaac aaattaaaga tggaccaag | 300 |
| attttcaagg ctattcatga gaataaatcg ttcgcatggg tccaattatg ggttctaggt | 360 |
| tgggctgctt tccagacac ccttgctagg gatggttttgc gttacgactc cgcttctgac | 420 |
| aacgtgtata tgaatgcaga acaagaagaa aaggctaaga aggctaacaa cccacaacac | 480 |

```
agtataacaa aggatgaaat taagcaatac gtcaaagaat acgtccaagc tgccaaaaac    540
tccattgctg ctggtgccga tggtgttgaa atccacagcg ctaacggtta cttgttgaac    600
cagttcttgg acccacactc caataacaga accgatgagt atggtggatc catcgaaaac    660
agagcccgtt tcaccttgga agtggttgat gcagttgtcg atgctattgg ccctgaaaaa    720
gtcggtttga gattgtctcc atatggtgtc ttcaacagta tgtctggtgg tgctgaaacc    780
ggtattgttc tcaatatgc ttatgtctta ggtgaactag aaagaagagc taaagctggc    840
aagcgtttgg ctttcgtcca tctagttgaa cctcgtgtca ccaacccatt tttaactgaa    900
ggtgaaggtg aatacaatgg aggtagcaac aaatttgctt attctatctg aagggccca    960 attattagag ctggtaactt tgctctgcac ccagaagttg tcagagaaga ggtgaaggat   1020
cctagaacat tgatcggtta cggtagattt tttatctcta atccagattt ggttgatcgt   1080
ttggaaaaag ggttaccatt aaacaaatat gacagagaca ctttctacaa aatgtcagct   1140
gagggataca ttgactaccc tacgtacgaa gaagctctaa aactcggttg gacaaaaat   1200 taa                                                                1203
```

<210> SEQ ID NO 39
<211> LENGTH: 1209
<212> TYPE: DNA
<213> ORGANISM: Pichia angusta

<400> SEQUENCE: 39

```
atgaccccaa gcacttctct tgcttccagc aatctgttca agcctatcaa ggtcggcaaa     60
gtcgagctga aaacagact tgttttcgct ccaaccacca gatacagagc ctcgaaggat    120
tttgttccta ccgactccat gctcaagtac tacgagcaaa gagcggaaaa taacggaggc    180
ttgctgactg ctgaggcaac ctacgtcgac ttcaattttg gcctctatcc gttcacgccg    240
atgatcaaga cgcctgcgca ggttgcggcc tgggccaaga tcatcgaggc tgtacacaag    300
cagggatcat atttctccat ccagctgtgg catctcggca gggctgccga ccccaagttc    360
aacaaggaga agggcgtgcc gttcgtggct ccgtcggcta tatacttgga ccaggactct    420
gagaaggcag cccgggaggc cggcaacgag cttagagaac tgacgatccc ggagattgag    480
gcgattgtca aagagtttgc tgcagccgcg aaaagagcca tccacgaggc caaggccgac    540
ttcatcgagc tgcacagcgc ccacggctat ctgctggacc agtttatcca gccaaacatc    600
aacaagagaa ccgacaagta cggtggttcg attgagaatc gcgcccggtt ggttctagag    660
gttgtcgacg cgtgcattga gcggtcggc gcagaacacg tgggtataag actgtcgccg    720
tacgccaagt tccaaggcag cgagggtgtt gacagcgaaa tcaacccgat cgcgtccttc    780
ggctacattt tgagcgagct cgagaaaaga gccagagacg gaaacaggct ggcgtatgtt    840
tccgtagtcg agccaagagt tagcggaaac gtagacagca acgaccagcg gaagtttgac    900
acttcctgga tcagagaaat ctggaagggt attctattta gggccggcgg atacctcaaa    960
gaaaacgagc agtcgctgga gcacgatgtc aaccaggacg acagaacgct tattggcgtc   1020
tcgagatatt acacttcgaa tccagatctc gtggagagat tgaaaaaggg tctgtcgctg   1080
acgccctacg atagatcccg cttctacaac cactcctcca acgacggcta cctcacatgg   1140
cctaagtatg gcgaggacga ggagaagtac aaagctgtgc tggatgtcga gccaaaggcc   1200
cttgcgtag                                                         1209
```

<210> SEQ ID NO 40
<211> LENGTH: 1206
<212> TYPE: DNA

<213> ORGANISM: Pichia angusta

<400> SEQUENCE: 40

```
atgtctcagc catcattaac agacacaaac ctattcaaac caatcaaggt cggtaatgtg      60
gagctcaagc acgattctt ctcggctcca accacgagat tcagagcatc tgatgatttc     120
gtgcctaccg actccatgct cagctactat gagcagcgcg cggagaacaa cggtggactt     180
atcgttgccg aagccacttt ccccgactac agctttggcc tgtatccaaa cgctcctatg     240
atcaagacgc cggagcaggt tgctgcctgg aagaaaatcg tggatgctgt ccataagcag     300
ggatctttct tctcgattca gctgtggcac ttgggaagag ttgccgtccc gcagctgaac     360
aagaagtaca acgttcccct tgttggtcct tccaaactct acgtcgacga gagcagcgag     420
aaggcagcaa aagaggcagg aaacgagcta cacgagctga ctatccctga aatcgaggcc     480
atcgtgaagg agtttgccgc cggcgccaag cgggtggttg acgaagccaa agcagacttt     540
gtggaaattc ttgctggagg aggctacttg ctggaccagt tcaaccactc aaacatcaac     600
aagagaaccg ataagtacgg tggctcgatc gaaaaccgtg ccagactgat tttggaggtt     660
gtcgacgcat gcatcgaggc ggtcggcgca agcatgtcg gcatcaagct gtcgccatac     720
gcagcggtca atggtctcca gggtgtcgat acggagatcc accctatttc cagatatgga     780
tacatcttga gcagttgga gagaagagga aggagggaa agagaatcgc gtacatcaca     840
atgatcgagc ctcgtgtcaa cggcacggag gacagcaagg acacgcgggc gttcgactcc     900
tcgtgggtgg gcgagatctg gaagagcact ctgttgaggg cgggcgccta tctcaaccag     960
ttctcgaatt acctgatcca ggacgtcaac aaggacgaca gaacgctaat ggagccgct    1020
agatacttta cctccaaccc ggaccttatc gagagactga gaaagggaca ggagctgact    1080
ccgtacgaca gatcgaagtt ctacaccccg gccaccaatg acggctacat cacgtggacc    1140
aagtatggcg aggatcccga aaagtacaag ggccttgttg ccgtgaagcc acagccgctg    1200
tcctga                                                                1206
```

<210> SEQ ID NO 41
<211> LENGTH: 1209
<212> TYPE: DNA
<213> ORGANISM: Pichia angusta

<400> SEQUENCE: 41

```
atgtccaaga caccaacgct agcaaacacg aatctgttca agcctattaa agtcggcaaa      60
gtcgagctga aaacagact tgttttcgct ccaaccacca gatacagagc ctcgaaggac     120
tttgttccta ccgactccat gctcaagtac tacgaacaga gagcagagaa caacggcggt     180
ctcctggtga ccgaggctac ttatccggac tatagctttg gtctgtaccc cgacaccccg     240
atgatcaaga cgccggctca ggttgctggc tggaaaaagg tgattgaggc cgtccacaac     300
aagggctcct tcgtctctat ccagctgtgg cacctgggaa gaactgccag cgccgagttc     360
aacaagtcca agggtcttcc cctggtcggt gcttcgccga tctacatgga cgaggactcc     420
gagaaggcgg ccaaggaggc tggcaacgag ctcagagcgc tcacgattcc tgaaatagag     480
aacattgtta ccgaatatgc tgctgccgcc aagcgtgcga tccacgaggc caaggccgac     540
ttcatcgagc tgcacggcgc ccacggctat cttctcgatc agttcaacca gcctggctcc     600
aataagagaa ccgacaagta tggtggatcc atcgagaacc gcgccagact gatcctggag     660
gctgttgacg cctgcatcga ggctgttggc gctgagcacg ttgccatcag actgtctccg     720
tatgcggccg ttcagggtat caaaggtgtt gacagcgaga tccaccccat ctcctacttt     780
```

```
ggctacgtgc tgagcgagct cgagcgcaga gcccaggagg gaaagagact ggcctacatc      840
tctgttgtcg agccaagagt caacggcatc tacgactcca aggacaagag agaattcaac      900
acctcgtgga tcagcgaaat ctggaagggt gttcttctga gatctggtgc ctacctgaac      960
gagaactaca agttcttgca gcatgacgtg gacgagaacg acagaaccct gattggagtt     1020
tccagatact acacgtccaa cccagacctt gctgaccggc tcaagaacgg ccacgagctg     1080
acaccatatg atagatctaa attctacaaa cactcctcca acgacggata cctgacctgg     1140
accagatacg gagagaaaga gcctcagtac aaggatctgg tggatgttgc tccagagcca     1200
ctggcctga                                                             1209

<210> SEQ ID NO 42
<211> LENGTH: 1077
<212> TYPE: DNA
<213> ORGANISM: Zymomonas mobilis

<400> SEQUENCE: 42
atgcctagct tgtttgatcc catccgcttc ggcgctttta ccgcaaaaaa tagaatttgg       60
atggcgcctc tgacccgtgg ccgtgccacg cgcgatcatg tccccactga ataatggcc      120 gaatattatg cccagagggc aagcgccgga ctgattattt cagaagcgac tggcattagt      180
caggaaggtt tgggctggcc ttatgctccg ggaatctgga gtgatgccca agtagaagcc      240
tggctgccga ttacgcaggc cgtgcatgat gccggcggtc ttatctttgc ccagctatgg      300
catatgggac gtatggtgcc gtctaatgtc agtgggatgc agcctgttgc gccttctgcc      360
agtcaggcac ccggattggg gcatacctat gatggtaaaa agccttatga tgttgcccgc      420
gctttgcgat tggatgaaat tccgcgtctt cttgatgatt atgaaaaggc tgcccgtcat      480
gccttgaagg ccggttttga tggcgtacag atccatgccg ctaatggtta tttgattgac      540
gaatttatac gggatagcac caaccatcgt catgatgaat atggggtgc agttgaaaac      600 cgtattcgtt tgctgaaaga cgtcaccgaa cgagttattg caaccattgg gaaagagcgg      660
acggccgtta ggttatcacc gaatggtgaa atacagggga cggttgatag tcatcccgaa      720
caggttttta taccggcggc caaaatgttg tctgatttgg atattgcctt tttagggatg      780
cgagaagggg ctgttgatgg caccttggc aaaacagatc agcccaaatt atcgcctgaa      840
atccgaaaag ttttcaaacc gccttttggtt cttaatcagg attatacttt tgaaaccgcg      900
caagctgctc ttgattccgg tgtggccgat gccatcagtt ttggaaggcc ttttatcggt      960
aatcctgatt tgccacggcg tttctttgag aaagcccccc ttaccaaaga tgtgattgag     1020
acttggtata cccaaacccc caagggatat acggattatc ctttgcttgg ggattga       1077

<210> SEQ ID NO 43
<211> LENGTH: 1098
<212> TYPE: DNA
<213> ORGANISM: Escherichia coli DH10B

<400> SEQUENCE: 43
atgtcatctg aaaaactgta ttccccactg aaagtgggcg cgatcacggc ggcaaaccgt       60 attttatgg caccgctgac gcgtctgcgc agtattgaac cgggtgacat tcctaccccg      120
ttgatggcgg aatactatcg ccaacgtgcc agtgccggtt tgattattag tgaagccacg      180
caaatttctg cccaggcaaa aggatatgca ggtgcgcctg gcatccatag tccggagcaa      240
attgccgcat ggaaaaaaat caccgctggc gttcatgctg aaaatggtca tatggccgtg      300
cagctgtggc acaccggacg catttctcac gccagcctgc aacctggcgg tcaggcaccg      360
```

-continued

| | |
|---|---|
| gtagcgcctt cagcacttag cgcgggaaca cgtacttctc tgcgcgatga aaatggtcag | 420 |
| gcgatccgtg ttgaaacatc catgccgcgt gcgcttgaac tggaagagat tccaggtatc | 480 |
| gtcaatgatt tccgtcaggc cattgctaac gcgcgtgaag ccggttttga tctggtagag | 540 |
| ctccactctg ctcacggtta tttgctgcat cagttccttt ctccttcttc aaaccatcgt | 600 |
| accgatcagt acggcggcag cgtggaaaat cgcgcacgtt tggtactgga agtggtcgat | 660 |
| gccgggattg aagaatgggg tgccgatcgc attggcattc gcgtttcacc aatcggtact | 720 |
| ttccagaaca cagataacgg cccgaatgaa gaagccgatg cactgtatct gattgaacaa | 780 |
| ctgggtaaac gcggcattgc ttatctgcat atgtcagaac agattgggc gggggtgaa | 840 |
| ccgtatactg atgcgttccg cgaaaaagta cgcgcccgtt tccacggtcc gattatcggc | 900 |
| gcaggtgcat acacagtaga aaagctgaa acgctgatcg gcaaagggtt aattgatgcg | 960 |
| gtggcatttg tcgtgactg gattgcgaac ccggatctgg tcgcccgctt gcagcgcaaa | 1020 |
| gctgagctta acccacagcg tgccgaaagt ttctacggtg gcggcgcgga aggctatacc | 1080 |
| gattacccga cgttgtaa | 1098 |

<210> SEQ ID NO 44
<211> LENGTH: 2019
<212> TYPE: DNA
<213> ORGANISM: Escherichia coli DH10B

<400> SEQUENCE: 44

| | |
|---|---|
| atgagctacc cgtcgctgtt cgccccgctg gatttaggtt ttaccacgtt aaaaaaccgc | 60 |
| gtgttgatgg gctcaatgca caccgggctg gaggaatacc cggacggtgc cgagcggctg | 120 |
| gcagcgtttt atgccgaacg cgcccgtcac ggcgtggcgc tgattgtcag cggcggcatt | 180 |
| gcaccagatt taacaggcgt tggcatggaa ggtggcgcaa tgctcaacga cgccagccag | 240 |
| atcccacacc atcgcaccat taccgaagcg gtacatcagg aaggcggcaa aatagccctg | 300 |
| caaattttgc ataccgggcg ctacagctac caaccgcatc tggtcgcccc gtccgcattg | 360 |
| caggcccca tcaaccgttt cgtgccccat gagttaagcc atgaagagat cctgcaactg | 420 |
| atcgacaatt tcgcccgctg cgcgcaactg gcgcgggagg caggatacga cggtgtagag | 480 |
| gtgatgggtt ccgaagggta tttgatcaac gaatttctga cgctgcgcac caatcagcgt | 540 |
| agtgaccagt ggggcggcga ttaccgcaac cggatgcgat ttgccgtaga agtagtgcgt | 600 |
| gcggtgcgcg aacgcgtcgg caacgacttc attattatct accgactgtc gatgctcgac | 660 |
| ctggtcgaag acgcgggac ttttgccgaa acggtagagc tggcgcaggc cattgaagcg | 720 |
| gcgggcgcga ccattatcaa caccggcatt ggctggcatg aagcacgtat tccgaccatt | 780 |
| gccacgcccg tgccgcgcgg cgcatttagc tgggtcacgc gcaaactgaa aggccacgtc | 840 |
| tcgctgccgc tggtaaccac caaccggatt aacgatccgc aggttgccga cgatattctc | 900 |
| tcgcgcggcg atgccgatat ggtatcgatg gcgcgaccgt tcttgctga tgcggagctg | 960 |
| ctgtcaaaag cgcaatcggg acgagccgat gagatcaaca cttgtattgg ctgcaatcag | 1020 |
| gcctgtctcg atcaaatctt cgttggcaaa gtcacctcgt gcctggtgaa tcctcgcgcc | 1080 |
| tgccacgaaa ccaaaatgcc aatccttccc gccgtgcaga aaaaaaatct ggcggtggtc | 1140 |
| ggtgcgggac tgctgggct ggcgtttgcc attaacgcgg cggcgcgtgg catcaggta | 1200 |
| acattgtttg acgctcatag cgagattggc gggcagttta atatcgccaa acagatcccc | 1260 |
| ggcaaagagg agttttacga aacgctcgcg tattaccgcc ggatgatcga agtgacgggc | 1320 |
| gtgacgctaa aactcaatca caccgtgacg gcggatcagt tacaggcttt cgatgaaacg | 1380 |

```
atcctcgcca gtgggatcgt gccgcgcact ccgcccatcg acgggatcga tcatccgaag    1440
gtattgagtt atctcgatgt actgcgcgac aaagcgccgg ttggcaacaa agttgccatc    1500
atcggttgtg gcgggattgg ttttgatacg gcgatgtatt taagtcagcc gggcgaatcc    1560
accagccaga atatcgccgg gttctgtaat gaatggggga tcgacagtag cctacaacag    1620
gctggtggct taagcccgca gggaatgcag atccccgta gcccacggca gattgtgatg    1680
ctccagcgca aagccagcaa accaggacag gggttaggca aaaccaccgg ctggatccat    1740
cgcaccaccc tgctctcgcg gggtgtgaaa atgatcccag gcgtaagtta tcagaagatt    1800
gacgatgacg ggctgcatgt ggtgatcaac ggcgaaacgc aggtattagc agtggacaat    1860
gtggtgatct gcgcagggca agagccaaac cgcgcgctgg cgcaaccgct gattgatagc    1920
gggaaaacgg tgcatttaat tggcggctgc gatgtggcta tggagctgga cgcacgacgg    1980
gcaattgccc agggaacacg gctggcgctg gagatttaa    2019

<210> SEQ ID NO 45
<211> LENGTH: 1098
<212> TYPE: DNA
<213> ORGANISM: Klebsiella pneumoniae MGH78578

<400> SEQUENCE: 45
atgtcggaag caaaattatt cagcccactg aaagtcggtg cggtcaccgt ccctaatcgc      60
gtatttatgg cgccgttgac gcgtctgcgc agcattgagc cgggcgatat ccctactccg     120
ctgatgggcg aatactaccg ccagcgcgcc agttccgggc tgatcatcac cgaagcgacg     180
cagatctccg cgcaggccaa aggctacgcc ggcgcgcctg gctgcacag cccggagcag     240 attgccgcct ggcagaaaat taccgccggc gttcatgccg aaaacggtca tatcgccgtc     300
cagctgtggc acaccgggcg tatttcccat agcagcctgc agcctggcgg cgccgccccg     360
gtagcgcctt ccgcgctgag cgcgggcacc cgtacctcac tgcgtgacga aaacggccac     420
gccattcgcg tcgacacctc aatgccccgc gccctggaaa ccgcagagat cccagggatc     480
gtcaacgatt ccgtcaggc ggtcggcaat gcccgtgacg ccggcttcga tctggttgag     540
ctgcactcag cccacggcta tctgctgcac caattcctct cgccatcggc gaaccagcgt     600
accgatcagt acggcggcag cgtggagaac cgtgcccgtc tggtgctgga agtggttgac     660
gccgtgagtc aagagtggag cgccgagcgc attggcatcc gcgtgtcgcc gattggcagc     720
ttccagaatg tggataatgg cccgaacgaa gaagaagacg cgctgtatct gattagcgag     780
ctggcgaaac gcgtatcgc ctatctgcac atgtccgagc cggactgggc gggcggcaaa     840
ccttacagtg aagctttccg tcagaaagtc cgcgaccgct tcccgggggt gatcattggc     900
gctggcgctt acacagtaga aaagccaac gatcttatca ataaagggct gattgatgcc     960
gtggcctttg ccgcgattta catcgccaac ccggatctgg tggctcgcct gcagaaaaaa    1020
gcgccgctta acccgcaacg cccggaatcc ttctacggcg cggcgcgga aggctacacc    1080 gattacccga ctctgtaa                                                  1098

<210> SEQ ID NO 46
<211> LENGTH: 2778
<212> TYPE: DNA
<213> ORGANISM: Klebsiella pneumoniae MGH78578

<400> SEQUENCE: 46
atgaccagta acgaacgtat tttgcagcca tttactttac caaatggtac cgagctgaaa      60
aaccgtttgc tcatggcgcc aatgaccacc tgcaccggtt atttcgatgg tactgtcacc     120
```

-continued

```
agcgagctgg tggagtacta ccgcgcgcgc gccggaagca tcggtaccat tattgtcgag    180
tgctgcttta ttgatgacta cggtctggcc ttcccgggcg cgatcggcat tgataatgat    240
gaaaaaattg ccggcctggc gaaaatcgct gaggcgatca agccgagggg ttcaaaagcg    300
attctgcaga tctaccacgg cggccgtatg gtcgacccgc agctgatcgg ggggcgccag    360
ccggtggcgc cgagcgctat tgccgcgccg cgtgagggcg ccgccatgcc gcgggcgctg    420
agcggagaag aagtggaagg gatgatcgcc aagtttggcg acggcgttcg tcgcgccatt    480
ctcgccggtt tcgacggggt cgaaattcac ggcgccaaca cctatctcat tcagcagttc    540
tattcgccga actccaacca gcgcgatgac gagtgggggcg gtagccgcga caaccgcgcc    600
cgtttcccac tggcggtgct ggatattacc cacaaaatgg cccgccagta cgccgacgat    660
gcctttatca tcggctatcg cttctcgccg gaggagatga aggtcccggg gatccgcttt    720
gacgacacca tgtatctgct ggaaaagctg gccgcccgcg tgtcgatta tctgcacttc    780
tcggtgggtg ccaccctgcg tccgtctatc gtcgatacca gcgatgcgac gccgctgatc    840
gagaaatact gcgcgatgcg ctctgacacc ctcgcccagg tgccggtgat gggcgtcggc    900
ggggtggtga acgccgctga tgccgagcag ggcctcgatc atggttatga cctgatcgcc    960
gtgggccgcg cctgcatcgc ctatccggac tgggcgtcac gtatcgccgc cggcgaagag   1020
ctggagctgt ttatcgacag cacccagcgt gaagcgctgc acattccgga accgctatgg   1080
cgtttctcgc tggtggaagc gatgatccgc gacatgagca tgggcgacgc caaatttaaa   1140
ccggggatgt ttgttgagac cgtccacgat gacgccaatg agctggtgat caacgtcagc   1200
ctcgaaaatg accatattgc cgatatcgaa ctggcggcga gcccggtcca gactgtggaa   1260
ttcaccacca gcttcgaaga gatccgcgaa cgtattctca ccgccaatac cccgcacgtc   1320
gatgccattt ccggggccac cagccagagc gaggcggtga aaaaagcggt cgccaaagcg   1380
atgctgaaat cgagtaaagc gctgcggcgc gaagagggcg gcaatgacgc cgcgccgaaa   1440
agctatgatg tggtggtagt cggcagcggc ggcgccggtc tggcggcagc cattcaggca   1500
cacgacgaag gggccagcgt gctgatcgtt gaaaaaatgc caaccatcgg cgggaacacc   1560
atcaaggctt ccgccgggat gaacgccgcg gaaacccgct tccagcgcgt gaaaggtatc   1620
gaagacagta aggagttgtt ctatcaggaa accctgaagg gcggccacaa caaaaacaac   1680
ccgcagctgc tgccccgttt cgttgaaaac gcgccgcaag ccattgagtg gctggcggac   1740
cggggcatta tgctcaacga cattaccacc accggtggga tgagcattga ccgtacccac   1800
cgtccgcgcg acgggtcagc ggttggcggc tatctgatta gcggctggt gcgcaacatc   1860
accaaacgcg gtattgacgt cctgctggat acctcggtgg aagagatcct gatgcgcggg   1920
gatgaggtta gcggtgtacg tctgatcaac gacgaaaaag aggtcattga agtacagacc   1980
aaaagcatcg tagtggccac cggcggcttc agcgctaaca gcgcgatggt cgtgaagtat   2040
cgtcctgacc ttgaaggctt cgtcaccact aaccacaaag gggctaccgg gagcggtatc   2100
gcgttgctgg aacgcatcgg cgccggcacc gtggacatgg gcgaaattca gattcacccg   2160
accgtcgagc agcagacctc gtatctgatt tccgaatcga ttcgcggcgg cggcgctatt   2220
ctcgtaaacc agcaggggaa ccgcttcttc aacgagatgg agacccgcga taaagtctcg   2280
gcggcgatta tcgctctgcc ggaacactat gcttgcatcg tcttcgacga gcatgtgcgg   2340
gcgaaaaaca aagctgccga cgagtacatc gccaaaggct tcgtcaccag cgccagctca   2400
ccgcgggaac tggcggagaa actggggatg gattaccatg ccttcctcgc caccctcgag   2460
tgctataacg gggcggtgga aaaacagcat gatgaacagt ttggccggac caccgcgcta   2520
```

-continued

| | |
|---|---|
| cgcgcgccga ttaacgaagg cccgttccac gccattcgca tcgcccccgg cgtgcaccac | 2580 |
| accatgggcg gcgtgaccat taataccgat ggcgaagtgc tgaatgtggc gcagcagccg | 2640 |
| atttgcggcg cctacgccgc cggtgaagtg gtgggcggga tccacggcgg caaccgtatc | 2700 |
| ggcggtaacg cggtggcgga tatcatcatc ttcggtaccc tcgcgggcca tcaggcggcg | 2760 |
| aaacgtgcca gaggataa | 2778 |

<210> SEQ ID NO 47
<211> LENGTH: 1050
<212> TYPE: DNA
<213> ORGANISM: Pseudomonas fleurescens Pf-5

<400> SEQUENCE: 47

| | |
|---|---|
| atgacgactc tctttgatcc gatcaaactc ggcgatctcg aactgtccaa ccgcatcatc | 60 |
| atggcgccgc tgacccgctg ccgcgccgat gccggccgcg tacccaacgc gctgatggcc | 120 |
| gaatactacg tacaacgggc ttccgccggc ctgatcctca gcgaggccac ctcggtgacc | 180 |
| cccatgggcg tgggctaccc ggacaccccc ggcatctggt ccaacgacca ggtgcgtggc | 240 |
| tgggccaatg tgaccaaggc agtacacggc gccgtggca agatattcct gcagctgtgg | 300 |
| cacgtcggac gcatctccca cccgtcctat ctgaacggcg aaaccccggt ggcacccagc | 360 |
| gccctgcagc caaggggca tgtcagcctg gtgcgcccgc tggccgactt cccaactccg | 420 |
| cgggccctgg aaaccgctga atcgccgac atcgtcgatg cctaccgggt cggcgcggaa | 480 |
| aacgccaagg ccgccggttt cgacggcgtg aaatccacg cgccaacgg ctacctgctg | 540 |
| gaccagttcc tgcaaagcag caccaaccag cgtaccgacc agtacggcgg ctccctggaa | 600 |
| aaccgtgccc gctgctgct ggaagtcacc gacgcggcca tcgagatctg gggtgccggc | 660 |
| cgggtaggcg tgcacctggc accacgtgcc gactcccatg acatgggtga tgccaacctg | 720 |
| gcggagacct tcacctacgt cgctcgggag ctggcaaac gcggtatcgc ctttatctgc | 780 |
| tcccgcgaga agaaggcgc cgacagcctg ggcccgcaac tcaaagaagc cttcggcggc | 840 |
| ccctacatcg ccaacgaacg cttcaccaag gacagcgcca acgcctggct ggccgctggc | 900 |
| aaggctgacg ccgtggcctt tggtgtgccc ttcatcgcca acccggacct gccagcccgc | 960 |
| ctgaaggccg atgcgccgtt gaacgaagcg cacccggaaa ccttctacgg caagggcccg | 1020 |
| gtcggctata tcgactaccc gactctgtaa | 1050 |

<210> SEQ ID NO 48
<211> LENGTH: 1101
<212> TYPE: DNA
<213> ORGANISM: Pseudomonas fleurescens Pf-5

<400> SEQUENCE: 48

| | |
|---|---|
| atgaccgatc agaatctgtt caccccttac acccttggcg ccctcgcgct ggcgaaccgc | 60 |
| atcgtcctcg cgccactgac ccgcaaccgc gcgggcgcag gctttgttcc cagcgaattc | 120 |
| gccgccacct attacagcca acgcgctagc gcaggcttgc tgatcagcga agccacgcag | 180 |
| atttcccaac agggccaggg ctatcaggac accccgggga tctacaccca ggcgcagatt | 240 |
| gatggctggc gcacggtgac cgacgcggtc cacgcccagg gcgcaaagat ctttgtgcaa | 300 |
| ctgtggcatg tcgccgcgt gtcccacgtt gatctgcaag aaaacggcgc cgcccccgtg | 360 |
| gccccttccg cgctgcgtgc ggccaccaag gtgttcgtca caaccgcttt gaagacgcc | 420 |
| agcgagcccc gcgcactgga catcagcgag ctgccgggga tcgtcgccga tttccgccag | 480 |
| gccgcggcaa acgctatcgc tgccgggttc gatggcgtgg aaattcacgg cgcgaacggc | 540 |

```
tatttgctgg atcagttcct caaggacagc gccaacgtac gcaccgatgc ttacggcggc    600
tcgattgaaa atcgtgcgcg tctgttgctc gaagtcaccg ctgccgtggt caatgaaatc    660
ggcgcggatc gcaccggggt gcgcttgtcg ccggtgtcgc cggccaacgg tgtctccagc    720
agcaatccgc aggcgcaatt caattacgtc gtcgatcaac tcgacgccct cgacgtcgtt    780
tacctgcaca tggtcgaagg cgcgaccggt ggcccacgtg acgtggcgcc attggatttc    840
accgccctgc gccagcgttt caaaaacacc tacatcgcca acaacggcta tgacctggag    900
ctggcaacct cacggctcgc cgaagaccag gccgatctga tcgcgttcgg tcgcccgttc    960
atcggcaacc cggatctggt ggagcgtctc aagaccggcg ccgccttgtc cgcattcaat   1020
cccgccaccc tctacggcgg cggcgcggca ggctacatcg actacccgac gctggttgat   1080
tcgagcgcca gcgcaagctg a                                              1101
```

<210> SEQ ID NO 49
<211> LENGTH: 1104
<212> TYPE: DNA
<213> ORGANISM: Pseudomonas fleurescens Pf-5

<400> SEQUENCE: 49

```
atgcctgttc aagccttgtt caaacccttt caactcggcg cgctggaact gccgactcgc     60
gtggtgatgg caccaatgac ccggtcgttt tccccggtg gcgtgcccaa ctccaaggtc    120
atcgagtatt accgccgccg cgctgctgcg ggtgtcggcc tgatcattac cgagggcacc    180
acggtgggtc accaggctgc caatggttac cccaatgtgc cgcagttcca tggcgaggcg    240
gccctggccg gctggaagaa ggtggtggat gcggtccacg ccgaaggcgg caagatcgtc    300
ccgcaactct ggcatgtggg caatgtgcgc cgcctgggca ccgagccgga cgccagcgtg    360
cccggctacg gccccaccga gaagctcaag gacggcaagg tgctggtgca cggcatgacc    420
caccaggaca tccaggaggt gatcgcagcc tttgcccagg ccgccaagga tgcccagagc    480
atcggcatgg acgcgtgga gatccatggc gcccatggtt acctggtgga ccagttcttc    540
tgggaaggca ccaaccagcg taccgatgaa tacggtggcg acctggccca gcgctcgcgc    600
ttcgccattg agctgatcca ggccgtgcgg gctgccgtcg gtccggattt cccgatcatc    660
ctgcgttttt cccagtggaa gcagcaggac tacagcgcgc gcctggtgca gaccccggaa    720
gctctggagg ccttcctcaa gccgctggcg gatgccggtg tggatatctt ccactgctcg    780
acccgccgct tctgggagcc tgagttcgaa ggttccgacc tcaacctggc gggctggact    840 cgcaaaactca ccggcaagcc caccatcacc gtgggcagcg tcggcctgga cggcgagttc    900
ctgcagttca tggtcaacac cgacaaggtg gcgcagccgg ccagcctgga aaacctgctg    960
cagcgtctga taacgacga gttcgatctg gtggccgtgg gcgtgcact gctggtggat   1020 ccggattggg cgcagaaagt ccgtgaaggt cgcgagcagg acatcctgcc gttcagccgt   1080
gacgctctga cgaccctggt ttaa                                          1104
```

<210> SEQ ID NO 50
<211> LENGTH: 1050
<212> TYPE: DNA
<213> ORGANISM: Pseudomonas putida

<400> SEQUENCE: 50

```
atgaccacgc ttttcgatcc gatcaaactg ggcgacctgc aactgcccaa ccgtatcatc     60
atggccccgc tcaccccgctg ccgtgccgat gaaggccgtg tgcccaatgc gctgatggcc    120
gaatactacg tacaacgtgc cagcgccggg ctgatcctca gcgaggccac ttcggtcagc    180
```

| | | |
|---|---|---|
| ccaatgggcg tcggctaccc agatacccccc ggcatctgga acgatgaaca ggtacgtggc | 240 | |
| tggaacaatg tgacaaaggc cgtacatgcc gcgggcggtc gcatcttcct gcagctgtgg | 300 | |
| cacgtgggtc gtatctccca ccccagctat ctgaatggcg aactgcctgt ggcccccagc | 360 | |
| gcgatccagc ccaagggcca tgtgagcctg gtgcgcccgc tgagtgacta ccctaccccg | 420 | |
| cgggcgctgg aaaccgaaga atcaacgac atcgtcgagg cctaccgcag tggtgccgaa | 480 | |
| aatgccaagg ctgccggttt cgatggtgtg agatccatg gcgccaacgg ttacctgctc | 540 | |
| gaccaattcc tgcaaagcag caccaaccag cgcaccgacc gttacggtgg ctcgctggaa | 600 | |
| aaccgcgcgc gcctgctgct ggaggtgacc gatgcggcca ttgaagtgtg gggcgcgcag | 660 | |
| cgtgtaggtg tgcacctggc accgcgagcc gacgcccatg acatgggcga cgccgaccgc | 720 | |
| gccgagacct tcacctatgt ggcccgagcg ctgggcaagc gcggcatcgc cttcatctgc | 780 | |
| tcgcgggagc gggaagccga cgacagcatc gggccgctga tcaaagaggc attcggtggc | 840 | |
| ccgtacatcg tcaacgagcg gttcgacaag gccagtgcca atgcggccct ggccagtggc | 900 | |
| aaagcggatg ccgtggcgtt tggtgtgccg ttcatcgcca accctgacct gccggcacgg | 960 | |
| ctggcagcgg atgcgccgtt gaatgaggcg cggcctgaga cttctatgg caaggggccg | 1020 | |
| gtggggtaca tcgattaccc gcggttgtaa | 1050 | |

<210> SEQ ID NO 51
<211> LENGTH: 747
<212> TYPE: DNA
<213> ORGANISM: Thermotoga maritima

<400> SEQUENCE: 51

| | | |
|---|---|---|
| atgatagagt acaggattga ggaggcagta gcgaagtaca gagagttcta cgaattcaag | 60 | |
| cccgtcagag aaagcgcagg tattgaagat gtgaaaagtg ctatagagca cacgaatctg | 120 | |
| aaaccgtttg ccacaccaga cgatataaaa aaactctgtc ttgaagcaag gaaaatcgt | 180 | |
| ttccatggag tctgtgtgaa tccgtgttat gtgaaactgg ctcgtgaaga actcgaagga | 240 | |
| accgatgtga aagtcgtcac cgttgttggt tttccactgg gagcgaacga aactcggacg | 300 | |
| aaagcccatg aggcgatttt cgctgttgag agtggagccg atgagatcga tatggtcatc | 360 | |
| aacgttggca tgctcaaggc aaaggagtgg gagtacgttt acgaggatat aagaagtgtt | 420 | |
| gtcgaatcgg tgaaaggaaa agttgtgaag gtgatcatcg aaacgtgcta tctggatacg | 480 | |
| gaagagaaga tagcggcgtg tgtcatttcc aaacttgctg gagctcattt cgtgaagact | 540 | |
| tccacgggat ttggaacagg aggggcgacc gcagaagacg ttcatctcat gaaatggatc | 600 | |
| gtgggagatg agatgggtgt aaaagcttcc ggagggatca gaaccttcga ggacgctgtt | 660 | |
| aaaatgatca tgtacggtgc tgatagaata ggaacgagtt cgggagttaa gatcgttcag | 720 | |
| gggggagaag agagatatgg aggttaa | 747 | |

<210> SEQ ID NO 52
<211> LENGTH: 837
<212> TYPE: DNA
<213> ORGANISM: Thermotoga maritima

<400> SEQUENCE: 52

| | | |
|---|---|---|
| atggtttaca caactccatg aacagaaag atcgagtttg aagaacgat ggttatggga | 60 | |
| ataataaacg tcacaccgga ctccttcttc gctgattcca gaaaacagag cgtactcgaa | 120 | |
| gcggtggaaa ccgcaaagaa gatgatgaa aaggtgctg acataataga cgtgggagga | 180 | |
| atgtccaccc gtcccggatc agatcccgtc gatgaggaag aagaattgaa cagagtgatt | 240 | |

```
cccgtgataa gagcgatcag atcgataacc gacgttccga tttccgtaga tacatacagg    300
tggagggtgg cttttgaaagc tcttgaagcc ggagcggata tcgtaaacga tatcagcggt    360
tatcaattcg aaccggatat cgtcagagta gtttctgaaa caacgtccc ttacgttctc    420 atgcacataa aaggaacgcc aaagacgatg caggaaaatc ctcattacga agatgtggtg    480
aaggagataa aagagtactt cacagaaaaa atagagtatc taaaagaaaa aggtgtgaac    540
cagatcgttc tggacccggg tatcgggttt ggaaaaagat acgaagacaa cctcgaaatt    600
cttcgaagga tcgacgaatt caaagagtta aaactgccca tcctcatagg tgcttcaaga    660
aaatctttca taggaatcac cttgggaaac gtgccccccg aagaaagact tgaaggtact    720
cttgcggtca ccgcgtactg cacgatgaaa ggagtagata taattcgggt acacgatgtc    780
ctccctaaca agagggtgat aagaatgatg gaggcgatac tctggcaaag gttgtaa       837

<210> SEQ ID NO 53
<211> LENGTH: 618
<212> TYPE: DNA
<213> ORGANISM: Thermotogo maritima

<400> SEQUENCE: 53
atgaagatgg aagagctctt caaaaaacac aagattgtag ccgtgctgag ggcaaacagt     60
gtggaagaag cgaaagaaaa ggcgttggct gttttttgaag gaggagttca cctcatcgaa    120
atcaccttca ctgttccaga cgctgacaca gtcatcaaag aactctcgtt cctcaaggaa    180
aaaggtgcca taataggtgc aggtacagtg acgagtgtcg aacagtgcag aaaagctgta    240
gaaagtggag cagagttcat cgtcagtcca caccttgacg aggaaatctc tcaattctgc    300
aaagaaaaag gtgtcttcta catgcccggt gtgatgacac ccaccgaact tgtaaaagcc    360
atgaaactcg gtcacacgat tttgaaactc ttccctggag aagtggtggg acctcagttt    420
gtaaaagcga tgaaaggacc gttcccccaat gtgaaattcg tgcccactgg aggcgtgaat    480
ctggacaacg tgtgtgagtg gttcaaagcc ggagtcctcg ctgttggtgt tggaagtgcg    540
cttgtgaaag gaacaccaga cgaggtgaga gaaaaagcaa aagcgttcgt agaaaagatc    600 aggggggtgca cagaataa                                                 618

<210> SEQ ID NO 54
<211> LENGTH: 948
<212> TYPE: DNA
<213> ORGANISM: Thermotoga maritima

<400> SEQUENCE: 54
atgacaatgc cttatgtaaa gaacacgaaa gaaattctgg aaaaagccag caagagagaa     60
tacgctatcg gtgcattcaa tttcaacaac atggaatttc tccaggcaat tcttgaagcc    120
gctgaggaag aaaaagcacc ggtcatcgtc gctacatcgg aaggagcgat aaagtacata    180
ggaaagggcg atatagaaac aggagcaaaa cttgccgttg aaatggtgag aacttacgct    240
gaaaaacttt cagttcccgt cgcactccac ctggaccacg gaagagactt taaagttatc    300
atggctgcca taaaagcggg ttactcttca gtgatgatcg acgcttcgca tcttcccttc    360
gaggaaaacc tcagagagac gaagaggatc gtggagatag ctcacgcggt tggtataagt    420
gtagaagcgg aactcggaaa actcaaggga atagaggaca atgtggtgga aaagagtcc    480 gtgctcgtcg atccggaaga agcaaaggta tttgtgaagg aaacagaagt ggatttcctg    540
gctccagcca ttgaaccagc cacggtgcg ttcaagttca aaggggaagc acagctcgac    600
tttgaacgac tgaagaaagt gaaagaatac acccagatac cgctcgttct tcacggagct    660
```

```
tccatggtac cgcaggatat tgtgaaactg gcgaacgaat acggtgccga gctttccggt    720
gcgaaaggcg ttccggaaga catgctgaag aaagctatag aacttggtat caacaagata    780
aacacagaca ccgatctgag aatccacttc gtcgcgtatc tcaggaaggt tctctcagaa    840
gacaagtctc agatagatcc cagaaaaatt ttcaaacctg tcttcgaaca ggtgaaagaa    900
atcgtcaagg agagaatcag aatattcgga tccagcggaa aggcgtaa                948
```

<210> SEQ ID NO 55
<211> LENGTH: 765
<212> TYPE: DNA
<213> ORGANISM: Thermotoga maritima

<400> SEQUENCE: 55

```
atgaggagta cagacaggtt actgtttata gattttctgt tgaagtttga aaacaaaaac     60
ggaactgtga taccttgttg tgtggataat tttgactgta cgtttaccca taaggaggt    120 aaaagcatgt acgaaaaaga aggaaagag ctatacaatg cccatcttct gttggaaaaa    180
tacggtcttg tcgcttacac aagcggtaac gtgagtgtga aatcggtga tcatgttctg    240 ataaagccct ccggtgttcc ataccaccgag ctgaaaccag aggacttcgt cgtggtggac    300
cttgaaggaa acgtgatcga gggagagaag aaaccctccg tcgatacagc tacacatctg    360
tatctctaca acaccctcga ctgggcaaaa tccgtgattc acactcattc aacattcgcc    420
atggtgtggg caattctcga aaaatcaatc cccgttcttt gcacggcaca tgcggatgtt    480
ttcggagagg agattcctct tacagaatac gctcctgtag atccgaggc gattggaaaa    540 gctgtcgtga agtgattgg aaaatccggt gctgttcttc tcagaaaaca cggtgttatg    600
atcgtgggga cctctgtgga cgatgcagtg aaaaaggcga ttttccttga ggaggtagca    660
aaggcagcgt actttgcgac acttgcagga aaacccacac cattgccacc tgacgaggtg    720
gatcatctct acaatcagta ccacaccaag tacggtcaga agtaa                   765
```

<210> SEQ ID NO 56
<211> LENGTH: 657
<212> TYPE: DNA
<213> ORGANISM: Thermotoga maritima

<400> SEQUENCE: 56

```
atgaagatct ttctggacac agcaaactta gaagagatca aaaaaggtgt tgaatggggt     60
atcgtggatg gagtaacgac gaatccaaca ctgatttcaa aggaaggagc agagttcaaa    120
cagagagtga aagagatctg cgatctggtg aaaggtcccg tttctgcgga ggttgtgtct    180
ctcgactacg aaggcatggt gagagaggcg agagaactcg ctcagatcag cgaatacgtg    240
gtgatcaaga taccaatgac acccgatggc atcaaagcgg tgaagactct ctctgcagag    300
ggtataaaga caaacgtgac actcgtgttc agcccagccc aggccattct ggccgcgaaa    360
gcgggagcaa cctacgtgag cccttcgtt ggaaggatgg acgatctttc aaacgacgga    420
atgagaatgc ttggagaaat cgtcgagatc tacaacaact acggtttcga aaccgagatc    480
atcgccgcaa gcatcagaca tccaatgcac gtggtggaag cagcacttat gggtgtggat    540
atcgtgacga tgccatttgc cgtgctggag aaactcttca acacccgat gacggatctt    600 ggaatagaaa ggttcatgga agactggaaa aagtatttgg agaacctgaa gaaataa      657
```

<210> SEQ ID NO 57
<211> LENGTH: 1017
<212> TYPE: DNA
<213> ORGANISM: Thermotoga maritima

<400> SEQUENCE: 57

```
atgatagtcg ttttgaaacc cggttccaca gaagaagata taaggaaggt ggtgaagttg    60
gccgagagtt acaacttgaa gtgtcacatt tccaaaggtc aggaaagaac ggttattggg   120
atcatcgggg acgacaggta cgtggtggcg acaagttcg agtcgctgga ttgcgtggaa    180
agcgttgtga gggtgctcaa accttacaaa ctcgtttctc gtgagttcca tccggaggac   240
acggtgatcg acctcggaga tgtgaagata ggaaacggct acttcaccat catagcggga   300
ccgtgctcag ttgaaggcag ggaaatgctc atggaaaccg cacactttt aagcgaactc    360
ggtgttaaag ttttgagggg aggggcctac aagcctcgaa catctcctta ctctttccaa   420
ggactcggag aaaaggggct ggaatacctg agagaggctg ccgacaagta cggtatgtac   480
gtggtgacga aggctctcgg agaagacgat cttccaaaag tggccgagta cgctgatatc   540
attcagatag gagcgagaaa cgctcagaac ttcagattgc tctctaaagc gggaagctac   600
aacaaacccg ttcttctgaa aaggggtttc atgaacacca tcgaagagtt ccttctctcc   660
gctgaataca ttgcaaactc tggaaacacg aagatcatac tgtgtgaaag gggaatcaga   720
acgttcgaaa aggccacgag gaacacactc gatatatccg ctgttcctat aatcagaaag   780
gaatcccatc ttcccattct ggtggatccg agccactctg ggggaagaag agacctcgtt   840
attccactct cccgggccgc tatagcggtt ggagctcatg gaatcattgt ggaggttcat   900
ccggagccgg agaaggcact ttcggatgga aaacagagtc ttgacttcga gctcttcaag   960
gaactggttc aggaaatgaa gaaactcgct gatgccctgg gggtgaaggt gaattaa    1017
```

<210> SEQ ID NO 58
<211> LENGTH: 1284
<212> TYPE: DNA
<213> ORGANISM: Thermotoga maritima

<400> SEQUENCE: 58

```
atgtggaagc atgtaaaaca ggttgatccc gaaatatacg aagttcttgt gaacgagttg    60
aagcgtcagg agtacggcct ggagctgatc gcctctgaga acttcgcgtc actcgctgtc   120
atagaaacca tgggaagcat gctcaccaac aagtatgcgg aaggataccc gaagaagaga   180
tactacggtg gctgcgagtg ggtggatcga gcagaagaac gtgctataga gagagcgaag   240
aggttgtttg gagccaaatt tgcgaacgtt cagccgcact ccggttctca ggcgaacatg   300
gcggtttatc tggcactcgc ccagcccgga gacacgatca tgggaatgtc cctgtcacac   360
gggggacatc tcacccatgg agcaccggtg aatttctcag ggaagatctt caaggtggta   420
ccttacggag tcaatctgga aacggaaacg atagattacg atgaggtcag aagactcgct   480
ctggaacaca gccgaagat aatcgttgcg ggtggaagtg cttacgccag gatcatcgat   540
ttcaaaagat tcagagagat agccgatgag gtgggagcat atttgatggt ggatatggct   600
cactttgccg gactcgtcgc tgctggaatt catccaaatc ccttggaata cgcccacgtg   660
gtgacttcca ccacacacaa gactctcagg ggccccagag gtggtttgat actcacgaac   720
gatccggaga tcgccaaagc cgtggataaa actatcttcc ccggtatcca gggtggtcct   780
ctcatgcacg tcatagcggc gaaagctgtc tgtttcaaag aagccatgac ggaggagttc   840
aaagagtacc agaagcaggt ggtcaaaaat gctaaaaaga tggctgaaga gttccagaaa   900
cgaggttaca ggatcgtttc tggaggaact gatacacacc tgttcctggt ggatctcaca   960
ccaaaagaca taacgggtaa agcggcggaa aaggccctgg aaagctgtgg tatcacagtg  1020
aacaaaaaca ccattcccaa cgaaaagaga ctctccgttcg tggcgagcgg tatcagaata  1080
```

| | |
|---|---|
| ggaacacccg ctgttacaac ccgcggaatg aaggaagaag agatggaaga gatcgccgag | 1140 |
| atgatagatc tggttctttc gaacgtgatc gatgaaaacg gaacggtgaa accagaggtg | 1200 |
| agggaagagg tttcaaagaa ggtaagggag ctctgcgaaa ggtttcctct gtaccgtgac | 1260 |
| aagatcgaag gggtggaaat ataa | 1284 |

<210> SEQ ID NO 59
<211> LENGTH: 711
<212> TYPE: DNA
<213> ORGANISM: Thermotoga maritima

<400> SEQUENCE: 59

| | |
|---|---|
| atgagagaga cgataagaga gattcaaaaa gtagcttact ggcttgccat aaagggcctt | 60 |
| tccgaggcga acgcagggaa catctctgtc agactggatg aaagaccaga aggatacgag | 120 |
| gtcaagagtg tgaacgaata cgggttcgat tacgacggtc ccgagatgta ccttctgatc | 180 |
| acggcaacgg gctcgagaat gagagaagtc tacgaagacg acagcaagat ctgtcttctt | 240 |
| cacgtccttc cggggaaaca ctacgaaatt ctccacggaa acggaaaacc caccagtgag | 300 |
| tttcccacac acctcatgat ccacgcaaaa ttcaaggaga tgaatccgga aaagaaagcc | 360 |
| atcgttcaca ctcatcctct gaacctgctc actctgatga acttagagga attccaggag | 420 |
| cttcttccga gatgatgaa gattcatccg gaagttttga tcttttttccc acagggaatc | 480 |
| tccgtcgtcg agttcgaaaa gccaggcagt gtggaactcg gcctgaagac ggtggagaag | 540 |
| tcagaaggga agatgcagt tctctgggac aagcacggtg ttgtggcttt cggaaaagat | 600 |
| gtcgcagaag cgtacgacag ggtcgagatc ctggaaaaag cggcggagat ccttttgaga | 660 |
| gtgctcagcc tcggaagaaa tcccacgggt gttccggagg atggctgta a | 711 |

<210> SEQ ID NO 60
<211> LENGTH: 1149
<212> TYPE: DNA
<213> ORGANISM: Thermotoga maritima

<400> SEQUENCE: 60

| | |
|---|---|
| atggtcaagg tcctgatcct cggtcagggc tacgttgcca gtacattcgt tgccggactt | 60 |
| gaaaagctca ggaaagggga aatagaacct tacggagtgc cccttgcaag ggaacttccc | 120 |
| atcggcttcg aagacatcaa gattgttgga agctacgacg tggacagagc gaagattgga | 180 |
| aagaaactga gcgaagtggt gaagcagtac tggaacgatg ttgactcgct gacgagtgat | 240 |
| cctgagattc gcaaaggagt acaccttgga agcgtgagga acctccccat cgaagctgaa | 300 |
| ggtctcgaag acagcatgac tctgaaggaa gcagttgata ctctcgtcaa ggaatggaca | 360 |
| gaactcgatc ccgatgtgat cgtgaacacc tgtactacag aagctttcgt gcccttcggg | 420 |
| aacaaagaag atcttctgaa agctatcgaa aacaacgaca agagagact cactgcaact | 480 |
| caggtgtacg cttacgcagc ggcactgtac gcgaacaagc gtggaggagc ggcttttgtg | 540 |
| aacgttattc cgaccttcat agcgaacgac ccggctttcg ttgaactcgc gaaggagaac | 600 |
| aacctcgtcg tttcggaga cgacggtgct accggtgcca caccgttcac agcgacgtt | 660 |
| ctcagccatc ttgcccagag aaacaggtac gtcaaagatg ttgcgcagtt caacatagga | 720 |
| gggaacatgg acttttctggc actcacagac gatggaaaga caagagtaa gaaattcacc | 780 |
| aaatccagta tagtgaagga cattctcggt tacgatgcac cgcattacat aaaacctaca | 840 |
| gggtatcttg aaccacttgg agataaaag ttcatagcca ttcacatcga gtacgtgagt | 900 |
| ttcaacggtg ctacagatga gctcatgata aacggaagaa taaacgacag cccggctctt | 960 |

```
ggaggtctcc ttgttgacct tgtgagactc ggaaagatcg cactcgacag gaaggagttc    1020
ggaacggtct acccagtgaa cgccttctac atgaagaacc cgggaccggc ggaagaaaag    1080
aacatcccaa gaatcattgc ttacgagaag atgagaatct gggcgggatt gaaaccgaag    1140
tggctgtaa                                                            1149

<210> SEQ ID NO 61
<211> LENGTH: 885
<212> TYPE: DNA
<213> ORGANISM: Thermotoga maritima

<400> SEQUENCE: 61
atgttcagag gagtaggaac tgctatcgtt acaccattca aaaatggtga gcttgatctt     60
gagtcttacg agaggcttgt caggtatcag ctcgaaaacg gcgtcaacgc gttgatcgtc    120
cttggaacga caggtgaatc accaaccgtc aacgaagacg agagagaaaa gctcgtttcc    180
agaactctcg agatcgtcga tgggaaaatc cctgtgatcg tgggagcggg aacgaattcc    240
accgaaaaaa cgctgaaact cgtcaagcag gcggaaaaac tcggagcgaa cggagttctt    300
gtggtcaccc cgtattacaa caagcccaca caggaaggac tctatcagca ctacaagtac    360
atctctgaga gaacggatct cgggatcgtt gtttacaacg tgcccggaag aaccggtgtg    420
aacgttctcc cggaaactgc tgcaaggatc gctgcggacc tcaagaacgt ggtgggaata    480
aaagaggcga acccggatat agaccagata gacaggacgg tatcactgac aaaacaggca    540
agaagcgatt tcatggtgtg gtccggcaac gatgatagaa cgttctatct cctctgcgcg    600
ggtggagacg gcgtcatctc tgttgtgtcg aacgtggcac cgaaacagat ggtagaactc    660
tgcgcagagt acttcagcgg aaacctcgaa aaatcgaggg aggttcacag aaaactcaga    720
cctctcatga aggcactgtt cgtggaaaca aatccgatac cagttaaagc cgctttgaat    780
ctcatgggat tcatcgagaa cgagctgaga ctaccgcttg tacctgccag tgaaaagacg    840
gtggaacttc tcagaaacgt tctcaaggag agtggattgc tataa                    885

<210> SEQ ID NO 62
<211> LENGTH: 1032
<212> TYPE: DNA
<213> ORGANISM: Thermotoga maritima

<400> SEQUENCE: 62
atgatcgatc tcaggtccga caccgttaca aaaccaacag aagagatgag aaaagccatg     60
gcacaggctg aggtgggaga cgatgtgtac ggagaagatc caaccatcaa cgaactcgaa    120
aggctcgccg cagagacctt tggaaaggaa gcggctctct ttgtacccct cggcaccatg    180
ggaaatcaag tgagcataat ggctcacacc cagaggggcg atgaagtgat actggaggca    240
gacagccaca tcttctggta cgaggtcgga gccatggcgg ttctctccgg agtcatgccc    300
catcctgtac ctggaaaaaa tggagccatg gaccccgatg atgtgaggaa ggccataaga    360
cccagaaaca tacacttccc cagaacttcg ctcattgcca tcgaaaacac acacaaccgt    420
tccggtggaa gagtggtccc gcttgaaaac ataaaagaga tttgcacgat agccaaagaa    480
cacggcataa acgttcacat agatggtgcg aggatcttca acgcctcaat cgcttcaggt    540
gttcccgtga aggagtacgc cgggtacgcc gattccgtga tgttctgtct ttcaaaaggt    600
ctctgcgcac ccgtcggttc ggtggttgta ggagacaggg acttcataga aagagcgaga    660
aaggcgagaa agatgctcgg tggagggatg agacaggcag tgttctcgc tgccgctgga    720 ataatcgcct tgacaaagat ggtagatcga ttgaaagaag atcatgaaaa cgccagattt    780
```

| | |
|---|---:|
| ctcgccctga agttgaaaga aatagggtac tccgtgaatc ccgaagatgt gaaaccaac | 840 |
| atggtgattc tgaggaccga caacctgaag gtgaacgcgc acgggttcat agaagcgctc | 900 |
| agaaacagcg gggtgctcgc gaacgccgta tccgacacgg agatcagact ggtaacccac | 960 |
| aaagacgttt caagaaacga catagaagag gctctgaaca tcttcgaaaa actcttcaga | 1020 |
| aaattctcct aa | 1032 |

<210> SEQ ID NO 63
<211> LENGTH: 954
<212> TYPE: DNA
<213> ORGANISM: Eschericia coli DH10B

<400> SEQUENCE: 63

| | |
|---|---:|
| atgacggaca aattgacctc ccttcgtcag tacaccaccg tagtggccga cactggggac | 60 |
| atcgcggcaa tgaagctgta tcaaccgcag gatgccacaa ccaacccttc tctcattctt | 120 |
| aacgcagcgc agattccgga ataccgtaag ttgattgatg atgctgtcgc ctgggcgaaa | 180 |
| cagcagagca acgatcgcgc gcagcagatc gtggacgcga ccgacaaact ggcagtaaat | 240 |
| attggtctgg aaatcctgaa actggttccg ggccgtatct caactgaagt tgatgcgcgt | 300 |
| cttttcctatg acaccgaagc gtcaattgcg aaagcaaaac gcctgatcaa actctacaac | 360 |
| gatgctggta ttagcaacga tcgtattctg atcaaactgg cttctacctg caggggtatc | 420 |
| cgtgctgcag aacagctgga aaagaaggc atcaactgta acctgaccct gctgttctcc | 480 |
| ttcgctcagg ctcgtgcttg tgcggaagcg ggcgtgttcc tgatctcgcc gtttgttggc | 540 |
| cgtattcttg actggtacaa agcgaatacc gataagaaag agtacgctcc ggcagaagat | 600 |
| ccgggcgtgg tttctgtatc tgaaatctac cagtactaca aagagcacgg ttatgaaacc | 660 |
| gtggttatgg gcgcaagctt ccgtaacatc ggcgaaattc tggaactggc aggctgcgac | 720 |
| cgtctgacca tcgcaccggc actgctgaaa gagctggcgg agagcgaagg gctatcgaa | 780 |
| cgtaaactgt cttacaccgg cgaagtgaaa gcgcgtccgg cgcgtatcac tgagtccgag | 840 |
| ttcctgtggc agcacaacca ggatccaatg gcagtagata aactggcgga aggtatccgt | 900 |
| aagtttgcta ttgaccagga aaaactggaa aaaatgatcg gcgatctgct gtaa | 954 |

<210> SEQ ID NO 64
<211> LENGTH: 663
<212> TYPE: DNA
<213> ORGANISM: Escherichia coli DH10B

<400> SEQUENCE: 64

| | |
|---|---:|
| atggaactgt atctggatac ttcagacgtt gttgcggtga aggcgctgtc acgtattttt | 60 |
| ccgctggcgg gtgtgaccac taacccaagc attatcgccg cgggtaaaaa accgctggat | 120 |
| gttgtgcttc cgcaacttca tgaagcgatg ggcggtcagg ggcgtctgtt tgcccaggta | 180 |
| atggctacca ctgccgaagg gatggttaat gacgcgctta gctgcgttc tattattgcg | 240 |
| gatatcgtgg tgaaagttcc ggtgaccgcc gaggggctgg cagctattaa gatgttaaaa | 300 |
| gcggaaggga ttccgacgct gggaaccgcg gtatatggcg cagcacaagg gctgctgtcg | 360 |
| gcgctggcag gtgcggaata tgttgcgcct tacgttaatc gtattgatgc tcagggcggt | 420 |
| agcggcattc agactgtgac cgacttacac cagttattga aatgcatgc gccgcaggcg | 480 |
| aaagtgctgg cagcgagttt caaaaccccg cgtcaggcgc tggactgctt actggcagga | 540 |
| tgtgaatcaa ttactctgcc actggatgtg cacaacagaa tgattagcta tccggcggtt | 600 |
| gatgccgctg tggcgaagtt tgagcaggac tggcagggag cgtttggcag aacgtcgatt | 660 |

```
taa                                                                         663
```

<210> SEQ ID NO 65
<211> LENGTH: 1002
<212> TYPE: DNA
<213> ORGANISM: Escherichia coli DH10B

<400> SEQUENCE: 65

```
atgattgatt tacgcagtga taccgttacc cgaccaagcc gcgccatgct cgaagcgatg     60
atggccgccc cggttgggga cgacgtttac ggagacgacc ctaccgttaa tgctctgcag    120
gactacgcag cagagctttc cggtaaagaa gccgccattt ttctgcctac cggcactcag    180
gccaacctgg tcgctctgct cagtcactgc gaacgcggcg aagagtatat tgtcggtcag    240
gccgcgcata actatctgtt tgaagccggt ggcgcggcgg tgctgggcag tattcaaccg    300
caacccatag acgcggctgc cgacggcacg ctaccgctgg ataaagtggc gatgaaaatc    360
aaacccgacg atatccattt cgcccgcacc aaattactca gtctggaaaa cacccacaac    420
ggcaaagtgt tgccgcggga atacctgaaa gaagcatggg aatttacccg cgagcgcaat    480
ctggcgctgc atgttgacgg tgcgcgcatc tttaatgccg tggtggctta cggctgcgaa    540
ctgaaagaga tcacgcaata ttgtgattcg ttcaccattt gcctgtcgaa aggtcttggg    600
acgccagtcg gttcattact cgtcggtaat cgtgattaca ttaaacgtgc cattcgctgg    660
cggaaaatga caggtggcgg gatgcgccag tccggcattc tggctgccgc cgggatatat    720
gccctgaaaa ataacgttgc gcgcttgcag gaagaccacg acaacgctgc ctggatggcg    780
gagcagctgc gtgaagcagg cgcggatgtg atgcgtcagg acaccaatat gctgtttgtt    840
cgcgtcgggg aagaaaatgc tgccgcgtta ggcgaataca tgaaagcgag aaacgtgctg    900
attaacgcct cgccgattgt ccgcctggtg acgcatcttg acgtctcgcg cgaacaactg    960
gcggaagtcg ccgcccactg gcgtgcattc ctggcgcgtt aa                      1002
```

<210> SEQ ID NO 66
<211> LENGTH: 876
<212> TYPE: DNA
<213> ORGANISM: Escherichia coli DH10B

<400> SEQUENCE: 66

```
atggcagatt tagacgatat taaagatggt aaagattttc gtaccgatca accgcaaaaa     60
aatatcccctt ttaccctgaa aggttgcggt gcgctggatt ggggaatgca gtcacgctta    120
tcgcggatat ttaatccgaa aacgggtaaa accgtgatgc tggcttttga ccatggttat    180
tttcagggac cgactaccgg acttgaacgc attgatataa atatcgcccc gctgtttgaa    240
catgccgatg tattaatgtg tacgcgcggc attttgcgca gcgtagttcc ccctgcgacc    300
aataggccgg tggtactgcg ggcgtcaggt gcgaactcta ttctggcgga attaagtaat    360
gaagccgtgg cgttatcgat ggatgacgcc gtgcgcctga acagttgcgc ggtggcggcg    420
caggtttata tcggcagcga atatgaacat cagtcgatca aaaatattat tcagctggtt    480
gatgccggaa tgaaagtggg aatgccgacc atggccgtga ctggcgtggg caaagatatg    540
gtgcgcgatc agcgttattt ctcgctcgcg actcgaatcg ccgctgaaat ggggcgcaa     600
attatcaaaa cctattatgt cgaaaaaggt tttgaacgga ttgttgccgg atgtccggta    660
cccattgtta ttgctggcgg taaaaaatta ccggagcgcg aggcgctgga aatgtgctgg    720
caggctatcg atcagggcgc ttctggtgtg gatatgggc gtaatatttt ccagtctgac    780
catccggtgg cgatgatgaa agccgtacag gcggtggttc accataacga aacggctgat    840
```

-continued

```
cgggcatatg aactctatct gagtgaaaaa cagtaa                             876
```

<210> SEQ ID NO 67
<211> LENGTH: 642
<212> TYPE: DNA
<213> ORGANISM: Escherichia coli DH10B

<400> SEQUENCE: 67

```
atgaaaaact ggaaaacaag tgcagaatca atcctgacca ccggcccggt tgtaccggtt    60
atcgtggtaa aaaaactgga acacgcggtg ccgatggcaa aagcgttggt tgctggtggg   120
gtgcgcgttc tggaagtgac tctgcgtacc gagtgtgcag ttgacgctat ccgtgctatc   180
gccaaagaag tgcctgaagc gattgtgggt gccggtacgg tgctgaatcc acagcagctg   240
gcagaagtca ctgaagcggg tgcacagttc gcaattagcc cgggtctgac cgagccgctg   300
ctgaaagctg ctaccgaagg gactattcct ctgattccgg ggatcagcac tgtttccgaa   360
ctgatgctgg gtatggacta cggttttgaaa gagttcaaat tcttcccggc tgaagctaac   420
ggcggcgtga aagccctgca ggcgatcgcg ggtccgttct cccaggtccg tttctgcccg   480
acgggtggta tttctccggc taactaccgt gactacctgg cgctgaaaag cgtgctgtgc   540
atcggtggtt cctggctggt tccggcagat gcgctggaag cgggcgatta cgaccgcatt   600
actaagctgg cgcgtgaagc tgtagaaggc gctaagctgt aa                     642
```

<210> SEQ ID NO 68
<211> LENGTH: 855
<212> TYPE: DNA
<213> ORGANISM: Escherichia coli DH10B

<400> SEQUENCE: 68

```
atgtacgtgg tatcgacaaa gcagatgctg aacaacgcac agcgcggcgg ttatgcggtt    60
ccggcattca atattcacaa tctcgaaacg atgcaagtgg tggtagaaac cgctgccaac   120
ctgcatgcgc cggtcatcat cgccggaacg cctggcacat ttactcatgc tggtacagaa   180
aatctgttgg cgctggtcag cgcgatggcg aagcaatatc accatccact ggcaattcat   240
ctcgaccatc acacgaaatt tgacgatatc gctcagaagg ttcgttctgg cgtgcgctca   300
gtcatgattg acgcctcgca tttgccttttt gcgcaaaata tttcacgggt caaagaggtg   360
gtggattttt gccatcgctt tgatgtcagc gtcgaggcgg agctggggca acttggcggc   420
caggaagatg atgtgcaagt caatgaagcc gatgcgttgt acaccaaccc cgctcaggcg   480
cgtgaatttg ccgaggcaac cggaattgat tccctggcgg tcgccatcgg cacggctcat   540
gggatgtatg ccagcgcacc ggcgcttgat tttttctagac tggagaacat cgccagtgg   600
gtgaacttac cgctggtgct gcatggcgcg tcagggttat cgactaagga tattcagcaa   660
accatcaaac tggggatatg caaaatcaac gttgcaacgg agctgaaaaa tgccttctcg   720
caggcgttaa aaaattacct gaccgagcac cctgaagcga ccgatccccg ggattatttg   780
cagtcggcta aatccgcaat gcgcgatgtg gtgagcaaag tgattgccga ttgtggctgc   840
gagggcaggg cataa                                                   855
```

<210> SEQ ID NO 69
<211> LENGTH: 1053
<212> TYPE: DNA
<213> ORGANISM: Escherichia coli DH10B

<400> SEQUENCE: 69

```
atgacagata ttgcgcagtt gcttggcaaa gacgccgaca accttttaca gcaccgttgt    60
```

-continued

```
atgacaattc cttctgacca gctttatctc cccggacatg actacgtaga ccgcgtaatg      120
attgacaata atcgcccgcc agcggtgtta cgtaatatgc agacgttgta caacaccggg      180
cgtctggctg gcacaggata tctttctatt ctgccggttg accagggcgt tgagcactct      240
gccggagctt catttgctgc taacccgctc tactttgacc cgaaaaacat tgttgaactg      300
gcgatcgaag cgggctgtaa ctgtgtggcg tcaacttacg gcgtgctggc gtcggtatcg      360
cggcgttatg cgcatcgcat tccattcctc gtcaaactta atcacaacga gacgctaagt      420
tacccgaata cctacgatca aacgctgtat gccagcgtgg agcaggcgtt caacatgggc      480
gcggttgcgg ttggtgcgac tatctatttt ggctcggaag agtcacgtcg ccagattgaa      540
gaaatttctg cggcttttga acgtgcgcac gagctgggta tggtgacagt gctgtgggcc      600
tatttgcgta actccgcctt taagaaagat ggcgttgatt accatgtttc cgccgacctg      660
accggtcagg caaaccatct ggcggcaacc atcggtgcag atatcgtcaa acaaaaaatg      720
gcggaaaata acgcggcta taaagcaatt aattacggtt acaccgacga tcgtgtttac      780
agcaaattga ccagcgaaaa cccgattgat ctggtgcgtt atcagttagc taactgctat      840
atgggtcggg ctgggttgat aaactccggc ggtgctgcgg gcggtgaaac tgacctcagc      900
gatgcagtgc gtactgcggt tatcaacaaa cgcgcaggcg gaatgggggct gattcttgga      960 cgtaaagcgt tcaagaaatc gatggctgac ggcgtgaaac tgattaacgc cgtgcaggac     1020
gtttatctcg atagcaaaat tactatcgcc tga                                  1053
```

<210> SEQ ID NO 70
<211> LENGTH: 804
<212> TYPE: DNA
<213> ORGANISM: Escherichia coli DH10B

<400> SEQUENCE: 70

```
atgaacgcat tattaagcaa tcccttaaa gaacgtttac gcaagggcga agtgcaaatt        60
ggtctgtggt taagctcaac gactgccatat atggcagaaa ttgccgccac ttctggttat      120
gactggttgc tgattgacgg ggagcacgcg ccaaacacca ttcaggatct ttatcatcag      180
ctacaggcgg tagcgcccta tgccagccaa cccgtgatcc gtccggtgga aggcagtaaa      240
ccgctgatta aacaagtcct ggatattggc gcgcaaactc tactgatccc gatggtcgat      300
actgccgaac aggcacgtca ggtggtgtct gccacgcgct atcctcccta cggtgagcgt      360
ggtgtcgggg ccagtgtggc acgggctgcg cgctggggac gcattgagaa ttacatggcg      420
caagttaacg attcgctttg tctgttggtg caggtgaaaa gtaaaacggc actggataac      480
ctggacgaaa tcctcgacgt cgaagggatt gatggcgtgt ttattggacc tgcggatctt      540
tctgcgtcgt tgggctaccc ggataacgcc gggcacccgg aagtgcagcg aattattgaa      600
accagtattc ggcggatccg tgctgcgggt aaagcggctg gttttctggc tgtggctcct      660
gatatggcgc agcaatgcct ggcgtgggga gcgaactttg tcgctgttgg cgttgacacg      720
atgctctaca gcgatgccct ggatcaacga ctggcgatgt ttaaatcagg caaaaatggg      780
ccacgcataa aaggtagtta ttga                                              804
```

<210> SEQ ID NO 71
<211> LENGTH: 363
<212> TYPE: DNA
<213> ORGANISM: Escherichia coli DH10B

<400> SEQUENCE: 71

```
atggcacaac ctgccgctat tattcgtata aagaaccttc gtttgcgtac gtttatcgga       60
```

```
attaaggaag aagaaattaa caaccgtcag gatattgtta tcaatgtgac gatccactac    120
cccgccgata aagcgcgcac tagcgaagat atcaacgatg cgctgaatta tcgcaccgta    180
acgaaaaaca ttattcagca tgtagagaat aaccgtttct ctttgctgga aaaattaact    240
caggatgtgc tcgatatcgc acgtgaacat cactgggtga cgtatgctga agtggagatc    300
gataaactgc acgcgctgcg ctacgccgat tcggtatcca tgaccttaag ctggcagcgt    360
taa                                                                  363
```

<210> SEQ ID NO 72
<211> LENGTH: 951
<212> TYPE: DNA
<213> ORGANISM: Escherichia coli DH10B

<400> SEQUENCE: 72

```
atgaacgagt tagacggcat caaacagttc accactgtcg tggcagacag cggcgatatt     60
gagtccattc gccattatca tccccaggat gccaccacca atccttcgct gttactcaaa    120
gctgccggat tatcacaata tgagcattta atagacgatg ctatcgcctg ggtaaaaaa    180 aatggcaaga cccaggaaca acaggtggtc gcagcgtgtg acaaactggc ggtcaatttc    240
ggtgctgaaa tcctcaaaat cgtacccggt cgcgtgtcaa cagaagttga tgcacgcctc    300
tcttttgata agaaaagag tattgagaag gcgcgccatc tggtggactt gtatcagcaa    360
caaggcgttg agaaatcacg cattctgatc aagctggctt cgacctggga aggaattcgc    420
gcggcagaag agctggaaaa agaaggtatt aactgcaacc tgacgctgct gttttctttt    480
gcacaggcac gggcctgtgc ggaagcaggc gttttctga tttcgccgtt tgtcgggcgt    540
atttatgact ggtatcaggc acgcaagccg atggacccgt atgtggtgga agaagatccg    600
ggcgttaaat cggtgcgcaa tatctacgac tactataagc aacaccacta tgaaaccatt    660
gtgatgggcg cgagcttccg tcgcaccgaa caaatcctcg ccttaaccgg ctgcgatcga    720
ctgactatcg caccgaattt actgaaggag ctgcaggaaa agtttcgcc agtggtacgt    780 aaattaatcc caccttctca gacgttccca cgcccagctc ccatgagcga agcggagttc    840
cgttgggagc acaatcagga tgcgatggcg gtagaaaaac tgtctgaagg cattcgtctg    900
ttcgccgttg atcaacgcaa actggaagat cttcttgccg ccaaactata a              951
```

<210> SEQ ID NO 73
<211> LENGTH: 648
<212> TYPE: DNA
<213> ORGANISM: Escherichia coli DH10B

<400> SEQUENCE: 73

```
atggaacgaa ataaacttgc tcgtcagatt attgacactt gcctggaaat gacccgcctg     60
ggactgaacc aggggacagc ggggaacgtc agtgtacgtt atcaggatgg gatgctgatt    120
acgcctacag gcattccata tgaaaaactg acggagtcgc atattgtctt tattgatggc    180
aacggtaaac atgaggaagg aaagctcccc tcaagcgaat ggcgtttcca tatggcagcc    240
tatcaaagca gaccggatgc caacgcggtt gttcacaatc atgccgttca ttgcacggca    300
gtttccattc ttaaccgatc gatccccgct attcactaca tgattgcggc ggctggcggt    360
aattctattc cttgcgcgcc ttatgcgacc tttggaacac gcgaactttc tgaacatgtt    420
gcgctggctc tcaaaaatcg taaggcaact ttgttacaac atcatgggct tatcgcttgt    480
gaggtgaatc tggaaaaagc gttatggctg gcgcatgaag ttgaagtgct ggcgcaactt    540
tacctgacga ccctggcgat tacggacccg gtgccagtgc tgagcgatga agagattgcc    600
```

```
gtagtgctgg agaaattcaa aacctatggg ttacgaattg aagagtaa             648

<210> SEQ ID NO 74
<211> LENGTH: 1080
<212> TYPE: DNA
<213> ORGANISM: Escherichia coli DH10B

<400> SEQUENCE: 74
atgtctaaga tttttgattt cgtaaaacct ggcgtaatca ctggtgatga cgtacagaaa    60
gttttccagg tagcaaaaga aaacaacttc gcactgccag cagtaaactg cgtcggtact   120
gactccatca acgccgtact ggaaaccgct gctaaagtta aagcgccggt tatcgttcag   180
ttctccaacg gtggtgcttc ctttatcgct ggtaaaggcg tgaaatctga cgttccgcag   240
ggtgctgcta tcctgggcgc gatctctggt gcgcatcacg ttcaccagat ggctgaacat   300
tatggtgttc cggttatcct gcacactgac cactgcgcga agaaactgct gccgtggatc   360
gacggtctgt tggacgcggg tgaaaaacac ttcgcagcta ccggtaagcc gctgttctct   420
tctcacatga tcgacctgtc tgaagaatct ctgcaagaga acatcgaaat ctgctctaaa   480
tacctggagc gcatgtccaa aatcggcatg actctggaaa tcgaactggg ttgcaccggt   540
ggtgaagaag acggcgtgga caacagccac atggacgctt ctgcactgta cacccagccg   600
gaagacgttg attacgcata caccgaactg agcaaaatca gccgcgtttt caccatcgca   660
gcgtccttcg gtaacgtaca cggtgtttac aagccgggta acgtggttct gactccgacc   720
atcctgcgtg attctcagga atatgtttcc aagaaacaca acctgccgca aacagcctg    780 aacttcgtat tccacggtgg ttccggttct actgctcagg aaatcaaaga ctccgtaagc   840
tacggcgtag taaaaatgaa catcgatacc gatacccaat gggcaacctg ggaaggcgtt   900
ctgaactact acaaagcgaa cgaagcttat ctgcagggtc agctgggtaa cccgaaaggc   960
gaagatcagc cgaacaagaa atactacgat ccgcgcgtat ggctgcgtgc cggtcagact  1020
tcgatgatcg ctcgtctgga gaaagcattc caggaactga cgcgatcga cgttctgtaa  1080

<210> SEQ ID NO 75
<211> LENGTH: 369
<212> TYPE: DNA
<213> ORGANISM: Escherichia coli DH10B

<400> SEQUENCE: 75
atggatattg tatttataga gcaactttcg gtaatcacca ctattggtgt ttacgactgg    60
gaacagacca tcgaacagaa gttagtgttc gatatcgaaa tggcgtggga taaccgtaaa   120
gcggcgaaaa gtgatgatgt ggcggattgc ctcagttacg ctgacattgc agaaacggtg   180
gtcagccacg tcgaggggc gcgttttgcg ctggtggaac gcgtggctga agaggtggcg   240
gagctgctgt tagcacgctt caactcgccg tgggtgcgta tcaaactcag caagccaggc   300
gcagtggcgc gggcggcgaa tgttggcgta atcattgagc gtggcaataa tctgaaagaa   360
aataattaa                                                          369

<210> SEQ ID NO 76
<211> LENGTH: 771
<212> TYPE: DNA
<213> ORGANISM: Escherichia coli DH10B

<400> SEQUENCE: 76
atgaataacg atgttttccc gaataaattc aaagccgcac tggctgcgaa acaggtacaa    60
attggttgct ggtcagcact ctctaacccg attagcactg aagttcttgg tttggctggg   120
```

| | |
|---|---|
| tttgactggc tggtgctgga tggcgaacat gcgccaaacg atatctccac gtttattccg | 180 |
| cagttaatgg ccttgaaagg cagcgccagc gcgccagtag tgcgagtgcc gaccaacgag | 240 |
| ccggtaatta ttaagcgtct tctggatatc ggtttctata acttcctgat tccttttgta | 300 |
| gaaacaaaag aggaagcaga gctggcggtg gcatcaaccc gttacccacc ggaaggcatt | 360 |
| cgcggcgtct ccgtttctca ccgcgccaat atgtttggca ccgtggcgga ttatttcgct | 420 |
| cagtcgaaca gaacatcac tattctggtc cagatagaaa gtcagcaggg cgtagataac | 480 |
| gtcgatgcca ttgccgctac cgaaggcgta gacggcatct tcgtcggccc cagcgatctg | 540 |
| gccgcggcat taggccatct cggcaatgca tcacacccgg atgtacaaaa agcaattcag | 600 |
| cacattttta accgtgccag cgcgcacggc aaacccagcg gtatcctcgc gccggtcgaa | 660 |
| gccgatgcgc gtcgttatct ggaatggggc gcgacgtttg tggctgtcgg cagcgatctc | 720 |
| ggcgtcttcc gctctgccac tcagaaactg gctgatacct ttaaaaaata a | 771 |

<210> SEQ ID NO 77
<211> LENGTH: 1281
<212> TYPE: DNA
<213> ORGANISM: Escherichia coli DH10B

<400> SEQUENCE: 77

| | |
|---|---|
| atgaaacatc tgacagaaat ggtgagacag cacaaagcgg gcaaaacaaa tggaatttat | 60 |
| gccgtttgtt ccgcacatcc gctggtgctg gaagctgcaa tccgctacgc cagtgcaaac | 120 |
| caaacgccgt tactgattga agcaacctcc aatcaggtag accagttcgg cggttatacc | 180 |
| ggaatgacgc ccgccgattt tcgcggcttt gtttgtcagc tcgccgactc gttgaatttc | 240 |
| ccgcaggatg cgttgattct gggtggtgac catctgggc caaaccgctg gcaaaacctg | 300 |
| ccggccgctc aggcaatggc caatgccgat gatttgatta aaagctacgt tgcggcagga | 360 |
| ttcaaaaaaa tccaccttga ttgcagcatg tcctgtcagg acgatccgat tcccttaact | 420 |
| gatgacatcg tggctgaacg cgccgcccgt ctggcgaaag tggcggaaga aacctgtctt | 480 |
| gaacactttg gcgaagccga tctggagtat gtcattggta ccgaagtgcc ggtacctggc | 540 |
| ggcgcgcatg aaaccttaag cgagctggcg gtcaccacgc cggatgccgc ccgcgccacg | 600 |
| ctggaagccc atcgtcacgc ctttgaaaag caaggtttga atgccatctg ccacgcatc | 660 |
| attgccctgg tggttcaacc cggcgtcgaa ttcgatcaca ccaacgttat tgattatcag | 720 |
| cccgccaaag cgagcgcctt aagccagatg gtcgaaaact acgaaacgct gattttcgaa | 780 |
| gcgcactcta ccgattatca aacgccgcaa tcgctgcgcc agctggtgat tgaccacttt | 840 |
| gccattctga agttggccc agcgctgacc ttcgccctgc gtgaagctct gttctctctg | 900 |
| gcggcgattg aagaagaact ggtgccagcg aaagcctgtt ctggtctgcg tcaggtgctg | 960 |
| gaagacgtga tgctcgaccg cccggaatac tggcaaagcc actaccacgg tgacggcaac | 1020 |
| gcgcgtcgtc tggcgcgtgg ttatagctac tcggatcgcg tgcgctatta ctggccggac | 1080 |
| agccagattg atgacgcttt cgctcatctg gtacgtaatc tggcggattc accaattccg | 1140 |
| ctgccgctga tcagccagta tctgccgctg cagtacgtga agttcgctc cggcgagctg | 1200 |
| cagccaacgc cacgggaact cattatcaac catattcagg acatcctggc gcagtaccac | 1260 |
| acagcctgtg aaggccaata a | 1281 |

<210> SEQ ID NO 78
<211> LENGTH: 861
<212> TYPE: DNA
<213> ORGANISM: Escherichia coli DH10B

```
<400> SEQUENCE: 78
atgagcatta tctccactaa atatctgtta caggacgccc aggccaatgg ctacgcggtg      60
cctgctttta acattcataa cgccgagacg atccaagcga tcctcgaagt gtgcagtgaa     120
atgcgatcgc cggtgatcct cgccggaacg ccggggacct ttaaacacat cgcgctggaa     180
gagatctacg ccctgtgtag cgcctattcc acaacctaca acatgccact ggcgctgcat     240
ctcgaccacc acgaatcgct ggatgatatt cgccgtaaag tccacgcagg tgtgcgcagt     300
gcgatgatcg acggcagcca cttcccgttt gccgagaacg tgaagctggt gaaatcggtt     360
gttgacttct gccactcaca agattgcagc gtggaagcag aactgggccg cctgggcggt     420
gttgaagatg acatgagcgt tgacgccgaa agtgcattcc tgaccgatcc acaagaagct     480
aaacgctttg tcgaactgac tggcgtcgac agcctggcgg tagcgattgg tacggcgcac     540
ggcttataca gcaaaacgcc gaagattgat ttccagcggc tggcggaaat cgtgaagtg      600 gtggatgttc ctctggtgct gcatggtgcc agcgatgttc cggatgaatt tgtccgtcgc     660
actattgaac ttggcgtcac aaaagtgaac gttgccacag aattaaaaat agccttcgct     720
ggcgcggtta aagcctggtt tgcggaaaat ccgcagggta atgatcctcg ttattatatg     780
cgcgtcggaa tggatgcgat gaaagaagtt gtcagaaata aaattaatgt ctgtggttca     840
gcgaatcgaa tttcagcata a                                               861

<210> SEQ ID NO 79
<211> LENGTH: 879
<212> TYPE: DNA
<213> ORGANISM: Escherichia coli DH10B

<400> SEQUENCE: 79
atgaataagt acaccatcaa cgacattacg cgcgcatcgg gcggttttgc catgctggcg      60
gtcgatcagc gcgaagccat gcgcatgatg tttgccgcgg ctgggcacc cgctccggta     120 gccgatagcg ttttaactga tttcaaagtt aacgctgcaa aggccctctc gccttatgcc     180
tcggcgattc tggtagatca acaattctgc taccgccagg tggttgagca aaacgcgatt     240
gccaaaagtt gcgccatgat tgtcgccgcc gatgagttca ttcctggcaa cggtattccg     300
gtcgatagcg tggttattga ccgcaaaatc aatccgctac agatcaaaca agacggtggc     360
aaagccttaa aactgctggt gctgtggcgt agtgatgaag atgcgcagca acgtctggat     420
atggtgaaag agttcaacga actgtgccac tcacacggtc tggtaagcat cattgagcca     480
gtcgtccgcc caccgcgtcg tggcgataaa ttcgatcgcg aacaagcgat catcgatgcc     540
gccaaagagc tgggcgacag tggcgctgac ctctacaaag ttgaaatgcc gctttatggc     600
aaaggtccgc aacaagagct tctctgtgct tcacaacgtc tgaatgacca tatcaatatg     660
ccatgggtga tcctctcttc cggtgtcgac gaaaaactgt tcccgcgtgc cgtacgcgtg     720
gcaatgacgg cgggcgcatc gggattcctg gcaggccgtg cagtctgggc atcggtcgtc     780
ggtttaccag acaacgagct gatgctgcgt gacgtttgcg caccgaaatt acaacaactt     840
ggcgatatcg tcgacgaaat gatggctaaa cgccgctaa                           879

<210> SEQ ID NO 80
<211> LENGTH: 825
<212> TYPE: DNA
<213> ORGANISM: Escherichia coli DH10B

<400> SEQUENCE: 80
atgcaaaaca ttactcagtc ctggtttgtc cagggaatga tcaaagccac caccgacgcc      60
```

-continued

```
tggctgaaag gctgggatga gcgcaacggc ggcaacctga cgctacgcct ggatgacgcc    120
gatatcgcac catatcacga caatttccac caacaaccgc gctatatccc gctcagccag    180
cccatgcctt tactggcaaa tacaccgttt attgtcaccg gctcgggcaa attcttccgt    240
aacgtccagc ttgatcctgc ggctaactta ggcatcgtaa aagtcgacag cgacggcgcg    300
ggctaccaca ttctttgggg gttaaccaac gaagccgtcc ccacttccga acttccggct    360
cacttccttt cccactgcga gcgcattaaa gccaccaacg gcaaagatcg ggtgatcatg    420
cactgccacg ccaccaacct gatcgccctc acctatgtac ttgaaaacga caccgcggtc    480
ttcactcgcc aactgtggga aggcagcacc gagtgtctgg tggtattccc ggatggcgtt    540
ggcattttgc cgtggatggt gcccggcacg gacgaaatcg gccaggcgac cgcacaagag    600
atgcaaaaac attcgctggt gttgtggccc ttccacggcg tcttcggcag cggaccgacg    660
ctggatgaaa ccttcggttt aatcgacacc gcagaaaaat cagcacaagt attagtgaag    720
gtttattcga tgggcggcat gaaacagacc atcagccgtg aagagttgat agcgctcggc    780
aagcgtttcg gcgttacgcc actcgccagt gcgctggcgc tgtaa                    825
```

<210> SEQ ID NO 81
<211> LENGTH: 663
<212> TYPE: DNA
<213> ORGANISM: Escherichia coli DH10B

<400> SEQUENCE: 81

```
atggaactgt atctggacac cgctaacgtc gcagaagtcg aacgtctggc acgcatattc     60
cccattgccg gggtgacaac taacccgagc attatcgctg ccagcaagga gtccatatgg    120
gaagtgctgc cgcgtctgca aaaagcgatt ggtgatgagg gcattctgtt tgctcagacc    180
atgagccgcg acgcgcaggg gatggtggaa gaagcgaagc gcctgcgcga cgctattccg    240
ggtattgtgg tgaaaatccc ggtgacttcc gaaggtctgg cagcaattaa aatactgaaa    300
aaagagggta ttactacact tggcactgct gtatatagcg ccgcacaagg gttattagcc    360
gcactggcag gggcaaaata cgttgctccg tatgttaacc gcgtagatgc ccagggcgga    420
gacggcattc gtacggttca ggagctgcaa acgcgttag aaatgcacgc gccagaaagc    480
atggtgctgg cagccagctt taaaacgccg cgtcaggcgc tggactgttt actggcagga    540
tgtgaatcca tcaccctgcc cttagatgta gcgcaacaaa tgctcaacac ccctgcggta    600
gagtcagcta tagagaagtt cgaacacgac tggaatgccg catttggcac tactcatctc    660
taa                                                                  663
```

<210> SEQ ID NO 82
<211> LENGTH: 780
<212> TYPE: DNA
<213> ORGANISM: Escherichia coli DH10B

<400> SEQUENCE: 82

```
atgactgatc tgaaagcaag cagcctgcgt gcactgaaat tgatggacct gaccaccctg     60
aatgacgacg acaccgacga gaaagtgatc gccctgtgtc atcaggccaa aactccggtc    120
ggcaataccg ccgctatctg tatctatcct cgctttatcc cgattgctcg caaaactctg    180
aaagagcagg gcaccccgga aatccgtatc gctacggtaa ccaacttccc acacggtaac    240
gacgacatcg acatcgcgct ggcagaaacc cgtgcggcaa tcgcctacgg tgctgatgaa    300
gttgacgttg tgttcccgta ccgcgcgctg atggcgggta acgagcaggt tggttttgac    360
ctggtgaaag cctgtaaaga ggcttgcgcg gcagcgaatg tactgctgaa agtgatcatc    420
```

```
gaaaccggcg aactgaaaga cgaagcgctg atccgtaaag cgtctgaaat ctccatcaaa      480
gcgggtgcgg acttcatcaa aacctctacc ggtaaagtgg ctgtgaacgc gacgccggaa      540
agcgcgcgca tcatgatgga agtgatccgt gatatgggcg tagaaaaaac cgttggtttc      600
aaaccggcgg cgggcgtgcg tactgcggaa gatgcgcaga aatatctcgc cattgcagat      660
gaactgttcg gtgctgactg ggcagatgcg cgtcactacc gctttggcgc ttccagcctg      720
ctggcaagcc tgctgaaagc gctgggtcac ggcgacggta agagcgccag cagctactaa      780

<210> SEQ ID NO 83
<211> LENGTH: 963
<212> TYPE: DNA
<213> ORGANISM: Pseudomonas putida

<400> SEQUENCE: 83
gtgaaggcat tgcaaggcgt tgacggacat gtggagtggg tcgaggccga acgcccgacc       60
tgtgacgcgg gccaagtgcg cattcgcgtg gccgctgcgg ggctgaaccg cgccgacctg      120
ctgcagatga aggtttgta cccgccacca ccaggtgcca gcccatacat ggggctggag      180
tgttccgggg tggttgaaga ggtggggggct ggtgccgcct ggcgcgtggg tgaccgcgtt      240
tgcgccctgc tggccagcgg cgccatggcc gaggaagtgg tggtcgatgc ccgtcacgta      300
ttgccggtac ccgaaggcct tggcctgcat gaggcggcag cgttgccgga ggtgtatgcc      360
accgcctggc tgaacatctt ccagctcggt gcagtgaagg ctggcgagaa ggtgctggtg      420
cacgccggcg ccagtggcgt tggctcggcc gccatccagc tgtgcaaggc gttcggcagc      480
ccggtatggg tcagcgtcgg ttcgcaggac cgcttggcct actgccaggc gctgggcgct      540
gcgggtggtg tggtacgtaa cgagaacctg gacgcgctgg aaggttttgg cccgttcgat      600
gtgattctcg accggtggg cgccagctac ggtgagctga acctcaagct gctggcccgt      660
gacgggcgct gggtgatcat cggcctgatg ggcggacgca agttcgagct ggacctggcc      720
caagtgctgg gcaagcgtct ggaaattacc ggttccaccc tgcgcaaccg tgatgacggc      780
ttcaaggccg agctgttgcg cgaactgcag cagcaagtat ggccgctgtt cgccgagggg      840
cggttgtcgc cgcagctggt cgacacctat ccggtggagt ttgcccaggc ggcgtatgcc      900
gagctggaga ccaaccaggt gtcgggcaag ctggtgatgg tgatcgaccc tagcctggtg      960
taa                                                                     963

<210> SEQ ID NO 84
<211> LENGTH: 1002
<212> TYPE: DNA
<213> ORGANISM: Pseudomonas putida

<400> SEQUENCE: 84
atgacccaga ccaaccgccg cttcctgctt gccaaacgcc cggtcggcgc cgtgcgccgt       60
gacgacttca gcttcgagac cgtacccgcc gaacaacccg cgaaggcca ggtactggtg      120 cgcaacctgt acctgtcgct ggacccggcc atgcgcggct ggatgaacga aggcaagtcc      180
tacatcccgc ccgtggccct gggccaggta atgcgtgcgc tgggtgtagg tgaagtggtt      240
gcctccaatc accccggcta ccagcccggc gaccatgtga gcggcgccct cggtgtgcag      300
gactacttca ccggcgagcc ccagggcctg cacaagatcg accccaagct ggccccctg      360 ccccgttacc tgtcagcctt gggcatgacc ggcatgaccg cctacttcgc cctgctggag      420
gttggccaac ccaaagctgg cgacaccgtg gtcatttccg gcgcggccgg tcggtgggc      480 agcattgtcg ggcagattgc caagatcaaa ggctgccgcg tggtcggcat tgccggcggt      540
```

```
gccgagaagt gccagtacct gaaggacgag ctgggctttg acggcgtgat cgactacaag    600
gccgaagacg tgctggccgg cctgaagcgc gaatgcccca aaggcgtgga cgtgtacttc    660
gacaacgtgg cggcgatat cctcgatgcc gtgctgacgc gcatcaactt caaggcacgc    720
attgtgattt gcgcgcgcat cagccagtac aacaacaaag aagcggtgaa aggcccggcc    780
aactacctgt cgctgctggt gaaccgcgcg cgcatggaag ttttgtggt gatggattac     840 accaaggact acggcaaggc cgcgcaggaa attgccggct ggttggccaa tggtcaggtg    900
aagagcaaag aggatgtggt ggaagggctg gaaaccttcc cggagacctt gttgaagctg    960
ttcagcgggg agaattttgg caagttggtg ttgaaggttt aa                      1002

<210> SEQ ID NO 85
<211> LENGTH: 1164
<212> TYPE: DNA
<213> ORGANISM: Pseudomonas putida

<400> SEQUENCE: 85
atgcagcctt tcagctttgc caccactgcg cagatcctct gcgaacccgg cgcggtgcag     60
cgccttgcag gtctgtgccg tgagcgcggt gccaagcgtg ttttgattat cagtgacccg    120
ggtatcgccc gccttggcat gctcgatgac ctgctgccgg ggttcacggc agccaaggtc    180
ggtgtggcga tcttcagtga ggttacggcc gaccccagcg aggcatgcgt gctggcggcc    240
gcccagcgcg cccggcatat cggcgccgac ctggtggtgg ggttcggcgg cggcagctcg    300
atggatgtgg ccaagctggt tgcgctgctg gcccaccgcg attgttcgca gcccatcgcc    360
gagctgtacg gcatcgacag ggccaagggc cgccggctgc cgttgatcca ggtgcccacc    420
acggcaggta ccggttcgga ggtgacgccg atcgccatcg tcaccaccgg cgccaccacc    480
aagatgggca ttgtttcgcc gctgctgttg ccagacctgg cagtgctcga cgccgtctgc    540
accctcggcc tgccatcggc ggtgactgct gctaccggta tcgatgccat ggtgcatgcc    600
atcgaagcct ataccagccg cctcaaacgt aaccgctgt ccagcctgct ggcccgtgag    660
gcgctgcggc tgctgcggga taaccttgac caggctgtgc acaacggcgg caacctgcag    720 gccgccagg ccatgctgtt ggggcttgc ctggccggcc aggcctttgc caatgcaccg     780
gtggcggcgg tgcatgccct ggcctatccg ctgggtgggc actttcatgt tccccatggc    840
ctggccaacg cgctggtgtt gccgcatgtg ctgcgcttca acctgccggt ggcggcagtg    900
gactacgccg aattggccgt gccgctgttg ggggcccgtt tgcagcccgg tgatcagcgc    960
cagcaggcag aacaattcgt ggccgagctg gccgcgctga gcagccgctg cgggttacct   1020
gaccgcctgc gcgacgccga tgtaccgcgt catcggcttg gccagctggc cgaagacgcg   1080
atgcaacagc agcgccttt ggtcaataac ccgcgtgaag tcacccaggc cgatgcgttg    1140
gccatctatg aggcagccta ctga                                          1164

<210> SEQ ID NO 86
<211> LENGTH: 1035
<212> TYPE: DNA
<213> ORGANISM: Pseudomonas putida

<400> SEQUENCE: 86
atgccccaat caaagctaat caatcggcgc gtcgttctgg cctcacgtcc ccacggtgcg     60
cctctcgaag cgaattttcg cattgagcaa agccccattc ctgagccagc agaagggcag    120
gttctgttgc gtaccgttta cctctcactt gaccccttaca tgcgtggtcg catgagtgat    180
gcaccgtcct atgctgcgcc ggtggaaatc ggtggagtga ttgtgggtgg cactgtatgc    240
```

```
cgtgtggagg cttcgaaaaa cccggcctac aaggtcggtg actgggtgct gtcctttgct      300
ggctggcagg actacacgct gtccgatgga agcgatctga ccgcgttggg tgagtcgccg      360
gcgcatcctt cttatgcctt gggcatcttt ggcatgccgg gcttcaccgc ttatatgggc      420
ttgctcgata ttggccggcc gcaggcgggt gaaaccctgg tggtggcggc ggccaccggg      480
ccggtcggcg cgactgtggg gcagatcggc aagatcaagg gctgccatgt ggtcggtgtc      540
gccggtggcg cggaaaaatg ccggcatgcg gtcgaggtgc tgggttttga tgcctgtcta      600
gatcaccgtg cgccggactt cgccgagcaa ctggccaagg cctgcccggc aggtatcgac      660
atctacttcg agaatgtcgg cggcaaggtc ttcgatgcgg tgctgccgct gctcaatacc      720
aaggcccgag tgcccgtctg cggcattatt gcgcactaca acgataccgc tttacccaac      780
gggccagatc gtttgcctgc tttgatgggc agcattctgc gcaagcgtat tcatgtgcag      840
ggtttcatta ttttttgatga ttacggccac cgctacaacg agttctttaa cgatatgtcg      900
agctggtttg cgcagggccg gattaaatac cgtgaagaat tagtgagtgg tctggaggag      960
gcgcctaagg cctttatcgg cctgctcgag gggcgaaatt ttggcaagtt agtggttcgc     1020
gtcagtgagg actga                                                     1035

<210> SEQ ID NO 87
<211> LENGTH: 1143
<212> TYPE: DNA
<213> ORGANISM: Pseudomonas putida

<400> SEQUENCE: 87
atgtccctga tcaactacat cacccagatc caattcgata tcggtgccat cgcctgcctg       60
cctgccgaat gtgagcgcat tggtataacc aggcctttga tcgtgaccga ccgtggcgtg      120
cgtgccgccg gtatcgtcga tacggcgttg aacaccttcg gcagcgacac cacacaactg      180
ccgatctacg acgtacgcc acccaacccc aacgagcatg ccgtgcgtga ggccgtggcc      240
atgttcaagg caaatggctg tgatggcatc atcgccattg tggtggctc ggcgatcgac      300 ctggccaagg gggtggccgt gtgtgcccgg cacgacggcc cgttgaagag ctttgcggtg      360
atcgagggcg gcctggcccg gatcacccg gcaaccgcgc cggtgattgc ggtgccgacc      420
acggccggca cggggagcga ggtcgggcgc ggtgccatcc tgatactcga tgacgggcgc      480
aaggtggggg tgatctcgcc ccatgtggtg cccaaggccg ccatctgtga cccgtcattg      540
accctcgggc tgccggcaca actcacggct gccaccggca tggacgcgat tgcccactgc      600
ctggaaacct tcatggcacc tgcgttcaac ccgcctgccg acggcattgc cctggacggc      660
ctgtggaggg cctggcgctt catcgaacga gccacccgcg cgccgggcaa cctggacggg      720
cgcatcaaca tgatgagcgc atcgctgcaa ggtgcgctgg ccttccagaa aggcctgggc      780
tgcgtgcaca gccttagcca cgcgctgggc gggatcaacc gcgcctgca ccacggcacc      840 ctcaatgcga tcttcctgcc tgccgtcatc cgcttcaacc gcacggccga aacggtggtg      900
aatgaacaca gatgcaacg catcgcccag gcgatggggc tggccgatga cagccagatc      960
gaagatgcca ttcgccacat gacccgtacg ctgggcctgc cgaccggcct tggcgaactg     1020
gatgtcaacc cggacctgtt cccgcgcatc gtccagggtg cgttggccga tcacagccac     1080
cgcaccaacc cgcgtgaggc atctgccgag gactaccagt ggctgcttga agcgtcgatg     1140
taa                                                                  1143

<210> SEQ ID NO 88
<211> LENGTH: 1164
<212> TYPE: DNA
```

<213> ORGANISM: Pseudomonas putida

<400> SEQUENCE: 88

```
atgagccaga gtttcagccc ccttcgcaag ttcgtatcgc ctgaaatcat ctttggtgcc      60
ggctgccggc acaatgtggc caattacgcc aaaaccttcg gtgcgcgcaa ggtactggtg     120
gtcagcgacc ctggcgtgat cgccgccggc tgggtggcgg atgtggaggc cagcctgcag     180
gcccagggta tcgactactg cctgtacaca gcggtgtcac ccaacccgcg ggtcgaggag     240
gtgatgctcg gcgccgagat ctatcggcag aaccactgtg acgtgatcgt cgccgtcggt     300
ggcggcagcc cgatggattg cggcaaggcc atcggtatcg tggtggccca tgggcgcagc     360
atcctcgaat tcgaaggcgt ggacatgatc cgcgtgccca gcccgccgct gatcctgatc     420
ccgaccaccg ccggcaccct cggcggacgt gtcgcagttc gtgatcatttc caaccagcag     480
gaacgcatga agttctccat cgtcagcaag gcggtggtgc cggacgtgtc gctgatcgac     540
ccgcagacca ccctgagcat ggacccgttc ctgtcggcct gcaccggcat cgatgcgttg     600
gtgcatgcca tcgaggcctt cgtgtctacc ggccacgggc cgctgaccga ccccatgcg     660
ctggaagcca tgcgcctgat caatggcaac ctggtggaga tgatcgccaa ccctactgat     720
attgcgctgc gcgagaagat catgctcggc agcatgcagg cggggctggc gttctccaat     780
gcgatcctgg gcgcagtgca cgccatgtcg cacagcctgg gcggcttcct cgacttgccc     840
catggcttgt gcaacgcggt gctggtggag cacgtggtgg cgttcaacta cagctcggcg     900
ccggagcgtt tcaaggtgat cgccgagtg tttggtatcg actgccgcgg tctcaatcac     960
cggcagatct gcgggcggct ggtggagcac ctgattgccc tgaagcgtgc catcggcttc    1020
catgaaaccc tgggcctgca cggggtgcgc acgtctgata tcccgttcct gtcgcaacac    1080
gcgatggacg acccgtgcat cctcaccaac ccccgtgcgt ccagccagcg tgatgtcgag    1140
gtggtctatg gcgaggccct ctga                                            1164
```

<210> SEQ ID NO 89
<211> LENGTH: 1023
<212> TYPE: DNA
<213> ORGANISM: Pseudomonas putida

<400> SEQUENCE: 89

```
atgtcccgca tgatccgttt ccacaagttt ggcgctgccg acgtgctccg ttgcgaagag      60
caggccgaac cgtcacccgc tgccgacgag gtgcagatcc gcgtcgaagc ggttggcgtc     120
agctggtatg acgtgctgtg cgccagaat ctggcaccgt cccaggcgcg tctgccagcg     180
gggatcggtc acgaaatggc aggggtggtg actgcggttg gtgaagggt cgatgatatt     240
gccgtcggtg accgggtcgc cagcttcccg gccaccagtg ccaacgacca cccggtgtac     300
ggcgatgtca tcgtactgcc ccgtacagcc atcacgcgct acccgaatgt gctcacccg     360
atcgaggcca gcgtgcacta cacccccgctg ctgatcgcct atttcgccta cgtcgacctg     420
gcacgtgcca aggccgggca gacagcactg gtcaccgatg ccagccattg cgccgggcct     480
gccttcgtgc agctgggcag ggccctgggg ctgaaagtgt cgccgccac caaggaagcg     540
gcgcagcgtg actacctgct gggcttgggc gcagacaaag tgatcgtcac cgaagagcaa    600
gacctgctgc tgcagattgg caagtacacc gatggccgtg tgtgacat ggtgctcgac     660
ggcatgggcg gcccgcagat gtcactgttg gtgatgtgc tggcgccgcg tggcagcctg     720
gtgctgtacg gtctgcaagg cggcaaccag acgccgttcc cggcttgcgc ggcattccag     780
aagaacattc agttctatgt gcactgcatc ggtaatttca ccggcaagcc agagcttggc     840
```

| | | |
|---|---|---|
| atcagccagg accaggtggc gctgcagcgt gccttgcgcg atatcaacca gttcacggcc | 900 | |
| gaccagctgc tgacaccgca gatcatcaag gtgtacccgt tcgagcaggt ggtcgaggcg | 960 | |
| catcgttaca tggaccaatg cccgtgcggc gggcgcgtcg tgctggacat ggcgcaacac | 1020 | |
| tga | 1023 | |

<210> SEQ ID NO 90
<211> LENGTH: 1008
<212> TYPE: DNA
<213> ORGANISM: Pseudomonas putida

<400> SEQUENCE: 90

| | |
|---|---|
| atgaaagcga tcagtttcat ccacaaaggc ttgcctatcg aagaccctgc gtctctccag | 60 |
| gacatcttca tgcccaagcc cagccctggg cccaggacc ttctggtcga ggtcaaagcc | 120 |
| gtgtcggtca accccgtaga caccaaggta cgcgcgggaa ctttcacggg agagccgaaa | 180 |
| atactcggct gggacgcggc cggtgtcgac cgcgaagtcg ggcgccaggt gaccctgttc | 240 |
| aagcccggag accaggtgta ctacgccggc tccatcgcca ggcccggcag ctacagcgaa | 300 |
| tatcacctgg ttgacgaacg catcgtcggg catcaaccgc gtagcctggg tgcagcacag | 360 |
| gcagccgcgc tgccgctgac ggccatcacc gcctgggaac tgctgttcga tcgcctgggg | 420 |
| atcgcggagg gcggcgggga gggcgatgcc ctgctgatcg ttggcgctgc cggtggcgtc | 480 |
| ggttcgatgc tggtgcagtt ggcccggcaa ctgacccgct tgacggttat cggcacggcc | 540 |
| tcccgcgccg agaccagcaa ctgggtacgc gaactgggcg cccatcacgt catcgatcac | 600 |
| agtgcgccgc tgcaagggca gctgcaggcc ttggggatcg agtcggtcag ccatgtcgcc | 660 |
| agccttaccc atactgatca acactttgcg caactggttg aagtgctgcg accacaaggt | 720 |
| cgcctgggcg tgatcgacga cccgcagacc ctggacgtca tgccgctcaa gcgcaagtcg | 780 |
| ctgtcgctgc actgggagct gatgttcacc cgctcgcttt acgaaaccga cgacatggtg | 840 |
| cgccagcacg agctgctcga gcgcgtggcc gggctgatcg atcaaggcac cctgcgtacc | 900 |
| accttgggcg agcatttcgg cgccatcaat gccgccaaca tgcgccgtgc ccatgcgctg | 960 |
| gtcgagagtg gcaaggcgcg cggcaagatc gtcctggaag gcttctga | 1008 |

<210> SEQ ID NO 91
<211> LENGTH: 1002
<212> TYPE: DNA
<213> ORGANISM: Pseudomonas putida

<400> SEQUENCE: 91

| | |
|---|---|
| atgaatcaga ccatgcttgc cgctatcgcc gaatccgccc agaccccgct ggtcgtgcgc | 60 |
| cacatcgccc gccctgtgcc cggtaagggg caggttttgg tgcggattca cgccgccggg | 120 |
| gtcaacccgc tcgacaccaa gattgcaatc ggtgcgggtg ctcacgcccg ccaggagttg | 180 |
| ccggccgtgc tcgcctgga tctcgccggt acggtcgtcg aactgggcga ggcagttgat | 240 |
| ggcttcacgc ctggccagga ggtcttcggc atggccggcg gaatcggcgg cgcccaaggc | 300 |
| accctggccg aatacatcgc cgtggatgcc aggctgattg catcaaagcc gcatgcactc | 360 |
| ggcatgcgtg aggctgccgc gctgccgttg gtattcatca ccgcctggga aggtttggta | 420 |
| gatcacgcaa atgttcgtag tggtcagcgt gtgctgattc atggcggcgc aggtggcgtc | 480 |
| ggccaagttg cggtgcaatt ggccaaggct cgaggtgccg aagtctacgc caccggctcc | 540 |
| gcgggcagtc tagacttcat tcgctcgctg ggggccacgg caattgacta tcaggcgcag | 600 |
| ggtgtagagg cctatgtcga acaatatacg gccggggaag gtttcgacat cgtttatgac | 660 |

```
accgtcggcg gcagcacgtt ggacgcgtca ttcaaggcag taaagcctta taccgggcac    720
gtactcagct gcctcggttg gggccagcac agtctcgcgc ctttatcctt caaaagtgcc    780
acctactcgg gcgtatttac cctggcaccg ctgctaaccg gcaagggacg cgaacaccat    840
ggaagtatcc tgcgcgaggc tgccgttctg gccaatgccg gcaactggc gatccgggtg     900 gacccgcaac agtttgcatt ggatgaggtc aacgacgcat tccgacaggt cgccgaaggt    960
cgcggcaggg gcaagacggt tatccagttg ataagtgaat ag                       1002

<210> SEQ ID NO 92
<211> LENGTH: 1017
<212> TYPE: DNA
<213> ORGANISM: Pseudomonas putida

<400> SEQUENCE: 92
atgatgaata gccgaatcat gcaagcactg accttcaagc gctacggcaa gtcacccgac    60
atcgggttgg ccgacgttcc ccgccccacg ccaaaggctg acgaattact ggtgcaagtc    120
cacgctgccg gcctgaaccc gatcgacaac atgattccaa cggggatgtt caagcctgta    180
ttgcatttcc agctgccagc caccctgggc agcgatctgg ccggcatcgt gaccgaggta    240
ggtagcaatg tgacccgctt caagccaggc gatgctgtct tcgccagcct cttcgatctt    300
ggcacagggg cgattgcgga gttcgcggtt gtgccggaaa gcgccgccgc gctgaaaccg    360
gccaatctga gcttcgagca ggcggcgtcg atcccgatgg tcggcctcac ctcatggcaa    420
gcgctgaaag agcgcctcaa gcttcaggcc gggcagaagg tgttcattcc tgccgggtcg    480
gggggcatcg gtacattcgc aatccagttg gccaaacacc tcggtgcaaa ggtgggcacc    540
actaccagta caggcaacgt tgacctggtg cgcgctctgg gggcggacga ggttgtggac    600
tacaagacgc aggatttcga gaccgtgctg cgcgactacg acgcggtgct cggaaccgta    660
aggggggatg cgattgaaaa atccttgtcc atcctcagac ccggaagcca gattgtctcg    720
ctcgttggcc cactggatgc tgcgttcgcc cgggccaaac gcctgaacct cctcctgacc    780
ttcgtgttcg gcctgatgag ccgcaagatc atgcgcctgg caagaggcg gaatgtccaa     840 tactcgtttc ttttcgtgca gcccgacggt gcccaactcg ccgaaatcgg caagcttctg    900
gacgcccagc aaattcagcc ggtgatcgac cgggtatttc cgttcgagga cgcaaagggt    960
gcgcttgagt accttgctca agggcgctcc aagggcaagg tcgtaatcaa gatgtga       1017

<210> SEQ ID NO 93
<211> LENGTH: 1011
<212> TYPE: DNA
<213> ORGANISM: Pseudomonas putida

<400> SEQUENCE: 93
atgaaagctg ctgtcgttgc accaggccgt cgcgtggacg tgatagagaa aagcctgcgc    60
cctctcgaac acggcgaagc gctgctgaag atgcagtgct gcggtgtgtg ccacaccgac    120
ctgcacgtca aaaatggcga cttttggtgac aagaccgggg tagtactggg ccacgaaggt   180
attggcgtgg ttcaggaagt tggccccggc gtcacctcgc tcaagccagg cgaccgagcc    240
agcgttgcct ggttctacca gggttgcgga cattgcgaat actgcaacag cggcaacgag    300
accctgtgcc gcgacgtgaa gaattccggt tacaccgtgg acggcggcat ggccgaggcc    360
tgcatcgtca aggccgacta ctcggttaaa gtgcccgacg gcctcgactc gccgccgcc     420 agcagcatca cctgcgccgg cgtcacgacc tacaaggcag tgaaaatctc caacgtccgc    480
cccggccaat ggatcgccat ctacgggctc ggcggcctgg gcaacctggc cctgcaatat    540
```

```
gccaagaatg tgttcaacgc caaagtcatc gccatcgacg tcaacgaaga gcaactgcgc        600
ttcgccagcg agatgggcgc ggatctggtc gtcaacccgc tcaacgaaga tgccgcgaag        660
gtcatccagg ccaaaaccgg cggtgcacat gctgccgtcg ttactgctgt ggccaaaggc        720
gcgttcaact cggctgtcga tgccttgcgc gctggcgggc gactggtggc cgtcgggctt        780
ccgtcggagt ccatggacct gaatattccc cgcctggtgc ttgatgggat cgaagtggtg        840
ggctcgctgg taggtacacg ccaggacctg caggaagcct tccagtttgc cgctgaaggc        900
aaagtggtgc ccaaggtaac gctgcgaccg atcgaggata tcaaccagat ctttgacgag        960
atgctggagg gcaagatcaa aggccggatg gtgatacagt tcgaaggctg a                1011

<210> SEQ ID NO 94
<211> LENGTH: 1203
<212> TYPE: DNA
<213> ORGANISM: Pseudomonas putida

<400> SEQUENCE: 94
atgagagcag tctcctacca cggtgctaac gatgtgcggg tcgattctgt cccagacccc         60
atcctccaag acgcagacga catcatctta agggtgacgg ccaccgccat ctgcggatcc        120
gacctccacc tctatcgagg caagatcccg gaaacagagc aaggcgacat cttcggccac        180
gagttcatgg gcatcgtgga agaggttggc agggacgtga cgaccctgca ggttggcgac        240
cgagtggtga ttccttttgt catcgcttgt ggaagttgct ttttctgcca gcaggatctc        300
ttcgctgcct gtgaaaccac caataccggg cgcggatcga tcatcaacaa aaagggcata        360
ccaccaggcg cagcgctgtt cggatacagc catctgtatg gagggatccc tggaggccaa        420
gctgattacg ttagggtgcc caaaggcaat gtcgggccat tcaaagtccc gacgaccctc        480
gcggatgaca aagtgctgtt cctatccgac atccttccca ccgcttggca agcggtcatc        540
aatgccgaga ttggcgaagg ctcatcggta gcgatctatg gcgcggggcc agtggggctg        600
ttgagtgccg cctgcgcacg gatgctgggc gcgcacaccg tcttcatggt ggatgacaac        660
gactaccggc tggcctatgc ccaggaagcc tatggcgtca tcccgatcaa cttcgaaaag        720
gatgatgatc ctgccgacag catcattcgc cagacaccgg gtatgcgtgg cgtggacgcg        780
gtcatcgatg cggtcgggtt tgaagccaaa ggcagcacca cggaaaccgt gatgacggcc        840
ttgaaactgg agggtagcag cggcaaggcc ctgcgccaga gcatcgcggc tgtgcgacgt        900
ggcggcgtag tcagcgtgcc cggcgtctat gcagggttca ttcacggctt catgttcggt        960
gatgccttcg acaaaggcct gaccttcaag atgggtcaga cccatgttca aaaatacctt       1020
cccgaactgc tggagcacat cgaagcaggg cgcctgcaac cggaactgat cgttactcac       1080
cgcttagccc tagaagaggc ggccatgggc tacaaaatgt tcgatcaaaa gcaggataac       1140
tgccgcaagg tcatcctcgt gccaggtgct gcacccggca ccttgggccc tgaccacctc       1200
tag                                                                   1203

<210> SEQ ID NO 95
<211> LENGTH: 1011
<212> TYPE: DNA
<213> ORGANISM: Pseudomonas putida

<400> SEQUENCE: 95
atgagcagca aggccatcta cgtacaaccc ggcggcggct acgacaaggt cgaggtcggc         60
acctgcgagg cccaggcccc ccaggccggc gagattaccg tgcgcctgca cgccagttcc        120
ctcaactacc acgatttcgc cgtggtcagc ggcatgtggg gcccgagcga gcgacgcatc        180
```

```
ccaatggccg atggcgccgg cgaggtggtt gcggtggggg ctggcgtcac tgagttccag    240
gtcggcgaca atgtggtcag caccttcttc cccgactggc tcgatggcca ggccaatgtc    300
gagggcttcg ccagggtgcc cggcgacggc atcgatggct acgcccgtga gcaagtgact    360
gcccgcgcca ccgccttcac cctggcaccc cagggtttca gccatgccga ggctgccacc    420
ctgaccaccg ccggccttac cgcctggcgc gcgctgatga gcgacgatca cctcaagccc    480
ggcgacacgt gctggtgca gggtaccggc ggtgtgtcga ttttcgccct gcagttcgcc    540
aagctggcgg gcgcgaccgt gatcgccacc tcgtccagcg atgccaagct ggagcgcctg    600
aaggccctgg gtgccgacca cctgatcaac tacaagagca ccccggcctg gggtgagaag    660
gtgcgcgagc tgactggcaa ccgtggtgtc gatcatgtga ttgaagtggg cggcccggcg    720
acgctggagc agtcgatgat tgctgcgcgc attggcgggc atgtttcgct gatcggcatc    780
cttaccgggg tggccgggca gttgccgctg gtgcaggcgc tggtgcggca gattcggctg    840
caaggggtgc tggttggcag ccgagcgcag cagcaggcga tggtacgggc gatcgatgcc    900
aacggcctgc ggccggtggt ggacaagcat ttcgaactgg aacagatcgt cgaggcgttc    960
cgttaccagg agagcaaccg gcatttcggc aagatctgcc tgacctggtg a            1011

<210> SEQ ID NO 96
<211> LENGTH: 978
<212> TYPE: DNA
<213> ORGANISM: Pseudomonas putida

<400> SEQUENCE: 96
atgaaagctg tgttgtgcaa aaccctgggt ccggcgcgca acctggtgct ggaagaggtg     60
gccagcccac tgccgaagaa gaacgagatc ctgctggacg tgcaagctgc cggggtcaac    120
ttccccgaca ccttgatcat cgaaggcaag taccagttcc agccgccgct gccgttctct    180
ccaggtggcg aggcagcggg cgtggtggcc gccgtcggcg aaaaggccgg cgcgttcaag    240
gtcggcgacc gggtcatggc gctcaccggc tggggtgcgt cgccgagca agtggcggtg    300 ccgttctata acgttctgcc gatcccggcg agcatggact tcaccaccgc tgcggccttc    360
ggcatgacct acgcacctc gatgcacgcc ctgcgccagc gtggccagtt gcaagccggc    420
gagaccctgc tggtactggg cgcttccggc ggggtgggcc tggcggcggt ggagatcggc    480
aaggccatgg gcgcgcgggt gatcgcggcg gccagcagtg ccgagaaact ggccgtggcc    540
aaggctgccg ggcggatga gctgatcgac tacagccagg ccaacctgcg cgaagaaatc    600
aaacgcctga ccggtggcca gggcgtggac gtgatctatg acccggtcgg tggcgagctg    660
ttcgaacaag cggtgcgcgg gttggcctgg aatggcaggc tgctggtggt gggttttgcc    720
agtggcagca ttccacagct ggcggccaac ctggtgctgc tcaagggcgc ggcggtactg    780
ggcgtgttct gggggggcatt tgcccagcgc cagccggagg acaacgcggc caacttccac    840 cagctgttg cctggcatgc cgagggcaag ttgaagccgc tggtgtcgca gacttatcca    900
ctggcagaag ccggggttgc tatcgagaag ctggggcaac ggcaggctgt gggtaagttg    960
gtggtgctgg ccaggtaa                                                  978

<210> SEQ ID NO 97
<211> LENGTH: 37
<212> TYPE: DNA
<213> ORGANISM: Artificial Sequence
<220> FEATURE:
<223> OTHER INFORMATION: Primer

<400> SEQUENCE: 97
```

```
catgccatgg ggatgacaat gccttatgta aagaaca                                     37
```

<210> SEQ ID NO 98
<211> LENGTH: 25
<212> TYPE: DNA
<213> ORGANISM: Artificial Sequence
<220> FEATURE:
<223> OTHER INFORMATION: Primer

<400> SEQUENCE: 98

```
ctgcggtacc atagaagctc cgtga                                                  25
```

<210> SEQ ID NO 99
<211> LENGTH: 25
<212> TYPE: DNA
<213> ORGANISM: Artificial Sequence
<220> FEATURE:
<223> OTHER INFORMATION: Primer

<400> SEQUENCE: 99

```
tcacggagct tctatggtac cgcag                                                  25
```

<210> SEQ ID NO 100
<211> LENGTH: 33
<212> TYPE: DNA
<213> ORGANISM: Artificial Sequence
<220> FEATURE:
<223> OTHER INFORMATION: Primer

<400> SEQUENCE: 100

```
gctctagatt acgcctttcc gctggatccg aat                                         33
```

<210> SEQ ID NO 101
<211> LENGTH: 37
<212> TYPE: DNA
<213> ORGANISM: Artificial Sequence
<220> FEATURE:
<223> OTHER INFORMATION: Primer

<400> SEQUENCE: 101

```
catgccatgg ggatgaggag tacagacagg ttactgt                                     37
```

<210> SEQ ID NO 102
<211> LENGTH: 25
<212> TYPE: DNA
<213> ORGANISM: Artificial Sequence
<220> FEATURE:
<223> OTHER INFORMATION: Primer

<400> SEQUENCE: 102

```
tgcccacacc atcgcgaatg ttgaa                                                  25
```

<210> SEQ ID NO 103
<211> LENGTH: 25
<212> TYPE: DNA
<213> ORGANISM: Artificial Sequence
<220> FEATURE:
<223> OTHER INFORMATION: Primer

<400> SEQUENCE: 103

```
ttcaacattc gcgatggtgt gggca                                                  25
```

<210> SEQ ID NO 104
<211> LENGTH: 33
<212> TYPE: DNA
<213> ORGANISM: Artificial Sequence
<220> FEATURE:

```
<223> OTHER INFORMATION: Primer

<400> SEQUENCE: 104
gctctagatt acttctgacc gtacttggtg tgg                                33

<210> SEQ ID NO 105
<211> LENGTH: 37
<212> TYPE: DNA
<213> ORGANISM: Artificial Sequence
<220> FEATURE:
<223> OTHER INFORMATION: Primer

<400> SEQUENCE: 105
catgccatgg ggatgtggaa gcatgtaaaa caggttg                            37

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
catgcttccc attgtttcta tgaca                                         25

<210> SEQ ID NO 107
<211> LENGTH: 25
<212> TYPE: DNA
<213> ORGANISM: Artificial Sequence
<220> FEATURE:
<223> OTHER INFORMATION: Primer

<400> SEQUENCE: 107
tgtcatagaa acaatgggaa gcatg                                         25

<210> SEQ ID NO 108
<211> LENGTH: 25
<212> TYPE: DNA
<213> ORGANISM: Artificial Sequence
<220> FEATURE:
<223> OTHER INFORMATION: Primer

<400> SEQUENCE: 108
caccggtgct ccgtgggtga gatgt                                         25

<210> SEQ ID NO 109
<211> LENGTH: 25
<212> TYPE: DNA
<213> ORGANISM: Artificial Sequence
<220> FEATURE:
<223> OTHER INFORMATION: Primer

<400> SEQUENCE: 109
acatctcacc cacggagcac cggtg                                         25

<210> SEQ ID NO 110
<211> LENGTH: 33
<212> TYPE: DNA
<213> ORGANISM: Artificial Sequence
<220> FEATURE:
<223> OTHER INFORMATION: Primer

<400> SEQUENCE: 110
gctctagatt atatttccac cccttcgatc ttg                                33

<210> SEQ ID NO 111
```

-continued

<211> LENGTH: 37
<212> TYPE: DNA
<213> ORGANISM: Artificial Sequence
<220> FEATURE:
<223> OTHER INFORMATION: Primer

<400> SEQUENCE: 111
catgccatgg ggatgataga gtacaggatt gaggagg                              37

<210> SEQ ID NO 112
<211> LENGTH: 25
<212> TYPE: DNA
<213> ORGANISM: Artificial Sequence
<220> FEATURE:
<223> OTHER INFORMATION: Primer

<400> SEQUENCE: 112
cacacagact ccgtggaaac gattt                                           25

<210> SEQ ID NO 113
<211> LENGTH: 25
<212> TYPE: DNA
<213> ORGANISM: Artificial Sequence
<220> FEATURE:
<223> OTHER INFORMATION: Primer

<400> SEQUENCE: 113
aaatcgtttc cacggagtct gtgtg                                           25

<210> SEQ ID NO 114
<211> LENGTH: 33
<212> TYPE: DNA
<213> ORGANISM: Artificial Sequence
<220> FEATURE:
<223> OTHER INFORMATION: Primer

<400> SEQUENCE: 114
gctctagatt aacctccata tctctcttct ccc                                  33

<210> SEQ ID NO 115
<211> LENGTH: 37
<212> TYPE: DNA
<213> ORGANISM: Artificial Sequence
<220> FEATURE:
<223> OTHER INFORMATION: Primer

<400> SEQUENCE: 115
catgccatgg ggatgatcga tctcaggtcc gacaccg                              37

<210> SEQ ID NO 116
<211> LENGTH: 25
<212> TYPE: DNA
<213> ORGANISM: Artificial Sequence
<220> FEATURE:
<223> OTHER INFORMATION: Primer

<400> SEQUENCE: 116
agcctgtgcc atcgcttttc tcatc                                           25

<210> SEQ ID NO 117
<211> LENGTH: 25
<212> TYPE: DNA
<213> ORGANISM: Artificial Sequence
<220> FEATURE:
<223> OTHER INFORMATION: Primer

<400> SEQUENCE: 117
gatgagaaaa gcgatggcac aggct                                         25

<210> SEQ ID NO 118
<211> LENGTH: 25
<212> TYPE: DNA
<213> ORGANISM: Artificial Sequence
<220> FEATURE:
<223> OTHER INFORMATION: Primer

<400> SEQUENCE: 118
ttgatttccc attgtgccgg agggt                                         25

<210> SEQ ID NO 119
<211> LENGTH: 25
<212> TYPE: DNA
<213> ORGANISM: Artificial Sequence
<220> FEATURE:
<223> OTHER INFORMATION: Primer

<400> SEQUENCE: 119
accctccggc acaatgggaa atcaa                                         25

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
gagaaccgcc atcgctccga cctcg                                         25

<210> SEQ ID NO 121
<211> LENGTH: 25
<212> TYPE: DNA
<213> ORGANISM: Artificial Sequence
<220> FEATURE:
<223> OTHER INFORMATION: Primer

<400> SEQUENCE: 121
cgaggtcgga gcgatggcgg ttctc                                         25

<210> SEQ ID NO 122
<211> LENGTH: 25
<212> TYPE: DNA
<213> ORGANISM: Artificial Sequence
<220> FEATURE:
<223> OTHER INFORMATION: Primer

<400> SEQUENCE: 122
atcggggtcc atcgctccat ttttt                                         25

<210> SEQ ID NO 123
<211> LENGTH: 25
<212> TYPE: DNA
<213> ORGANISM: Artificial Sequence
<220> FEATURE:
<223> OTHER INFORMATION: Primer

<400> SEQUENCE: 123
aaaaaatgga gcgatggacc ccgat                                         25

<210> SEQ ID NO 124
<211> LENGTH: 33
<212> TYPE: DNA
<213> ORGANISM: Artificial Sequence
<220> FEATURE:

<223> OTHER INFORMATION: Primer

<400> SEQUENCE: 124
gctctagatt aggagaattt tctgaagagt ttt                33

<210> SEQ ID NO 125
<211> LENGTH: 36
<212> TYPE: DNA
<213> ORGANISM: Artificial Sequence
<220> FEATURE:
<223> OTHER INFORMATION: Primer

<400> SEQUENCE: 125
catgccatgg tttacacaac tccctggaac agaaag              36

<210> SEQ ID NO 126
<211> LENGTH: 33
<212> TYPE: DNA
<213> ORGANISM: Artificial Sequence
<220> FEATURE:
<223> OTHER INFORMATION: Primer

<400> SEQUENCE: 126
gctctagatt acaacctttg ccagagtatc gcc                 33

<210> SEQ ID NO 127
<211> LENGTH: 37
<212> TYPE: DNA
<213> ORGANISM: Artificial Sequence
<220> FEATURE:
<223> OTHER INFORMATION: Primer

<400> SEQUENCE: 127
catgccatgg ggatgaagat ggaagagctc ttcaaaa             37

<210> SEQ ID NO 128
<211> LENGTH: 33
<212> TYPE: DNA
<213> ORGANISM: Artificial Sequence
<220> FEATURE:
<223> OTHER INFORMATION: Primer

<400> SEQUENCE: 128
gctctagatt attctgtgca cccctgatc ttt                  33

<210> SEQ ID NO 129
<211> LENGTH: 37
<212> TYPE: DNA
<213> ORGANISM: Artificial Sequence
<220> FEATURE:
<223> OTHER INFORMATION: Primer

<400> SEQUENCE: 129
catgccatgg ggatgacaat gccttatgta aagaaca             37

<210> SEQ ID NO 130
<211> LENGTH: 33
<212> TYPE: DNA
<213> ORGANISM: Artificial Sequence
<220> FEATURE:
<223> OTHER INFORMATION: Primer

<400> SEQUENCE: 130
gctctagatt acgcctttcc gctggatccg aat                 33

<210> SEQ ID NO 131

```
<211> LENGTH: 37
<212> TYPE: DNA
<213> ORGANISM: Artificial Sequence
<220> FEATURE:
<223> OTHER INFORMATION: Primer

<400> SEQUENCE: 131
catgccatgg ggatgaggag tacagacagg ttactgt                              37

<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132
gctctagatt acttctgacc gtacttggtg tgg                                  33

<210> SEQ ID NO 133
<211> LENGTH: 37
<212> TYPE: DNA
<213> ORGANISM: Artificial Sequence
<220> FEATURE:
<223> OTHER INFORMATION: Primer

<400> SEQUENCE: 133
catgccatgg ggatgaagat ctttctggac acagcaa                              37

<210> SEQ ID NO 134
<211> LENGTH: 33
<212> TYPE: DNA
<213> ORGANISM: Artificial Sequence
<220> FEATURE:
<223> OTHER INFORMATION: Primer

<400> SEQUENCE: 134
gctctagatt atttcttcag gttctccaaa tac                                  33

<210> SEQ ID NO 135
<211> LENGTH: 37
<212> TYPE: DNA
<213> ORGANISM: Artificial Sequence
<220> FEATURE:
<223> OTHER INFORMATION: Primer

<400> SEQUENCE: 135
catgccatgg ggatgatagt cgttttgaaa cccggtt                              37

<210> SEQ ID NO 136
<211> LENGTH: 33
<212> TYPE: DNA
<213> ORGANISM: Artificial Sequence
<220> FEATURE:
<223> OTHER INFORMATION: Primer

<400> SEQUENCE: 136
gctctagatt aattcacctt caccccagg gca                                   33

<210> SEQ ID NO 137
<211> LENGTH: 37
<212> TYPE: DNA
<213> ORGANISM: Artificial Sequence
<220> FEATURE:
<223> OTHER INFORMATION: Primer

<400> SEQUENCE: 137
```

```
catgccatgg ggatgtggaa gcatgtaaaa caggttg                              37
```

<210> SEQ ID NO 138
<211> LENGTH: 33
<212> TYPE: DNA
<213> ORGANISM: Artificial Sequence
<220> FEATURE:
<223> OTHER INFORMATION: Primer

<400> SEQUENCE: 138

```
gctctagatt atatttccac cccttcgatc ttg                                  33
```

<210> SEQ ID NO 139
<211> LENGTH: 37
<212> TYPE: DNA
<213> ORGANISM: Artificial Sequence
<220> FEATURE:
<223> OTHER INFORMATION: Primer

<400> SEQUENCE: 139

```
catgccatgg ggatgagaga gacgataaga gagattc                              37
```

<210> SEQ ID NO 140
<211> LENGTH: 33
<212> TYPE: DNA
<213> ORGANISM: Artificial Sequence
<220> FEATURE:
<223> OTHER INFORMATION: Primer

<400> SEQUENCE: 140

```
gctctagatt acagccatcc ctccggaaca ccc                                  33
```

<210> SEQ ID NO 141
<211> LENGTH: 31
<212> TYPE: DNA
<213> ORGANISM: Artificial Sequence
<220> FEATURE:
<223> OTHER INFORMATION: Primer

<400> SEQUENCE: 141

```
catgccatgg tcaaggtcct gatcctcggt c                                    31
```

<210> SEQ ID NO 142
<211> LENGTH: 33
<212> TYPE: DNA
<213> ORGANISM: Artificial Sequence
<220> FEATURE:
<223> OTHER INFORMATION: Primer

<400> SEQUENCE: 142

```
gctctagatt acagccactt cggtttcaat ccc                                  33
```

<210> SEQ ID NO 143
<211> LENGTH: 37
<212> TYPE: DNA
<213> ORGANISM: Artificial Sequence
<220> FEATURE:
<223> OTHER INFORMATION: Primer

<400> SEQUENCE: 143

```
catgccatgg ggatgttcag aggagtagga actgcta                              37
```

<210> SEQ ID NO 144
<211> LENGTH: 33
<212> TYPE: DNA
<213> ORGANISM: Artificial Sequence
<220> FEATURE:

<223> OTHER INFORMATION: Primer

<400> SEQUENCE: 144
gctctagatt atagcaatcc actctccttg aga    33

<210> SEQ ID NO 145
<211> LENGTH: 37
<212> TYPE: DNA
<213> ORGANISM: Artificial Sequence
<220> FEATURE:
<223> OTHER INFORMATION: Primer

<400> SEQUENCE: 145
catgccatgg ggatgataga gtacaggatt gaggagg    37

<210> SEQ ID NO 146
<211> LENGTH: 33
<212> TYPE: DNA
<213> ORGANISM: Artificial Sequence
<220> FEATURE:
<223> OTHER INFORMATION: Primer

<400> SEQUENCE: 146
gctctagatt aacctccata tctctcttct ccc    33

<210> SEQ ID NO 147
<211> LENGTH: 37
<212> TYPE: DNA
<213> ORGANISM: Artificial Sequence
<220> FEATURE:
<223> OTHER INFORMATION: Primer

<400> SEQUENCE: 147
catgccatgg ggatgatcga tctcaggtcc gacaccg    37

<210> SEQ ID NO 148
<211> LENGTH: 33
<212> TYPE: DNA
<213> ORGANISM: Artificial Sequence
<220> FEATURE:
<223> OTHER INFORMATION: Primer

<400> SEQUENCE: 148
gctctagatt aggagaattt tctgaagagt ttt    33

<210> SEQ ID NO 149
<211> LENGTH: 37
<212> TYPE: DNA
<213> ORGANISM: Artificial Sequence
<220> FEATURE:
<223> OTHER INFORMATION: Primer

<400> SEQUENCE: 149
catgccatgg ggatggcaga tttagacgat attaaag    37

<210> SEQ ID NO 150
<211> LENGTH: 25
<212> TYPE: DNA
<213> ORGANISM: Artificial Sequence
<220> FEATURE:
<223> OTHER INFORMATION: Primer

<400> SEQUENCE: 150
ctgaaaataa ccgtggtcaa aagcc    25

<210> SEQ ID NO 151

```
<211> LENGTH: 25
<212> TYPE: DNA
<213> ORGANISM: Artificial Sequence
<220> FEATURE:
<223> OTHER INFORMATION: Primer

<400> SEQUENCE: 151
ggcttttgac cacggttatt ttcag                                             25

<210> SEQ ID NO 152
<211> LENGTH: 26
<212> TYPE: DNA
<213> ORGANISM: Artificial Sequence
<220> FEATURE:
<223> OTHER INFORMATION: Primer

<400> SEQUENCE: 152
cagtcacggc catcgtcggc attccc                                            26

<210> SEQ ID NO 153
<211> LENGTH: 26
<212> TYPE: DNA
<213> ORGANISM: Artificial Sequence
<220> FEATURE:
<223> OTHER INFORMATION: Primer

<400> SEQUENCE: 153
gggaatgccg acgatggccg tgactg                                            26

<210> SEQ ID NO 154
<211> LENGTH: 30
<212> TYPE: DNA
<213> ORGANISM: Artificial Sequence
<220> FEATURE:
<223> OTHER INFORMATION: Primer

<400> SEQUENCE: 154
gctctagatt actgtttttc actcagatag                                        30

<210> SEQ ID NO 155
<211> LENGTH: 33
<212> TYPE: DNA
<213> ORGANISM: Artificial Sequence
<220> FEATURE:
<223> OTHER INFORMATION: Primer

<400> SEQUENCE: 155
catgccatgg ggatgtacgt ggtatcgaca aag                                    33

<210> SEQ ID NO 156
<211> LENGTH: 25
<212> TYPE: DNA
<213> ORGANISM: Artificial Sequence
<220> FEATURE:
<223> OTHER INFORMATION: Primer

<400> SEQUENCE: 156
gttctccagt ctcgaaaaat caagc                                             25

<210> SEQ ID NO 157
<211> LENGTH: 25
<212> TYPE: DNA
<213> ORGANISM: Artificial Sequence
<220> FEATURE:
<223> OTHER INFORMATION: Primer

<400> SEQUENCE: 157
```
gcttgatttt tcgagactgg agaac                                              25

<210> SEQ ID NO 158
<211> LENGTH: 28
<212> TYPE: DNA
<213> ORGANISM: Artificial Sequence
<220> FEATURE:
<223> OTHER INFORMATION: Primer

<400> SEQUENCE: 158
gctctagatt atgccctgcc ctcgcagc                                           28

<210> SEQ ID NO 159
<211> LENGTH: 33
<212> TYPE: DNA
<213> ORGANISM: Artificial Sequence
<220> FEATURE:
<223> OTHER INFORMATION: Primer

<400> SEQUENCE: 159
catgccatgg ggatgaataa gtacaccatc aac                                     33

<210> SEQ ID NO 160
<211> LENGTH: 27
<212> TYPE: DNA
<213> ORGANISM: Artificial Sequence
<220> FEATURE:
<223> OTHER INFORMATION: Primer

<400> SEQUENCE: 160
gaggatcacc cacggcatat tgatatg                                            27

<210> SEQ ID NO 161
<211> LENGTH: 27
<212> TYPE: DNA
<213> ORGANISM: Artificial Sequence
<220> FEATURE:
<223> OTHER INFORMATION: Primer

<400> SEQUENCE: 161
catatcaata tgccgtgggt gatcctc                                            27

<210> SEQ ID NO 162
<211> LENGTH: 27
<212> TYPE: DNA
<213> ORGANISM: Artificial Sequence
<220> FEATURE:
<223> OTHER INFORMATION: Primer

<400> SEQUENCE: 162
gctctagatt agcggcgttt agccatc                                            27

<210> SEQ ID NO 163
<211> LENGTH: 32
<212> TYPE: DNA
<213> ORGANISM: Artificial Sequence
<220> FEATURE:
<223> OTHER INFORMATION: Primer

<400> SEQUENCE: 163
catgccatgg ggatgacgga caaattgacc tc                                      32

<210> SEQ ID NO 164
<211> LENGTH: 27
<212> TYPE: DNA
<213> ORGANISM: Artificial Sequence
<220> FEATURE:

<223> OTHER INFORMATION: Primer

<400> SEQUENCE: 164
gctctagatt acagcagatc gccgatc                                27

<210> SEQ ID NO 165
<211> LENGTH: 32
<212> TYPE: DNA
<213> ORGANISM: Artificial Sequence
<220> FEATURE:
<223> OTHER INFORMATION: Primer

<400> SEQUENCE: 165
catgccatgg ggatggaact gtatctggat ac                          32

<210> SEQ ID NO 166
<211> LENGTH: 30
<212> TYPE: DNA
<213> ORGANISM: Artificial Sequence
<220> FEATURE:
<223> OTHER INFORMATION: Primer

<400> SEQUENCE: 166
gctctagatt aaatcgacgt tctgccaaac                             30

<210> SEQ ID NO 167
<211> LENGTH: 35
<212> TYPE: DNA
<213> ORGANISM: Artificial Sequence
<220> FEATURE:
<223> OTHER INFORMATION: Primer

<400> SEQUENCE: 167
catgccatgg ggatgattga tttacgcagt gatac                       35

<210> SEQ ID NO 168
<211> LENGTH: 28
<212> TYPE: DNA
<213> ORGANISM: Artificial Sequence
<220> FEATURE:
<223> OTHER INFORMATION: Primer

<400> SEQUENCE: 168
gctctagatt aacgcgccag gaatgcac                               28

<210> SEQ ID NO 169
<211> LENGTH: 37
<212> TYPE: DNA
<213> ORGANISM: Artificial Sequence
<220> FEATURE:
<223> OTHER INFORMATION: Primer

<400> SEQUENCE: 169
catgccatgg ggatggcaga tttagacgat attaaag                     37

<210> SEQ ID NO 170
<211> LENGTH: 30
<212> TYPE: DNA
<213> ORGANISM: Artificial Sequence
<220> FEATURE:
<223> OTHER INFORMATION: Primer

<400> SEQUENCE: 170
gctctagatt actgttttc actcagatag                              30

<210> SEQ ID NO 171

```
<211> LENGTH: 32
<212> TYPE: DNA
<213> ORGANISM: Artificial Sequence
<220> FEATURE:
<223> OTHER INFORMATION: Primer

<400> SEQUENCE: 171
catgccatgg ggatgaaaaa ctggaaaaca ag                                    32

<210> SEQ ID NO 172
<211> LENGTH: 29
<212> TYPE: DNA
<213> ORGANISM: Artificial Sequence
<220> FEATURE:
<223> OTHER INFORMATION: Primer

<400> SEQUENCE: 172
gctctagatt acagcttagc gccttctac                                        29

<210> SEQ ID NO 173
<211> LENGTH: 33
<212> TYPE: DNA
<213> ORGANISM: Artificial Sequence
<220> FEATURE:
<223> OTHER INFORMATION: Primer

<400> SEQUENCE: 173
catgccatgg ggatgtacgt ggtatcgaca aag                                   33

<210> SEQ ID NO 174
<211> LENGTH: 28
<212> TYPE: DNA
<213> ORGANISM: Artificial Sequence
<220> FEATURE:
<223> OTHER INFORMATION: Primer

<400> SEQUENCE: 174
gctctagatt atgccctgcc ctcgcagc                                         28

<210> SEQ ID NO 175
<211> LENGTH: 33
<212> TYPE: DNA
<213> ORGANISM: Artificial Sequence
<220> FEATURE:
<223> OTHER INFORMATION: Primer

<400> SEQUENCE: 175
catgccatgg ggatgacaga tattgcgcag ttg                                   33

<210> SEQ ID NO 176
<211> LENGTH: 28
<212> TYPE: DNA
<213> ORGANISM: Artificial Sequence
<220> FEATURE:
<223> OTHER INFORMATION: Primer

<400> SEQUENCE: 176
gctctagatc aggcgatagt aattttgc                                         28

<210> SEQ ID NO 177
<211> LENGTH: 37
<212> TYPE: DNA
<213> ORGANISM: Artificial Sequence
<220> FEATURE:
<223> OTHER INFORMATION: Primer

<400> SEQUENCE: 177
```

```
catgccatgg ggatggcaca acctgccgct attattc                              37
```

<210> SEQ ID NO 178
<211> LENGTH: 28
<212> TYPE: DNA
<213> ORGANISM: Artificial Sequence
<220> FEATURE:
<223> OTHER INFORMATION: Primer

<400> SEQUENCE: 178

```
gctctagatt aacgctgcca gcttaagg                                        28
```

<210> SEQ ID NO 179
<211> LENGTH: 33
<212> TYPE: DNA
<213> ORGANISM: Artificial Sequence
<220> FEATURE:
<223> OTHER INFORMATION: Primer

<400> SEQUENCE: 179

```
catgccatgg ggatgaacga gttagacggc atc                                  33
```

<210> SEQ ID NO 180
<211> LENGTH: 29
<212> TYPE: DNA
<213> ORGANISM: Artificial Sequence
<220> FEATURE:
<223> OTHER INFORMATION: Primer

<400> SEQUENCE: 180

```
gctctagatt atagtttggc ggcaagaag                                       29
```

<210> SEQ ID NO 181
<211> LENGTH: 32
<212> TYPE: DNA
<213> ORGANISM: Artificial Sequence
<220> FEATURE:
<223> OTHER INFORMATION: Primer

<400> SEQUENCE: 181

```
catgccatgg ggatggaacg aaataaactt gc                                   32
```

<210> SEQ ID NO 182
<211> LENGTH: 28
<212> TYPE: DNA
<213> ORGANISM: Artificial Sequence
<220> FEATURE:
<223> OTHER INFORMATION: Primer

<400> SEQUENCE: 182

```
gctctagatt actcttcaat tcgtaacc                                        28
```

<210> SEQ ID NO 183
<211> LENGTH: 33
<212> TYPE: DNA
<213> ORGANISM: Artificial Sequence
<220> FEATURE:
<223> OTHER INFORMATION: Primer

<400> SEQUENCE: 183

```
catgccatgg ggatgtctaa gattttgat ttc                                   33
```

<210> SEQ ID NO 184
<211> LENGTH: 30
<212> TYPE: DNA
<213> ORGANISM: Artificial Sequence
<220> FEATURE:

<223> OTHER INFORMATION: Primer

<400> SEQUENCE: 184
gctctagatt acagaacgtc gatcgcgttc                              30

<210> SEQ ID NO 185
<211> LENGTH: 33
<212> TYPE: DNA
<213> ORGANISM: Artificial Sequence
<220> FEATURE:
<223> OTHER INFORMATION: Primer

<400> SEQUENCE: 185
catgccatgg ggatggatat tgtatttata gag                          33

<210> SEQ ID NO 186
<211> LENGTH: 33
<212> TYPE: DNA
<213> ORGANISM: Artificial Sequence
<220> FEATURE:
<223> OTHER INFORMATION: Primer

<400> SEQUENCE: 186
gctctagatt aattattttc tttcagatta ttg                          33

<210> SEQ ID NO 187
<211> LENGTH: 32
<212> TYPE: DNA
<213> ORGANISM: Artificial Sequence
<220> FEATURE:
<223> OTHER INFORMATION: Primer

<400> SEQUENCE: 187
catgccatgg ggatgaataa cgatgttttc cc                           32

<210> SEQ ID NO 188
<211> LENGTH: 28
<212> TYPE: DNA
<213> ORGANISM: Artificial Sequence
<220> FEATURE:
<223> OTHER INFORMATION: Primer

<400> SEQUENCE: 188
gctctagatt attttttaaa ggtatcag                                28

<210> SEQ ID NO 189
<211> LENGTH: 33
<212> TYPE: DNA
<213> ORGANISM: Artificial Sequence
<220> FEATURE:
<223> OTHER INFORMATION: Primer

<400> SEQUENCE: 189
catgccatgg ggatgaaaca tctgacagaa atg                          33

<210> SEQ ID NO 190
<211> LENGTH: 42
<212> TYPE: DNA
<213> ORGANISM: Artificial Sequence
<220> FEATURE:
<223> OTHER INFORMATION: Primer

<400> SEQUENCE: 190
gctcatatat atatcctcct ttattggcct tcacaggctg tg                42

<210> SEQ ID NO 191

```
<211> LENGTH: 45
<212> TYPE: DNA
<213> ORGANISM: Artificial Sequence
<220> FEATURE:
<223> OTHER INFORMATION: Primer

<400> SEQUENCE: 191
caataaagga ggatatatat atgagcatta tctccactaa atatc            45

<210> SEQ ID NO 192
<211> LENGTH: 28
<212> TYPE: DNA
<213> ORGANISM: Artificial Sequence
<220> FEATURE:
<223> OTHER INFORMATION: Primer

<400> SEQUENCE: 192
gctctagatt atgctgaaat tcgattcg                               28

<210> SEQ ID NO 193
<211> LENGTH: 33
<212> TYPE: DNA
<213> ORGANISM: Artificial Sequence
<220> FEATURE:
<223> OTHER INFORMATION: Primer

<400> SEQUENCE: 193
catgccatgg ggatgaataa gtacaccatc aac                         33

<210> SEQ ID NO 194
<211> LENGTH: 27
<212> TYPE: DNA
<213> ORGANISM: Artificial Sequence
<220> FEATURE:
<223> OTHER INFORMATION: Primer

<400> SEQUENCE: 194
gctctagatt agcggcgttt agccatc                                27

<210> SEQ ID NO 195
<211> LENGTH: 32
<212> TYPE: DNA
<213> ORGANISM: Artificial Sequence
<220> FEATURE:
<223> OTHER INFORMATION: Primer

<400> SEQUENCE: 195
catgccatgg ggatgcaaaa cattactcag tc                          32

<210> SEQ ID NO 196
<211> LENGTH: 28
<212> TYPE: DNA
<213> ORGANISM: Artificial Sequence
<220> FEATURE:
<223> OTHER INFORMATION: Primer

<400> SEQUENCE: 196
gctctagatt acagcgccag cgcactgg                               28

<210> SEQ ID NO 197
<211> LENGTH: 32
<212> TYPE: DNA
<213> ORGANISM: Artificial Sequence
<220> FEATURE:
<223> OTHER INFORMATION: Primer

<400> SEQUENCE: 197
```
catgccatgg ggatggaact gtatctggac ac                                    32

<210> SEQ ID NO 198
<211> LENGTH: 31
<212> TYPE: DNA
<213> ORGANISM: Artificial Sequence
<220> FEATURE:
<223> OTHER INFORMATION: Primer

<400> SEQUENCE: 198
gctctagatt agagatgagt agtgccaaat g                                     31

<210> SEQ ID NO 199
<211> LENGTH: 32
<212> TYPE: DNA
<213> ORGANISM: Artificial Sequence
<220> FEATURE:
<223> OTHER INFORMATION: Primer

<400> SEQUENCE: 199
catgccatgg ggatgactga tctgaaagca ag                                    32

<210> SEQ ID NO 200
<211> LENGTH: 27
<212> TYPE: DNA
<213> ORGANISM: Artificial Sequence
<220> FEATURE:
<223> OTHER INFORMATION: Primer

<400> SEQUENCE: 200
gctctagatt agtagctgct ggcgctc                                          27

<210> SEQ ID NO 201
<211> LENGTH: 31
<212> TYPE: DNA
<213> ORGANISM: Artificial Sequence
<220> FEATURE:
<223> OTHER INFORMATION: Primer

<400> SEQUENCE: 201
cccgagctct taggaggatt agtcatggaa c                                     31

<210> SEQ ID NO 202
<211> LENGTH: 32
<212> TYPE: DNA
<213> ORGANISM: Artificial Sequence
<220> FEATURE:
<223> OTHER INFORMATION: Primer

<400> SEQUENCE: 202
gctctagatt attttgaata atcgtagaaa cc                                    32

<210> SEQ ID NO 203
<211> LENGTH: 42
<212> TYPE: DNA
<213> ORGANISM: Artificial Sequence
<220> FEATURE:
<223> OTHER INFORMATION: Primer

<400> SEQUENCE: 203
gctctagagg aggatatata tatgaaaaat tgtgtcatcg tc                         42

<210> SEQ ID NO 204
<211> LENGTH: 30
<212> TYPE: DNA
<213> ORGANISM: Artificial Sequence
<220> FEATURE:

```
<223> OTHER INFORMATION: Primer

<400> SEQUENCE: 204
aactgcagtt aattcaaccg ttcaatcacc                                    30

<210> SEQ ID NO 205
<211> LENGTH: 46
<212> TYPE: DNA
<213> ORGANISM: Artificial Sequence
<220> FEATURE:
<223> OTHER INFORMATION: Primer

<400> SEQUENCE: 205
cgagctcagg aggatatata tatgaaaaat tgtgtcatcg tcagtg                  46

<210> SEQ ID NO 206
<211> LENGTH: 50
<212> TYPE: DNA
<213> ORGANISM: Artificial Sequence
<220> FEATURE:
<223> OTHER INFORMATION: Primer

<400> SEQUENCE: 206
ggttgaatta aggaggatat atatgaat aaagacacac taatacctac                50

<210> SEQ ID NO 207
<211> LENGTH: 50
<212> TYPE: DNA
<213> ORGANISM: Artificial Sequence
<220> FEATURE:
<223> OTHER INFORMATION: Primer

<400> SEQUENCE: 207
gtctttattc atatatatat cctccttaat tcaaccgttc aatcaccatc              50

<210> SEQ ID NO 208
<211> LENGTH: 30
<212> TYPE: DNA
<213> ORGANISM: Artificial Sequence
<220> FEATURE:
<223> OTHER INFORMATION: Primer

<400> SEQUENCE: 208
cccaagctta gccggcaagt acacatcttc                                    30

<210> SEQ ID NO 209
<211> LENGTH: 46
<212> TYPE: DNA
<213> ORGANISM: Artificial Sequence
<220> FEATURE:
<223> OTHER INFORMATION: Primer

<400> SEQUENCE: 209
cgagctcagg aggatatata tatgaaaaat tgtgtcatcg tcagtg                  46

<210> SEQ ID NO 210
<211> LENGTH: 30
<212> TYPE: DNA
<213> ORGANISM: Artificial Sequence
<220> FEATURE:
<223> OTHER INFORMATION: Primer

<400> SEQUENCE: 210
cccaagctta gccggcaagt acacatcttc                                    30

<210> SEQ ID NO 211
```

```
<211> LENGTH: 40
<212> TYPE: DNA
<213> ORGANISM: Artificial Sequence
<220> FEATURE:
<223> OTHER INFORMATION: Primer

<400> SEQUENCE: 211
aaggaaaaaa gcggccgccc ctgaaccgac gaccgggtcg                          40

<210> SEQ ID NO 212
<211> LENGTH: 33
<212> TYPE: DNA
<213> ORGANISM: Artificial Sequence
<220> FEATURE:
<223> OTHER INFORMATION: Primer

<400> SEQUENCE: 212
cggggtacca cttttcatac tcccgccatt cag                                33

<210> SEQ ID NO 213
<211> LENGTH: 35
<212> TYPE: DNA
<213> ORGANISM: Artificial Sequence
<220> FEATURE:
<223> OTHER INFORMATION: Primer

<400> SEQUENCE: 213
cggggtaccg cggatacata tttgaatgta tttag                              35

<210> SEQ ID NO 214
<211> LENGTH: 44
<212> TYPE: DNA
<213> ORGANISM: Artificial Sequence
<220> FEATURE:
<223> OTHER INFORMATION: Primer

<400> SEQUENCE: 214
aaggaaaaaa gcggccgcgc ggatacatat ttgaatgtat ttag                    44

<210> SEQ ID NO 215
<211> LENGTH: 1248
<212> TYPE: DNA
<213> ORGANISM: Cuphea hookeriana

<400> SEQUENCE: 215
atggtggctg ctgcagcaag ttccgcattc ttccctgttc cagcccccgg agcctcccct    60
aaacccggga gttcggaaa ttggccctcg agcttgagcc cttccttcaa gcccaagtca    120
atccccaatg gcggatttca ggttaaggca aatgacagcg cccatccaaa ggctaacggt    180
tctgcagtta gtctaaagtc tggcagcctc aacactcagg aggacacttc gtcgtccct    240 cctcctcgga ctttccttca ccagttgcct gattggagta ggcttctgac tgcaatcacg    300
accgtgttcg tgaaatctaa gaggcctgac atgcatgatc ggaaatccaa gaggcctgac    360
atgctggtgg actcgtttgg gttggagagt actgttcagg atgggctcgt gttccgacag    420 agttttcga ttaggtctta tgaaataggc actgatcgaa cggcctctat agagacactt    480
atgaaccact gcaggaaac atctctcaat cattgtaaga gtaccggtat tctccttgac    540
ggcttcggtc gtactcttga tgtgtaaa agggacctca tttgggtggt aataaaaatg    600
cagatcaagg tgaatcgcta tccagcttgg ggcgatactg tcgagatcaa tacccggttc    660
tcccggttgg ggaaaatcgg tatgggtcgc gattggctaa taagtgattg caacacagga    720
gaaattcttg taagagctac gagcgcgtat gccatgatga atcaaaagac gagaagactc    780
```

```
tcaaaacttc catacgaggt tcaccaggag atagtgcctc tttttgtcga ctctcctgtc     840
attgaagaca gtgatctgaa agtgcataag tttaaagtga agactggtga ttccattcaa     900
aagggtctaa ctccggggtg gaatgacttg gatgtcaatc agcacgtaag caacgtgaag     960
tacattgggt ggattctcga gagtatgcca acagaagttt tggagaccca ggagctatgc    1020
tctctcgccc ttgaatatag gcgggaatgc ggaagggaca gtgtgctgga gtccgtgacc    1080
gctatggatc cctcaaaagt tggagtccgt tctcagtacc agcaccttct gcggcttgag    1140
gatgggactg ctatcgtgaa cggtgcaact gagtggcggc cgaagaatgc aggagctaac    1200
ggggcgatat caacgggaaa gacttcaaat ggaaactcgg tctcttag                 1248
```

<210> SEQ ID NO 216
<211> LENGTH: 1260
<212> TYPE: DNA
<213> ORGANISM: Cuphea lanceolata

<400> SEQUENCE: 216

```
atggtggctg ctgcagcaac ttctgcattc ttccccgttc cagccccggg aacctcccct      60
aaacccggga gtccggcaa ctggccatcg agcttgagcc ctaccttcaa gcccaagtca     120
atccccaatg ctggatttca ggttaaggca aatgccagtg cccatcctaa ggctaacggt     180
tctgcagtaa atctaaagtc tggcagcctc aacactcagg aggacacttc gtcgtcccct     240
cctccccggg cttcccttaa ccagttgcct gattggagta tgcttctgac tgcaatcacg     300
accgtcttcg tggcggcaga gaagcagtgg actatgcttg ataggaaatc taagaggcct     360
gacatgctcg tggactcggt tgggttgaag agtattgttc gggatgggct cgtgtccaga     420
cagagttttt tgattagatc ttatgaaata ggcgctgatc gaacagcctc tatagagacg     480
ctgatgaacc acttgcagga acatctatc aatcattgta agagtttggg tcttctcaat     540
gacggctttg gtcgtactcc tgggatgtgt aaaaacgacc tcatttgggt gcttacaaaa     600
atgcagatca tggtgaatcg ctacccaact tggggcgata ctgttgagat caatacctgg     660
ttctctcagt cggggaaaat cggtatggct agcgattggc taataagtga ttgcaacaca     720
ggagaaattc ttataagagc aacgagcgtg tgggctatga tgaatcaaaa gacgagaaga     780
ttctcaagac ttccatacga ggttcgccag gagttaacac ctcattttgt ggactctcct     840
catgtcattg aagacaatga tcagaaattg cataagtttg atgtgaagac tggtgattcc     900
attcgcaagg gtctaactcc gaggtggaat gacttggatg tgaatcagca cgtaagcaac     960
gtgaagtaca ttgggtggat tctcgagagt atgccaatag aagttttgga gacccaggag    1020
ctatgctctc tcaccgttga atataggcgg gaatgcggaa tggacagtgt gctggagtcc    1080
gtgactgctg tggatccctc agaaaatgga ggccggtctc agtacaagca ccttttgcgg    1140
cttgaggatg ggactgatat cgtgaagagc agaactgagt ggcgaccgaa gaatgcagga    1200
actaacgggg cgatatcaac atcaacagca aagacttcaa atggaaactc ggcctcttag    1260
```

<210> SEQ ID NO 217
<211> LENGTH: 1617
<212> TYPE: DNA
<213> ORGANISM: Cuphea lanceolata

<400> SEQUENCE: 217

```
atggcggcgg cctcttccat ggctgcgtca ccgttctgta cgtggctcgt agctgcttgc      60
atgtccactt ccttcgaaaa caacccacgt tcgccctcca tcaagcgtct ccccgccgg     120 aggagggttc tctcccattg ctccctccgt ggatccacct tccaatgcct cgtcacctca     180
```

-continued

```
cacatcgacc cttgcaatca gaactgctcc tccgactccc ttagcttcat cggggttaac      240
ggattcggat ccaagccatt ccggtccaat cgcggccacc ggaggctcgg ccgtgcttcc      300
cattccgggg aggccatggc tgtggctctg caacctgcac aggaagtcgc cacgaagaag      360
aaacctgcta tcaagcaaag gcgagtagtt gttacaggaa tgggtgtggt gactcctcta      420
ggccatgaac ctgatgtttt ctacaacaat ctcctagatg gagtaagcgg cataagtgag      480
atagagaact tcgacagcac tcagtttccc acgagaattg ccggagagat caagtctttt      540
tccacagatg gctgggtggc cccaaagctc tccaagagga tggacaagct catgctttac      600
ttgttgactg ctggcaagaa agcattagca gatgctggaa tcaccgatga tgtgatgaaa      660
gagcttgata aagaaagtg tggagttctc attggctccg gaatgggcgg catgaagttg      720
ttctacgatg cgcttgaagc cctgaaaatc tcttacagga gatgaaccc tttttgtgta      780 ccttttgcca ccacaaatat gggatcagct atgcttgcaa tggatctggg atggatgggt      840
ccaaactact ctatttcaac tgcctgtgca acaagtaatt tctgtatact gaatgctgca      900
aaccacataa tcagaggcga agctgacatg atgctttgtg gtggctcgga tgcggtcatt      960
atacctatcg gtttgggagg ttttgtggcg tgccgagctt tgtcacagag gaataatgac     1020
cctaccaaag cttcgagacc atgggatagt aatcgtgatg gatttgtaat gggcgaagga     1080
gctggagtgt tacttctcga ggagttagag catgcaaaga aaagaggtgc aaccatttat     1140
gcagaatttt taggggcag tttcacttgc gatgcctacc acatgaccga gcctcaccct     1200
gaaggagctg gagtgatcct ctgcatagag aaggccatgg ctcaggccgg agtctctaga     1260
gaagatgtaa attacataaa tgcccatgca acttccactc ctgctggaga tatcaaagaa     1320
taccaagctc tcgcccactg tttcggccaa acagcgagc tgagagtgaa ttccactaaa     1380
tcgatgatcg gtcatcttct tggagcagct ggtggcgtag aagcagttac tgtaattcag     1440
gcgataagga ctgggtggat ccatccaaat cttaatttgg aagacccgga caaagccgtg     1500
gatgcaaaat ttctcgtggg acctgagaag gagagactga atgtcaaggt cggtttgtcc     1560
aattcatttg ggttcggtgg gcataactcg tctatactct tcgcccctta caattag       1617
```

<210> SEQ ID NO 218
<211> LENGTH: 1641
<212> TYPE: DNA
<213> ORGANISM: Cuphea lanceolata

<400> SEQUENCE: 218

```
atgcctgccg cctcttccct gctcgcttcc cctctctgta cgtggctcct tgccgcctgc       60
atgtctacct ccttccaccc ctccgaccct cttccgcctt ccatctcctc tcctcgccga      120
cgcctctccc gccgcggat tctctcccaa tgcgccccac taccttctgc ttcctccgcc      180
ctccgcggat ccagtttcca taccctcgtc acctcttacc tcgcctgctt cgagccctgc      240
catgactact atacatccgc atccttgttc ggatccagac ccattcgcac cacccgcagg      300
caccggaggc tcaatcgagc ttccccttcc agggaggcaa tggccgtggc tctgcaacct      360
gaacaggaag ttaccacaaa gaagaagcca agtatcaaac agcggcgagt agttgtgact      420
ggaatgggtg tggtgactcc tctaggccat gaccctgatg ttttctacaa taatctgctt      480 gatgaacga gtggcataag cgagatagag acctttgatt gtgctcaatt tcctacgaga      540
attgctggag agatcaagtc tttctccaca gatggttggg tggccccgaa gctctctaag      600
aggatggaca agttcatgct atacatgctg accgctggca agaaagcatt aacagatggt      660
ggaatcaccg aagatgtgat gaaagagcta gataaaagaa aatgcggagt tctcattggc      720
```

```
tcagcaatgg gtggaatgaa ggtattcaat gatgccattg aagccctaag gatttcatat    780
aagaagatga atccctttg tgtacctttc gctaccacaa atatgggatc agctatgctt    840
gcaatggact tgggatggat ggggcccaac tactcgatat ctactgcttg tgcaacgagt    900
aacttttgta taatgaatgc tgcgaaccat ataatcagag gcgaagcaga tgtgatgctt    960
tgcgggggct cagatgcggt aatcatacct attggtatgg gaggttttgt tgcatgccga   1020
gctttgtccc agagaaattc cgaccctact aaagcttcaa gaccatggga cagtaatcgt   1080
gatggatttg ttatggggga aggagctgga gtgctactac tagaggagtt ggagcatgca   1140
aagaaaagag gtgcgactat ttacgcagaa tttctaggtg ggagtttcac ttgcgatgcc   1200
taccacatga ccgagcctca ccctgatgga gctggagtga ttctctgcat agagaaggct   1260
ttggctcagt caggagtctc tagggaagac gtaaattaca taaatgccca tgccacatcc   1320
actccggctg agatatcaa agagtaccaa gctcttatcc actgtttcgg ccaaaacaga   1380
gagttaaaag ttaattcaac caaatcaatg attggtcacc ttctcggagc agccggtggt   1440
gtggaagcag tttcagtagt tcaggcaata aggactgggt ggatccatcc gaatattaat   1500
ttggaaaacc cagatgaagg cgtggataca aaattgctcg tgggtcctaa gaaggagaga   1560
ctgaacgtta aggtcggttt gtctaattca tttgggtttg gtgggcacaa ctcgtccata   1620
ctcttcgccc cttacatcta g                                             1641

<210> SEQ ID NO 219
<211> LENGTH: 414
<212> TYPE: DNA
<213> ORGANISM: Cuphea lanceolata

<400> SEQUENCE: 219
atggcgtccg cagctcccgc ttcttcgatc tgcatcaaat ccgcctcctg ctcggctctg     60
gcgccgggta gaatctcgag cttgagatca gtctcactac ctgtcagtcg gaaaagcttc    120
ttctctcgca ggggttcgtt ctccctccga gtcaactgtc aggctaaacc agaaccgtg    180 acaaaggtct gcaatatagt gaagaagcag ttggccttac cagacgactc tgatgtttcc    240
ggagtgtcca agttcagtgc tcttggagca gattcttggg acacggtgga gattgtcatg    300
ggactagagg aggagtttgg gatcagtgtg gaggaagaaa gtgcacagag catccagacc    360
gtccaagatg ccgccgatct catcgagaag ctcatggaga agaagggcca ttga          414

<210> SEQ ID NO 220
<211> LENGTH: 432
<212> TYPE: DNA
<213> ORGANISM: Cuphea lanceolata

<400> SEQUENCE: 220
atggctaccg ccgccgccgg atcttccctc atctgcatca agtccgcttc ctgctcccct     60
aaccgggctc aggtaccaag tggactttca agcctgagat ctgtctcgct acctatcagt    120
ggcaaaatct ttccctctct caggtcatcc agggaccttt tgagcttccg cgtctgctgt    180
caggctaagc aagaaaccgt aacgagggtc tgcgaaatag tcaagaagca gttggccttg    240
ccagaggact ctgaggttaa cggactgtca agttctctg ctctcggtgc agactctttg     300
gacacggtgg agattgtcat gggactagag gaagagtttg gatcagtgt ggaggaagag    360 agtgctcaga gcatccaaac cgtccaagac gctgcagatc tcatcgagaa gctcgttggg    420
aataagaaat aa                                                        432

<210> SEQ ID NO 221
```

```
<211> LENGTH: 423
<212> TYPE: DNA
<213> ORGANISM: Cuphea lanceolata

<400> SEQUENCE: 221
atggcttccg cagctgccgg tgcttccatc tgcatcaagt ccgcctcctt ctcgcctctg     60
gcaccgggta gaatttcaag cttgagatct gtctcattac ctgtgagtcg gaaaagcttt    120
ccctctctca agtcatccaa gagttcgttc gctctccggg tcagctgtca ggctaaacca    180
gaaaccgtgg cgaaggtctg cggcatagtg aagaaacaat tggccttacc agacgactct    240
gaggttaatg gactatccaa gtttagtgct ctcggagcag attctctcga cacggtggag    300
attgtcatgg gactagagga ggaatttggg atcagcgtgg aggaagaaag tgcacagagc    360
atccagaccg tccaagatgc tgccgatctc atcgagaagc tcatggagaa gagggccat     420 tga                                                                  423

<210> SEQ ID NO 222
<211> LENGTH: 420
<212> TYPE: DNA
<213> ORGANISM: Cuphea lanceolata

<400> SEQUENCE: 222
atggcttccg cagctgccgg tgcttccatc tgcatcaagt ccgcctcctg ctcgcctctg     60
gcaccgggta gaatttcaag cttgagatca gtctcattac ctgtgagtcg gaaaagcttt    120
ccctctctca ggtcatccaa gggttcgttt gcccgggtca gctgtcaggc taaaccagaa    180
accgtggcga aggtctgccg catagtgaag aaacaattgg ccttaccaga cgactctgag    240
gttaatggac tatccaagtt tagtgctctc ggagcagatt ctctcgacac ggtggagatt    300
gtcatgggac tagaggagga atttgggatc agcgtggagg aagaaagtgc acagagcatc    360
cagaccgtcc aagatgctgc cgatctcatc gagaagctca tggagaagaa gggccattga    420

<210> SEQ ID NO 223
<211> LENGTH: 8
<212> TYPE: PRT
<213> ORGANISM: Eschericia coli DH10B
<220> FEATURE:
<221> NAME/KEY: VARIANT
<222> LOCATION: 1
<223> OTHER INFORMATION: Xaa = Asp, Gly, or His
<220> FEATURE:
<221> NAME/KEY: VARIANT
<222> LOCATION: 2
<223> OTHER INFORMATION: Xaa = Ile, Val, Ser, Ala, or Cys
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 7
<223> OTHER INFORMATION: Xaa = Ser, Thr, or Ala
<220> FEATURE:
<221> NAME/KEY: VARIANT
<222> LOCATION: 8
<223> OTHER INFORMATION: Xaa = Leu, Ile, Val, Met, or Phe

<400> SEQUENCE: 223

Xaa Xaa Thr Xaa Asn Pro Xaa Xaa
 1               5

<210> SEQ ID NO 224
<211> LENGTH: 18
<212> TYPE: PRT
<213> ORGANISM: Escherichia coli DH10B
```

```
<220> FEATURE:
<221> NAME/KEY: VARIANT
<222> LOCATION: 1
<223> OTHER INFORMATION: Xaa = Leu, Ile, Val, Met, or Ala
<220> FEATURE:
<221> NAME/KEY: VARIANT
<222> LOCATION: 2
<223> OTHER INFORMATION: Xaa = Any amino acid
<220> FEATURE:
<221> NAME/KEY: VARIANT
<222> LOCATION: 3
<223> OTHER INFORMATION: Xaa = Leu, Ile, Val, or Met
<220> FEATURE:
<221> NAME/KEY: VARIANT
<222> LOCATION: 5
<223> OTHER INFORMATION: Xaa = Leu, Ile, Val, or Met
<220> FEATURE:
<221> NAME/KEY: VARIANT
<222> LOCATION: 6
<223> OTHER INFORMATION: Xaa = Pro, Ala, or Ser
<220> FEATURE:
<221> NAME/KEY: VARIANT
<222> LOCATION: 7
<223> OTHER INFORMATION: Xaa = Any amino acid
<220> FEATURE:
<221> NAME/KEY: VARIANT
<222> LOCATION: 8
<223> OTHER INFORMATION: Xaa = Ser, Thr, or Cys
<220> FEATURE:
<221> NAME/KEY: VARIANT
<222> LOCATION: 9
<223> OTHER INFORMATION: Xaa = Any amino acid
<220> FEATURE:
<221> NAME/KEY: VARIANT
<222> LOCATION: 10
<223> OTHER INFORMATION: Xaa = Asp, Glu, Asn, Gln, Pro, Ala, or Ser
<220> FEATURE:
<221> NAME/KEY: VARIANT
<222> LOCATION: 11
<223> OTHER INFORMATION: Xaa = Gly or Cys
<220> FEATURE:
<221> NAME/KEY: VARIANT
<222> LOCATION: 12
<223> OTHER INFORMATION: Xaa = Leu, Ile, Val, or Met
<220> FEATURE:
<221> NAME/KEY: VARIANT
<222> LOCATION: 13
<223> OTHER INFORMATION: Xaa = Any amino acid
<220> FEATURE:
<221> NAME/KEY: VARIANT
<222> LOCATION: 14
<223> OTHER INFORMATION: Xaa = Ala, Gly, or Val
<220> FEATURE:
<221> NAME/KEY: VARIANT
<222> LOCATION: 15
<223> OTHER INFORMATION: Xaa = Any amino acid
<220> FEATURE:
<221> NAME/KEY: VARIANT
<222> LOCATION: 16
<223> OTHER INFORMATION: Xaa = Gln, Glu, Lys, Arg, Ser, Thr, or His
<220> FEATURE:
<221> NAME/KEY: VARIANT
<222> LOCATION: 17
<223> OTHER INFORMATION: Xaa = Any amino acid
<220> FEATURE:
<221> NAME/KEY: VARIANT
<222> LOCATION: 18
<223> OTHER INFORMATION: Xaa = Leu, Ile, Val, Met, or Phe

<400> SEQUENCE: 224

Xaa Xaa Xaa Lys Xaa Xaa Xaa Xaa Xaa Xaa Xaa Xaa Xaa Xaa Xaa Xaa
 1               5                  10                  15

Xaa Xaa

<210> SEQ ID NO 225
<211> LENGTH: 10
<212> TYPE: PRT
```

```
<213> ORGANISM: Escherichia coli DH10B
<220> FEATURE:
<221> NAME/KEY: VARIANT
<222> LOCATION: 2
<223> OTHER INFORMATION: Xaa = Leu, Ile, Val, or Met
<220> FEATURE:
<221> NAME/KEY: VARIANT
<222> LOCATION: (3)...(5)
<223> OTHER INFORMATION: Xaa = Any amino acid
<220> FEATURE:
<221> NAME/KEY: VARIANT
<222> LOCATION: 7
<223> OTHER INFORMATION: Xaa = Leu, Ile, or Val
<220> FEATURE:
<221> NAME/KEY: VARIANT
<222> LOCATION: 9
<223> OTHER INFORMATION: Xaa = Leu or Phe

<400> SEQUENCE: 225

Gly Xaa Xaa Xaa Xaa Glu Xaa Thr Xaa Arg
 1               5                  10

<210> SEQ ID NO 226
<211> LENGTH: 14
<212> TYPE: PRT
<213> ORGANISM: Escherichia coli DH10B
<220> FEATURE:
<221> NAME/KEY: VARIANT
<222> LOCATION: 2-4, 11-13
<223> OTHER INFORMATION: Xaa = Any amino acid
<220> FEATURE:
<221> NAME/KEY: VARIANT
<222> LOCATION: 5
<223> OTHER INFORMATION: Xaa = Leu, Ile, Val, Met, or Phe
<220> FEATURE:
<221> NAME/KEY: VARIANT
<222> LOCATION: 7
<223> OTHER INFORMATION: Xaa = Leu or Phe
<220> FEATURE:
<221> NAME/KEY: VARIANT
<222> LOCATION: 10
<223> OTHER INFORMATION: Xaa = Ser or Ala

<400> SEQUENCE: 226

Gly Xaa Xaa Xaa Xaa Lys Xaa Phe Pro Xaa Xaa Xaa Xaa Gly
 1               5                  10

<210> SEQ ID NO 227
<211> LENGTH: 12
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2
<223> OTHER INFORMATION: Xaa = Any amino acid
<220> FEATURE:
<221> NAME/KEY: VARIANT
<222> LOCATION: 3
<223> OTHER INFORMATION: Xaa = Leu, Ile, Val, Met, or His
<220> FEATURE:
<221> NAME/KEY: VARIANT
<222> LOCATION: 4
<223> OTHER INFORMATION: Xaa = Ala, Pro, Asn, or Thr
<220> FEATURE:
<221> NAME/KEY: VARIANT
<222> LOCATION: 5
<223> OTHER INFORMATION: Xaa = Leu, Ile, Val, or Met
<220> FEATURE:
<221> NAME/KEY: VARIANT
<222> LOCATION: 6
<223> OTHER INFORMATION: Xaa = Any amino acid
<220> FEATURE:
```

```
<221> NAME/KEY: VARIANT
<222> LOCATION: 7
<223> OTHER INFORMATION: Xaa = Leu, Ile, Val, or Met
<220> FEATURE:
<221> NAME/KEY: VARIANT
<222> LOCATION: 9
<223> OTHER INFORMATION: Xaa = Any amino acid
<220> FEATURE:
<221> NAME/KEY: VARIANT
<222> LOCATION: 12
<223> OTHER INFORMATION: Xaa = Gly, Ala, Cys, or His

<400> SEQUENCE: 227

Xaa Xaa Xaa Xaa Xaa Xaa Xaa His Xaa Asp His Xaa
 1               5                  10

<210> SEQ ID NO 228
<211> LENGTH: 12
<212> TYPE: PRT
<213> ORGANISM: Escherichia coli DH10B
<220> FEATURE:
<221> NAME/KEY: VARIANT
<222> LOCATION: 1
<223> OTHER INFORMATION: Xaa = Leu, Ile, Val, or Met
<220> FEATURE:
<221> NAME/KEY: VARIANT
<222> LOCATION: 3, 7, 8, 11
<223> OTHER INFORMATION: Xaa = Any amino acid
<220> FEATURE:
<221> NAME/KEY: VARIANT
<222> LOCATION: 5
<223> OTHER INFORMATION: Xaa = Leu, Ile, Val, or Met
<220> FEATURE:
<221> NAME/KEY: VARIANT
<222> LOCATION: 9
<223> OTHER INFORMATION: Xaa = Gly or Met
<220> FEATURE:
<221> NAME/KEY: VARIANT
<222> LOCATION: 10
<223> OTHER INFORMATION: Xaa = Gly, Ser, Thr, or Ala

<400> SEQUENCE: 228

Xaa Glu Xaa Glu Xaa Gly Xaa Xaa Xaa Xaa Xaa Glu
 1               5                  10

<210> SEQ ID NO 229
<211> LENGTH: 9
<212> TYPE: PRT
<213> ORGANISM: Escherichia coli DH10B

<400> SEQUENCE: 229

Asp Ala Thr Thr Asn Pro Ser Leu Ile
 1               5

<210> SEQ ID NO 230
<211> LENGTH: 18
<212> TYPE: PRT
<213> ORGANISM: Escherichia coli DH10B

<400> SEQUENCE: 230

Ile Leu Ile Lys Leu Ala Ser Thr Trp Gln Gly Ile Arg Ala Ala Glu
 1               5                  10                  15

Gln Leu

<210> SEQ ID NO 231
<211> LENGTH: 9
<212> TYPE: PRT
<213> ORGANISM: Escherichia coli DH10B

<400> SEQUENCE: 231
```

```
Gly Val Thr Thr Asn Pro Ser Ile Ile
1               5
```

<210> SEQ ID NO 232
<211> LENGTH: 17
<212> TYPE: PRT
<213> ORGANISM: Escherichia coli DH10B

<400> SEQUENCE: 232

```
Ile Val Val Lys Val Pro Val Thr Ala Glu Gly Leu Ala Ala Ile Lys
1               5                   10                  15

Met
```

<210> SEQ ID NO 233
<211> LENGTH: 9
<212> TYPE: PRT
<213> ORGANISM: Escherichia coli DH10B

<400> SEQUENCE: 233

```
Asp Ala Thr Thr Asn Pro Ser Leu Leu
1               5
```

<210> SEQ ID NO 234
<211> LENGTH: 18
<212> TYPE: PRT
<213> ORGANISM: Escherichia coli DH10B

<400> SEQUENCE: 234

```
Ile Leu Ile Lys Leu Ala Ser Thr Trp Glu Gly Ile Arg Ala Ala Glu
1               5                   10                  15

Glu Leu
```

<210> SEQ ID NO 235
<211> LENGTH: 9
<212> TYPE: PRT
<213> ORGANISM: Escherichia coli DH10B

<400> SEQUENCE: 235

```
Gly Val Thr Thr Asn Pro Ser Ile Ile
1               5
```

<210> SEQ ID NO 236
<211> LENGTH: 17
<212> TYPE: PRT
<213> ORGANISM: Escherichia coli DH10B

<400> SEQUENCE: 236

```
Ile Val Val Lys Ile Pro Val Thr Ser Glu Gly Leu Ala Ala Ile Lys
1               5                   10                  15

Ile
```

<210> SEQ ID NO 237
<211> LENGTH: 10
<212> TYPE: PRT
<213> ORGANISM: Escherichia coli DH10B

<400> SEQUENCE: 237

```
Gly Val Arg Val Leu Glu Val Thr Leu Arg
1               5                   10
```

<210> SEQ ID NO 238
<211> LENGTH: 14
<212> TYPE: PRT
<213> ORGANISM: Escherichia coli DH10B -continued

<400> SEQUENCE: 238

Gly Leu Lys Glu Phe Lys Phe Phe Pro Ala Glu Ala Asn Gly
1               5                   10

<210> SEQ ID NO 239
<211> LENGTH: 12
<212> TYPE: PRT
<213> ORGANISM: Escherichia coli DH10B

<400> SEQUENCE: 239

Tyr His His Pro Leu Ala Ile His Leu Asp His His
1               5                   10

<210> SEQ ID NO 240
<211> LENGTH: 12
<212> TYPE: PRT
<213> ORGANISM: Escherichia coli DH10B

<400> SEQUENCE: 240

Val Glu Ala Glu Leu Gly Gln Leu Gly Gly Gln Glu
1               5                   10

<210> SEQ ID NO 241
<211> LENGTH: 12
<212> TYPE: PRT
<213> ORGANISM: Escherichia coli DH10B

<400> SEQUENCE: 241

Tyr Gly Val Pro Val Ile Leu His Thr Asp His Cys
1               5                   10

<210> SEQ ID NO 242
<211> LENGTH: 11
<212> TYPE: PRT
<213> ORGANISM: Escherichia coli DH10B

<400> SEQUENCE: 242

Leu Glu Ile Glu Leu Gly Cys Thr Gly Gly Glu
1               5                   10

<210> SEQ ID NO 243
<211> LENGTH: 14
<212> TYPE: PRT
<213> ORGANISM: Escherichia coli DH10B

<400> SEQUENCE: 243

Thr Thr Tyr Asn Met Pro Leu Ala Leu His Leu Asp His His
1               5                   10

<210> SEQ ID NO 244
<211> LENGTH: 12
<212> TYPE: PRT
<213> ORGANISM: Escherichia coli DH10B

<400> SEQUENCE: 244

Val Glu Ala Glu Leu Gly Arg Leu Gly Gly Val Glu
1               5                   10

<210> SEQ ID NO 245
<211> LENGTH: 6
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.

```
<220> FEATURE:
<221> NAME/KEY: VARIANT
<222> LOCATION: 1, 6
<223> OTHER INFORMATION: Xaa = Ala, Gly, or Ser
<220> FEATURE:
<221> NAME/KEY: VARIANT
<222> LOCATION: 2, 5
<223> OTHER INFORMATION: Xaa = Any amino acid

<400> SEQUENCE: 245

Xaa Xaa Gly Gly Xaa Xaa
 1               5

<210> SEQ ID NO 246
<211> LENGTH: 7
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 7
<223> OTHER INFORMATION: Xaa = Ala, Gly, or Ser
<220> FEATURE:
<221> NAME/KEY: VARIANT
<222> LOCATION: 2, 3, 6
<223> OTHER INFORMATION: Xaa = Any amino acid

<400> SEQUENCE: 246

Xaa Xaa Xaa Gly Gly Xaa Xaa
 1               5

<210> SEQ ID NO 247
<211> LENGTH: 8
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 8
<223> OTHER INFORMATION: Xaa = Ala, Gly, or Ser
<220> FEATURE:
<221> NAME/KEY: VARIANT
<222> LOCATION: 2, 3, 4, 7
<223> OTHER INFORMATION: Xaa = Any amino acid

<400> SEQUENCE: 247

Xaa Xaa Xaa Xaa Gly Gly Xaa Xaa
 1               5

<210> SEQ ID NO 248
<211> LENGTH: 6
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 6
<223> OTHER INFORMATION: Xaa = Ala, Gly, or Ser
<220> FEATURE:
<221> NAME/KEY: VARIANT
<222> LOCATION: 2, 4, 5
<223> OTHER INFORMATION: Xaa = Any amino acid

<400> SEQUENCE: 248

Xaa Xaa Gly Xaa Xaa Xaa
 1               5
```

```
<210> SEQ ID NO 249
<211> LENGTH: 8
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 8
<223> OTHER INFORMATION: Xaa = Ala, Gly, or Ser
<220> FEATURE:
<221> NAME/KEY: VARIANT
<222> LOCATION: 2, 3, 6, 7
<223> OTHER INFORMATION: Xaa = Any amino acid

<400> SEQUENCE: 249

Xaa Xaa Xaa Gly Gly Xaa Xaa Xaa
 1               5

<210> SEQ ID NO 250
<211> LENGTH: 8
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 8
<223> OTHER INFORMATION: Xaa = Ala, Gly, or Ser
<220> FEATURE:
<221> NAME/KEY: VARIANT
<222> LOCATION: 2-4, 6-7
<223> OTHER INFORMATION: Xaa = Any amino acid

<400> SEQUENCE: 250

Xaa Xaa Xaa Xaa Gly Xaa Xaa Xaa
 1               5

<210> SEQ ID NO 251
<211> LENGTH: 5
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 5
<223> OTHER INFORMATION: Xaa = Ala, Gly, or Ser
<220> FEATURE:
<221> NAME/KEY: VARIANT
<222> LOCATION: 2, 4
<223> OTHER INFORMATION: Xaa = Any amino acid

<400> SEQUENCE: 251

Xaa Xaa Gly Xaa Xaa
 1               5

<210> SEQ ID NO 252
<211> LENGTH: 6
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 6
<223> OTHER INFORMATION: Xaa = Ala, Gly, or Ser
<220> FEATURE:
<221> NAME/KEY: VARIANT
```

```
<222> LOCATION: 2, 3, 5
<223> OTHER INFORMATION: Xaa = Any amino acid

<400> SEQUENCE: 252

Xaa Xaa Xaa Gly Xaa Xaa
 1               5

<210> SEQ ID NO 253
<211> LENGTH: 7
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 7
<223> OTHER INFORMATION: Xaa = Ala, Gly, or Ser
<220> FEATURE:
<221> NAME/KEY: VARIANT
<222> LOCATION: 2-4, 6
<223> OTHER INFORMATION: Xaa = Any amino acid

<400> SEQUENCE: 253

Xaa Xaa Xaa Xaa Gly Xaa Xaa
 1               5

<210> SEQ ID NO 254
<211> LENGTH: 8
<212> TYPE: PRT
<213> ORGANISM: Artificial Sequence
<220> FEATURE:
<223> OTHER INFORMATION: Example sequence of a possible NAD+, NADH,
      NADP+, or NADPH binding motif.
<220> FEATURE:
<221> NAME/KEY: VARIANT
<222> LOCATION: 1, 8
<223> OTHER INFORMATION: Xaa = Ala, Gly, or Ser
<220> FEATURE:
<221> NAME/KEY: VARIANT
<222> LOCATION: 2-5, 7
<223> OTHER INFORMATION: Xaa = Any amino acid

<400> SEQUENCE: 254

Xaa Xaa Xaa Xaa Xaa Gly Xaa Xaa
 1               5

<210> SEQ ID NO 255
<211> LENGTH: 17
<212> TYPE: PRT
<213> ORGANISM: Escherichia coli DH10B
<220> FEATURE:
<221> NAME/KEY: VARIANT
<222> LOCATION: 1
<223> OTHER INFORMATION: Xaa = Leu, Ile, Val, Met, or Ala
<220> FEATURE:
<221> NAME/KEY: VARIANT
<222> LOCATION: 2
<223> OTHER INFORMATION: Xaa = Any amino acid
<220> FEATURE:
<221> NAME/KEY: VARIANT
<222> LOCATION: 3
<223> OTHER INFORMATION: Xaa = Leu, Ile, Val, or Met
<220> FEATURE:
<221> NAME/KEY: VARIANT
<222> LOCATION: 5
<223> OTHER INFORMATION: Xaa = Leu, Ile, Val, or Met
<220> FEATURE:
<221> NAME/KEY: VARIANT
<222> LOCATION: 6
<223> OTHER INFORMATION: Xaa = Pro, Ala, or Ser
<220> FEATURE:
<221> NAME/KEY: VARIANT
<222> LOCATION: 7
```

-continued

```
<223> OTHER INFORMATION: Xaa = Any amino acid
<220> FEATURE:
<221> NAME/KEY: VARIANT
<222> LOCATION: 8
<223> OTHER INFORMATION: Xaa = Ser, Thr, or Cys
<220> FEATURE:
<221> NAME/KEY: VARIANT
<222> LOCATION: 9
<223> OTHER INFORMATION: Xaa = Any amino acid
<220> FEATURE:
<221> NAME/KEY: VARIANT
<222> LOCATION: 10
<223> OTHER INFORMATION: Xaa = Asp, Glu, Asn, Gln, Pro, Ala, or Ser
<220> FEATURE:
<221> NAME/KEY: VARIANT
<222> LOCATION: 11
<223> OTHER INFORMATION: Xaa = Gly or Cys
<220> FEATURE:
<221> NAME/KEY: VARIANT
<222> LOCATION: 12
<223> OTHER INFORMATION: Xaa = Leu, Ile, Val, or Met
<220> FEATURE:
<221> NAME/KEY: VARIANT
<222> LOCATION: 13
<223> OTHER INFORMATION: Xaa = Any amino acid
<220> FEATURE:
<221> NAME/KEY: VARIANT
<222> LOCATION: 14
<223> OTHER INFORMATION: Xaa = Ala, Gly, or Val
<220> FEATURE:
<221> NAME/KEY: VARIANT
<222> LOCATION: 15
<223> OTHER INFORMATION: Xaa = Gln, Glu, Lys, Arg, Ser, Thr, or His
<220> FEATURE:
<221> NAME/KEY: VARIANT
<222> LOCATION: 16
<223> OTHER INFORMATION: Xaa = Any amino acid
<220> FEATURE:
<221> NAME/KEY: VARIANT
<222> LOCATION: 17
<223> OTHER INFORMATION: Xaa = Leu, Ile, Val, Met, or Phe

<400> SEQUENCE: 255

Xaa Xaa Xaa Lys Xaa Xaa Xaa Xaa Xaa Xaa Xaa Xaa Xaa Xaa Xaa Xaa
  1               5                  10                  15

Xaa

<210> SEQ ID NO 256
<211> LENGTH: 13
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2
<223> OTHER INFORMATION: Xaa = Any amino acid
<220> FEATURE:
<221> NAME/KEY: VARIANT
<222> LOCATION: 3
<223> OTHER INFORMATION: Xaa = Leu, Ile, Val, Met, or His
<220> FEATURE:
<221> NAME/KEY: VARIANT
<222> LOCATION: 4
<223> OTHER INFORMATION: Xaa = Ala, Pro, Asn, or Thr
<220> FEATURE:
<221> NAME/KEY: VARIANT
<222> LOCATION: 5
<223> OTHER INFORMATION: Xaa = Leu, Ile, Val, or Met
<220> FEATURE:
<221> NAME/KEY: VARIANT
<222> LOCATION: 6, 7
<223> OTHER INFORMATION: Xaa = Any amino acid
<220> FEATURE:
<221> NAME/KEY: VARIANT
```

<222> LOCATION: 8
<223> OTHER INFORMATION: Xaa = Leu, Ile, Val, or Met
<220> FEATURE:
<221> NAME/KEY: VARIANT
<222> LOCATION: 10
<223> OTHER INFORMATION: Xaa = Any amino acid
<220> FEATURE:
<221> NAME/KEY: VARIANT
<222> LOCATION: 13
<223> OTHER INFORMATION: Xaa = Gly, Ala, Cys, or His

<400> SEQUENCE: 256

Xaa Xaa Xaa Xaa Xaa Xaa Xaa Xaa His Xaa Asp His Xaa
 1               5                  10

<210> SEQ ID NO 257
<211> LENGTH: 13
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2,3
<223> OTHER INFORMATION: Xaa = Any amino acid
<220> FEATURE:
<221> NAME/KEY: VARIANT
<222> LOCATION: 4
<223> OTHER INFORMATION: Xaa = Leu, Ile, Val, Met, or His
<220> FEATURE:
<221> NAME/KEY: VARIANT
<222> LOCATION: 5
<223> OTHER INFORMATION: Xaa = Ala, Pro, Asn, or Thr
<220> FEATURE:
<221> NAME/KEY: VARIANT
<222> LOCATION: 6
<223> OTHER INFORMATION: Xaa = Leu, Ile, Val, or Met
<220> FEATURE:
<221> NAME/KEY: VARIANT
<222> LOCATION: 7
<223> OTHER INFORMATION: Xaa = Any amino acid
<220> FEATURE:
<221> NAME/KEY: VARIANT
<222> LOCATION: 8
<223> OTHER INFORMATION: Xaa = Leu, Ile, Val, or Met
<220> FEATURE:
<221> NAME/KEY: VARIANT
<222> LOCATION: 10
<223> OTHER INFORMATION: Xaa = Any amino acid
<220> FEATURE:
<221> NAME/KEY: VARIANT
<222> LOCATION: 13
<223> OTHER INFORMATION: Xaa = Gly, Ala, Cys, or His

<400> SEQUENCE: 257

Xaa Xaa Xaa Xaa Xaa Xaa Xaa Xaa His Xaa Asp His Xaa
 1               5                  10

<210> SEQ ID NO 258
<211> LENGTH: 14
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2, 3
<223> OTHER INFORMATION: Xaa = Any amino acid
<220> FEATURE:
<221> NAME/KEY: VARIANT
<222> LOCATION: 4
<223> OTHER INFORMATION: Xaa = Leu, Ile, Val, Met, or His

```
<220> FEATURE:
<221> NAME/KEY: VARIANT
<222> LOCATION: 5
<223> OTHER INFORMATION: Xaa = Ala, Pro, Asn, or Thr
<220> FEATURE:
<221> NAME/KEY: VARIANT
<222> LOCATION: 6
<223> OTHER INFORMATION: Xaa = Leu, Ile, Val, or Met
<220> FEATURE:
<221> NAME/KEY: VARIANT
<222> LOCATION: 7, 8
<223> OTHER INFORMATION: Xaa = Any amino acid
<220> FEATURE:
<221> NAME/KEY: VARIANT
<222> LOCATION: 9
<223> OTHER INFORMATION: Xaa = Leu, Ile, Val, or Met
<220> FEATURE:
<221> NAME/KEY: VARIANT
<222> LOCATION: 11
<223> OTHER INFORMATION: Xaa = Any amino acid
<220> FEATURE:
<221> NAME/KEY: VARIANT
<222> LOCATION: 14
<223> OTHER INFORMATION: Xaa = Gly, Ala, Cys, or His

<400> SEQUENCE: 258

Xaa Xaa Xaa Xaa Xaa Xaa Xaa Xaa Xaa His Xaa Asp His Xaa
 1               5                  10

<210> SEQ ID NO 259
<211> LENGTH: 14
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2-4
<223> OTHER INFORMATION: Xaa = Any amino acid
<220> FEATURE:
<221> NAME/KEY: VARIANT
<222> LOCATION: 5
<223> OTHER INFORMATION: Xaa = Leu, Ile, Val, Met, or His
<220> FEATURE:
<221> NAME/KEY: VARIANT
<222> LOCATION: 6
<223> OTHER INFORMATION: Xaa = Ala, Pro, Asn, or Thr
<220> FEATURE:
<221> NAME/KEY: VARIANT
<222> LOCATION: 7
<223> OTHER INFORMATION: Xaa = Leu, Ile, Val, or Met
<220> FEATURE:
<221> NAME/KEY: VARIANT
<222> LOCATION: 8
<223> OTHER INFORMATION: Xaa = Any amino acid
<220> FEATURE:
<221> NAME/KEY: VARIANT
<222> LOCATION: 9
<223> OTHER INFORMATION: Xaa = Leu, Ile, Val, or Met
<220> FEATURE:
<221> NAME/KEY: VARIANT
<222> LOCATION: 11
<223> OTHER INFORMATION: Xaa = Any amino acid
<220> FEATURE:
<221> NAME/KEY: VARIANT
<222> LOCATION: 14
<223> OTHER INFORMATION: Xaa = Gly, Ala, Cys, or His

<400> SEQUENCE: 259

Xaa Xaa Xaa Xaa Xaa Xaa Xaa Xaa His Xaa Asp His Xaa
 1               5                  10

<210> SEQ ID NO 260
<211> LENGTH: 15
```

```
<212> TYPE: PRT
<213> ORGANISM: Escherichia coli
<220> FEATURE:
<221> NAME/KEY: VARIANT
<222> LOCATION: 1
<223> OTHER INFORMATION: Xaa = Phe, Tyr, Val, Met, or Thr
<220> FEATURE:
<221> NAME/KEY: VARIANT
<222> LOCATION: 2-4
<223> OTHER INFORMATION: Xaa = Any amino acid
<220> FEATURE:
<221> NAME/KEY: VARIANT
<222> LOCATION: 5
<223> OTHER INFORMATION: Xaa = Leu, Ile, Val, Met, or His
<220> FEATURE:
<221> NAME/KEY: VARIANT
<222> LOCATION: 6
<223> OTHER INFORMATION: Xaa = Ala, Pro, Asn, or Thr
<220> FEATURE:
<221> NAME/KEY: VARIANT
<222> LOCATION: 7
<223> OTHER INFORMATION: Xaa = Leu, Ile, Val, or Met
<220> FEATURE:
<221> NAME/KEY: VARIANT
<222> LOCATION: 8, 9
<223> OTHER INFORMATION: Xaa = Any amino acid
<220> FEATURE:
<221> NAME/KEY: VARIANT
<222> LOCATION: 10
<223> OTHER INFORMATION: Xaa = Leu, Ile, Val, or Met
<220> FEATURE:
<221> NAME/KEY: VARIANT
<222> LOCATION: 12
<223> OTHER INFORMATION: Xaa = Any amino acid
<220> FEATURE:
<221> NAME/KEY: VARIANT
<222> LOCATION: 15
<223> OTHER INFORMATION: Xaa = Gly, Ala, Cys, or His

<400> SEQUENCE: 260

Xaa Xaa Xaa Xaa Xaa Xaa Xaa Xaa Xaa Xaa His Xaa Asp His Xaa
1               5                   10                  15
```